US010000452B1

(12) United States Patent
Manetsch et al.

(10) Patent No.: US 10,000,452 B1
(45) Date of Patent: Jun. 19, 2018

(54) QUINOLONE-BASED COMPOUNDS, FORMULATIONS, AND USES THEREOF

(71) Applicants: Roman Manetsch, Boston, MA (US); Dennis E. Kyle, Lithia, FL (US); Raghupathi Neelarapu, Newark, DE (US); Jordany R. Maignan, Land O Lakes, FL (US); Cynthia L. Lichorowic, Durham, NC (US); Alexis N. LaCrue, Temple Terrace, FL (US)

(72) Inventors: Roman Manetsch, Boston, MA (US); Dennis E. Kyle, Lithia, FL (US); Raghupathi Neelarapu, Newark, DE (US); Jordany R. Maignan, Land O Lakes, FL (US); Cynthia L. Lichorowic, Durham, NC (US); Alexis N. LaCrue, Temple Terrace, FL (US)

(73) Assignees: University of South Florida, Tampa, FL (US); Northeastern University, Boston, MA (US)

( * ) Notice: Subject to any disclaimer, the term of this patent is extended or adjusted under 35 U.S.C. 154(b) by 0 days. days.

(21) Appl. No.: 15/412,667

(22) Filed: Jan. 23, 2017

Related U.S. Application Data

(60) Provisional application No. 62/281,833, filed on Jan. 22, 2016.

(51) Int. Cl.
*C07D 215/56* (2006.01)

(52) U.S. Cl.
CPC .................................. *C07D 215/56* (2013.01)

(58) Field of Classification Search
CPC .................................................. C07D 215/56
See application file for complete search history.

(56) References Cited

U.S. PATENT DOCUMENTS

| 3,947,449 | A | 3/1976 | Durckheimer | |
|---|---|---|---|---|
| 8,598,354 | B2 * | 12/2013 | Riscoe | C07D 215/233 546/153 |
| 8,877,752 | B2 * | 11/2014 | Manetsch | C07D 215/233 514/235.2 |
| 9,206,131 | B2 * | 12/2015 | Riscoe | C07D 215/233 |

OTHER PUBLICATIONS

Ressurreicao et al (2013): STN International, HCAPLUS database (Columbus, Ohio), Accession No. 2013: 1417905.*
Jimenez et al (2013): STN International, HCAPLUS database (Columbus, Ohio), Accession No. 2013: 1795646.*
Devine et al (2015): STN International, HCAPLUS database (Columbus, Ohio), Accession No. 2015: 1023981.*
Ryley, et al., Trop. Med. Parasitol. 1970, 64, 209-222.
Nilsen, et al., Quinolone-3-Diarylethers: A New Class of Antimalarial Drug. Sci. Transl. Med. 2013, 5, 1-11.
World Malaria Report 2013; World Health Organization, pp. ii-255.
World Health Organization. Malaria Fact Sheet. http://www.who.int/mediacentre/factsheets/fs094/en/(accessed Jun 22, 2015). pp. 1-9.
Control, C. f. D. Malaria Parasites. http://www.cdc.gov/malaria/about/biology/parasites.html (Sep. 16, 2014). pp. 1-2.
Lacrue, et al., 4(1H)-Quinolones with liver stage activity against Plasmodium berghei. Antimicrobial agents and chemotherapy 2013, 57, 417-24.
Teixeira, et al., "Recycling" Classical Drugs for Malaria. Chemical Reviews 2014, 114, 11164-11220.
Monastyrskyi, et al., 4(1H)-Pyridone and 4(1H)-Quinolone Derivatives as Antimalarials with Erythrocytic, Exoerythrocytic, and Transmission Blocking Activities. Current Topics in Medicinal Chemistry 2014, 14, 1693-1705.
Cross, et al., Orally Bioavailable 6-Chloro-7-methoxy-4(1H)-quinolones Efficacious against Multiple Stages of Plasmodium. Journal of Medicinal Chemistry 2014, 57, 8860-8879.
Puri, et al., Quinoline esters as potential antimalarial drugs: effect on relapses of Plasmodium cynomolgi infections in monkeys. Transactions of the Royal Society of Tropical Medicine and Hygiene 1990, 84, 759-60.
Zhang, et al. Lead optimization of 3-carboxyl-4(1H)-quinolones to deliver orally bioavailable antimalarials. J Med Chem 2012, 55, 4205-19.
Zhang et al. Synthesis and structure-activity relationships of antimalarial 4-oxo-3-carboxyl quinolones. Bioorganic & medicinal chemistry 2010, 18, 2756-66.
Cross, et al., Synthesis, antimalarial activity, and structure-activity relationship of 7-(2-phenoxyethoxy)-4(1H)-quinolones. J Med Chem 2011, 54, 8321-7.
Reddy, et al., Discovery of 8-Cyclopentyl-2[4-(4-methyl-piperazin-1-yl)-phenylamino]-7-oxo-7,8-dihydro-pyrido[2,3-d]pyrimidine-6-carbonitrile (7x) as a Potent Inhibitor of Cyclin-Dependent Kinase 4 (CDK4) and AMPK-Related Kinase 5 (ARK5). Journal of Medicinal Chemistry 2014, 57, 578-599.
Liu, et al, A general and convenient synthesis of N-aryl piperazines. Tetrahedron Letters 2005, 46, 7921-7922.
Kühhorn, et al., Bivalent Dopamine D2 Receptor Ligands: Synthesis and Binding Properties. Journal of Medicinal Chemistry 2011, 54, 4896-4903.
Rossi, et al., Alkyl piperidine and piperazine hydroxamic acids as HDAC inhibitors. Bioorganic & Medicinal Chemistry Letters 2011, 21, 2305-2308.
Ghosh, et al., Discovery of 4-(4-(2-((5-Hydroxy-1,2,3,4-tetrahydronaphthalen-2-yl)(propyl)amino)ethyl)piperazin-1-yl)quinolin-8-ol and Its Analogues as Highly Potent Dopamine D2/D3 Agonists and as Iron Chelator: In Vivo Activity Indicates Potential Application in Symptomatic and Neuroprotective Therapy for Parkinson's Disease. Journal of Medicinal Chemistry 2010, 53, 2114-2125.

(Continued)

*Primary Examiner* — Golam M Shameem
(74) *Attorney, Agent, or Firm* — Thomas | Horstemeyer, LLP

(57) ABSTRACT

Provided herein are quinolone-based compounds that can be used for treatment and/or prevention of malaria and formulations thereof. Also provided herein are methods of treating and/or preventing malaria in a subject by administering a quinolone-based compound or formulation thereof provided herein.

17 Claims, 23 Drawing Sheets

(56) References Cited

OTHER PUBLICATIONS

World Malaria Report 2015; World Health Organization: Geneva, Switzerland, 2015. pp. ii-243.
Centers for Disease Control and Prevention. Biology. http://www.cdc.gov/malaria/about/biology/ (accessed Jun. 22, 2015). pp. 1-2.
Cross, et al., Optimization of 1,2,3,4-Tetrahydroacridin-9(10H)-Ones as Antimalarials Utilizing Structure-Activity and Structure-Property Relationships. J. Med. Chem. 2011, 54 (13), 4399-4426.
Cross, et al., Optimization: Structure-Activity and Structure-Property Relationship Studies of 3-Substituted 2-Methyl-4 (1H)-Quinolones with Antimalarial Activity. J. Med. Chem. 2010, 53 (19), 7076-7094.
Saenz, et al., 4-(1H)-Quinolones and 1,2,3,4-Tetrahydroacridin-9(10H)-Ones Prevent the Transmission of Plasmodium Falciparum to Anopheles Freeborn. Antimicrob. Agents Chemother. 2013, 57 (12), 6187-6195.
Bueno, et al., Potent Antimalarial 4-Pyridones with Improved Physico-Chemical Properties. Bioorg. Med. Chem. Lett. 2011, 21 (18), 5214-5218.
Winter, et al., Antimalarial Quinolones: Synthesis, Potency, and Mechanistic Studies. Exp. Parasitol. 2008, 118 (4), 487-497.
Winter, et al., Optimization of Endochin-like Quinolones for Antimalarial Activity. Exp. Parasitol. 2011, 127 (2), 545-551.
Cowley, et al., The Development of Quinoloneesters as Novel Antimalarial Agents Targeting the Plasmodium Falciparum Bc 1 Protein Complex. Med. Chem. Commun. 2012, 3 (1), 39-44.
Maignan, et al., Manetsch, R. ICI 56,780 Optimization: Structural-Activity and Relationship Studies of 7-(2-Phenoxyethoxy)-4(1H)-Quinolones with Antimalarial Activity. J. Med. Chem. 2016, 4.
Gould, et al., The Synthesis of Certain Substituted Quinolines and 5,6-Benzoquinolines. J. Am. Chem. Soc. 1939, 61 (10), 2890-2895.
Dess, et al., Readily Accessible 12-I-5 Oxidant for the Conversion of Primary and Secondary Alcohols to Aldehydes and Ketones. J. Org. Chem. 1983, 48 (22), 4155-4156.
Plowe, C. V. Resistance Nailed. Nature 2014, 505, 30-31.
Looareesuwan, et al., Clinical Studies of Atovaquone, Alone or in Combination with Other Antimalarial Drugs, for Treatment of Acute Uncomplicated Malaria in Thailand. Am. J. Trop. Med. Hyg. 1996, 54 (1), 62-66.
Milhous, et al., In Vitro Strategies for Circumventing Antimalarial Drug Resistance. Prog. Clin. Biol. Res. 1989, 313 (Malar. Red Cell, 2), 61-72.
Van Horn, et al., Antileishmanial Activity of a Series of N 2 , N 4-Disubstituted Quinazoline-2,4-Diamines. J. Med. Chem. 2014, 57 (12), 5141-5156.
Van Horn, et al., Antibacterial Activity of a Series of N 2 , N 4-Disubstituted Quinazoline-2,4-Diamines. J. Med. Chem. 2014, 57 (7), 3075-3093.
Gamo, et al., Antimalarial Drug Resistance: New Treatments Options for Plasmodium. Drug Discover Today: Technol. 2014, 11, 81-88.
Fujioka, et al., Structure and Life Cycle. Chem Immunol. 2002, 80, 1-26.
Centers for Disease Control and Prevention. Malaria. http://www.cdc.gov/malaria/ (accessed Jun. 22, 2015). pp. 1-2.
White, et al., Primaquine to Prevent Transmission of Falciparum Malaria. Lancet Infect. Dis. 2013, 13, 175-181.
University of the Sciences, Techniques and Technologies of Bamako. Phase 2 Proof of Concept Study of a Candidate Aminoquinoline Antimalarial (AQ-13). NLM Identifier: NCT01614964. https://clinicaltrials.gov/ct2/show/NCT01614964 (cited 2015 Jun. 22, 2015). pp. 1-4.
Cross, et al., Endochin Optimization: Structure-Activity and Structure-Property Relationship Studies of 3 Substituted 2-Methyl-4(1H)-Quinolines with Antimalarial Activity. J. Med. Chem. 2010, 53, 7076-7094.
Donovan, et al., Method for Measuring the Logarithm of the Octanol-water Partition Coefficient by Using Short Octadecyl-poly(vinyl Alcohol) High-Performance Liquid Chromatography Columns. J. Chromatogr. A 2002, 952, 47-61.
Stephen, et al., Tetrahydroacridones and Related Compounds as Antimalarials. J. Chem. Soc. 1947, 1034-1039.
Mzayek, et al., Randomized Dose-Ranging Controlled Trial of AQ-13, a Candidate Antimalarial, and Chloroquine in Healthy Volunteers. PLoS Clin. Trials 2007, 2, 1-15.
Donovan, et al., Elaboration of Diaryl Ketones into Naphthalenes Focused on Two or Four Sides: A Naphthoannulation Procedure. J. Am. Chem. Soc. 2004, 126, 3108-3112.
Sørensen, et al, Copper-Free Palladium-Catalyzed Sonogashira-Type Coupling of Aryl Halides and 1-Aryl-2-(Trimethylsilyl)acetylenes. Tetrahedron 2005, 61, 2697-2703.
Zheng, et al., Microwave-Assisted Synthesis of Ethynylarylboronates for the Construction of Boronic Acid-Based Fluorescent Sensors for Carbohydrates. Tetrahedron Lett. 2006, 47, 2331-2335.
Levin, et al., An Alternative Procedure for the Aluminum-Mediated Conversion of Esters to Amides. Synth. Commun. 1982, 12, 989-993.
Bradbury, et al., New Nonpeptide Angiotensin II Receptor Antagonists. Synthesis, Biological Properties, and Structure-Activity Relationships of 2-Alkyl-4-(Biphenylylmethoxy)pyridine Derivatives. J. Med. Chem. 1993, 36, 1245-1254.
Conrad, et al., Synthesen von Chinolinderivaten Mittelst Acetessigester. Ber. Dtsch. Chem. Ges. 1887, 20, 944-948.

* cited by examiner

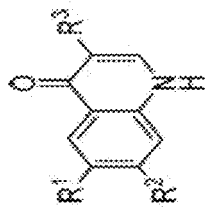

| compd | R¹ | R² | R³ | EC₅₀ W2 (nM) | EC₅₀ TM90-C2B (nM) | EC₉₀ Pb (nM) | EC₅₀ J774 (μM) | RI[b] | LBI[c] | LBI[d] |
|---|---|---|---|---|---|---|---|---|---|---|
| 6b | (CH₂)₃CH₃ | O(CH₂)₂OPh | CO₂CH₃ | 0.039 | 7.89 | 0.052 | >20.0 | 202 | 0.75 | 152 |
| 9b | (CH₂)₃CH₃ | O(CH₂)₂OPh | H | 328 | 430 | 5.82 | >20.0 | 1.31 | 56.4 | 73.9 |
| 8c | (CH₂)₃CH₃ | H | H | 552 | >12400 | 3.95 | >20.0 | >33.2 | 0.89 | >31.4 |
| 6c | (CH₂)₃CH₃ | H | CO₂CH₃ | 1.53 | 2.22 | 0.819 | >20.0 | 1.41 | 1.93 | 27.1 |
| 8a | H | O(CH₂)₂OPh | H | 5960 | 7680 | >35.4 | >20.0 | 1.29 | <16.8 | <21.7 |
| 6a | H | O(CH₂)₂OPh | CO₂CH₃ | 2.80 | 73.6 | 0.286 | >20.0 | 26.3 | 9.79 | 257 |
| 6d | H | H | CO₂CH₃ | 2.00 | 65.90 | 3.65 | >20.0 | 33.0 | 54.9 | 1810 |

"Chloroquine (CQ), atovaquone (ATO), and dihydroartemisinin (DHA) are internal controls for each in vitro assay: CQ, 42.1 nM W2, 229 nM TM90-C2B, and 47.2 μM J774; ATO, 1.39 nM W2, 18.4 μM TM90-C2B and 28.3 μM J774; DHA, 5.47 nM W2, 3.86 nM TM90-C2B and 1.53 μM J774. [b]RI = TM90-C2B/W2. [c]LBI = W2/Pb. [d]LBI = TM90-C2B/Pb.

FIG. 6

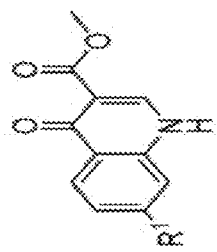

| compd | R¹ | EC₅₀ W2 (nM) | EC₅₀ TM90-C2B (nM) | EC₅₀ Pb (nM) | EC₅₀ J774 (μM) | RI[b] | LBI[c] | LBI[d] |
|---|---|---|---|---|---|---|---|---|
| 6d | H | 2.00 | 6590 | 3.65 | >20.0 | 33.0 | 54.8 | 181.0 |
| 6e | O(CH₂)₂OPh | 2.80 | 73.6 | 0.286 | >20.0 | 26.3 | 9.79 | 25.7 |
| 6f | O(CH₂)₃Ph | 0.711 | >794 | 5.26 | 3.48 | >1100 | 0.14 | >149 |
| 6g | O(CH₂)₃Ph | 1.39 | 7740 | ND[e] | 17.2 | 55.7 | ND[e] | ND[e] |
| 6h | OCH₂Ph | 18.30 | 8080 | ND[e] | 18.9 | 4.42 | ND[e] | ND[e] |
| 6i | OPh | 16.6 | 1950 | 1.10 | 9.12 | 11.7 | 0.15 | 17.7 |
| 6m | Br | 2.560 | 11300 | ND[e] | >20.0 | 4.41 | ND[e] | ND[e] |
| 6n | Cl | 2.340 | 5800 | ND[e] | >20.0 | 2.46 | ND[e] | ND[e] |
| 6o | F | 26.2 | 395 | >100 | >20.0 | 15.1 | <0.262 | <3.95 |

[a] Chloroquine (CQ), atovaquone (ATO), and dihydroartemisinin (DHA) are internal controls for each in vitro assay: CQ, 421 nM W2, 229 nM TM90-C2B, and 47.23 mM J774; ATO, 1.4 nM W2, 18.4 nM TM90-C2B, and 23.83 mM J774; DHA, 5.5 nM W2, 5.9 nM TM90-C2B, and 1.53 mM J774. [b] RI = TM90-C2B/W2. [c] LBI = W2/Pb. [d] LBI = TM90-C2B/Pb. [e] ND: not determined.

FIG. 9

"Chloroquine (CQ), atovaquone (ATO), and dihydroartemisinin (DHA) are internal controls for each in vitro assay: CQ, 421 nM W2, 229 nM TM90-C2B, and 47.23 mM J774; ATO, 1.4 nM W2, 18.4 nM TM90-C2B, and 23.83 mM J774; DHA, 5.5 nM W2, 5.9 nM TM90-C2B, and 1.53 nM J774. [b] RI = TM90-C2B/W2. [c] LBI = W2/Pb. [d] LBI = TM90-C2B/Pb. [e] ND: not determined.

| compd | R¹ | EC₅₀ W2 (nM) | EC₅₀ TM90-C2B (nM) | EC₅₀ J774 (nM) | EC₅₀ J774 (μM) | RI[b] | LBI[c] | LBI[d] |
|---|---|---|---|---|---|---|---|---|
| 6ac | CH₃ | 20.1 | 49.9 | 15.2 | >20.0 | 2.48 | 0.013 | 3.28 |
| 6aa | OCH₃ | 6.93 | 11.1 | 17.3 | >20.0 | 1.60 | 0.396 | 0.634 |
| 6ab | Cl | 9.93 | 6.17 | 0.063 | >20.0 | 0.621 | 1.30 | 97.90 |
| 6a | Br | 4.47 | 8.47 | 0.336 | >20.0 | 1.895 | 13.3 | 25.20 |

[a]Chloroquine (CQ), atovaquone (ATO), and dihydroartemisinin (DHA) are internal controls for each in vitro assay: CQ, 4.21 nM W2, 229 nM TM90-C2B, and 47.23 nM J774; ATO, 1.4 nM W2, 18.4 nM TM90-C2B, and 23.83 nM J774; DHA, 5.5 nM W2, 5.9 nM TM90-C2B, and 1.53 nM J774. [b]RI = TM90-C2B/W2. [c]LBI = W2/Ph. [d]LBI = TM90-C2B/Ph.

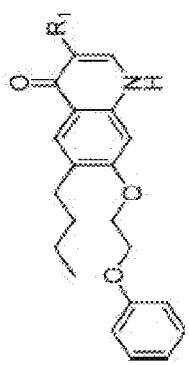

| compd | R₁ | EC₅₀ W2 (nM) | EC₅₀ TM90-C2B (nM) | EC₅₀ Pb (nM) | EC₅₀ J774 (μM) | RI[b] | LBI₉₀₀[c] | LBI₂₂[d] |
|---|---|---|---|---|---|---|---|---|
| 8b | H | 328 | 430 | 5.82 | >20.0 | 1.31 | 56.4 | 73.9 |
| 7b | CO₂H | 64.0 | 1110 | 0.267 | >20.0 | 17.3 | 240 | 4160 |
| 6b | CO₂CH₃ | 0.039 | 789 | 0.052 | >20.0 | 202 | 0.75 | 15.2 |
| 6af | CO₂CH₂CH₃ | 0.143 | 108 | 0.007 | >20.0 | 699 | 19.6 | 14300 |
| 6ae | CH₂CH₃ | 0.440 | 1.92 | 2.63 | 0.350 | 4.36 | 0.166 | 0.723 |
| 6d | CN | 97.2 | 3170 | 6.09 | >20.0 | 32.6 | 13.7 | 521 |
| 13a | CONHCH₃ | 13.3 | 3980 | 2.57 | >20.0 | 299 | 4.03 | 1390 |
| 13b | CON(CH₃)₂ | 56.7 | >6120 | 12.2 | 15.3 | >108 | 0.46 | >27.7 |
| 13c | CONHCH₂CH₃ | 206 | >6120 | ND[e] | >20.0 | >29.7 | ND[e] | ND[e] |
| 13d | CONH(CH₂)₂OH | 253 | 5890 | 12.8 | >20.0 | 23.3 | 19.8 | 460 |
| 13e | CONHCH(CH₃)₂ | 3340 | 5140 | ND[e] | >20.0 | 1.54 | ND[e] | ND[e] |
| 6ag | COCH₃ | 9.67 | 378 | ND[e] | ND[e] | 39.1 | ND[e] | ND[e] |

[a]Chloroquine (CQ), atovaquone (ATO), and dihydroartemisinin (DHA) are internal controls for each in vitro assay: CQ, 421 nM W2, 229 nM TM90-C2B, and 47.23 mM J774; ATO, 1.4 nM W2, 18.4 nM TM90-C2B, and 23.83 mM J774; DHA, 5.5 nM W2, 5.9 nM TM90-C2B, and 1.53 mM J774. [b]RI = TM90-C2B/W2. [c]LBI = W2/Pb. [d]LBI = TM90-C2B/Pb. [e]ND: not determined.

FIG. 20

| compd | R¹ | R² | EC₅₀ W2 (nM) | EC₅₀ TM90-C2B (nM) | EC₅₀ 7b (nM) | EC₅₀ J774 (μM) | RI[b] | LBI[c]₅₀ | LBI[d]₉₀ |
|---|---|---|---|---|---|---|---|---|---|
| 16a | I | CH₃ | 0.867 | 5.87 | ND[e] | ND[e] | 6.77 | ND[e] | ND[e] |
| 16b | I | H | 1.23 | 6.04 | 2.55 | >10.0 | 4.91 | 0.482 | 1.37 |
| 16c | Br | CH₃ | 2.60 | 12.3 | 2.12 | >10.0 | 4.60 | 1.23 | 5.75 |
| 16d | Br | H | 4.64 | 48.7 | 18.7 | 8.07 | 10.5 | 0.248 | 2.60 |
| 16e | Cl | CH₃ | 6.92 | 67.7 | 11.2 | >10.0 | 9.79 | 0.616 | 6.03 |

[a] Chloroquine (CQ), atovaquone (ATQ), and dihydroartemisinin (DHA) are internal controls for each in vitro assay. CQ, 42.1 nM W2, 229 nM TM90-C2B, and 47.23 nM J774; ATQ, 1.4 nM W2, 18.4 nM TM90-C2B, and 23.83 nM J774; DHA, 5.5 nM W2, 3.9 nM TM90-C2B, and 1.53 nM J774. [b] RI = TM90-C2B/W2. [c] LBI = W2/J774. [d] LBI = TM90-C2B/J774. [e] ND, not determined.

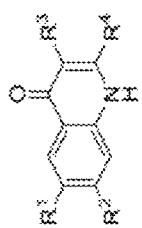

| Compound | R¹ | R² | R³ | R⁴ | Solubility pH 6.5 | Log D pH 7.4 |
|---|---|---|---|---|---|---|
| 6h | (CH₂)₃CH₃ | O(CH₂)₂OPh | CO₂CH₃ | H | * | 3.68 |
| 6k | H | OPh | CO₂CH₃ | H | *** | 2.36 |
| 6i | H | O(CH₂)₂Ph | CO₂CH₃ | H | ***** | 2.65 |
| 6j | H | O(CH₂)₃Ph | CO₂CH₃ | H | *** | 2.99 |
| 6e | OCH₂Ph | H | CO₂CH₃ | H | ** | 2.42 |
| 6f | O(CH₂)₂Ph | H | CO₂CH₃ | H | ** | 2.69 |
| 6g | O(CH₂)₃Ph | H | CO₂CH₃ | H | * | 2.98 |
| 6ab | Cl | O(CH₂)₂OPh | CO₂CH₃ | H | * | 2.97 |
| 6ae | (CH₂)₃CH₃ | O(CH₂)₂OPh | CH₂CH₃ | H | * | 4.07 |
| 13d | (CH₂)₃CH₃ | O(CH₂)₂OPh | CONH(CH₂)₂OH | H | ND | 3.48 |
| 16a | (CH₂)₃CH₃ | O(CH₂)₂OPh | I | CH₃ | ND | ND |
| 16c | (CH₂)₃CH₃ | O(CH₂)₂OPh | Br | CH₃ | ** | 4.20 |

ᵃ(*) Solubility < 1 μM, () 1μM < solubility < 1.9 μM, (*) 2μM < solubility < 3.9 μM, (**) 4μM < solubility < 9.9 μM, (*) 10μM < solubility < 20 μM, (****) > 20μM. ND, not determined.

FIG. 22

| compd | % inhibition, day 3 PE | % inhibition, day 6 PE | compd | % inhibition, day 3 PE | % inhibition, day 6 PE |
|---|---|---|---|---|---|
| 6b | 76.9 | 49.0 | 6i | 60.0 | <1 |
| 6c | 46.2 | <1 | 6ab | <1 | <1 |
| 6f | 7.69 | <1 | 6ae | 69.2 | 17.7 |
| 6g | 76.9 | <1 | 13d | 40.0 | <1 |
| 6j | 69.2 | 47.1 | 16c | 100 | 49.5 |
| 6k | 40.0 | 29.8 | 16a | 53.9 | 19.6 |
| amodiaquine | 95.5 | 99.9 | atovaquone | 96.3 | 99.8 |

*aPercent inhibition compared to untreated animals.*

FIG. 23

| compd | dose (mg/kg) | inhibition (%), day 6 PE[a] | av day of death |
|---|---|---|---|
| 6b | 10 | <1 | 13 |
| 16c | 10 | 61 | 13 |
| atovaquone | 10 | 99 | 30 |

[a]Percent inhibition as compared to untreated control animals.

FIG. 24

QUINOLONE-BASED COMPOUNDS, FORMULATIONS, AND USES THEREOF

CROSS-REFERENCE TO RELATED APPLICATIONS

This application claims the benefit of and priority to U.S. Provisional Patent Application No. 62/281,833, filed on Jan. 22, 2016, entitled "7-Piperazine Substituted 4(1H)-quinolones," the contents of which is incorporated by reference herein in its entirety.

STATEMENT REGARDING FEDERALLY SPONSORED RESEARCH OR DEVELOPMENT

This invention was made with government support under grant number RO1 GM097118 awarded by the National Institutes of Health. The government has certain rights in the invention.

BACKGROUND

Malaria is considered endemic in 97 countries and is one of the largest worldwide public health problem. Although therapeutics to treat malaria have been developed and have been successful in reducing deaths from the disease, parasite resistance to current antimalarial agents is a problem limiting the effectiveness of current treatments. As such, there exists an urgent need for the development of new antimalarial compounds.

SUMMARY

Provided herein are compounds that can have a structure according to Formula A

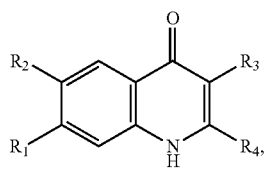

Formula A wherein $R_1$ can be selected from the group of: H, Cl, F, Ph, $O(CH_2)_2OPh$, $O(CH_2)_3Ph$, $OCH_2Ph$, Ph, $O(CH_2)_2Ph$, and,

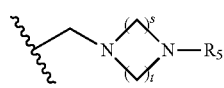

wherein s can be 1-4 and t can be 1-4, wherein $R_2$ can be selected from the group of: $CH_3$, $OCH_3$, $OCH_2Ph$, $O(CH_2)_m$ Ph wherein m can be 1-4, Ph, $CH_2CH_3$, $(CH_2)_2CH_3$, $(CH_2)_3CH_3$, $(CH_2)_4CH_3$, OPh, O(p-F)Ph, $CH(CH_3)_2$, Br, Cl, $OCH_2CH_3$, $O(CH_2)_3Ph$, and

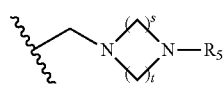

wherein s can be 1-4 and t can be 1-4, wherein $R_3$ can be selected from the group of H, Cl, Br, I, $CO_2H$, $CH_3$, $CO_2CH_2CH_3$, $CO_2CH_3$, $CH_2CH_3$, CN, $CONHCH_3$, $CON(CH_3)_2$, $CONHCH_2CH_3$, $CONH(CH_2)_2OH$, $CONHCH(CH_3)_2$, and $COCH_3$, wherein $R_4$ can be selected from the group of H and $CH_3$, wherein $R_5$ can be selected from the group consisting of: H, F, Bn, para-methoxybenzyl, a piperonyl, 4-$OCH_3Ph$, 4-F-Ph, 4-$CF_3$-Ph, $OCH_3$,

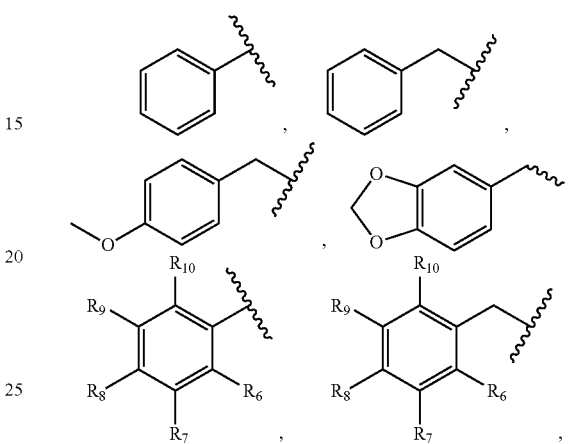

an alkyl, an alkylene, an alkenyl, a heterocycle, a heteroaryl, a heteroalkyl, an alkoxyl, an alkoxy, an amine, an amido, an aryl, an aralkyl, an aralkyloxy, an carbocycle, an carbonyl, a nitro, a halogen, a sulfhydryl, a hydroxyl, and a sulfonyl, wherein $R_5$ can be further optionally substituted, wherein $R_6$, $R_7$, $R_8$, $R_9$, and $R_{10}$ can each be independently selected from the group of F, $OCH_3$, $CF_3$, H, an alkyl, an alkylene, an alkenyl, a heterocycle, a heteroaryl, a heteroalkyl, an alkoxyl, an alkoxy, an amine, an amido, an aryl, an aralkyl, an aralkyloxy, an carbocycle, an carbonyl, a nitro, a halogen, a sulfhydryl, a hydroxyl, a sulfonyl, wherein $R_6$, $R_7$, $R_8$, $R_9$, and $R_{10}$ can each be further optionally substituted, wherein n can be 0, 1, or 2, and wherein the compound is not according to Formula B

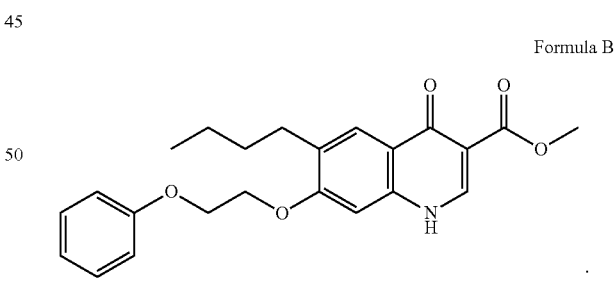

Formula B

In some embodiments, $R_1$ can be

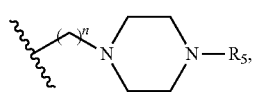

wherein $R_5$ can be selected from the group consisting of: H, F, Bn, para-methoxybenzyl, a piperonyl, 4-$OCH_3Ph$, 4-F-Ph, 4-$CF_3$-Ph, $OCH_3$, $CF_3$,

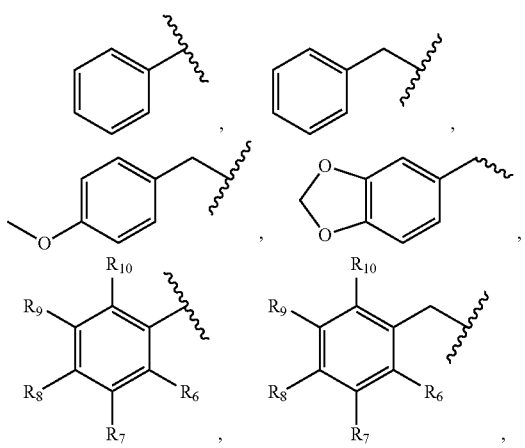

an alkyl, an alkylene, an alkenyl, a heterocycle, a heteroaryl, a heteroalkyl, an alkoxyl, an alkoxy, an amine, an amido, an aryl, an aralkyl, an aralkyloxy, a carbocycle, an carbonyl, a nitro, a halogen, a sulfhydryl, a hydroxyl, and a sulfonyl, wherein $R_5$ can be further optionally substituted, wherein $R_6$, $R_7$, $R_8$, $R_9$, and $R_{10}$ can each be independently selected from the group of F, $OCH_3$, $CF_3$, H, an alkyl, an alkylene, an alkenyl, a heterocycle, a heteroaryl, a heteroalkyl, an alkoxyl, an alkoxy, an amine, an amido, an aryl, an aralkyl, an aralkyloxy, an carbocycle, an carbonyl, a nitro, a sulfhydryl, a hydroxyl, a sulfonyl, wherein $R_6$, $R_7$, $R_8$, $R_9$, and $R_{10}$ can each be further optionally substituted, and wherein n can be 0, 1, or 2.

In some embodiments, the compound can have a structure according to Formula C

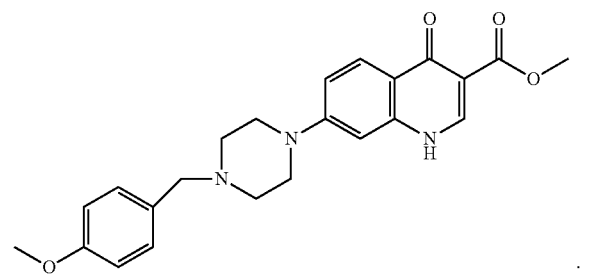

Formula C

In some embodiments, the compound can have a structure according to Formula D

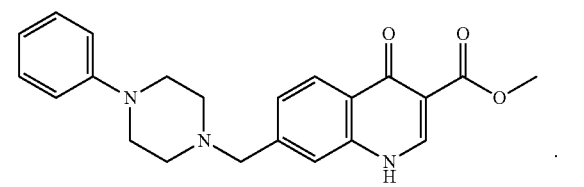

Formula D

In embodiments, the compound can have an $EC_{50}$ against the malarial strain W2, wherein the $EC_{50}$ against malarial strain W2 of the compound can range from 0 to about 1 μM. In embodiments, the $EC_{50}$ against malarial strain W2 of the compound can range from 0 to about 100 nM. In embodiments, the compound can have an $EC_{50}$ against the malarial strain TM90-C2B, wherein the $EC_{50}$ against malarial strain TM90-C2B of the compound can range from 0 to about 1 μM. In embodiments, the resistive index (RI) of the compound can range from about 0 to 200, wherein the resistive index is ($EC_{50}$ for TM90C2B)/($EC_{50}$ for W2).

Also provided herein are pharmaceutical compositions that can contain a compound according to Formula

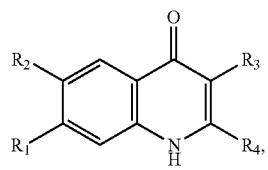

Formula A wherein $R_1$ can be selected from the group of: H, Cl, F, Ph, $O(CH_2)_2OPh$, $O(CH_2)_3Ph$, $OCH_2Ph$, Ph, $O(CH_2)_2Ph$, and

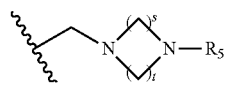

wherein s can be 1-4 and t can be 1-4, wherein $R_2$ can be selected from the group of: $CH_3$, $OCH_3$, $OCH_2Ph$, $O(CH_2)_m Ph$ wherein m can be 1-4, Ph, $CH_2CH_3$, $(CH_2)_2CH_3$, $(CH_2)_3 CH_3$, $(CH_2)_4CH_3$, OPh, O(p-F)Ph, $CH(CH_3)_2$, Br, Cl, $OCH_2CH_3$, $O(CH_2)_3Ph$, and

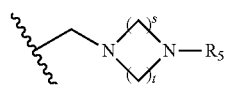

wherein s can be 1-4 and t can be 1-4, wherein $R_3$ can be selected from the group of H, Cl, Br, I, $CO_2H$, $CH_3$, $CO_2CH_2CH_3$, $CO_2CH_3$, $CH_2CH_3$, CN, $CONHCH_3$, $CON(CH_3)_2$, $CONHCH_2CH_3$, $CONH(CH_2)_2OH$, $CONHCH(CH_3)_2$, and $COCH_3$, wherein $R_4$ can be selected from the group of H and $CH_3$, wherein $R_5$ can be selected from the group consisting of: H, F, Bn, para-methoxybenzyl, a piperonyl, $4-OCH_3Ph$, $4-F-Ph$, $4-CF_3-Ph$, $OCH_3$, $CF_3$,

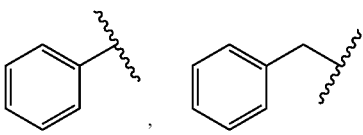

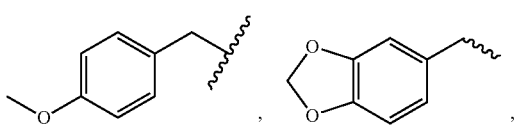

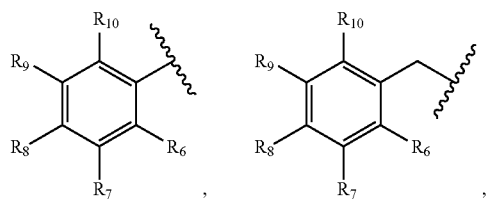
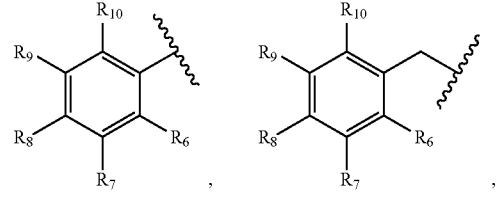

an alkyl, an alkylene, an alkenyl, a heterocycle, a heteroaryl, a heteroalkyl, an alkoxyl, an alkoxy, an amine, an amido, an aryl, an aralkyl, an aralkyloxy, an carbocycle, an carbonyl, a nitro, a halogen, a sulfhydryl, a hydroxyl, and a sulfonyl, wherein $R_5$ can be further optionally substituted, wherein $R_6$, $R_7$, $R_8$, $R_9$, and $R_{10}$ can each be independently selected from the group of F, $OCH_3$, $CF_3$, H, an alkyl, an alkylene, an alkenyl, a heterocycle, a heteroaryl, a heteroalkyl, an alkoxyl, an alkoxy, an amine, an amido, an aryl, an aralkyl, an aralkyloxy, an carbocycle, an carbonyl, a nitro, a halogen, a sulfhydryl, a hydroxyl, a sulfonyl, wherein $R_6$, $R_7$, $R_8$, $R_9$, and $R_{10}$ can each be further optionally substituted, wherein n can be 0, 1, or 2, and wherein the compound is not according to Formula B Formula B

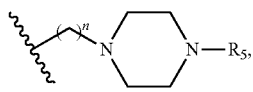

and a pharmaceutically acceptable carrier.

In some embodiments, $R_1$ can be

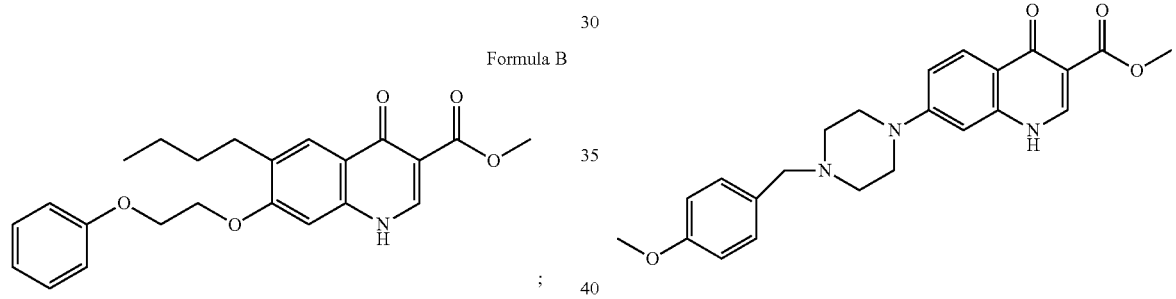

wherein $R_5$ can be selected from the group consisting of: H, F, Bn, para-methoxybenzyl, a piperonyl, 4-$OCH_3$-Ph, 4-F-Ph, 4-$CF_3$-Ph, $OCH_3$, $CF_3$,

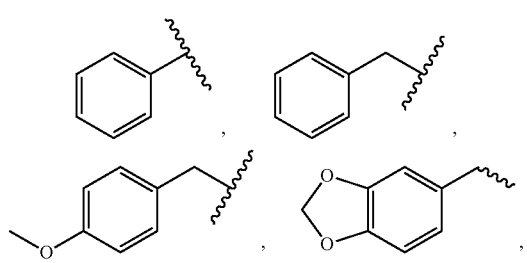

an alkyl, an alkylene, an alkenyl, a heterocycle, a heteroaryl, a heteroalkyl, an alkoxyl, an alkoxy, an amine, an amido, an aryl, an aralkyl, an aralkyloxy, an carbocycle, an carbonyl, a nitro, a halogen, a sulfhydryl, a hydroxyl, and a sulfonyl, wherein $R_5$ can be further optionally substituted, wherein $R_6$, $R_7$, $R_8$, $R_9$, and $R_{10}$ can each be independently selected from the group of F, $OCH_3$, $CF_3$, H, an alkyl, an alkylene, an alkenyl, a heterocycle, a heteroaryl, a heteroalkyl, an alkoxyl, an alkoxy, an amine, an amido, an aryl, an aralkyl, an aralkyloxy, an carbocycle, an carbonyl, a nitro, a halogen, a sulfhydryl, a hydroxyl, a sulfonyl, wherein $R_6$, $R_7$, $R_8$, $R_9$, and $R_{10}$ can each be further optionally substituted, and wherein n can be 0, 1, or 2.

In some embodiments, the compound can have a structure according to Formula C

Formula C

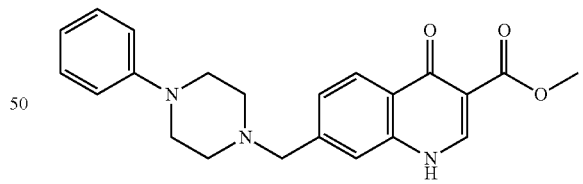

In some embodiments, the compound can have a structure according to Formula D

Formula D

In embodiments, the pharmaceutical formulation can have an $EC_{50}$ against the malarial strain W2, wherein the $EC_{50}$ against malarial strain W2 of the pharmaceutical formulation can range from 0 to about 1 μM. In embodiments, the $EC_{50}$ against malarial strain W2 of the pharmaceutical formulation can range from 0 to about 100 nM. In embodiments, the pharmaceutical formulation can have an $EC_{50}$ against the malarial strain TM90-C2B, wherein the $EC_{50}$ against malarial strain TM90-C2B of the pharmaceutical formulation can range from 0 to about 1 μM. In embodiments, the resistive index (RI) of the pharmaceutical formulation can range. from about 0 to 200, wherein the resistive index is ($EC_{50}$ for TM90C2B)/($EC_{50}$ for W2).

Also provided herein are methods of treating and/or preventing malaria and/or plasmodium infection in a subject that can include the step of administering a compound or pharmaceutical formulation as provided herein to a subject in need thereof.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 6 shows a table demonstrating sequential removal of original hit compound substituents[a].

FIG. 9 shows a table demonstrating the structure-activity relationship of the 7-position[a].

FIG. 20 shows a table demonstrating the structure-activity relationship of the 3-position using ester isosteres[a].

FIG. 22 shows a table demonstrating the solubility and Log d for select 4(1H)-quinolones.

FIG. 23 shows a table demonstrating results of an in vivo efficacy scout screening[a].

FIG. 24 shows a table demonstrating results of a Thompson Test.

DETAILED DESCRIPTION

Figure 1:
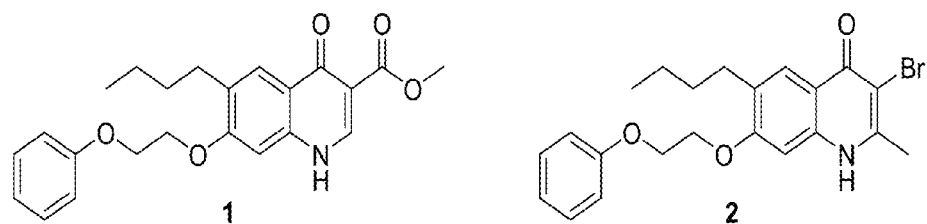
FIG. 1 shows the formulas for Compounds 1 and 2, which are ICI 56,780 (Compound 1) and an analogue there of (Compound 2).
Figure 2:
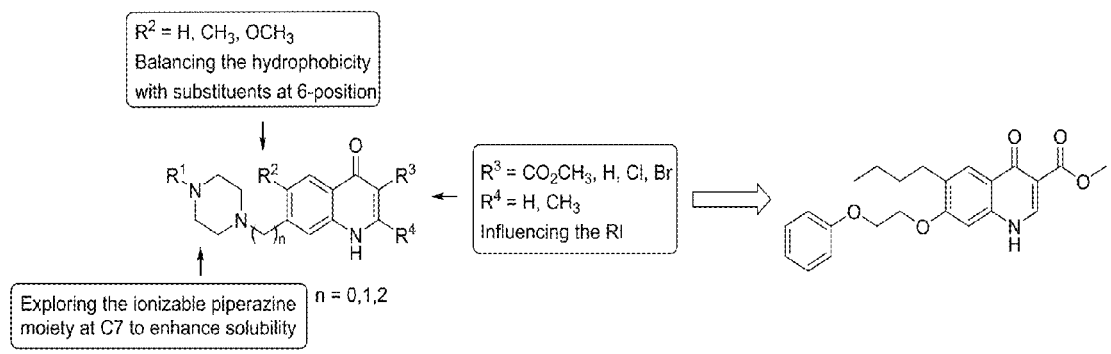
FIG. 2 shows an embodiment of a strategy for the design of piperazinyl-substituted scaffolds based on Compound 1 (ICI 56,780).

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value or range in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of biology, physiology, microbiology, parasitology, chemistry organic chemistry, biochemistry, and the like, which are within the skill of the art. Such techniques are explained fully in the literature.

Definitions

As used herein, "about," "approximately," and the like, when used in connection with a numerical variable, can refer to the value of the variable and to all values of the variable that are within the experimental error (e.g., within the 95% confidence interval for the mean) or within +/−10% of the indicated value, whichever is greater.

As used herein, "additive effect" can refer to an effect arising between two or more molecules, compounds, substances, factors, or compositions that is equal to or the same as the sum of their individual effects.

As used herein, "active derivative" and the like can refer to a modified compound containing a quinolone-based compound as provided herein. The term "active derivative" and the like can also refer to an analogue provided herein that can be effective at killing a parasite of the genus *Plasmodium* (including killing any life-cycle stage of the parasite), reducing parasite load, parasite infection ability, parasite transmission ability, and the ability to kill the parasite when it is in the liver stage and/or blood stage. Assays for testing the ability of an active derivative to perform in this fashion are known to those of ordinary skill in the art and provided herein. The assays can include, but are not limited to, in vitro and in vivo assays.

As used herein, "administering" can refer to any administration route, including but not limited to, administration that is oral, topical, intravenous, subcutaneous, transcutaneous, transdermal, intramuscular, intra-articular, parenteral, intra-arterial, intradermal, intraventricular, intracranial, intraperitoneal, intralesional, intranasal, rectal, vaginal, by inhalation, or via an implanted reservoir. The term "parenteral" includes subcutaneous, intravenous, intramuscular, intra-articular, intra-synovial, intrasternal, internasal, intrathecal, intrahepatic, intralesional, and intracranial injections or infusion techniques.

As used interchangeably herein, "biocompatible," "biocompatibility," and "biologically compatible" can refer to materials that are, with any metabolites or degradation products thereof, generally non-toxic to the recipient, and cause no significant adverse effects to the recipient. Generally speaking, biocompatible materials are materials which do not elicit a significant inflammatory or immune response when administered to a patient. In some embodiments, a biocompatible material elicits no detectable change in one or more biomarkers indicative of an immune response. In some embodiments, a biocompatible material elicits no greater than a 10% change, no greater than a 20% change, or no greater than a 40% change in one or more biomarkers indicative of an immune response.

As used herein, "a compound of formula (1), (2), (3), (4), (5), (6), (6a), (6b) (7), (8), (9), (10), (11), (12), (13), (14), (A), (B), (C), (D), and so forth and so on," or "a compound having a structure according to formula (1), (2), (3), (4), (5), (6), (6a), (6b) (7), (8), (9), (10), (11), (12), (13), (14), (A), (B), (C), (D), etc.," compound (1), (2), (3), (4), (5), (6), (6a), (6b) (7), (8), (9), (10), (11), (12), (13), (14), (A), (B), (C), (D), and so forth and so on," or a "compound" can include all or any sub-group of solvates, complexes, polymorphs, derivatives thereof (including but not limited to, radiolabeled derivatives (including deuterated derivatives where one or more H are replaced by D)), tautomers, stereoisomers, and optical isomers of the compound of the formulas listed above and salts thereof.

As used herein, "control" can refer to an alternative subject or sample used in an experiment for comparison purposes and included to minimize or distinguish the effect of variables other than an independent variable. A control can be positive or negative.

As used herein, "concentrated" can refer to an amount of a molecule, compound, or composition, including, but not limited to, a chemical compound, polynucleotide, peptide, polypeptide, protein, antibody, or fragments thereof, that indicates that the sample is distinguishable from its naturally occurring counterpart in that the concentration or number of molecules per volume is greater than that of its naturally occurring counterpart.

As used herein, "derivative" can refer to substituting, deleting, and/or adding one or more atoms or functional groups. The term "derivative" does not mean that the derivative is synthesized from the parent compound either as a starting material or intermediate, although this may be the case. The term "derivative" can include salts, prodrugs, or metabolites of the parent compound. Derivatives include compounds in which free amino groups in the parent compound have been derivatized to form amine hydrochlorides, p-toluene sulfonamides, benzoxycarboamides, t-butyloxycarboamides, thiourethane-type derivatives, trifluoroacetylamides, chloroacetylamides, or formamides. Derivatives include compounds in which carboxyl groups in the parent compound have been derivatized to form salts, methyl and ethyl esters, or other types of esters or hydrazides. Derivatives include compounds in which hydroxyl groups in the parent compound have been derivatized to form O-acyl or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imines, thiones, sulfones, tertiary amides, and sulfides. "Derivatives" also includes extensions of the replacement of the cyclopentane ring with saturated or unsaturated cyclohexane or other more complex, e.g., nitrogen-containing rings, and extensions of these rings with various side groups.

As used herein, "diluted" can refer to an amount of a molecule, compound, or composition including but not limited to, a chemical compound, polynucleotide, peptide, polypeptide, protein, antibody, or fragments thereof, that indicates that the sample is distinguishable from its naturally occurring counterpart in that the concentration or number of molecules per volume is less than that of its naturally occurring counterpart.

As used herein, "dose," "unit dose," or "dosage" can refer to physically discrete units suitable for use in a subject, each unit containing a predetermined quantity of a compound as provided herein and/or a pharmaceutical formulation thereof calculated to produce the desired response or responses in association with its administration.

As used herein, "effective amount" can refer to an amount sufficient to effect beneficial or desired results. An effective amount can be administered in one or more administrations, applications, or dosages. "Effective amount" can refer to an amount of a compound, derivative, and/or formulation thereof provided herein that can treat or prevent malaria, infection with and/or transmission of a parasite of the genus *Plasmodium*, or a symptom thereof. The term "effective amount" can refer to the amount effective to kill and or reduce a parasite of the genus *Plasmodium* in the liver stage and/or blood stage of the parasite infection. The term "effective amount" can refer to the amount effective to reduce or kill the amount of any stage of a parasite of the genus *Plasmodium* when in a host or vector.

As used herein, "hydrate" can refer to a compound formed by the addition of water. Typically, but not always, this will be crystalline lattice structures that incorporate water molecules. Hydrates include stoichiometric hydrates, as well as compositions containing variable amounts of water.

As used herein, "mitigate" can refer to reducing a particular characteristic, symptom, or other biological or physiological parameter associated with a disease or disorder.

The term "molecular weight", as used herein, can generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

As used herein, "negative control" can refer to a "control" that is designed to produce no effect or result, provided that all reagents are functioning properly and that the experiment is properly conducted. Other terms that are interchangeable with "negative control" include "sham," "placebo," and "mock."

As used herein, "pharmaceutical formulation" can refer to the combination of an active agent, compound, or ingredient with a pharmaceutically acceptable carrier or excipient, making the composition suitable for diagnostic, therapeutic, or preventive use in vitro, in vivo, or ex vivo.

As used herein "pharmaceutically effective amount", "effective amount" and the like can refer to an amount of a compound or formulation thereof provided herein that can treat or prevent malaria or symptom thereof malaria or symptom thereof and/or infection (at any stage (e.g. liver or blood stages) and/or transmission of a parasite of the genus *Plasmodium* in a subject. In embodiments, the "pharmaceutically effective amount" can be the least amount of a compound or formulation thereof provided herein needed to treat, prevent, or elicit the desired biological and/or medical effect in the response of a cell, tissue, organ, system, or subject that is being sought by the researcher, veterinarian, medical doctor or other clinician. In some embodiments, the "pharmaceutically effective amount" can be the least amount that can treat or prevent malaria or symptom thereof and/or infection (at any stage (e.g. liver or blood stages) and/or transmission of a parasite of the genus *Plasmodium*. "Pharmaceutically effective amount" or "pharmaceutically effective dose," can refer to the amount of a compound or formulation thereof provided herein that will elicit the biological and/or medical response of a cell, tissue, organ, system, or subject that is being sought by the researcher, veterinarian, medical doctor or other clinician. The pharmaceutically effective amount can vary depending on the compound, formulation the disorder or condition (normal or abnormal) and its severity, the route of administration, time of administration, rate of excretion, drug or compound, judgment of the researcher, veterinarian, medical doctor or other clinician, dosage form, and the age, weight, general health, sex and/or diet of the subject to be treated.

As used herein, "pharmaceutically acceptable" can refer to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration.

As used herein, "pharmaceutically acceptable carrier or excipient" can refer to a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used herein also includes both one and more than one such carrier or excipient. Pharmaceutically acceptable carriers include, but are not limited to, diluents, preservatives, binders, lubricants, disintegrators, swelling agents, fillers, stabilizers, and combinations thereof.

As used herein, "pharmaceutically acceptable salt" can refer to any salt derived from organic and inorganic acids of a compound described herein. Pharmaceutically acceptable salt also refers to a salt of a compound described having an acidic functional group, such as a carboxylic acid functional group, and a base. Pharmaceutically acceptable salt also includes hydrates of a salt of a compound described herein.

As used herein, "positive control" can refer to a "control" that is designed to produce the desired result, provided that all reagents are functioning properly and that the experiment is properly conducted.

As used herein, "preventative," "preventing," "prevent" and the like can refer to partially or completely delaying and/or precluding the onset or recurrence of a disorder or conditions and/or one or more of its attendant symptoms or barring a subject from acquiring or reacquiring a disorder or condition or reducing a subject's risk of acquiring or reacquiring a disorder or condition or one or more of its attendant symptoms including, but not limited to, malaria, infection and/or transmission of a parasite of the genus *Plasmodium* or a symptom thereof.

As used herein, "purified" or "purify" can be used in reference to a nucleic acid sequence, peptide, or polypeptide that has increased purity relative to the natural environment.

As used herein, "separated" can refer to the state of being physically divided from the original source or population such that the separated compound, agent, particle, chemical compound, or molecule can no longer be considered part of the original source or population.

As used herein, "solvate" refers to a complex of variable stoichiometry formed by a solute (e.g. formulas (1)-(1) (A), (B), (C), (D), or any other compound herein or a salt thereof) and a solvent. Pharmaceutically acceptable solvates may be formed for crystalline compounds wherein solvent molecules are incorporated into the crystalline lattice during crystallization. The incorporated solvent molecules can be water molecules or non-aqueous molecules, such as but not limited to, ethanol, isopropanol, dimethyl sulfoxide, acetic acid, ethanolamine, and ethyl acetate molecules.

As used interchangeably herein, "subject," "individual," or "patient," can refer to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

As used herein, "substantially pure" can mean an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

The terms "sufficient" and "effective," as used interchangeably herein, can refer to an amount (e.g. mass, volume, dosage, concentration, and/or time period) needed to achieve one or more desired result(s). For example, a therapeutically effective amount refers to an amount needed to achieve one or more therapeutic effects.

As used herein, "synergistic effect," "synergism," or "synergy" can refer to an effect arising between two or more molecules, compounds, substances, factors, or compositions that that is greater than or different from the sum of their individual effects.

As used herein, "tangible medium of expression" can refer to a medium that is physically tangible and is not a mere abstract thought or an unrecorded spoken word. Tangible medium of expression includes, but is not limited to, words on a cellulosic or plastic material or data stored on a suitable device such as a flash memory or CD-ROM.

As used herein, "therapeutic", "treating", "treat," and the like can refer to include partially or completely delaying, alleviating, mitigating or reducing the intensity of one or more attendant symptoms of a disease or condition including, but not limited to, malaria, infection and/or transmission of a parasite of the genus *Plasmodium* or a symptom thereof.

As used herein, "alkyl" and "alkylene" refer to a saturated hydrocarbon chain having the specified number of member atoms.

The term "alkyl" can also refer to the radical of saturated aliphatic groups (i.e., an alkane with one hydrogen atom removed), including straight-chain alkyl groups, branched-chain alkyl groups, cycloalkyl (alicyclic) groups, alkyl-substituted cycloalkyl groups, and cycloalkyl-substituted alkyl groups. "Alkyl" also refers to a saturated hydrocarbon chain having the specified number of atoms.

The term "alkyl" (or "lower alkyl") as used herein can include both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein can refer to an alkyl group, as defined above, but having from one to ten carbons in its backbone structure. Likewise, "lower alkenyl" and "lower alkynyl" have similar chain lengths.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF$_3$, —CN and the like. Cycloalkyls can be substituted in the same manner.

As used herein, "C$_{1-6}$alkyl" can refer to an alkyl group having any number of member atoms from 1 to 6 member atoms, such as for example 1 to 4 atoms. Other alkyl groups may have any number of member atoms as indicated by the numbers given in the formula, which, like the previous example, can refer to an alkyl group having any number of member atoms within the specified range of member atoms. Alkyl groups may be straight or branched. Representative branched alkyl groups have one, two, or three branches. Alkyl includes methyl, ethyl, propyl (n-propyl and isopropyl), butyl (n-butyl, isobutyl, and t-butyl), pentyl (n-pentyl, isopentyl, and neopentyl), and hexyl.

As used herein, "heterocyclic group" can refer to a non-aromatic ring and having the specified number of member atoms being saturated or having one or more degrees of unsaturation and, unless otherwise specified, containing one or more heteroatoms.

As used herein, "heteroaryl" can refer to an aromatic ring having the specified number of member atoms and, unless otherwise specified, containing one or more heteroatoms. Bicyclic and other polycyclic ring systems having a heteroaryl ring are described as fused systems.

The term "heteroalkyl," as used herein, can refer to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "heteroalkyl," as used herein, can refer to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

As used herein, "alkoxyl" or "alkoxy," as used herein, can refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl is an ether or resembles an alkoxyl, such as can be represented by one of —O-alkyl, —O-alkenyl, and —O-alkynyl. The terms "aroxy" and "aryloxy", as used interchangeably herein, can be represented by —O-aryl or O-heteroaryl, wherein aryl and heteroaryl are as defined below. The alkoxy and aroxy groups can be substituted as described above for alkyl.

As used herein, "amine" and "amino" (and its protonated form) are art-recognized and refer to both unsubstituted and substituted amines, e.g., a moiety that can be represented by the general formula:

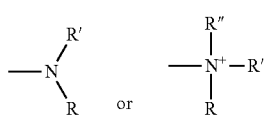

wherein R, R', and R" each independently represent a hydrogen, an alkyl, an alkenyl, —(CH2)$_m$—R$_C$ or R and R' taken together with the N atom to which they are attached complete a heterocycle having from 4 to 8 atoms in the ring structure; R$_C$ represents an aryl, a cycloalkyl, a cycloalkenyl, a heterocycle or a polycycle; and m is zero or an integer in the range of 1 to 8. In some embodiments, only one of R or R' can be a carbonyl, e.g., R, R' and the nitrogen together do not form an imide. In other embodiments, the term "amine" does not encompass amides, e.g., wherein one of R and R' represents a carbonyl. In further embodiments, R and R' (and optionally R") each independently represent a hydrogen, an alkyl or cycloakly, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of R and R' is an alkyl group.

As used herein, "amido" is art-recognized as an amino-substituted carbonyl and includes a moiety that can be represented by the general formula:

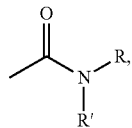

wherein R and R' are as defined above.

As used herein, "Aryl" can refer to C$_5$-C$_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those aryl groups having heteroatoms in the ring structure may also be referred to as "aryl heterocycles" or "heteroaromatics." The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, and combinations thereof.

The term "aryl" can also include polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. One or more of the rings can be substituted as defined above for "aryl."

As used herein, "aralkyl," can refer to an alkyl group substituted with an aryl group (e.g., an aromatic or heteroaromatic group).

As used herein, "aralkyloxy" can be represented by —O-aralkyl, wherein aralkyl is as defined above.

As used herein, "carbocycle," can refer to an aromatic or non-aromatic ring(s) in which each atom of the ring(s) is carbon.

As used herein, "heterocycle" or "heterocyclic" can refer to a monocyclic or bicyclic structure containing 3-10 ring atoms, and in some embodiments, containing from 5-6 ring atoms, wherein the ring atoms are carbon and one to four heteroatoms each selected from the following group of non-peroxide oxygen, sulfur, and N(Y) wherein Y is absent or is H, O, (C$_1$-C$_{10}$) alkyl, phenyl or benzyl, and optionally containing 1-3 double bonds and optionally substituted with one or more substituents. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbonyl" is art-recognized and includes such moieties as can be represented by the general formula:

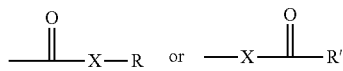

wherein X is a bond or represents an oxygen or a sulfur, and R and R' are as defined above. Where X is an oxygen and R or R' is not hydrogen, the formula represents an "ester". Where X is an oxygen and R is as defined above, the moiety is referred to herein as a carboxyl group, and particularly when R is a hydrogen, the formula represents a "carboxylic acid." Where X is an oxygen and R' is hydrogen, the formula represents a "formate." In general, where the oxygen atom of the above formula is replaced by sulfur, the formula represents a "thiocarbonyl" group. Where X is a sulfur and R or R' is not hydrogen, the formula represents a "thioester." Where X is a sulfur and R is hydrogen, the formula represents a "thiocarboxylic acid." Where X is a sulfur and R' is hydrogen, the formula represents a "thioformate." On the other hand, where X is a bond, and R is not hydrogen, the above formula represents a "ketone" group. Where X is a bond, and R is hydrogen, the above formula represents an "aldehyde" group.

As used herein, "heteroatom" as used herein can refer to an atom of any element other than carbon or hydrogen. Exemplary heteroatoms include, but are not limited to, boron, nitrogen, oxygen, phosphorus, sulfur, silicon, arsenic, and selenium.

As used herein, "nitro" can refer to —NO$_2$; the term "halogen" designates —F, —Cl, —Br, or —I; the term "sulfhydryl" refers to —SH; the term "hydroxyl" refers to —OH; and the term "sulfonyl" refers to —SO$_2$—.

The term "substituted" as used herein, can refer to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, e.g. 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, C$_3$-C$_{20}$ cyclic, substituted C$_3$-C$_{20}$ cyclic, heterocyclic, substituted heterocyclic, amino acid, peptide, and polypeptide groups.

Heteroatoms, such as nitrogen, can have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e., a compound that does not spontaneously undergo transformation such as by rearrangement, cyclization, elimination, etc.

As used herein, "suitable substituent" can refer to a chemically and pharmaceutically acceptable group, i.e., a moiety that does not significantly interfere with the preparation of or negate the efficacy of the inventive compounds. Such suitable substituents may be routinely chosen by those skilled in the art. Suitable substituents include but are not limited to the following: a halo, C$_1$-C$_6$ alkyl, C$_2$-C$_6$ alkenyl, C$_1$-C$_6$ haloalkyl, C$_1$-C$_6$ alkoxy, C$_1$-C$_6$ haloalkoxy, C$_2$-C$_6$ alkynyl, C$_3$-C$_8$ cycloalkenyl, (C$_3$-C$_8$ cycloalkyl)C$_1$-C$_6$ alkyl, (C$_3$-C$_8$ cycloalkyl)C$_2$-C$_6$ alkenyl, (C$_3$-C$_8$ cycloalkyl) C$_1$-C$_6$ alkoxy, C$_3$-C$_7$ heterocycloalkyl, (C$_3$-C$_7$ heterocycloalkyl) C$_1$-C$_6$ alkyl, (C3-C$_7$ heterocycloalkyl)C$_2$-C$_6$ alkenyl, (C$_3$-C$_7$ heterocycloalkyl)C$_1$-C$_6$ alkoxyl, hydroxy, carboxy, oxo, sulfanyl, C$_1$-C$_6$ alkylsulfanyl, aryl, heteroaryl, aryloxy, heteroaryloxy, arylalkyl, heteroaralkyl, arylalkoxy, heteroaralkoxy, nitro, cyano, amino, C$_1$-C$_6$ alkylamino, di-(C$_1$-C$_6$ alkyl)amino, carbamoyl, (C$_1$-C$_6$ alkyl)carbonyl, (C$_1$-C$_6$ alkoxy)carbonyl, (C$_1$-C$_6$ alkyl)aminocarbonyl, di-(C$_1$-C$_6$ alkyl)aminocarbonyl, arylcarbonyl, aryloxycarbonyl, (C$_1$-C$_6$ alkyl)sulfonyl, and arylsulfonyl. The groups listed above as suitable substituents are as defined hereinafter except that a suitable substituent may not be further optionally substituted.

As used herein, "optionally substituted" can indicate that a group may be unsubstituted or substituted with one or more substituents as defined herein.

Unless otherwise defined herein, all technical and scientific terms used herein have the same meaning as commonly understood by one of ordinary skill in the art.

DISCUSSION

Malaria is one of the deadliest diseases worldwides and accounts for about half a million deaths annually. A protozoan parasitic species, *Plasmodium* is responsible for transmitting the disease to humans through a mosquito vector. There are significant challenges plaguing the development of antimalarial agents. The various developmental stages of the parasite with in the host makes the design makes the design and development of antimalarial agents difficult. The development of resistance to antiamalarial compounds by the parasites further complicates the design makes the design and development of antimalarial agents. Widespread resistance to almost all current antiamalarial agents in use today underscores the immediate need for new antimalarial agents against the parasites that have developed resistance to current therapeutics.

With that said, described herein are antimalarial compounds and formulations thereof that can be used to treat and/or prevent malaria at one or more life stages and/or transmission of the parasite from host to mosquito. Also provided herein are methods of treating and/or preventing malaria and/or the transmission of a *Plasmodium* parasite that can include the step of administering a compound or formulation thereof provided herein to a subject. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Compounds and Formulations Thereof

Quinolone-Based Compounds

Malaria can be caused by many parasites of the genus *Plasmodium*, of which *P. faliciparum* is the most common cause for infections in humans. Malaria begins its life cycle in a host when an infected femal *Anopheles* mosquito takes a blood meal from a host. Sporozoites are injected from the salivary gland of the mosquito into the host and first infect the liver cells, where they mature into schizonts. This can also be referred to as the liver stage of the life cycle of the infecting parasite and is one point at which therapeutic intervention can be effective at treating and/or preventing malaria infection and disease. The schizonts then rupture and release merozoites, which rapidly infect red blood cells causing the clinical symptoms of the disease. When the red blood cells are infected this can be referred to as the blood stage of the disease. The time between the liver stage and the blood stage can vary based on the species of *Plasmodium* infecting the host. Some species can remain dormant in liver cells and cause disease weeks, months or even years later. Other species can move from liver stage to blood stage in only a couple of days or less. The life cycle completes and repeats when transmission from the blood of the infected host is injested by a mosquito and the parasite is transmitted from the blood the mosquito. This can be referred to as the transmission phase. While compounds that are effective at one or two of the stages, it is desirable to have a compound that is effective against the parasite when in the liver stage, blood stange, and at preventing transmission. Further, given the prevalent resistance that has developed against one or more current antimalarial agents, it is desirable to have compounds that are effective against resistant strains.

Provided herein are compounds and formulations thereof that can be effective at killing a parasite of the genus *Plasmodium* and/or can be effective to reduce *Plasmodium* parasite load in a host and/or eliminate *Plasmodium* parasites from an infected subject. The compounds and formulations thereof can be effective against a *Plasmodium* parasite when the parasite is in the liver stage, blood stage, and/or can be effective at preventing or reducing transmission of the parasite to the mosquito.

The compound can have a structure according to Formula A

Formula A

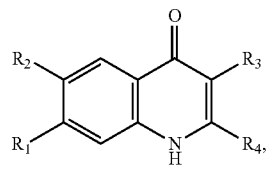

wherein $R_1$ can be selected from the group of: H, Cl, F, Ph, $O(CH_2)_2OPh$, $O(CH_2)_3Ph$, $OCH_2Ph$, Ph, $O(CH_2)_2Ph$, and

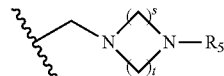

wherein s can be 1-4 and t can be 1-4, wherein $R_2$ can be selected from the group of: $CH_3$, $OCH_3$, $OCH_2Ph$, $O(CH_2)_m Ph$ wherein m can be 1-4, Ph, $CH_2CH_3$, $(CH_2)_2CH_3$, $(CH_2)_3 CH_3$, $(CH_2)_4CH_3$, OPh, O(p-F)Ph, $CH(CH_3)_2$, Br, Cl, $OCH_2CH_3$, $O(CH_2)_3Ph$, and

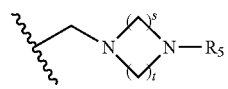

wherein s can be 1-4 and t can be 1-4, wherein $R_3$ can be selected from the group of H, Cl, Br, I, $CO_2H$, $CH_3$, $CO_2CH_2CH_3$, $CO_2CH_3$, $CH_2CH_3$, CN, $CONHCH_3$, $CON(CH_3)_2$, $CONHCH_2CH_3$, $CONH(CH_2)_2OH$, $CONHCH(CH_3)_2$, and $COCH_3$, wherein $R_4$ can be selected from the group of H and $CH_3$, wherein $R_5$ can be selected from the group consisting of: H, F, Bn, para-methoxybenzyl, a piperonyl, $4-OCH_3Ph$, $4-F-Ph$, $4-CF_3-Ph$, $OCH_3$, $CF_3$, O

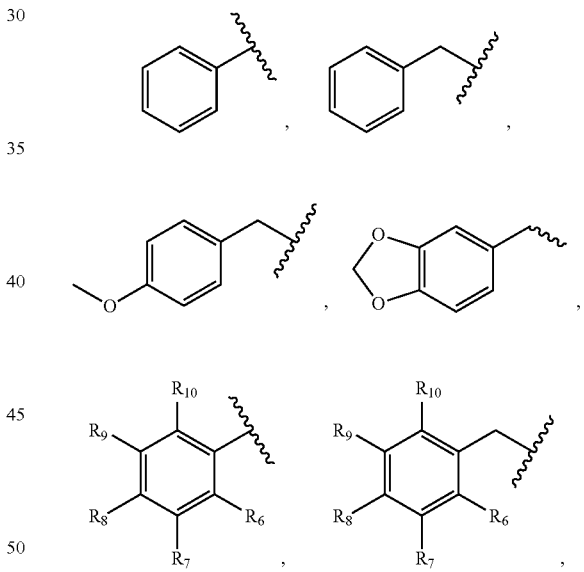

an alkyl, an alkylene, an alkenyl, a heterocycle, a heteroaryl, a heteroalkyl, an alkoxyl, an alkoxy, an amine, an amido, an aryl, an aralkyl, an aralkyloxy, an carbocycle, an carbonyl, a nitro, a halogen, a sulfhydryl, a hydroxyl, and a sulfonyl, wherein $R_5$ can be further optionally substituted, wherein $R_6$, $R_7$, $R_8$, $R_9$, and $R_{10}$ can each be independently selected from the group of F, $OCH_3$, $CF_3$, H, an alkyl, an alkylene, an alkenyl, a heterocycle, a heteroaryl, a heteroalkyl, an alkoxyl, an alkoxy, an amine, an amido, an aryl, an aralkyl, an aralkyloxy, an carbocycle, an carbonyl, a nitro, a halogen, a sulfhydryl, a hydroxyl, a sulfonyl, wherein $R_6$, $R_7$, $R_8$, $R_9$, and $R_{10}$ can each be further optionally substituted, wherein n can be 0, 1, or 2, and wherein the compound is not according to Formula B Formula B

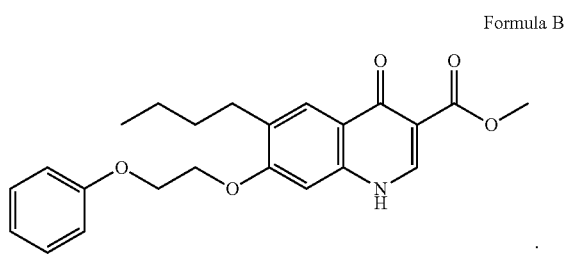 [SMILES: CCCCc1cc2c(=O)c(C(=O)OC)c[nH]c2cc1OCCOc1ccccc1]

In some embodiments, $R_1$ can be

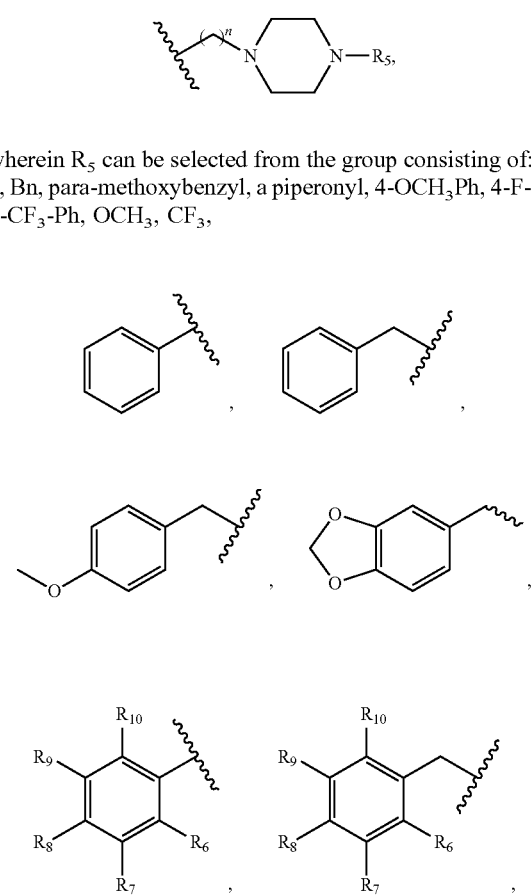

wherein $R_5$ can be selected from the group consisting of: H, F, Bn, para-methoxybenzyl, a piperonyl, 4-OCH$_3$Ph, 4-F-Ph, 4-CF$_3$-Ph, OCH$_3$, CF$_3$, an alkyl, an alkylene, an alkenyl, a heterocycle, a heteroaryl, a heteroalkyl, an alkoxyl, an alkoxy, an amine, an amido, an aryl, an aralkyl, an aralkyloxy, an carbocycle, an carbonyl, a nitro, a halogen, a sulfhydryl, a hydroxyl, and a sulfonyl, wherein $R_5$ can be further optionally substituted, wherein $R_6$, $R_7$, $R_8$, $R_9$, and $R_{10}$ can each be independently selected from the group of F, OCH$_3$, CF$_3$, H, an alkyl, an alkylene, an alkenyl, a heterocycle, a heteroaryl, a heteroalkyl, an alkoxyl, an alkoxy, an amine, an amido, an aryl, an aralkyl, an aralkyloxy, an carbocycle, an carbonyl, a nitro, a halogen, a sulfhydryl, a hydroxyl, a sulfonyl, wherein $R_6$, $R_7$, $R_8$, $R_9$, and $R_{10}$ can each be further optionally substituted, and wherein n can be 0, 1, or 2.

In some embodiments, the compound can have a structure according to Formula C

Formula C

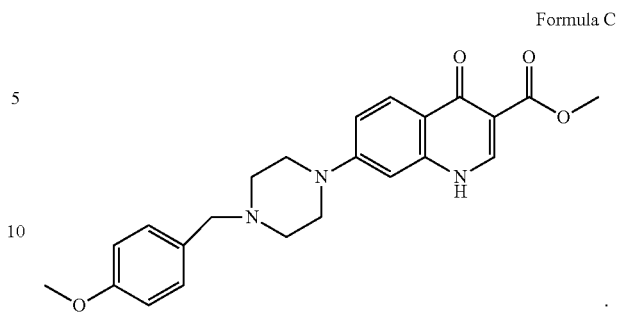

In some embodiments, the compound can have a structure according to Formula D

Formula D

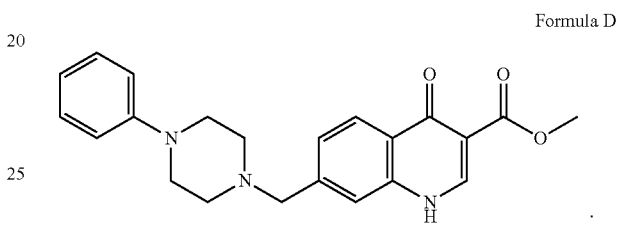

The effective concentration where about 50% of the population is reduced (EC$_{50}$) against malarial strain W2 of the compound can range from 0 to about 1 µM. The EC$_{50}$ against malarial strain W2 of the compound can range from 0 to about 100 nM. The effective concentration where about 50% of the population is reduced (EC$_{50}$) against malarial strain TM90-C2B of the compound can range from 0 to about 1 µM. The EC$_{50}$ against malarial strain TM90-C2B of the compound can range from 0 to about 100 nM.

Due to the emergence and rapid acquisition of cross-resistance of the parasites, the compounds can be evaluated on its resistive index (RI), which is the ratio of the effective concentrations needed to kill 50% of a parasite population for TN90-C2B and W2 strains and is a measure of the effectiveness of a compound against resistant strains. In some embodiments, the RI can from about 0 to 500, 0-200, 0-100, 0-50, 0-40, 0-30, 0-20, 0-10, 0-5, 0-3, or less than 1, where the resistive index is (EC$_{50}$ for TM90C2B)/(EC$_{50}$ for W2).

The compound can be effective against the liver stage of the parasite. The effectiveness of a compound against the liver stage of the parasite can be determined in vitro using hepatocytes infected *P. berghei* sporozoites expressing luciferase (Nilsen et al. 2013. Transl. Med. 5: 177ra37.). Liver blood indices (LBI) can be used to relate activity against *P. berghei* with activity against resistant strains (e.g. W2 and TM90-C2B). For example, when using W2 or TM90-C2B the LBI=(EC$_{50}$ W2)/(E$_{50}$ *P. berghei*) and (E$_{50}$ TM90-C2B)/(E$_{50}$ *P. berghei*), respectively. If strains other than W2 or TM90-C2B are used, the LBI for those strains can be determined in the same way. In embodiments, the LBI can range from 0 to 200.

Pharmaceutical Formulations

The compounds (e.g. compounds having a structure according to any one of formulas A, B, C, and D or any other compound provided herein and derivatives thereof) described herein can be provided to a subject in need thereof as an ingredient, such as an active ingredient, in a pharmaceutical formulation. As such, also described are pharmaceutical formulations containing one or more of the compounds and salts thereof, or pharmaceutically acceptable salts thereof described herein. Suitable salts include, but are not limited to, sulfate, citrate, acetate, oxalate, chloride, hydrochloride, bromide, hydrobromide, iodide, nitrate, bisulfate, phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, napthalenesulfonate, propionate, malonate, mandelate, malate, phthalate, and pamoate.

The pharmaceutical formulations or salts thereof can be administered to a subject in need thereof. In some embodiments, the subject is infected with a parasite of the genus *Plasmodium*. In some embodiments, the subject suffers from liver stage infection of a parasite of the genus *Plasmodium*. In some embodiments, the subject suffers from blood stage infection of a parasite of the genus *Plasmodium*. In some embodiments, the subject suffers from malaria or a symptom thereof.

Pharmaceutically Acceptable Carriers and Auxiliary Ingredients and Agents

The pharmaceutical formulations containing an effective amount of a compound described herein (e.g. compounds having a structure according to any one of Formulas A, B, C, or D, or other formula provided herein) or a derivative thereof can further include a pharmaceutically acceptable carrier. Suitable pharmaceutically acceptable carriers include, but are not limited to water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active compound.

In addition to the effective amount of a compound and/or derivative thereof, the pharmaceutical formulations can also include an effective amount of auxiliary active agents, including but not limited to, antisense or RNA interference molecules, chemotherapeutics, or antineoplastic agents, hormones, antibiotics, antivirals, immunomodulating agents, antinausea, pain modifying compounds (such as opiates), anti-inflammatory agents, antipyretics, antibiotics, and/or antibodies or fragments thereof.

Effective Amounts of the Compounds, Derivatives Thereof, and Auxiliary Active Agents The effective amount of the compound (e.g. compounds having a structure according to any one of Formulas A, B, C, or D, or other formula provided herein), or derivative thereof contained in the pharmaceutical formulation can range from about 0.001 micrograms to about 1000 grams. In some embodiments, the effective amount of the compound and/or derivative thereof can range from about 0.001 micrograms to about 0.01 micrograms. In other embodiments, the effective amount of compound and/or derivative thereof can range from about 0.01 micrograms to about 0.1 micrograms. In further embodiments, the effective amount of the compound and/or derivative thereof can range from about 0.1 micrograms to about 1.0 grams. In yet further embodiments, the effective amount of the compound and/or derivative thereof can range from about 1.0 grams to about 10 grams. In other embodiments, the effective amount of the compound and/or derivative thereof can range from about 10 grams to about 100 grams. In still other embodiments, the effective amount of the compound and/or derivative thereof can range from about 100 grams to about 1000 grams.

In embodiments where there is an auxiliary active agent contained in the compound or derivative thereof pharmaceutical formulation, the effective amount of the auxiliary active agent will vary depending on the auxiliary active agent. In some embodiments, the effective amount of the auxiliary active agent can range from 0.001 micrograms to about 1000 grams. In other embodiments, the effective amount of the auxiliary active agent can range from about 0.01 IU to about 1000 IU. In further embodiments, the effective amount of the auxiliary active agent can range from 0.001 mL to about 1000 mL. In yet other embodiments, the effective amount of the auxiliary active agent can range from about 1% w/w to about 50% w/w of the total pharmaceutical formulation. In additional embodiments, the effective amount of the auxiliary active agent can range from about 1% v/v to about 50% v/v of the total pharmaceutical formulation. In still other embodiments, the effective amount of the auxiliary active agent can range from about 1% w/v to about 50% w/v of the total pharmaceutical formulation.

The auxiliary active agent can be included in the pharmaceutical formulation or can exist as a stand-alone compound or pharmaceutical formulation that can be administered contemporaneously or sequentially with the compound, derivative thereof, or pharmaceutical formulation thereof. In embodiments where the auxiliary active agent is a stand-alone compound or pharmaceutical formulation, the effective amount of the auxiliary active agent can vary depending on the auxiliary active agent used. In some of these embodiments, the effective amount of the auxiliary active agent can range from 0.001 micrograms to about 1000 grams. In other embodiments, the effective amount of the auxiliary active agent can range from about 0.01 IU to about 1000 IU. In further embodiments, the effective amount of the auxiliary active agent can range from 0.001 mL to about 1000 mL. In yet other embodiments, the effective amount of the auxiliary active agent can range from about 1% w/w to about 50% w/w of the total auxiliary active agent pharmaceutical formulation. In additional embodiments, the effective amount of the auxiliary active agent can range from about 1% v/v to about 50% v/v of the total pharmaceutical formulation. In still other embodiments, the effective amount of the auxiliary active agent can range from about 1% w/v to about 50% w/v of the total auxiliary agent pharmaceutical formulation.

Dosage Forms

In some embodiments, the pharmaceutical formulations described herein can be in a dosage form. The dosage form can be administered to a subject in need thereof. In some embodiments, the subject can be infected with a parasite of the genus *Plasmodium*. In some embodiments, the subject can suffer from liver stage infection of a parasite of the genus *Plasmodium*. In some embodiments, the subject can suffer from blood stage infection of a parasite of the genus *Plasmodium*. In some embodiments, the subject suffers from malaria or a symptom thereof.

The dosage forms can be adapted for administration by any appropriate route. Appropriate routes include, but are not limited to, oral (including buccal or sublingual), rectal, intraocular, inhaled, intranasal, topical (including buccal, sublingual, or transdermal), vaginal, parenteral, subcutaneous, intramuscular, intravenous, internasal, and intradermal. Such formulations can be prepared by any method known in the art.

Dosage forms adapted for oral administration can discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as a foam, spray, or liquid solution. The oral dosage form can be administered to a subject in need thereof. In some embodiments, the subject can be infected with a parasite of the genus *Plasmodium*. In some embodiments, the subject can suffer from liver stage infection of a parasite of the genus *Plasmodium*. In some embodiments, the subject can suffer from blood stage infection of a parasite of the genus *Plasmodium*. In some embodiments, the subject suffers from malaria or a symptom thereof.

Where appropriate, the dosage forms described herein can be microencapsulated. The dosage form can also be prepared to prolong or sustain the release of any ingredient. In some embodiments, the compound or derivative thereof is the ingredient whose release is delayed. In other embodiments, the release of an auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings may be formed with a different ratio of water soluble polymer, water insoluble polymers, and/or pH dependent polymers, with or without water insoluble/water soluble non polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Where appropriate, the dosage forms described herein can be a liposome. In these embodiments, compound, derivative thereof, auxiliary active ingredient, and/or pharmaceutically acceptable salt thereof are incorporated into a liposome. In some embodiments, a compound, derivative thereof, auxiliary active ingredient, and/or pharmaceutically acceptable salts thereof is integrated into the lipid membrane of the liposome. In other embodiments, a compound, derivative thereof, auxiliary active ingredient, and/or pharmaceutically acceptable salt thereof are contained in the aqueous phase of the liposome. In embodiments where the dosage form is a liposome, the pharmaceutical formulation is thus a liposomal formulation. The liposomal formulation can be administered to a subject in need thereof. In some embodiments, the subject can be infected with a parasite of the genus *Plasmodium*. In some embodiments, the subject can suffer from liver stage infection of a parasite of the genus *Plasmodium*. In some embodiments, the subject can suffer from blood stage infection of a parasite of the genus *Plasmodium*. In some embodiments, the subject suffers from malaria or a symptom thereof.

Dosage forms adapted for topical administration can be formulated as ointments, creams, suspensions, lotions, powders, solutions, pastes, gels, sprays, aerosols, or oils. In some embodiments for treatments of the eye or other external tissues, for example the mouth or the skin, the pharmaceutical formulations are applied as a topical ointment or cream. When formulated in an ointment, the compound, derivative thereof, auxiliary active ingredient, and/or pharmaceutically acceptable salt thereof can be formulated with a paraffinic or water-miscible ointment base. In other embodiments, the active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some embodiments, the compound, derivative thereof, auxiliary active ingredient, and/or pharmaceutically acceptable salt thereof in a dosage form adapted for inhalation is in a particle-size-reduced form that is obtained or obtainable by micronization. In some embodiments, the particle size of the size reduced (e.g. micronized) compound or salt or solvate thereof, is defined by a $D_{50}$ value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active ingredient, which may be generated by various types of metered dose pressurized aerosols, nebulizers, or insufflators. The nasal/inhalation formulations can be administered to a subject in need thereof. In some embodiments, the subject can be infected with a parasite of the genus *Plasmodium*. In some embodiments, the subject can suffer from liver stage infection of a parasite of the genus *Plasmodium*. In some embodiments, the subject can suffer from blood stage infection of a parasite of the genus *Plasmodium*. In some embodiments, the subject suffers from malaria or a symptom thereof.

In some embodiments, the dosage forms are aerosol formulations suitable for administration by inhalation. In some of these embodiments, the aerosol formulation contains a solution or fine suspension of a compound, derivative thereof, auxiliary active ingredient, and/or pharmaceutically acceptable salt thereof a pharmaceutically acceptable aqueous or non-aqueous solvent. Aerosol formulations can be presented in single or multi-dose quantities in sterile form in a sealed container. For some of these embodiments, the sealed container is a single dose or multi-dose nasal or an aerosol dispenser fitted with a metering valve (e.g. metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of a compound, derivative thereof, auxiliary active ingredient, and/or pharmaceutically acceptable salt thereof. In further embodiments, the aerosol formulation also contains co-solvents and/or modifiers incorporated to improve, for example, the stability and/or taste and/or fine particle mass characteristics (amount and/or profile) of the formulation. Administration of the aerosol formulation can be once daily or several times daily, for example 2, 3, 4, or 8 times daily, in which 1, 2, or 3 doses are delivered each time. The aerosol formulations can be administered to a subject in need thereof. In some embodiments, the subject can be infected with a parasite of the genus *Plasmodium*. In some embodiments, the subject can suffer from liver stage infection of a parasite of the genus *Plasmodium*. In some embodiments, the subject can suffer from blood stage infection of a parasite of the genus *Plasmodium*. In some embodiments, the subject suffers from malaria or a symptom thereof.

For some dosage forms suitable and/or adapted for inhaled administration, the pharmaceutical formulation is a dry powder inhalable formulations. In addition to the compound, derivative thereof, auxiliary active ingredient, and/or pharmaceutically acceptable salt thereof, such a dosage form can contain a powder base such as lactose, glucose, trehalose, manitol, and/or starch. In some of these embodiments, the compound, derivative thereof, auxiliary active ingredient, and/or pharmaceutically acceptable salt thereof is in a particle-size reduced form. In further embodiments, a performance modifier, such as L-leucine or another amino acid, cellobiose octaacetate, and/or metals salts of stearic acid, such as magnesium or calcium stearate.

In some embodiments, the aerosol formulations are arranged so that each metered dose of aerosol contains a predetermined amount of an active ingredient, such as the one or more of the compounds described herein.

Dosage forms adapted for vaginal administration can be presented as pessaries, tampons, creams, gels, pastes, foams, or spray formulations. Dosage forms adapted for rectal administration include suppositories or enemas. The vaginal formulations can be administered to a subject in need thereof. In some embodiments, the subject can be infected with a parasite of the genus *Plasmodium*. In some embodiments, the subject can suffer from liver stage infection of a parasite of the genus *Plasmodium*. In some embodiments, the subject can suffer from blood stage infection of a parasite of the genus *Plasmodium*. In some embodiments, the subject suffers from malaria or a symptom thereof.

Dosage forms adapted for parenteral administration and/or adapted for injection can include aqueous and/or non-aqueous sterile injection solutions, which can contain antioxidants, buffers, bacteriostats, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and re-suspended in a sterile carrier to reconstitute the dose prior to administration. Extemporaneous injection solutions and suspensions can be prepared in some embodiments, from sterile powders, granules, and tablets. The parenteral formulations can be administered to a subject in need thereof. In some embodiments, the subject can be infected with a parasite of the genus *Plasmodium*. In some embodiments, the subject can suffer from liver stage infection of a parasite of the genus *Plasmodium*. In some embodiments, the subject can suffer from blood stage infection of a parasite of the genus *Plasmodium*. In some embodiments, the subject suffers from malaria or a symptom thereof.

For some embodiments, the dosage form contains a predetermined amount of a compound and/or derivative thereof per unit dose. In an embodiment, the predetermined amount of the compound or derivative thereof is an effective amount of the compound and/or derivative thereof to treat, prevent, or mitigate one or more symptoms of infection with a species of the genus *Plasmodium* and/or malaria. In other embodiments, the predetermined amount of the compound and/or derivative thereof can be an appropriate fraction of the effective amount of the active ingredient. Such unit doses may therefore be administered once or more than once a day (e.g. 1, 2, 3, 4, 5, 6, or more times per day). Such pharmaceutical formulations may be prepared by any of the methods well known in the art.

Methods of Making the Compounds and Derivatives Thereof

The compounds (e.g. compounds having a structure according to any one of formulas A, B, C, or D or any other compound provided herein) and derivatives thereof can be synthesized via many methods generally known to those of ordinary skill in the art. The present disclosure is not intended to be limited by the particular methods of synthesizing the compounds described herein. The skilled artisan will recognize additional methods of synthesizing the compounds described herein.

Methods of Using the Compounds and Formulations Thereof

Any amount of the compounds (e.g. compounds having a structure according to any one of formulas A, B, C, or D or any other compound provided herein) or derivatives thereof, pharmaceutical formulations, and/or salts thereof described herein can be administered to a subject in need thereof one or more times per day, week, month, or year. In some embodiments, the amount administered is the effective amount of the compound, derivative thereof, pharmaceutical formulation, and/or salt thereof. For example, the compounds, formulations, or salts thereof, can be administered in a daily dose. This amount may be given in a single dose per day. In other embodiments, the daily dose may be administered over multiple doses per day, in which each containing a fraction of the total daily dose to be administered (sub-doses). In some embodiments, the amount of doses delivered per day is 2, 3, 4, 5, or 6. In further embodiments, the compounds, formulations, or salts thereof are administered one or more times per week, such as 1, 2, 3, 4, 5, or 6 times per week. In other embodiments, the compounds, formulations, or salts thereof are administered one or more times per month, such as 1 to 5 times per month. In still further embodiments, the compounds, formulations, or salts thereof are administered one or more times per year, such as 1 to 11 times per year.

In some embodiments, the subject can be infected with a parasite of the genus *Plasmodium*. In some embodiments, the subject can suffer from liver stage infection of a parasite of the genus *Plasmodium*. In some embodiments, the subject can suffer from blood stage infection of a parasite of the genus *Plasmodium*. In some embodiments, the subject suffers from malaria or a symptom thereof.

In embodiments where more than one of compounds, formulations, additional therapeutic agents, salts thereof, or pharmaceutically acceptable salts thereof are administered to a subject in need thereof sequentially; the sequential administration may be close in time or remote in time. For example, administration of the second compound, formulation, or other therapeutic agent can occur within seconds or minutes (up to about 1 hour) after administration of the first agent (close in time). In other embodiments, administration of the second compound, formulation, or other therapeutic agent occurs at some other time that is more than an hour after administration of the first agent.

The amount of compounds, formulations, salts thereof (including pharmaceutically acceptable formulations and salts thereof) described herein can be administered in an amount ranging from about 0.001 mg to about 1000 mg per day, as calculated as the free or unsalted compound. In some embodiments the amount of the compound, formulation, or salt thereof (including pharmaceutically acceptable formulations and salts thereof) can range from 0.001 mg/kg bodyweight to 1000 mg/kg bodyweight. In some embodiments the amount is about 25, 50, or 100 mg/kg bodyweight. In some embodiments, the effective amount of the compound can range from 0.001 mg to about 1000 mg per day. In some embodiments, the effective amount of the compound can range from 5, 50, or 100 mg/kg bodyweight.

The compounds and formulations described herein can be administered in combinations with or include one or more other auxiliary agents. Suitable auxiliary agents include, but are not limited to antisense or RNA interference molecules, chemotherapeutics, anti-neoplastic agents, hormones, antibiotics, antivirals, immunomodulating agents, anti-nausea, pain modifying compounds (such as opiates), anti-inflammatory agents, antipyretics, antibiotics, and/or antibodies or fragments thereof. The compound(s), and/or formulation(s), and/or additional therapeutic agent(s) can be administered simultaneously or sequentially by any convenient route in separate or combined pharmaceutical formulations. The additional therapeutic agents can be provided in their optically pure form or a pharmaceutically acceptable salt thereof.

Kits

The compounds (e.g. compounds having a structure according to any one of formulas A, B, C, D, or any of the compound provided herein), including derivatives thereof) and pharmaceutical formulations described herein can be presented as a combination kit. As used herein, the terms "combination kit" or "kit of parts" refers to the compounds, or pharmaceutical formulations and additional components that are used to package, sell, market, deliver, and/or administer the combination of elements or a single element, such as the active ingredient, contained therein. Such additional components include but are not limited to, packaging, syringes, blister packages, bottles, and the like. When one or more of the components (e.g. active agents) contained in the kit are administered simultaneously, the combination kit can contain the active agents in a single pharmaceutical formulation (e.g. a tablet) or in separate pharmaceutical formulations.

When the agents are not administered simultaneously, the combination kit can contain each agent in separate pharmaceutical formulations. The separate pharmaceutical formulations can be contained in a single package or in separate packages within the kit.

In some embodiments, the combination kit also includes instructions printed on or otherwise contained in a tangible medium of expression. The instructions can provide information regarding the content of the compound or pharmaceutical formulations contained therein, safety information regarding the content of the compound(s) or pharmaceutical formulation(s) contained therein, information regarding the dosages, indications for use, and/or recommended treatment regimen(s) for the compound(s) and/or pharmaceutical formulations contained therein. In some embodiments, the instructions provide directions for administering the compounds, pharmaceutical formulations, or salts thereof to a subject that can be infected with a parasite of the genus *Plasmodium*, a subject that can be suffering from liver stage infection of a parasite of the genus *Plasmodium*, a subject that can be suffering from blood stage infection of a parasite of the genus *Plasmodium*, a subject that can be suffering from malaria or a symptom thereof, and/or a subject that is expecting to be exposed to a parasite of the genus *Plasmodium*. In some embodiments, the instructions provide directions for administering the compounds, pharmaceutical formulations, or salts thereof to reduce, mitigate, eliminate and/or prevent transmission of a parasite of the genus *Plasmodium*.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Introduction

Malaria is one of the deadliest public health problems in the world, accounting for nearly half a million casualties annually.[1] A protozoan parasitic species, *Plasmodium* is responsible for transmitting the disease to humans through a mosquito vector. The various developmental stages of the parasite within the host makes the design and development of curative antimalarial agents challenging.[2] In addition, the widespread parasite resistance to almost all antimalarial drugs in-use emphasizes the pressing need for new drugs with novel chemotypes that are safe and effective against multiple stages of highly resistant parasites.[3,4] In the past few years, several research groups reported their optimization efforts in developing antimalarial 4(1H)-pyridone- and 4(1H)-quinolone-based agents.[3,5-14] One of the major challenges in advancing these 4(1H)-quinolones into antimalarial drugs is the poor aqueous solubility of these scaffolds, which limits the oral bioavailability.[15] Quinolone ester ICI 56,780 (FIG. 1, Compound 1) is one of these antimalarial 4(1H)-quinolones displaying very potent activity against blood, liver, and transmission stages of the parasite.[3,7-11,16] Quinolone ester 1 even produced radical cures (eradicated dormant exoerythrocytic stages of the parasite) in *Plasmo*-

*dium cynomolgi* infected rhesus monkeys.[17] However, the development of 1 was halted as resistance emerged after only one passage in *Plasmodium berghei* (Pb) infected mice.[16] Nevertheless, recent improvements in preclinical efficacy models and compound property assessment motivated the laboratories of Guy,[5,6] Ward and O'Neill,[18] and Manetsch and Kyle[9,19] to reexamine studies on the antimalarial 4(1H)-quinolone ester from slightly different angles. Previous work completed in a set of 46 compounds with in vitro activities against clinically relevant W2 and TM90-C2B. Lead compound 3-bromo-6-butyl-2-methyl-7-(2-phenoxyethoxy)quinolin-4(1H)-one (FIG. 1, Compound 2) addressed atovaquone cross-resistance concerns over 1 by lowering the resistance index (RI) to 4.69 and exemplified a potent liver stage activity of 2.12 nM.[19] It further exemplified the need to not only improve potency but also for optimize aqueous solubility. Therefore, the main objective for the next phase focused on the design and synthesis of a series of 6- and 7-substituted 4(1H)-quinolones with enhanced aqueous solubility without compromising blood and liver stage activity. This Example demonstrates a detailed structure-activity relationship and structure-property relationship studies leading to a set of analogues with improved aqueous solubility and oral bioavailability for which a subset have been further assessed for in vivo efficacy in targeting the blood and liver stages of the parasite.

Results

Design and Synthesis.

The rationale for the design of the next generation 4(1H)-quinolones was based on insights gained from SAR studies on 4(1H)-quinolone esters reported by us and others.[9,17,18] The 4(1H)-quinolone core, the ester group in the 3-position, and the phenoxyethoxy substituent in the 7-position were identified to be key structural elements rendering this chemotype potent antimalarial activity. Substituents in 2- and 6-position were considered to be of secondary importance, with a negligible influence on the RI and/or the overall hydrophobicity of the 4(1H)-quinolone ester analogues. For the next compound design, a 4(1H)-quinolone pharmacophore containing a 3-carboxylic acid ester and a 7-piperazinyl group. The piperazinyl moiety was selected for the following reasons: (1) an ionizable piperazine can enhance the aqueous solubility of 4(1H)-quinolones; (2) a straightforward, base-mediated or reductive N-alkylation of a piperazine can provide an easy route to access highly functionalized 4(1H)-quinolone ester analogues; and (3) the commercial availability of various N-substituted piperazines allows the straightforward synthesis of a diversified set of piperazinyl-substituted 4(1H)-quinolones.

Initially, a set of 7-piperazinyl-4(1H)-quinolone esters with differing alkyl chain lengths between the 4(1H)-quinolone core and the piperazinyl moiety were synthesized. The connectivity ranged from a direct attachment of the piperazine to the 4(1H)-quinolone's 7-position, to a methylene or ethylene chain with each linker requiring a different synthetic path. The nucleophilic aromatic substitution was initially attempted for analogues with the piperazinyl moiety directly attached to the 4(1H)-quinolone core, using substituted nitrobenzenes 3 along with the required substituted piperazine. The substitution reaction was followed by a reduction of the nitro group and a thermal cyclization to yield 4(1H)-quinolones 8a-8b. This synthetic approach, however, was only successful when the 4(1H)-quinolone core was sufficiently electron deficient (Scheme 1).[20]

Scheme 1: Synthesis of 4(1H)-Quinolones with Direct Attachment of Piperazinyl Moiety

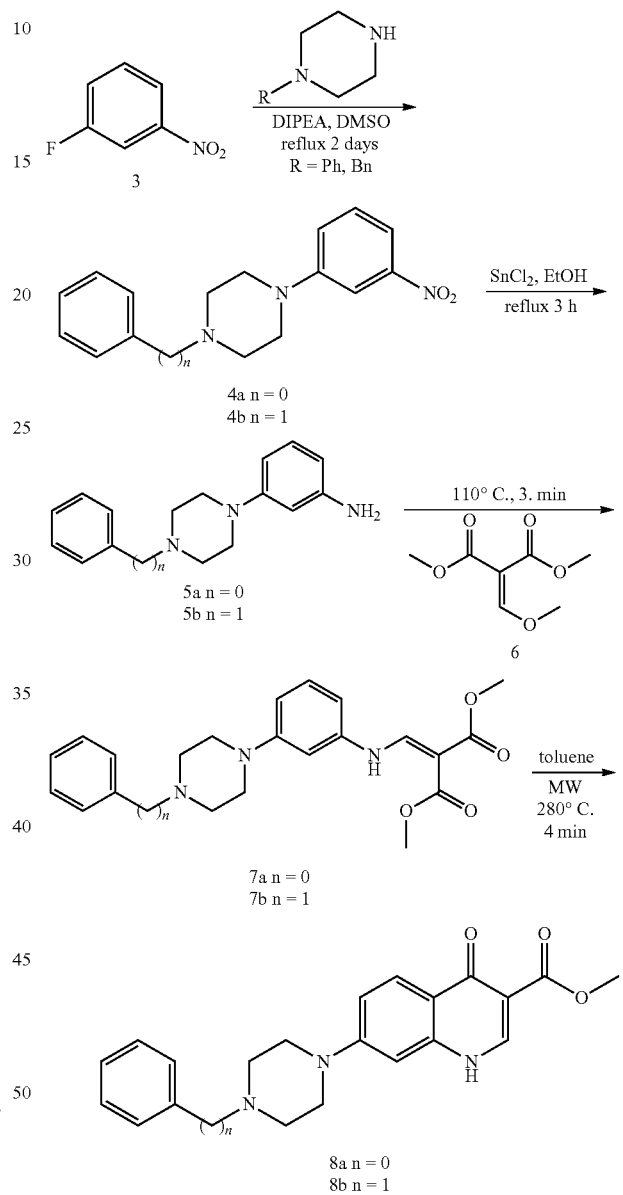

For analogues in which the 4(1H)-quinolone core was not sufficiently electron deficient, a two-step sequence was required to obtain the necessary nitro intermediates 4. First, the corresponding para-substituted aniline or benzylamine 9 was reacted with two equivalents of 2-chloroethanol to give diols 10. Diols 10 were chlorinated and their products were reacted with substituted nitroanilines to yield piperazines 4.[21] Subsequent reduction with tin(II)chloride gave piperazine-substituted anilines 5, which were further reacted using standard Gould-Jacob sequence of reactions to afford final products 8c-8i (Scheme 2).[9,22]

Scheme 2: Additional Scheme for Synthesis of 4(1H)-Quinolones with Direct Attachment of the Piperazinyl Moeity to the 4(1H)-Quinolone Core

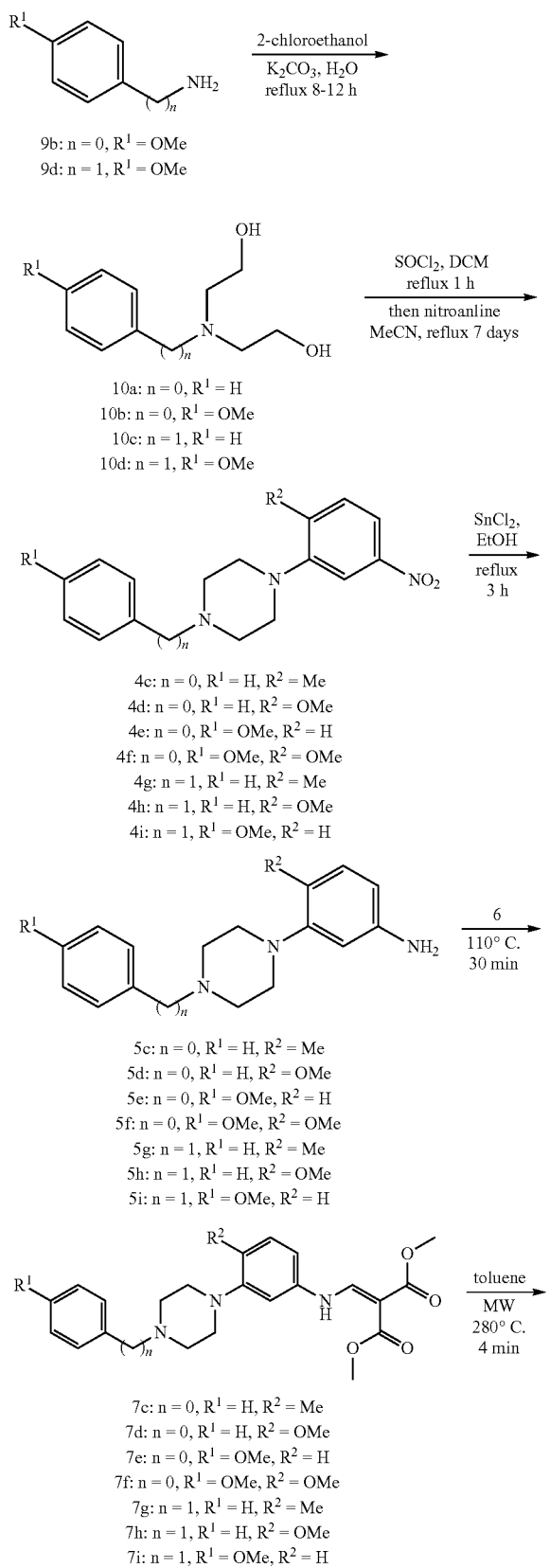

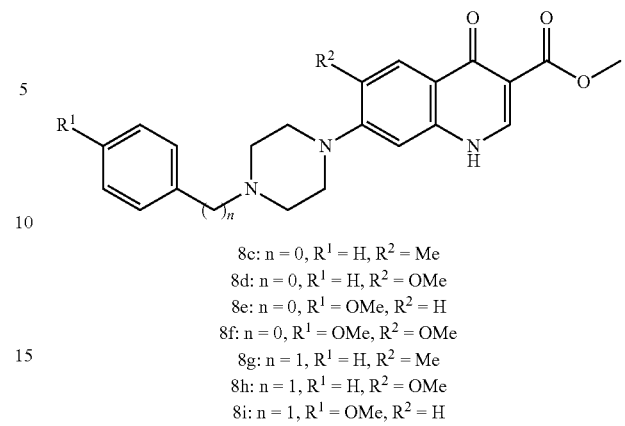

Compounds with a methylene unit between the 4(1H)-quinolone core and the piperazine were synthesized starting with 3-amino-benzyl alcohol 11, which was reacted with dimethyl 2-(methoxymethylene)malonate (6) to yield the corresponding enamines 12. The alcohol was oxidized using Dess-Martin periodinane[23] to the corresponding benzaldehyde, which was subjected to direct reductive amination conditions to yield substituted piperazines 7j-7ab.[24] These piperazinyl-substituted enamines were then cyclized using a microwave reactor to yield 4(1H)-quinolones 8j-8ab (Scheme 3).

Scheme 3: Synthesis of 4(1H)-Quinolones with a Methylene Between the Piperazinyl Moiety to the 4(1H)-Quinolone Core

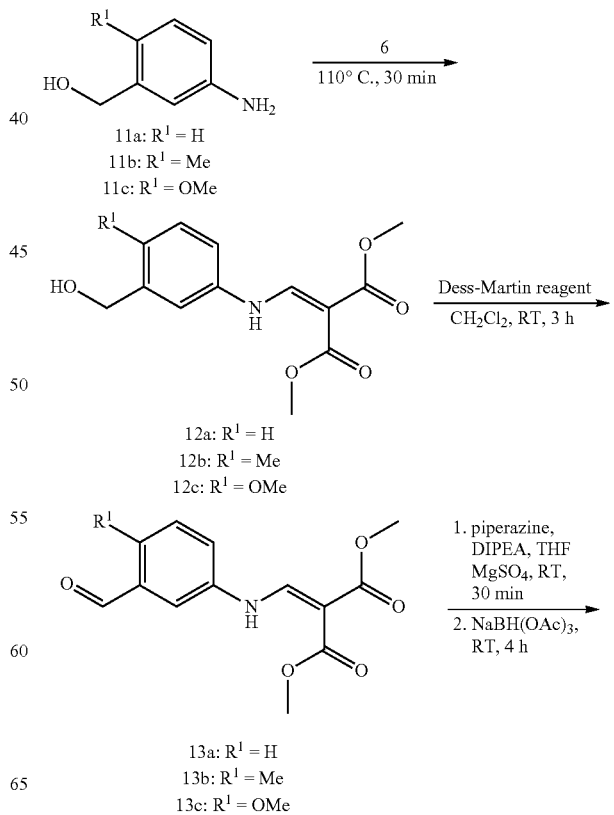

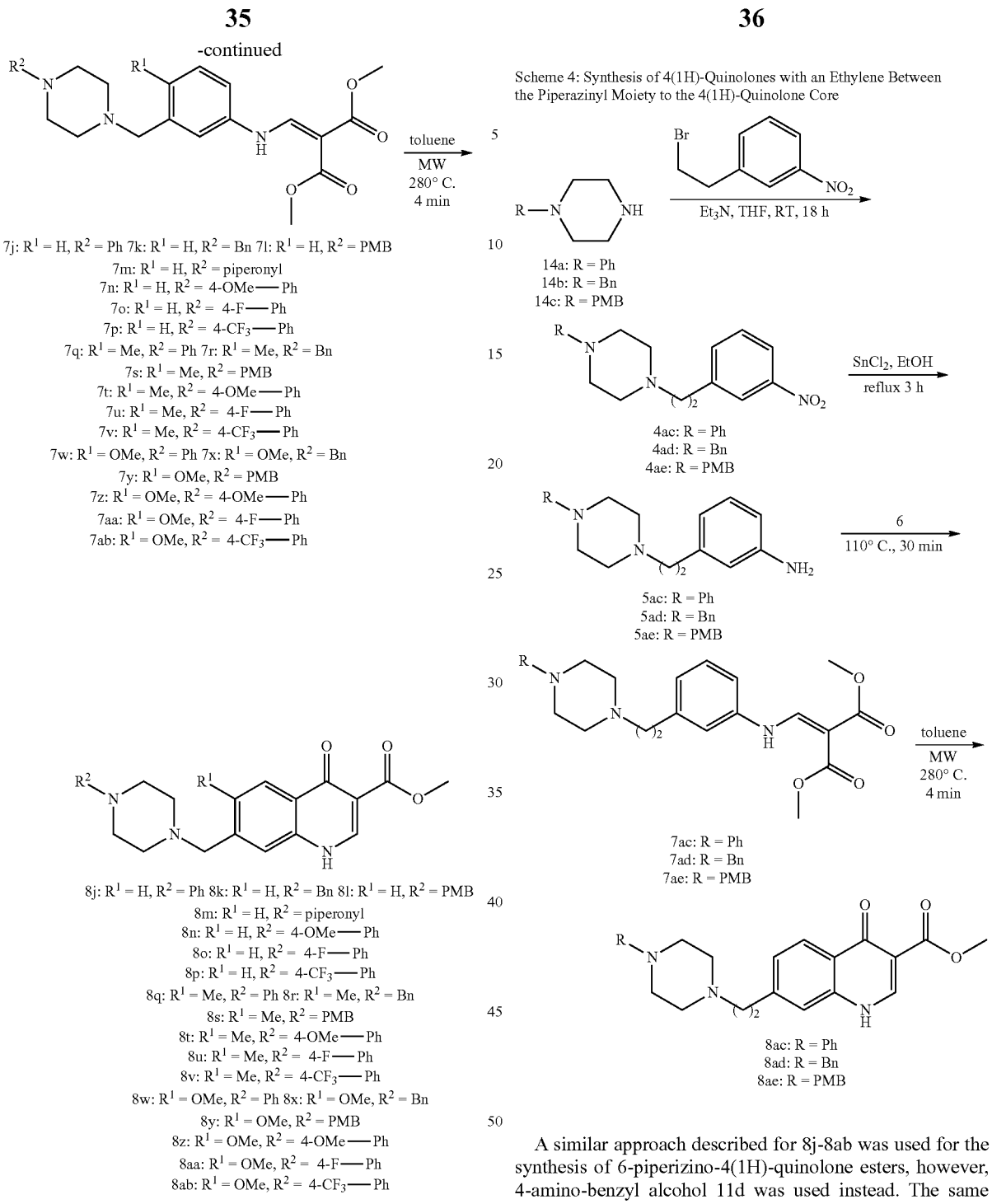

7j: $R^1$ = H, $R^2$ = Ph 7k: $R^1$ = H, $R^2$ = Bn 7l: $R^1$ = H, $R^2$ = PMB
7m: $R^1$ = H, $R^2$ = piperonyl
7n: $R^1$ = H, $R^2$ = 4-OMe—Ph
7o: $R^1$ = H, $R^2$ = 4-F—Ph
7p: $R^1$ = H, $R^2$ = 4-CF$_3$—Ph
7q: $R^1$ = Me, $R^2$ = Ph 7r: $R^1$ = Me, $R^2$ = Bn
7s: $R^1$ = Me, $R^2$ = PMB
7t: $R^1$ = Me, $R^2$ = 4-OMe—Ph
7u: $R^1$ = Me, $R^2$ = 4-F—Ph
7v: $R^1$ = Me, $R^2$ = 4-CF$_3$—Ph
7w: $R^1$ = OMe, $R^2$ = Ph 7x: $R^1$ = OMe, $R^2$ = Bn
7y: $R^1$ = OMe, $R^2$ = PMB
7z: $R^1$ = OMe, $R^2$ = 4-OMe—Ph
7aa: $R^1$ = OMe, $R^2$ = 4-F—Ph
7ab: $R^1$ = OMe, $R^2$ = 4-CF$_3$—Ph 8j: $R^1$ = H, $R^2$ = Ph 8k: $R^1$ = H, $R^2$ = Bn 8l: $R^1$ = H, $R^2$ = PMB
8m: $R^1$ = H, $R^2$ = piperonyl
8n: $R^1$ = H, $R^2$ = 4-OMe—Ph
8o: $R^1$ = H, $R^2$ = 4-F—Ph
8p: $R^1$ = H, $R^2$ = 4-CF$_3$—Ph
8q: $R^1$ = Me, $R^2$ = Ph 8r: $R^1$ = Me, $R^2$ = Bn
8s: $R^1$ = Me, $R^2$ = PMB
8t: $R^1$ = Me, $R^2$ = 4-OMe—Ph
8u: $R^1$ = Me, $R^2$ = 4-F—Ph
8v: $R^1$ = Me, $R^2$ = 4-CF$_3$—Ph
8w: $R^1$ = OMe, $R^2$ = Ph 8x: $R^1$ = OMe, $R^2$ = Bn
8y: $R^1$ = OMe, $R^2$ = PMB
8z: $R^1$ = OMe, $R^2$ = 4-OMe—Ph
8aa: $R^1$ = OMe, $R^2$ = 4-F—Ph
8ab: $R^1$ = OMe, $R^2$ = 4-CF$_3$—Ph Compounds with an ethylene between the piperazine and 4(1H)-quinolone core were synthesized through a four-step reaction sequence that was initiated by an alkylation of 3-nitrophenethyl bromide with corresponding piperazines 14 to yield intermediates 4.[25] The nitrophenyl intermediates 4 were reduced to anilines 5 using tin(II)chloride, which were subjected to the standard Gould-Jacob reaction sequence to give 4(1H)-quinolone esters 8ac-8ae (Scheme 4).

A similar approach described for 8j-8ab was used for the synthesis of 6-piperizino-4(1H)-quinolone esters, however, 4-amino-benzyl alcohol 11d was used instead. The same four-step reaction sequence involving the enamine formation, a Dess-Martin oxidation, a direct reductive amination, followed by the cyclization was performed to yield 6-piperizino-4(1H)-quinolone esters 8af-8ai (Scheme 5).

Scheme 5: Synthesis of 6-Piperazinyl-4(1H)-Quinolones

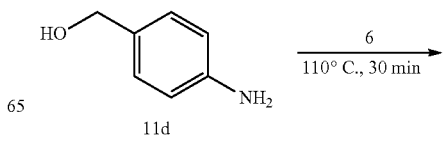

11d

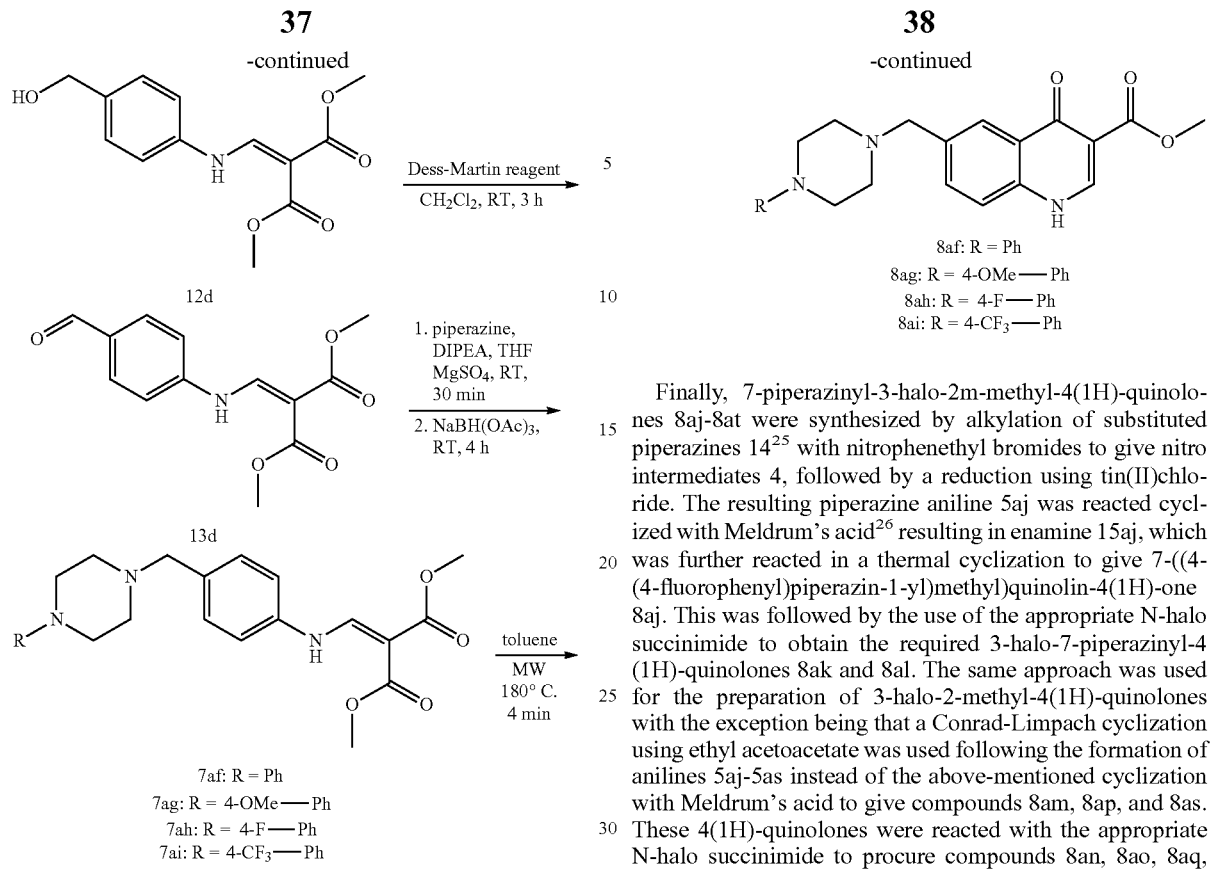

Finally, 7-piperazinyl-3-halo-2m-methyl-4(1H)-quinolones 8aj-8at were synthesized by alkylation of substituted piperazines 14[25] with nitrophenethyl bromides to give nitro intermediates 4, followed by a reduction using tin(II)chloride. The resulting piperazine aniline 5aj was reacted cyclized with Meldrum's acid[26] resulting in enamine 15aj, which was further reacted in a thermal cyclization to give 7-((4-(4-fluorophenyl)piperazin-1-yl)methyl)quinolin-4(1H)-one 8aj. This was followed by the use of the appropriate N-halo succinimide to obtain the required 3-halo-7-piperazinyl-4(1H)-quinolones 8ak and 8al. The same approach was used for the preparation of 3-halo-2-methyl-4(1H)-quinolones with the exception being that a Conrad-Limpach cyclization using ethyl acetoacetate was used following the formation of anilines 5aj-5as instead of the above-mentioned cyclization with Meldrum's acid to give compounds 8am, 8ap, and 8as. These 4(1H)-quinolones were reacted with the appropriate N-halo succinimide to procure compounds 8an, 8ao, 8aq, 8ar, and 8at (Scheme 6).

Scheme 6: Synthesis of 3-Halo Substituted 4(1H)-Quinolones

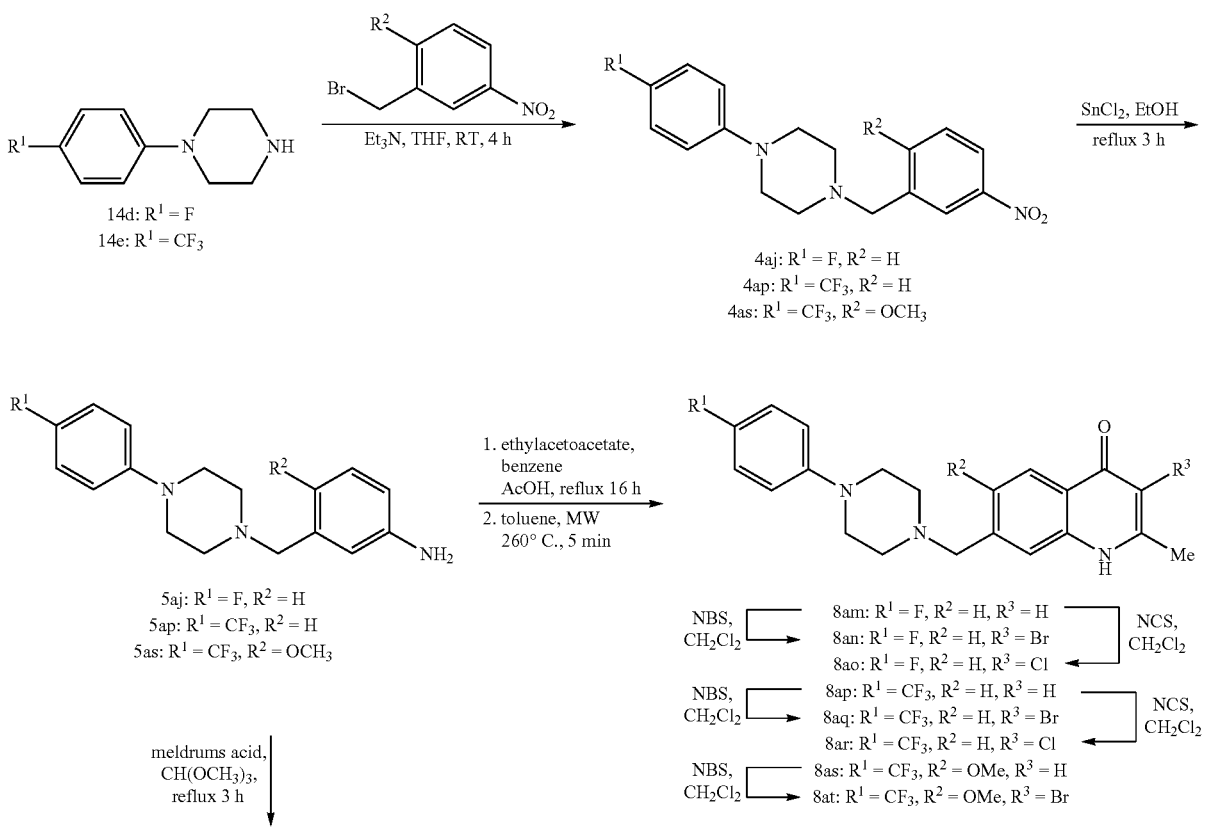

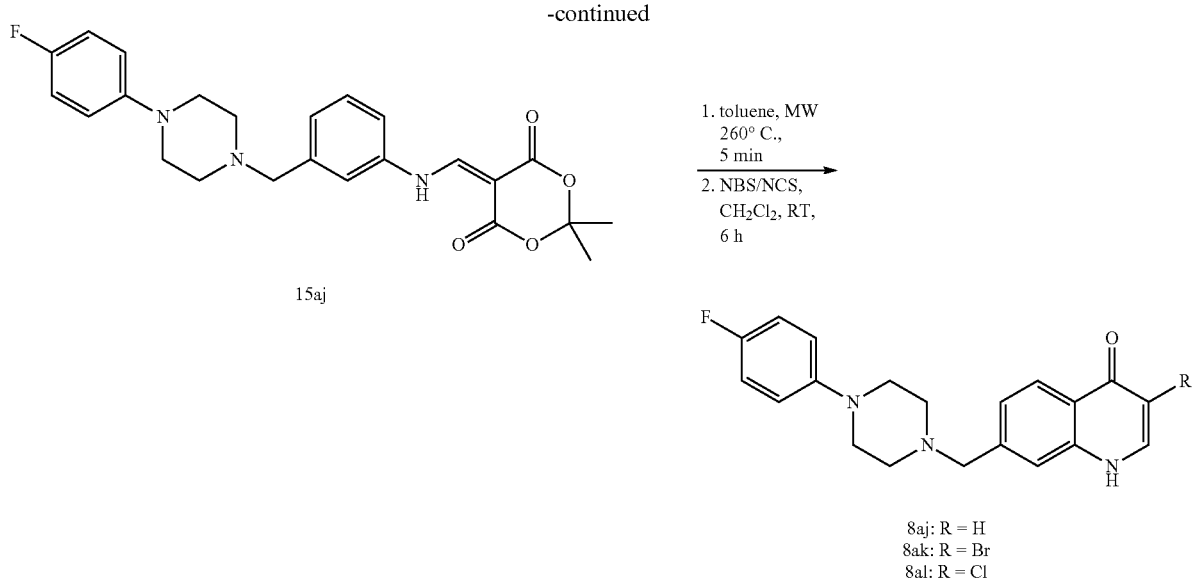

Antimalarial Activity and Cytotoxicity.

All compounds were tested against clinically relevant multidrug resistant malarial strains W2 (pyrimethamine and chloroquine-resistant) and TM90-C2B (mefloquine, chloroquine, atovaquone, and pyrimethamine-resistant) as previously reported.[7,10,27] Due to the emergence and rapid acquisition of cross-resistance,[28] each compound was also evaluated based on its RI, ($EC_{50}$) for TM90-C2B and W2 strains (RI=$EC_{50}$ TM90-C2B/$EC_{50}$ W2). Ideally, the RI of a compound should lie between 0.3 and 3.0 in order to avoid rapidly inducing resistance in the parasite. This range was based upon the natural resistance patterns observed for drugs like chloroquine and mefloquine.[29,30] Selected compounds were also tested for in vitro liver stage activity using Pb sporozoites expressing luciferase, harvested from mosquito salivary glands and allowed to infect HEPG2 hepatoma cells in order to assess if the compounds possessed causal prophylactic activity.[27] Additionally, each compound was tested for cytotoxicity using mammalian J774 cell lines in a 96 well plate format.[7,8,10,27]

Structural Activity Relationships.

The poor aqueous solubility of our 4(1H)-quinolone esters[9] motivated us to design and prepare a set of ionizable piperazinyl-substituted analogues with the primary aim being to significantly enhance the aqueous solubility without compromising antimalarial activity. The initial, small set of 6-hydrogen-7-piperazinyl-4(1H)-quinolones containing various linkages between the piperazinyl moiety and the 4(1H)-quinolone's benzenoid ring was prepared to identify the optimal spacer length (Table 1). In general, compounds with an ethylene between the 4(1H)-quinolone core and the piperazine showed the poorest blood stage activity of the group with N-phenylpiperazinyl-4(1H)-quinolone 8ac displaying $EC_{50}$ values of 25.6 nM for W2 and 1500 nM for TM90-C2B, while benzyl-substituted analogue 8ad was less active with $EC_{50}$ values of 116 nM for W2 and 6170 nM for TM90-C2B. In contrast, p-methoxybenzylpiperazinyl-4 (1H)-quinolone 8ae was the most active for W2 with $EC_{50}$ values of 11.6 nM but the least active for TM90-C2B showing activities greater than 5740 nM.

TABLE 1

Exploration of Various N-Substituted Piperazinyl Moieties on 7-Position of 4(1H)-Quinolone Benzenoid Ring to Enhance the Solubility and Antimalarial Activity

| Compound | R | n | $EC_{50}$ W2 (nM) | $EC_{50}$ TM90-C2B (nM) | RI[b] | $EC_{50}$ Pb (nM) | $EC_{50}$ J774 (μM) |
|---|---|---|---|---|---|---|---|
| 8ac | 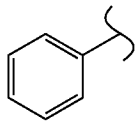 | 2 | 25.6 | 1500 | 58.6 | ND[c] | >20 |

TABLE 1-continued

Exploration of Various N-Substituted Piperazinyl Moieties on 7-Position of 4(1H)-Quinolone Benzenoid Ring to Enhance the Solubility and Antimalarial Activity

| Compound | R | n | $EC_{50}$ W2 (nM) | $EC_{50}$ TM90-C2B (nM) | $RI^b$ | $EC_{50}$ Pb (nM) | $EC_{50}$ J774 (μM) |
|---|---|---|---|---|---|---|---|
| 8ad | benzyl | 2 | 116 | 6170 | 53.2 | 157 | >20 |
| 8ae | 4-methoxybenzyl | 2 | 11.6 | >5740 | >495 | $ND^c$ | >20 |
| 8a | phenyl | 0 | 4.45 | 248 | 55.7 | 74.1 | >20 |
| 8b | benzyl | 0 | 16.2 | 860 | 53.1 | 84.5 | >20 |
| 8i | 4-methoxyphenyl | 0 | 19.9 | 1340 | 67.3 | $ND^c$ | $ND^c$ |
| 8j | phenyl | 1 | 1.25 | 483 | 386 | 4.74 | 3.94 |
| 8k | benzyl | 1 | 1.41 | 153 | 109 | 43.7 | 10.4 |
| 8l | 4-methoxybenzyl | 1 | 2.50 | 799 | 320 | 83.4 | 5.13 |
| 8m | 3,4-methylenedioxybenzyl | 1 | 157 | >5740 | >36.6 | $ND^c$ | >20 |

$^a$Chloroquine (CQ), atovaquone (ATO), and dihydroartemisinin (DHA) are internal controls for each in vitro assay: CQ, 421 nM W2, 229 nM TM90-C2B and 47.2 μM J774;
ATO, 1.39 nM W2, 18.4 μM TM90-C2B and 28.3 μM J774;
DHA, 5.47 nM W2, 5.86 nM TM90-C2B and 1.53 μM J774.
$^b$RI = TM90-C2B/W2.
$^c$ND: not determined.

Compounds with piperazines directly attached to the 4(1H)-quinolone core were more active than compounds containing an ethylene linker. N-Phenylpiperazinyl-4(1H)-quinolone 8a was the most active member with $EC_{50}$ values of 4.45 nM and 248 nM for W2 and TM90-C2B. N-Benzylpiperazinyl-4(1H)-quinolone 8b and its p-methoxybenzylpiperazinyl analogue 8i had nearly identical $EC_{50}$ of 16.2 nM and 19.9 nM for W2, along with 860 nM and 1340 nM for TM90-C2B.

Compounds with a methylene spacer between the piperazine and 4(1H)-quinolone were the most active analogues of this first set of 4(1H)-quinolones. Compounds 8j, 8k, and 8l were similarly potent with low single digit nM inhibitory concentrations for W2, whereas benzo[1,3]dioxolylpiperazinyl-4(1H)-quinolone 8m was significantly less potent. However, the same compounds displayed poor activity against TM90-C2B producing RI values ranging from 109-386 for analogues 8j, 8k, and 8l, and >36.6 for 8m.

A selection of this first set of piperazinyl-4(1H)-quinolones (Table 1) was tested for in vitro liver stage activity using *P. berghei* sporozoites expressing luciferase as previously described.[19] The best results were obtained with analogues whose piperazinyl moiety was attached to the quinolone's benzenoid ring via a methylene unit. N-Phenylpiperazinyl-4(1H)-quinolone 8j was the most potent compound with an $EC_{50}$ of 4.74 nM for Pb, while its benzyl analogue 8k or its 4-methoxybenyl analogue 8l were approximately 10-fold less potent with $EC_{50}$ values of 43.7 and 83.4 nM. All the other analogues 8a, 8b, and 8ad with the piperazinyl group substituted to the 4(1H)-quinolone's core directly or via an ethylene were slightly less potent.

Follow-up SAR studies focused solely on piperazines directly attached to the 4(1H)-quinolone core or via a methylene unit, as the antimalarial activity of the N-phenyl or N-benzylpiperazinyl-4(1H)-quinolones followed a trend with the ethylene-connected analogues being less potent than the methylene-linked compounds or the 4(1H)-quinolones to which the piperazine is directly attached. This, in conjunction with previous observations that substituents in 6-position alter antimalarial activity, lead to the design of a small series of 6-methyl- or 6-methoxy-4(1H)-quinolone esters retaining in 7-position, an N-phenyl-, N-benzyl-, or 4-methoxybenzyl-substituted piperazine.

Piperazinyl-4(1H)-quinolones 8q, 8r, 8w and 8x with a methylene spacer were approximately 10-fold more potent against W2 than their structurally related analogues 8c, 8g, 8d, and 8h whose 4(1H)-quinolone core is directly substituted with the piperazine moiety (Table 2). In contrast, the 7-piperazinyl-4(1H)-quinolones 8c, 8g, 8d and 8h possessed approximately 10-fold more favorable RI values in comparison to the analogues 8q, 8r, 8w and 8x with a methylene spacer. Furthermore, for both the N-phenylpiperazinyl- or N-benzylpiperazinyl-substituted 4(1H)-quinolones, the 6-methyl substituent appeared to slightly increase the antimalarial activity whereas the opposite effect was true for the 6-methoxy substituent, and the effect appeared consistent.

6-Methyl-7-phenylpiperazinyl-4(1H)-quinolone 8q was the most potent of the group against W2 with an $EC_{50}$ value of 0.435 nM and 147 nM against TM90-C2B. When the N-phenylpiperazinyl moiety of 8q was exchanged by an N-benzylpiperazine, activity for analogue 8r fell slightly for W2 with an $EC_{50}$ value of 1.45 nM and more noticeable for TM90-C2B with an $EC_{50}$ value of 890 nM. Additional potency losses were observed with compound 8s when the N-phenylpiperazinyl moiety of 8q was exchanged by a 4-methoxybenzylpiperazine. Exchange of the 6-methyl group of compound 8q by a 6-methoxy substituent in compound 8w dropped the potency approximately threefold for W2 and TM90-C2B with $EC_{50}$ values of 1.62 nM and 493 nM. p-Methoxybenzyl piperazines 8s and 8y were the least active ones with $EC_{50}$ values of 2.40 nM and 1022 nM for W2 and TM90-C2B for the 6-methyl analogue 8s and $EC_{50}$ values of 9.97 nM and 2750 nM for the 6-methoxy analogue 8y.

The compounds displaying the best W2 activity were also tested for in vitro liver stage activity. Analogues 8q, 8r and 8x were the most potent ones with $EC_{50}$ values of 6.92 nM, 9.46 nM, and 9.26 nM.

TABLE 2

Effect of Various Substitutions in 6-Position of the 4(1H)-Quinolone's Benzenoid Ring on Antimalarial Activity

| Compound | $R^1$ | $R^2$ | n | $EC_{50}$ W2 (nM) | $EC_{50}$ TM90-C2B (nM) | $RI^b$ | $EC_{50}$ Pb (nM) | $EC_{50}$ J774 (μM) |
|---|---|---|---|---|---|---|---|---|
| 8q | 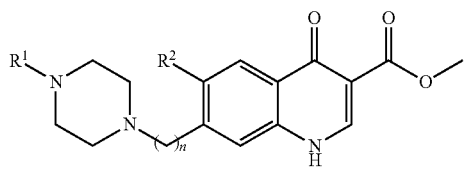 | —CH$_3$ | 1 | 0.435 | 147 | 338 | 6.92 | 11.9 |
| 8r |  | —CH$_3$ | 1 | 1.45 | 890 | 614 | 9.46 | >20 |

TABLE 2-continued

Effect of Various Substitutions in 6-Position of the 4(1H)-Quinolone's Benzenoid Ring on Antimalarial Activity

| Compound | R[1] | R[2] | n | $EC_{50}$ W2 (nM) | $EC_{50}$ TM90-C2B (nM) | RI[b] | $EC_{50}$ Pb (nM) | $EC_{50}$ J774 (μM) |
|---|---|---|---|---|---|---|---|---|
| 8s | 4-methoxybenzyl | —CH₃ | 1 | 2.40 | 1022 | 426 | ND[c] | >20 |
| 8w | benzyl | OCH₃ | 1 | 1.62 | 493 | 304 | 113 | >20 |
| 8x | phenethyl | OCH₃ | 1 | 5.45 | 2830 | 519 | 9.26 | >20 |
| 8y | 4-methoxybenzyl | OCH₃ | 1 | 9.97 | 2750 | 276 | 52.4 | >20 |
| 8c | benzyl | —CH₃ | 0 | 45.5 | 1110 | 24.4 | ND[c] | 16.7 |
| 8g | phenethyl | —CH₃ | 0 | 13.2 | 982 | 74.4 | >100 | >20 |
| 8d | benzyl | OCH₃ | 0 | 37.2 | 804 | 21.6 | ND[c] | 16.8 |
| 8h | phenethyl | OCH₃ | 0 | 63.5 | 198 | 3.11 | ND[c] | 12.4 |

[a]Chloroquine (CQ), atovaquone (ATO), and dihydroartemisinin (DHA) are internal controls for each in vitro assay:
CQ, 421 nM W2, 229 nM TM90-C2B and 47.2 μM J774;
ATO, 1.39 nM W2, 18.4 μM TM90-C2B and 28.3 μM J774;
DHA, 5.47 nM W2, 5.86 nM TM90-C2B and 1.53 μM J774.
[b]RI = TM90-C2B/W2.
[c]ND: not determined.

Next, a subseries was designed to determine whether steric and/or electronic effects of the N-phenylpiperazinyl moiety influenced the antimalarial activity (Table 3). The para position of the N-phenylpiperazinyl group was substituted with a fluorine, a trifluoromethyl, or a methoxy group, while simultaneously the quinolone's 6-position was probed with a hydrogen, a methyl, or a methoxy group. A previously observed trend was confirmed as analogues 8n and 8z with the methylene spacer between the piperazine and the 4(1H)-quinolone's core were more potent against W2 than compounds 8e and 8f with a directly attached piperazine. Activity data against W2 indicated the general trend that, independently of the 4-substituent of the N-phenylpiperazine moiety, the 6-methyl-substituted compounds are slightly more potent than the 6-methoxy analogues, which are equipotent or less potent than the 6-hydrogen analogues. Furthermore, substituting the 4-position of the N-phenylpiperazinyl moiety with the electron donating methoxy group generally produced compounds that were about half as potent as compounds with the electron withdrawing group.

The fluorinated methylene-spaced compounds 8o, 8u, and 8aa showed significant antimalarial activity against all strains. Analogues 8o and 8aa were equipotent against W2 with $EC_{50}$ values of 1.75 nM and 1.79 nM respectively, whereas compound 8u was about twice as potent with an $EC_{50}$ value of 843 pM. The trifluoromethylphenylpiperazinyl-4(1H)-quinolones 8p, 8v, and 8ab were more potent than the fluorophenyl-substituted analogues 8o, 8u, and 8aa suggesting a strong electron-withdrawing effect on the phenyl group to be beneficial. Compound 8v was very potent with an $EC_{50}$ value of 66 pM against W2 and an $EC_{50}$ value of 101 nM against TM90-C2B. Trifluoromethyl analogues 8ab and 8p were slightly less potent than compound 8v with $EC_{50}$ values of 6.42 and 0.315 nM against W2 and $EC_{50}$ values of 209 nM and 122 nM against TM90-C2B.

Compounds in this series also displayed very potent liver stage activity. Of the compounds chosen for testing, p-methoxyphenyl-substituted analogue 8n was the most potent one with an $EC_{50}$ value of 123 pM. Fluorophenyl- or methoxyphenyl-substituted 4(1H)-quinolones 8o, 8u, and 8t displayed single digit nanomolar activity with $EC_{50}$ values of 1.06 nM, 2.64 nM, and 4.11 nM.

We next considered whether a positional change of the piperazine moiety from the 7-position to the 6-position would retain or improve the antimalarial activity and possibly improve the RI value. A set of analogues 8af-8ai was prepared by switching the piperazine moiety from the 7-position to 6-position of the 4(1H)-quinolone's benzenoid ring and evaluated for their activity against W2, TM90-C2B, and Pb (Table 4). These piperazinyl analogues 8af-8ai lost significantly in activity in comparison to their 7-substituted counterparts with $EC_{50}$ values ranging from 45.2 nM to 164 nM against W2, whereas the compounds were considered to be nearly inactive against TM90-C2B. Surprisingly, compounds 8af and 8ai showed moderate activity against Pb with $EC_{50}$ values of 90.5 nM and 85 nM. However, the lack of potency against W2, TM90-C2B, and Pb further substantiated our initial hypothesis that for antimalarial activity the piperazine moiety must be attached at the 4(1H)-quinolone's 7-position.

TABLE 3

Steric and Electronic Effects of the Phenylpiperazine Moiety and the 4(1H)-Quinolone 6-Position of Antimalarial Activity

| Compound | $R^1$ | $R^2$ | n | $EC_{50}$ W2 (nM) | $EC_{50}$ TM90-C2B (nM) | $RI^b$ | $EC_{50}$ Pb (nM) | $EC_{50}$ J774 (µM) |
|---|---|---|---|---|---|---|---|---|
| 8o | F | H | 1 | 1.75 | 131 | 74.9 | 1.06 | 2.00 |
| 8u | F | —$CH_3$ | 1 | 0.843 | 348 | 413 | 2.64 | 15.7 |
| 8aa | F | —$OCH_3$ | 1 | 1.79 | 218 | 122 | 32.3 | >20 |
| 8e | $OCH_3$ | H | 0 | 7.76 | 154 | 19.8 | ND | >20 |
| 8f | $OCH_3$ | —$OCH_3$ | 0 | 42.9 | 1980 | 46.2 | >100 | >20 |
| 8n | $OCH_3$ | —H | 1 | 3.56 | 222 | 62.4 | 0.123 | 4.73 |
| 8t | $OCH_3$ | —$CH_3$ | 1 | 0.575 | 177 | 308 | 4.11 | >20 |
| 8z | $OCH_3$ | —$OCH_3$ | 1 | 3.38 | 861 | 255 | 10.4 | 15.7 |
| 8p | $CF_3$ | —H | 1 | 0.315 | 122 | 387 | 15.6 | 10.7 |
| 8v | $CF_3$ | —$CH_3$ | 1 | 0.066 | 101 | 1530 | $ND^c$ | >20 |
| 8ab | $CF_3$ | —$OCH_3$ | 1 | 6.42 | 209 | 32.5 | 9.58 | >20 |

$^a$Chloroquine (CQ), atovaquone (ATO), and dihydroartemisinin (DHA) are internal controls for each in vitro assay:

CQ, 421 nM W2, 229 nM TM90-C2B and 47.2 µM J774;

ATO, 1.39 nM W2, 18.4 µM TM90-C2B and 28.3 µM J774;

DHA, 5.47 nM W2, 5.86 nM TM90-C2B and 1.53 µM J774.

$^b$RI = TM90-C2B/W2.

$^c$ND: not determined.

TABLE 4

4(1H)-Quinolones Substituted in 6-Positions with the Piperazine Moiety

| Compound | R | EC$_{50}$ W2 (nM) | EC$_{50}$ TM90-C2B (nM) | RI[b] | EC$_{50}$ Pb (nM) | EC$_{50}$ J774 (μM) |
| --- | --- | --- | --- | --- | --- | --- |
| 8af | —H | 151 | 3200 | 21.2 | 90.5 | >20 |
| 8ag | —OCH$_3$ | 164 | 2900 | 17.7 | >100 | >20 |
| 8ah | —F | 106 | 2900 | 27.4 | ND[c] | >20 |
| 8ai | —CF$_3$ | 45.2 | 2900 | 64.2 | 85.0 | >20 |

[a]Chloroquine (CQ), atovaquone (ATO), and dihydroartemisinin (DHA) are internal controls for each in vitro assay:
CQ, 421 nM W2, 229 nM TM90-C2B and 47.2 μM J774;
ATO, 1.39 nM W2, 18.4 μM TM90-C2B and 28.3 μM J774;
DHA, 5.47 nM W2, 5.86 nM TM90-C2B and 1.53 μM J774.
[b]RI = TM90-C2B/W2.
[c]ND: not determined.

Previously, 3-halo-substituted 4(1H)-quinolones were shown to significantly improve the RI values for the antimalarial 4(1H)-quinolone ester series and several piperazinyl-substituted analogues were prepared for this purpose (Table 5). With the exception of compounds 8ar and 8at, all other 3-halo-4(1H)-quinolones 8ak-8aq possessed acceptable RI values smaller than 3.

The 3-chloro analogue 8al was among the least active at 1060 nM and 2290 nM, however with an RI of 2.16, it gave hope that the 3-halo effect could be distributed to the piperazine analogues. When the 3-chloro substituent was replaced with a 3-bromo 8ak, activity was increased to 812 nM for W2 and slightly decreased for TM90-C2B dropping to 2430 for TM90-C2B. Like the 7-phenoxyethoxy-4(1H)-quinolone analogues, the addition of a 2-methyl substituent gave rise to more potent compounds with the chloro-substituted 8ao having activities of 38.5 nM and 52.1 nM for W2 and TM90-C2B, giving it an RI of 1.35. The 3-bromo 8an was even more potent with EC$_{50}$s of 25.1 nM for W2 and 25.5 nM for TM90-C2B, and RI of 1.01. There was, however, a 30-fold difference in Pb activities between the 2-unsubstituted and 2-methyl substituted with 8ak having an EC$_{50}$ 0.858 nM while 8an had an EC$_{50}$ of 26.2 nM. Finally, trifluoromethylphenyl-substituted piperazine variants were synthesized to give 3-chloro 8ar and 3-bromo 8aq. Both compounds showed a significant decrease in activity compared to their fluoro-substituted piperazine counterparts 8ao and 8an.

TABLE 5

3-Halo-Substituted 4(1H)-Quinolones

| Compound | R$^1$ | R$^2$ | R$^3$ | R$^4$ | EC$_{50}$ W2 (nM) | EC$_{50}$ TM90-C2B (nM) | RI[b] | EC$_{50}$ Pb (nM) | EC$_{50}$ J774 (μM) |
| --- | --- | --- | --- | --- | --- | --- | --- | --- | --- |
| 8ak | —F | —H | —Br | —H | 812 | 2430 | 2.99 | 0.858 | >20 |
| 8al | —F | —H | —Cl | —H | 1060 | 2290 | 2.16 | ND[c] | >20 |
| 8am | —F | —H | —H | —CH$_3$ | 1220 | 1450 | 1.19 | ND[c] | >20 |
| 8an | —F | —H | —Br | —CH$_3$ | 25.1 | 25.5 | 1.02 | 26.2 | >20 |
| 8ao | —F | —H | —Cl | —CH$_3$ | 38.5 | 52.1 | 1.35 | ND[c] | >20 |
| 8aq | —CF$_3$ | —H | —Br | —CH$_3$ | 121 | 95.4 | 0.79 | ND[c] | >20 |

TABLE 5-continued

3-Halo-Substituted 4(1H)-Quinolones

| Compound | R¹ | R² | R³ | R⁴ | $EC_{50}$ W2 (nM) | $EC_{50}$ TM90-C2B (nM) | RI[b] | $EC_{50}$ Pb (nM) | $EC_{50}$ J774 (μM) |
|---|---|---|---|---|---|---|---|---|---|
| 8ar | —CF₃ | —H | —Cl | —CH₃ | 139 | 1510 | 10.9 | ND[c] | >20 |
| 8at | —CF₃ | —OCH₃ | —Br | —CH₃ | 128 | >5000 | >39.1 | ND[c] | >20 |

[a]Chloroquine (CQ), atovaquone (ATO), and dihydroartemisinin (DHA) are internal controls for each in vitro assay:
CQ, 421 nM W2, 229 nM TM90-C2B and 47.2 μM J774;
ATO, 1.39 nM W2, 18.4 μM TM90-C2B and 28.3 μM J774;
DHA, 5.47 nM W2, 5.86 nM TM90-C2B and 1.53 μM J774.
[b]RI = TM90-C2B/W2.
[c]ND: not determined.

Cytotoxicity.

All compounds were tested in vitro for cytotoxicity to J774 mammalian cells as previously reported (Tables 1-5).[7-10,19] Of all the compounds tested, only a few compounds displayed signs of cytotoxicity at concentrations lower than 20 μM. Onset of cytotoxicity was recorded for compounds 8j, 8l, 8n, and 8o with $EC_{50}$ values of 3.94 μM, 5.13 μM, 4.73 μM, and 2.00 μM. Nevertheless, these analogues and the majority of the piperazinyl-4(1H)-quinolones can be considered selective chemotypes as they display single digit nanomolar or sub-nanomolar activity against W2.

Structure-Property Relationships.

Calculated properties such as molecular weight, polar surface area, number of H-bond donors and acceptors were within the recommended ranges typically needed for good oral bioavailability suggesting that the piperazinyl-4(1H)-quinolone design provided excellent spatial leeway for structural modifications to occupy physicochemical space unique for orally bioavailable compounds. Furthermore, to profile the properties of the piperazinyl-4(1H)-quinolones, and to identify potential limitations, aqueous solubility and lipophilicity log D were experimentally determined via LC/MS-based assays as described by the Manetsch laboratory previously[8,10,31,32] (Tables 9-12). Encouragingly, the piperazinyl-4(1H)-quinolones were much more soluble than the previously described phenoxyethoxy-4(1H)-quinolone analogues.[19] As expected, the solubility of all compounds was affected by pH, with better solubility under more acidic conditions.

TABLE 9

Solubility and LogD of Piperazinyl-Substituted 4(1H)-Quinolones

| Compound | R¹ | R² | n | Solubility pH 2.0 (μM) | Solubility pH 6.5 (μM) | LogD pH 7.4 |
|---|---|---|---|---|---|---|
| 8ac | benzyl | —H | 2 | ≥80 | ≥80 | 5.11 |
| 8ad | phenethyl | —H | 2 | ≥80 | ≥80 | 1.72 |
| 8ae | 4-methoxyphenethyl | —H | 2 | ≥80 | ≥80 | 1.68 |

TABLE 9-continued

Solubility and LogD of Piperazinyl-Substituted 4(1H)-Quinolones

| Compound | R¹ | R² | n | Solubility pH 2.0 (μM) | Solubility pH 6.5 (μM) | LogD pH 7.4 |
|---|---|---|---|---|---|---|
| 8a | phenyl (CH₂)₀ | —H | 0 | 1-19.9 | 1-19.9 | 2.58 |
| 8b | benzyl | —H | 0 | 60-79.9 | 60-79.9 | 2.21 |
| 8i | 4-methoxyphenyl | —H | 0 | ≥80 | 40-59.9 | 2.08 |
| 8j | benzyl | —H | 1 | ≥80 | ≥80 | 0.86 |
| 8k | phenethyl | —H | 1 | ≥80 | ≥80 | 2.06 |
| 8l | 4-methoxybenzyl | —H | 1 | ≥80 | ≥80 | 1.66 |
| 8m | 3,4-methylenedioxybenzyl | —H | 1 | ≥80 | ≥80 | 0.87 |
| 8q | benzyl | —CH₃ | 1 | ≥80 | 60-79.9 | 2.81 |
| 8r | phenethyl | —CH₃ | 1 | ≥80 | ≥80 | 1.94 |
| 8s | 4-methoxybenzyl | —CH₃ | 1 | ≥80 | ≥80 | 2.03 |
| 8w | benzyl | —OCH₃ | 1 | ≥80 | ≥80 | 1.32 |

TABLE 9-continued

Solubility and LogD of Piperazinyl-Substituted 4(1H)-Quinolones

| Compound | R¹ | R² | n | Solubility pH 2.0 (µM) | Solubility pH 6.5 (µM) | LogD pH 7.4 |
|---|---|---|---|---|---|---|
| 8x | phenethyl | —OCH₃ | 1 | ≥80 | 60-79.9 | 1.28 |
| 8c | phenyl | —CH₃ | 0 | ≥80 | 40-59.9 | 2.31 |
| 8g | benzyl | —CH₃ | 0 | ≥80 | ≥80 | 2.37 |
| 8d | phenyl | —OCH₃ | 0 | ≥80 | 1-19.9 | 2.64 |
| 8h | benzyl | —OCH₃ | 0 | 60-79.9 | 40-59.9 | 2.03 |

TABLE 10

Solubility and LogD of Piperazinyl-Substituted 4(1H)-Quinolones

| Compound | R | R¹ | n | Solubility pH 2.0 (µM) | Solubility pH 6.5 (µM) | LogD pH 7.4 |
|---|---|---|---|---|---|---|
| 8o | —F | —H | 1 | ≥80 | ≥80 | 2.38 |
| 8u | —F | —CH₃ | 1 | ≥80 | 40-59.9 | 2.90 |
| 8aa | —F | —OCH₃ | 1 | 60-79.9 | ≥80 | 1.31 |
| 8e | —OCH₃ | —H | 0 | 40-59.9 | 20-39.9 | 2.44 |
| 8f | —OCH₃ | —OCH₃ | 0 | 60-79.9 | 20-39.9 | 2.48 |
| 8n | —OCH₃ | —H | 1 | ≥80 | 40-59.9 | 2.11 |
| 8t | —OCH₃ | —CH₃ | 1 | ≥80 | 20-39.9 | 2.61 |
| 8z | —OCH₃ | —OCH₃ | 1 | ≥80 | ≥80 | 2.19 |
| 8p | —CF₃ | —H | 1 | ≥80 | 1-19.9 | 3.23 |
| 8v | —CF₃ | —CH₃ | 1 | ≥80 | 1-19.9 | 3.73 |
| 8ab | —CF₃ | —OCH₃ | 1 | 1-19.9 | 1-19.9 | 1.29 |

TABLE 11

Solubility and LogD of Piperazinyl-Substituted 4(1H)-Quinolones

| Compound | R | Solubility pH 2.0 (µM) | Solubility pH 6.5 (µM) | LogD pH 7.4 |
|---|---|---|---|---|
| 8af | —H | ≥80 | 20-39.9 | 2.03 |
| 8ag | —OCH₃ | ≥80 | 20-39.9 | 1.91 |
| 8ah | —F | ≥80 | ≥80 | 2.17 |
| 8ai | —CF₃ | ≥80 | 1-19.9 | 3.01 |

Solubility and LogD of Piperazinyl-Substituted 4(1H)-Quinolones

| Compound | R | R² | Solubility pH 2.0 (μM) | Solubility pH 6.5 (μM) | LogD pH 7.4 |
|---|---|---|---|---|---|
| 8ak | —Br | —H | ≥80 | 20-39.9 | 2.91 |
| 8al | —Cl | —H | ≥80 | 40-59.9 | 2.57 |
| 8am | —H | —CH₃ | ≥80 | ≥80 | 2.44 |
| 8an | —Br | —CH₃ | ≥80 | 1-19.9 | 2.83 |
| 8ao | —Cl | —CH₃ | ≥80 | 1-19.9 | 2.73 |

The piperazine analogues such as 8ac, 8ad, 8ae, 8j or 8k with an ethylene or methylene spacer between the piperazine and the quinolone moiety displayed good aqueous solubility of 80 μM or more at both pH 2.0 and pH 6.5. Only compounds such as 8a with an N-phenylpiperazinyl group directly attached to the 4(1H)-quinolone core had reduced solubility below 20 μM at pH 2.0 and pH 6.5. Replacement of the N-phenylpiperazinyl group in 4(1H)-quinolone 8a by an N-benzylpiperazinyl group in compound 8b reestablished the solubility in the ranges of 60-80 μM.

Additional solubility dependencies were observed with the various 4(1H)-quinolone compound series. Analogues, in which the piperazinyl moiety was moved from the 4(1H)-quinolone's 7-position to the 6-position were slightly less soluble at pH 6.5 (see Supporting information, Tables 10 and 11). Furthermore, 3-halo-4(1H)-quinolones had marked solubility differences between pH 2.0 and pH 6.5, displaying significantly higher solubility at low pH. The addition of a 2-methyl group to the 4(1H)-quinolone further lowered solubility, with 3-bromo-2-methyl-4(1H)-quinolone 8an being greater than 20 times less soluble at pH 6.5 compared to its 2-hydrogen counterpart 8ak (Table 12).

In Vivo Efficacy Evaluation of Selected Compounds in an Efficacy Scouting Assay Against Blood Stages of the Parasite.

Of all prepared and tested 4(1H)-quinolones, 29 with potent in vitro activity against both P. falciparum strains were chosen to undergo a scouting assay in Pb-infected mice. The screening involved a single oral 50 mg/kg dose 1 day post infection (PI) and an assessment of parasitemia on days 3 PI and 6 PI (Table 6). The threshold for active compounds was inhibition greater than 50% on days 3 and 6 PI. Compounds 8h, 8m, 8t, and 8ad all showed no inhibition on day 6 PI, whereas 4(1H)-quinolones 8b and 8l were just under the 50% threshold of activity with both showing inhibition in the low 40% ranges. Compounds 8a, 8c, 8d, 8k, 8n, 8q, 8r, 8s, 8x, 8y, and 8ag displayed little to moderate protection on day 6 PI, delaying the parasites growth. Lastly, compounds 8o, 8p, 8u, 8v, 8w, 8z, 8aa, 8ab, 8ak, 8al, 8an, and 8ao all showed excellent activities in these scout assays with trifluoromethylpiperazinyl-4(1H)-quinolone esters 8p, 8v, and 8ab, and 3-bromo-4(1H)-quinolone 8an having completely inhibited parasite growth even on day 6 PI. These results clearly underscore the significant advantages the piperazinyl-substituted 4(1H)-quinolones have over the previously reported 4(1H)-quinolone esters.[19]

TABLE 6

In Vivo Efficacy Scout Screening

| Compound | % Inhibition Day 3 PI[a] | % Inhibition Day 6 PI[a] | Compound | % Inhibition Day 3 PI[a] | % Inhibition Day 6 PI[a] |
|---|---|---|---|---|---|
| 8a | 38.5 | 27.5 | 8u | 100 | 98.3 |
| 8b | 46.2 | 43.1 | 8v | 100 | 100 |
| 8c | 80.0 | 31.6 | 8w | 100 | 82.4 |
| 8d | 70.0 | 33.0 | 8x | 80.0 | 19.3 |
| 8h | 100 | <1 | 8y | 100 | 24.6 |
| 8k | 100 | 12.3 | 8z | 100 | 70.6 |
| 8l | 69.2 | 41.2 | 8aa | 100 | 56.9 |
| 8m | 40.0 | <1 | 8ab | 100 | 100 |
| 8n | 100 | 39.2 | 8ad | 46.2 | <1 |
| 8o | 100 | 98.0 | 8ag | 84.6 | 31.4 |
| 8p | 100 | 100 | 8ak | 100 | 94.2 |
| 8q | 46.2 | 15.7 | 8al | 100 | 71.9 |
| 8r | 100 | 24.6 | 8an | 100 | 100 |
| 8s | 80.0 | 14.0 | 8aO | 100 | 86.4 |
| 8t | 100 | <1 | Atovaquone | 96.3 | 99.8 |
| Amodiaquine | 95.5 | 99.9 | | | |

[a]percent inhibition compared to untreated animals

In Vivo Efficacy Evaluation of Frontrunner Compounds Against Blood Stages of the Parasite.

Using a modified Thompson test model, frontrunner compounds 8o, 8p, 8u, 8v, 8ab, 8ak, 8an, and 8ao were evaluated in vivo. These frontrunner compounds were selected for further in vivo efficacy testing as they displayed full inhibition on day 3 PI and over 85% inhibition on day 6 PI in the scouting assay. Mice were infected with 1×10⁶ P. berghei-GFP parasites and compounds were dosed orally on days 3, 4 and 5 PI with a dose of 10 mg/kg of compound suspended or dissolved in HEC/Tween or PEG 400. Parasitemia was observed by flow cytometry on days 3, 6, 9, 13, 21, and 30 PI. Compounds with animal survival up to day 30 PI and parasitemia levels of less than 1% on day 30 PI were considered to be cures. Lastly, animals with more than 40% parasitemia levels were euthanized. For all experiments, atovaquone was used as the positive control.[7,27]

4(1H)-Quinolone esters 8ak and 8ao, and 3-bromo-4(1H)-quinolone 8an all had the same day of death as the untreated control animals. While 4(1H)-quinolone esters 8ak and 8ao displayed a low inhibition on day 6 PI, analogue 8an was much more potent with a 90.9% inhibition on day 6 PI. These results suggest that compound 8an is possibly rapidly cleared after day 6 PI. Compounds 8o, 8p, and 8u had greater 100% inhibition on day 6 PI, nevertheless, all animals succumbed to the parasite by day 21 PI possibly indicating a longer half-life than 3-bromo-4(1H)-quinolone 8an. The remaining compounds, 8v and 8ab, both produced cures in more than half of the animals, curing 3 of the 5 animals (Table 7).

TABLE 7

In Vivo Efficacy Thompson Test

| Compound | Dose (mg/kg) | % Inhibition Day 6 PI[a] | Avg. Day of Death | No. of Cures |
|---|---|---|---|---|
| 8o | 10 | 100 | 21 | 0/5 |
| 8p | 10 | 100 | 21 | 0/5 |
| 8u | 10 | 100 | 21 | 0/5 |
| 8v | 10 | 100 | N/A | 3/5 |
| 8ab | 10 | 100 | N/A | 3/5 |
| 8ak | 10 | 33.0 | 13 | 0/5 |
| 8an | 10 | 90.9 | 13 | 0/5 |

TABLE 7-continued

In Vivo Efficacy Thompson Test

| Compound | Dose (mg/kg) | % Inhibition Day 6 PI[a] | Avg. Day of Death | No. of Cures |
|---|---|---|---|---|
| 8ao | 10 | 11.0 | 13 | 0/5 |
| Atovaquone | 10 | 100 | N/A | 5/5 |

[a]Percent inhibition as compared to untreated control animals

In Vivo Efficacy Evaluation of Frontrunner Compounds Against Liver Stages of the Parasite.

Figure 3A:
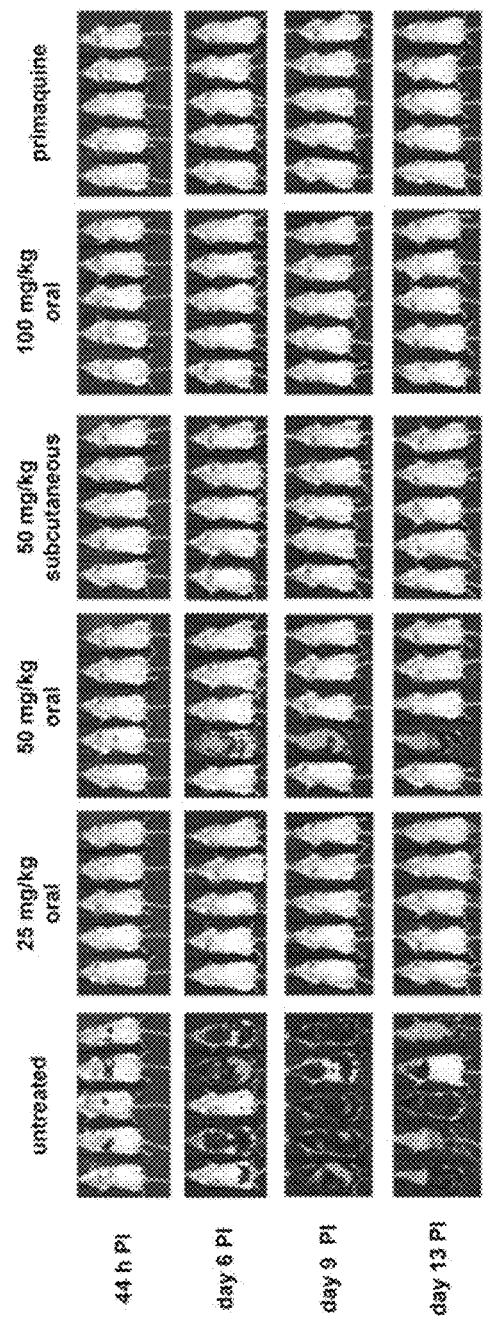
FIGS. 3A-3B show images demonstrating the results from: Whole-animal bioluminescence imaging of mice infected with luciferase-transfected P. berghei sporozoites. Mice were treated with different doses of 8j (FIG. 3A), 8l (Panel FIG. 3B), and primaquine (50 mg/kg, oral). Animals (n=5 per group) received a single dose by gavage 1 hour after inoculation with sporozoites. Representative images taken at 44 h, day 6, day 9, and day 13 after infection are shown. At 44 h, bioluminescent signal was detected in control untreated animals, with the highest intensity noted in the area overlaying the liver, consistent with the presence of liver-stage parasites.
Figure 3B:
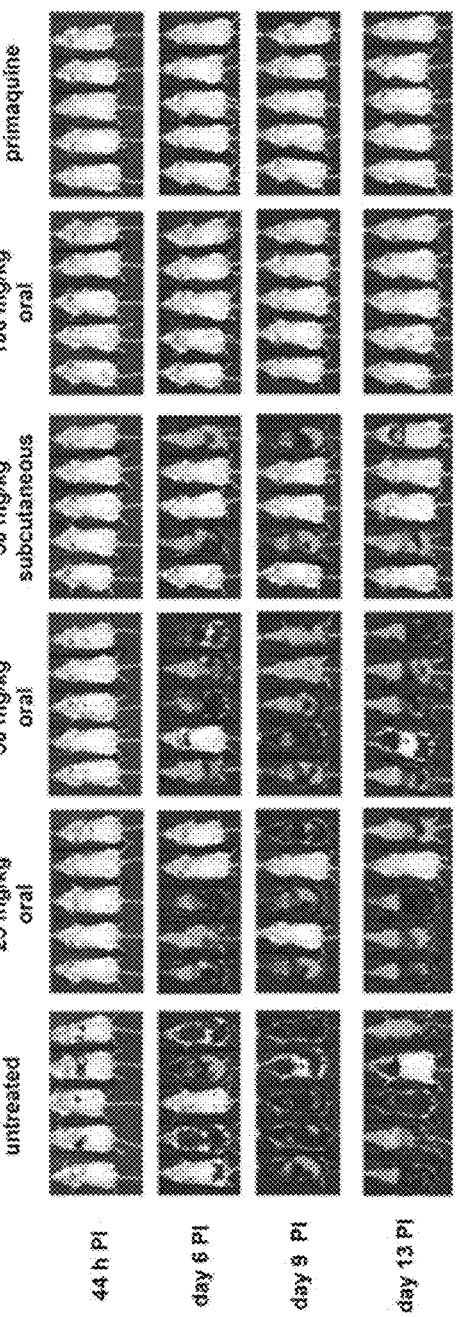
Figure 4A:
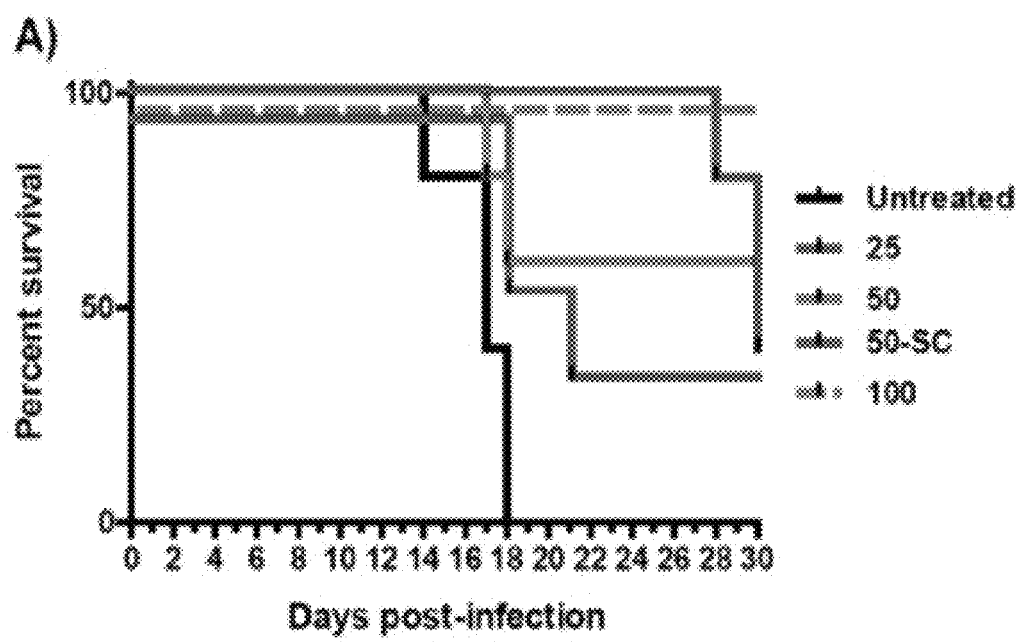
FIGS. 4A-4B show survival Curves for 4(1H)-quinolones 8j (FIG. 4A) and 8l (FIG. 4B) that demonstrate antimalarial activity against liver stages of the parasite. Compounds have been tested oral at 25 mg/kg (25), 50 mg/kg (50), and 100 mg/kg (100) and subcutaneous at 50 mg/kg (50-SC) doses.
Figure 4B:
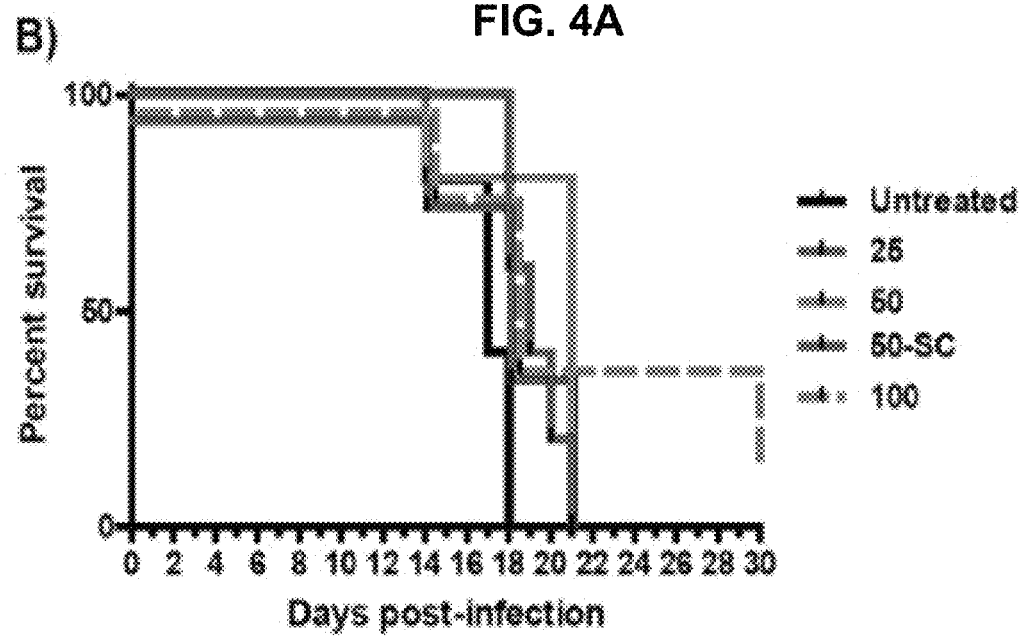

The potent in vitro activity of piperazinyl-substituted 4(1H)-quinolones against liver stages of the parasite prompted a study to determine how in vivo efficacious these compounds are in *P. berghei* sporozoite infected mice. Five animals per group were dosed as previously reported only 1 hour after infection[27] with piperazinyl-substituted 4(1H)-quinolones 8j and 8l. At 44 h PI, day 6 PI, day 9 PI, and day 13 PI, compound efficacy was determined by bioluminescence imaging via injection of D-luciferin. Both compounds were administered orally or subcutaneously at increasing doses of 25 mg/kg, 50 mg/kg, and 100 mg/kg in PEG 400. Of the two piperazinyl-substituted 4(1H)-quinolones, 8j performed significantly better than 8l (FIGS. 3A-3B). With the exception of an infection on days 6, 9, 13 PI of a single mouse, which was orally dosed with 50 mg/kg, no luminescence was observed for 8j at any other doses and time points. In comparison, compound 8l displayed full protection at all time points only at an oral dose of 100 mg/kg. Progression of parasitemia was monitored up to 30 days after infection (Table 8). Differences between the two test 4(1H)-quinolones were more obvious following survival cures (FIGS. 4A-4B) as 8j cured two or more out of five animals. In contrast, one of five animals was cured only at a high dose of 100 mg/kg of 8l. These results with 8j and 8l underscore that piperazinyl-substituted 4(1H)-quinolones have potential as single-dose prophylactic and curative agents.

TABLE 8

In Vivo Efficacy of Compounds 8j and 8l Against Liver Stages of the Parasite

| Compound | Dose (mg/kg) | Route | % Inhibition Day 9 PI[a] | No. of Cures |
|---|---|---|---|---|
| 8j | 25 | oral | 65.3 | 2/5 |
| 8j | 50 | oral | 85.1 | 2/5 |
| 8j | 50 | subcutaneous | >99.0 | 3/5 |
| 8j | 100 | oral | >99.0 | 5/5 |
| 8l | 25 | oral | 49.1 | 0/5 |
| 8l | 50 | oral | 38.8 | 0/5 |
| 8l | 50 | subcutaneous | 20.1 | 0/5 |
| 8l | 100 | oral | 43.9 | 1/5 |
| Primaquine | 50 | oral | >99.0 | 2/5 |

[a]Percent inhibition as compared to untreated control animals

Experimental Section

General.

All reagents and solvents were obtained from Aldrich Chemical Co. and used without further purification. NMR spectra were recorded at ambient temperature on a 400 MHz or 500 MHz Varian NMR spectrometer in the solvent indicated. All $^1$H NMR experiments are reported in δ units, parts per million (ppm) downfield of TMS, and were measured relative to the signals of chloroform (7.26 ppm) and dimethyl sulfoxide (39.5 ppm) with $^1$H decoupled observation. Data for $^1$H NMR are reported as follows: chemicals shift (δ ppm), multiplicity (s=singlet, d=doublet, t=triplet, q=quartet, p=pentet, m=multiplet), integration and coupling constant (Hz) whereas $^{13}$C NMR analyses were reported in terms of chemical shift. NMR data was analyzed by using MestReNova Software version 6.0.2-5475. The purity of the final compounds was determined to be ≥95% by high-performance liquid chromatography (HPLC) using an Agilent 1100 LC/MSD-VL with electrospray ionization. Low-resolution mass spectra were performed on an Agilent 1100 LC/MSD-VL with electrospray ionization. Analytical thin layer chromatography (TLC) was performed on silica gel 60 F254 precoated plates (0.25 mm) from EMD Chemical Inc., and components were visualized by ultraviolet light (254 nm). EMD silica gel 230-400 (particle size 40-63 μm) mesh was used for all flash column chromatography. Microwave heating was performed in a single-mode Anton Paar Monowave 300 and all microwave-irradiated reactions were conducted in heavy-walled glass vials sealed with Teflon septa.

General Procedure A:

A mixture of piperazine (1 eq), 3-nitrobenzyl bromide/3-nitrophenethyl bromide (1.1 eq) and Et$_3$N (1.5 eq) in anhydrous THF was stirred for overnight at RT. The reaction mixture was diluted with water (20 mL) and extracted with EtOAc (3×20 mL). The combined organic extracts were dried over Na$_2$SO$_4$, filtered, and concentrated under reduced pressure. The crude was purified by flash chromatography (90:20→70:30, hexanes/EtOAc) to afford the title compounds.

General Procedure B:

A mixture of nitro compound (1 eq) and SnCl$_2$ (3 eq) in absolute ethanol was refluxed for 3 h. The reaction was neutralized with 4N KOH solution and extracted with EtOAc. The combined organic extracts were dried over Na$_2$SO$_4$, filtered, and concentrated under reduced pressure. The crude was purified by flash chromatography using 100% EtOAc.

General Procedure C:

A neat mixture of aniline/aminobenzyl alcohol (1 eq) and dimethyl 2-(methoxymethylene)malonate (1.05 eq) was heated at 110° C. for 30 min. The reaction mixture was allowed to cool to RT while precipitation arose. Diethyl ether was added to the mixture to improve the precipitation. The solid was filtered off and washed with diethyl ether, dried under vacuum, and used directly for the further transformations.

General Procedure D:

To a solution of alcohol (1 eq) in anhydrous CH$_2$Cl$_2$ was added the Dess-Martin periodinane (1.5 eq) at RT. The resulting mixture was stirred for 3 h at RT. The mixture was treated with aqueous NaHCO$_3$ solution and filtered through a sintered funnel while washing with CH$_2$Cl$_2$. The organic phase was separated, dried over Na$_2$SO$_4$, filtered, and concentrated to give the aldehyde in an almost pure form which was used directly for further transformations.

General Procedure E:

To a mixture of aldehyde (1 eq) and piperazine/piperazine hydrochloride (1.2 eq) in anhydrous THF was added anhydrous MgSO$_4$ (2 eq) followed by N,N-diisopropylethylamine (2.5 eq) at RT, and the resulting solution was stirred vigorously for 30 min. To this was then added sodium triacetoxyborohydride (2 eq). The reaction was stirred for an additional 4 h at RT, quenched with saturated NaHCO$_3$ solution, and extracted with EtOAc. The combined organic fractions were washed with brine, dried over Na$_2$SO$_4$, and concentrated under reduced pressure. The crude was purified by flash chromatography gradient elution (80:20→30:70, hexanes/EtOAc) to afford the title compounds.

General Procedure F:

The enamine in toluene was subjected to microwave heating at 280° C. for 4 min. The reaction mixture was allowed to cool to RT while precipitation arose. Diethyl ether was added to the mixture to improve the precipitation. The solid was filtered off and washed with diethyl ether. The solid containing the unreacted enamine and quinolone regioisomers was then refluxed in methanol (in most of the cases unless it is mentioned otherwise) for 1 h and filtered hot to give the title quinolones in purest form.

General Procedure G:

To a solution of quinolone (1 eq) in anhydrous $CH_2Cl_2$ was added freshly recrystallized NBS/NCS (1.2 eq) at RT, and the resulting mixture was stirred overnight. The reaction was concentrated and the crude was purified by either recrystallization or HPLC.

General Procedure H:

To a stirred solution of diol 10 (12.5 mmol) in anhydrous $CH_2Cl_2$ (50 mL) was added thionyl chloride (2.5 mL, 34.7 mmol) dropwise. The mixture was heated at reflux for 1 h. The reaction was concentrated and the residue was diluted with MeCN (200 mL). To this was then added KI (100 mg, 0.62 mmol) followed by nitroaniline (13 mmol), and the resulting mixture was refluxed for 7 days. The reaction was concentrated and the crude product was used for next reaction without further purification.

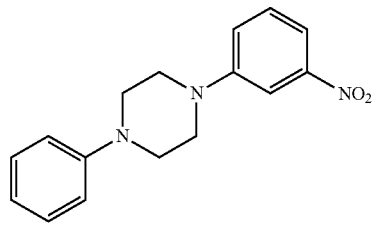

1-(3-nitrophenyl)-4-phenylpiperazine 4a. To a solution of 1-fluoro-3-nitrobenzene (2 g, 14.2 mmol) in DMSO (28.5 mL) was added 1-phenylpiperazine (6.5 mL, 42.5 mmol) and DIPEA (9.9 mL, 56.8 mmol). The reaction was refluxed for 2 days. DI water was added, then extracted with EtOAa 3 times. The organic layer was dried over sodium sulfate, filtered, and concentrated under reduced pressure followed by separation by flash column chromatography to give 4a as a yellow solid in 50% yield. $^1H$ NMR (399 MHz, $(CD_3)_2CO$) δ 7.77 (t, J=2.3 Hz, 1H), 7.63 (ddd, J=7.9, 2.1, 1.0 Hz, 1H), 7.50 (t, J=8.1 Hz, 1H), 7.44 (ddd, J=8.3, 2.5, 0.9 Hz, 1H), 7.29-7.23 (m, 2H), 7.05-7.00 (m, 2H), 6.84 (tt, J=7.4, 1.0 Hz, 1H), 3.49 (dd, J=6.3, 3.9 Hz, 4H), 3.37 (dd, J=6.3, 3.9 Hz, 4H). $^{13}C$ NMR (100 MHz, $(CD_3)_2CO$) δ 153.1, 152.4, 150.5, 131.0, 130.1, 122.4, 120.7, 117.2, 114.2, 110.1, 49.9, 49.2.

1-Benzyl-4-(3-nitrophenyl)piperazine 4b. To a solution of 1-fluoro-3-nitrobenzene (2 g, 14.2 mmol) in DMSO (28.5 mL) was added 1-benzylpiperazine (7.4 mL, 42.5 mmol) and DIPEA (9.9 mL, 56.8 mmol). The reaction was refluxed for 2 days. DI water was added, then extracted with EtOAc 3 times. The organic layer was dried over sodium sulfate, filtered, and concentrated under reduced pressure followed by separation by flash column chromatography to give 4a as a yellow solid in 65% yield. $^1H$ NMR (399 MHz, $(CD_3)_2CO$) δ 7.69 (t, J=2.3 Hz, 1H), 7.59 (ddd, J=8.0, 2.1, 0.8 Hz, 1H), 7.45 (t, J=8.2 Hz, 1H), 7.40-7.31 (m, 5H), 7.29-7.23 (m, 1H), 3.57 (s, 2H), 3.35-3.31 (m, 4H), 2.62-2.58 (m, 4H). $^{13}C$ NMR (100 MHz, $(CD_3)_2CO$) δ 152.4, 149.6, 138.7, 130.1, 129.1, 128.4, 127.2, 121.2, 112.9, 109.0, 62.7, 52.9, 48.3.

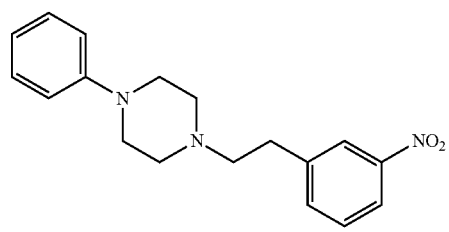 [SMILES: O=[N+]([O-])c1cccc(CCN2CCN(c3ccccc3)CC2)c1]

1-(3-Nitrophenethyl)-4-phenylpiperazine 4ac was obtained as a pale yellow semi-solid (600 mg, 62% yield) by alkylation of 1-phenylpiperazine (500 mg, 3.08 mmol) with 3-nitrophenethyl bromide (780 mg, 3.4 mmol) following general procedure A. $^1H$ NMR (400 MHz, $CDCl_3$): δ 8.16-8.04 (m, 2H), 7.57 (d, J=7.6 Hz, 1H), 7.46 (t, J=7.9 Hz, 1H), 7.33-7.23 (m, 2H), 7.00-6.82 (m, 3H), 3.31-3.17 (m, 4H), 2.96 (t, J=7.8 Hz, 2H), 2.73-2.69 (m, 6H). $^{13}C$ NMR (101 MHz, $CDCl_3$): δ 151.2, 148.3, 142.3, 135.0, 129.2, 129.1 (2C), 123.6, 121.3, 119.8, 116.1 (2C), 59.5, 53.2 (2C), 49.1 (2C), 33.1.

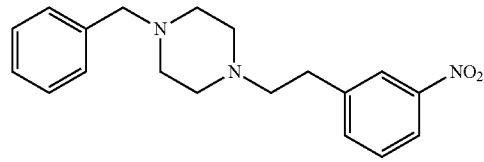 [SMILES: O=[N+]([O-])c1cccc(CCN2CCN(Cc3ccccc3)CC2)c1]

1-benzyl-4-(3-nitrophenethyl)piperazine 4ad was obtained as an orange yellow oil (800 mg, 63% yield) by alkylation of 1-benzylpiperazine (690 mg, 4.0 mmol) with 3-nitrophenethyl bromide (1.0 g, 4.3 mmol) following general procedure A. $^1H$ NMR (400 MHz, $CDCl_3$): δ 8.06 (t, J=2.0 Hz, 1H), 8.03 (ddd, J=8.1, 2.4, 1.1 Hz, 1H), 7.54-7.50 (m, 1H), 7.41 (t, J=7.9 Hz, 1H), 7.32-7.20 (m, 5H), 3.51 (s, 2H), 2.91-2.85 (m, 2H), 2.65-2.59 (m, 2H), 2.59-2.45 (m, 8H). $^{13}C$ NMR (101 MHz, $CDCl_3$): δ 148.3, 142.5, 138.0, 135.0, 129.2 (2C), 129.1, 128.2 (2C), 127.0, 123.6, 121.2, 63.0, 59.6, 53.1 (2C), 53.0 (2C), 33.1.

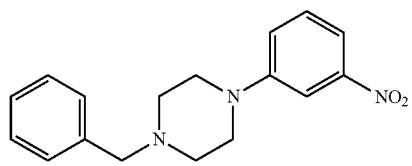

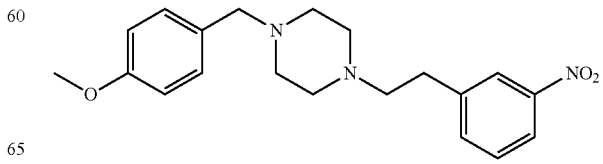

1-(4-methoxybenzyl)-4-(3-nitrophenethyl)piperazine 4ae was obtained as an orange yellow oil (1.3 g, 59% yield) by alkylation of 1-(4-methoxybenzyl)piperazine (1.3 g, 6.3 mmol) with 3-nitrophenethyl bromide (1.5 g, 6.9 mmol) following general procedure A. $^1$H NMR (400 MHz, CDCl$_3$): δ 8.07-7.95 (m, 2H), 7.48 (t, J=8.3, 1H), 7.37 (dd, J=16.5, 8.6, 1H), 7.23-7.15 (m, 2H), 6.86-6.78 (m, 2H), 3.74 (s, 3H), 3.42 (s, 2H), 2.87-2.80 (m, 2H), 2.59 (dd, J=9.0, 6.7, 2H), 2.54-2.40 (m, 8H). $^{13}$C NMR (101 MHz, CDCl$_3$): δ 158.7, 148.2, 142.5, 135.0, 130.3 (2C), 130.0, 129.1, 123.5, 121.1, 113.5 (2C), 62.4, 59.5, 55.2, 53.1 (2C), 52.9 (2C), 33.1.

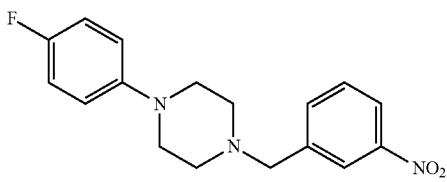

1-(4-Fluorophenyl)-4-(3-nitrobenzyl)piperazine 4aj was obtained as white solid (8.5 g, 97% yield) by alkylation of 1-(4-(trifloromethyl)phenyl)piperazine (5.0 g, 27.7 mmol) with 3-nitrobenzyl bromide (6.6 g, 30.5 mmol) following general procedure A. $^1$H NMR (400 MHz, CDCl$_3$): δ 8.21 (t, J=2.0 Hz, 1H), 8.09 (ddd, J=8.2, 2.4, 1.1 Hz, 1H), 7.68 (dt, J=7.7, 1.3 Hz, 1H), 7.47 (t, J=7.9 Hz, 1H), 6.95-6.89 (m, 2H), 6.87-6.81 (m, 2H), 3.63 (s, 2H), 3.16-3.05 (m, 4H), 2.65-2.56 (m, 4H). $^{13}$C NMR (101 MHz, CDCl$_3$): δ 158.2, 155.8, 148.3, 147.8, 140.5, 134.9, 129.1, 123.6, 122.1, 117.7, 115.5, 115.3, 61.8, 53.0 (2C), 50.0 (2C).

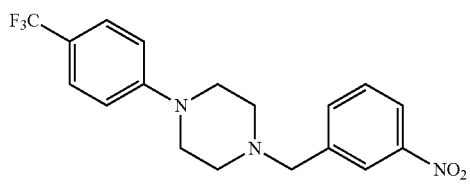 [SMILES: O=[N+]([O-])c1cccc(CN2CCN(c3ccc(C(F)(F)F)cc3)CC2)c1]

1-(3-Nitrobenzyl)-4-(4-(trifluoromethyl)phenyl)piperazine 4ao was obtained as a pale yellow solid (3.7 g, 90% yield) by alkylation of 1-(4-(trifluoromethyl)phenyl)piperazine (3 g, 13.0 mmol) with 3-nitrobenzyl bromide (2.2 g, 14.3 mmol) following general procedure A. $^1$H NMR (399 MHz, CDCl$_3$) δ 8.25 (s, 1H), 8.12 (d, J=8.2 Hz, 1H), 7.72 (d, J=7.6 Hz, 1H), 7.51 (d, J=7.9 Hz, 1H), 7.47 (d, J=8.7 Hz, 2H), 6.91 (d, J=8.7 Hz, 2H), 3.65 (s, 2H), 3.34-3.26 (m, 4H), 2.69-2.55 (m, 4H). $^{13}$C NMR (100 MHz, CDCl$_3$) δ 153.3, 148.5, 140.5, 135.1, 129.3, 126.4 (dd, J=7.4, 3.7 Hz), 124.9 (d, J=270.5 Hz), 123.7, 122.4, 120.4 (d, J=32.7 Hz), 114.6, 62.0, 52.8, 48.0.

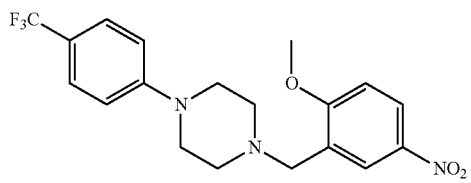 [SMILES: COc1ccc([N+](=O)[O-])cc1CN1CCN(c2ccc(C(F)(F)F)cc2)CC1]

1-(2-Methoxy-5-nitrobenzyl)-4-(4-(trifluoromethyl)phenyl)piperazine 4as was obtained as a white solid (1.4 g, 90% yield) by alkylation of 1-(4-(trifluoromethyl)phenyl)piperazine (850 mg, 3.7 mmol) with 2-(bromomethyl)-1-methoxy-4-nitrobenzene (1 g, 4.1 mmol) following general procedure A. $^1$H NMR (500 MHz, CDCl$_3$) δ 8.37 (d, J=2.8 Hz, 1H), 8.19 (dd, J=9.0, 2.8 Hz, 1H), 7.49 (d, J=8.8 Hz, 2H), 6.95 (t, J=8.1 Hz, 3H), 3.97 (s, 3H), 3.65 (s, 2H), 3.38-3.29 (m, 4H), 2.73-2.65 (m, 4H). $^{13}$C NMR (126 MHz, CDCl$_3$) δ 162.7, 153.4, 141.5, 127.7, 126.4 (q, J=3.9 Hz), 125.6, 124.9 (d, J=270.9 Hz), 124.6, 120.4 (d, J=32.7 Hz), 114.6, 110.1, 56.23, 55.5, 53.0, 48.1.

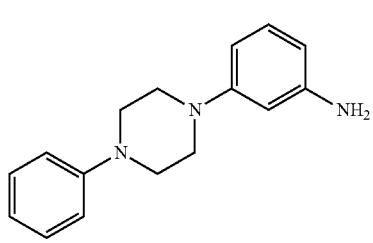 [SMILES: Nc1cccc(N2CCN(c3ccccc3)CC2)c1]

3-(4-Phenylpiperazin-1-yl)aniline 5a. A nitro reduction reaction of 4a (178 mg, 0.63 mmol) following general procedure B resulted in 5a, isolated as a crude orange solid which was used in the next step without further purification.

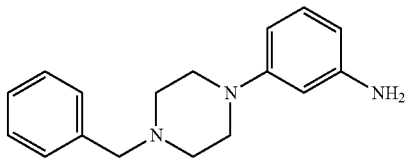 [SMILES: Nc1cccc(N2CCN(Cc3ccccc3)CC2)c1]

3-(4-Benzylpiperazin-1-yl)aniline 5b. A nitro reduction reaction of 4b (658 mg, 2.21 mmol) following general procedure B resulted in 5b, isolated as a crude orange solid which was used in the next step without further purification.

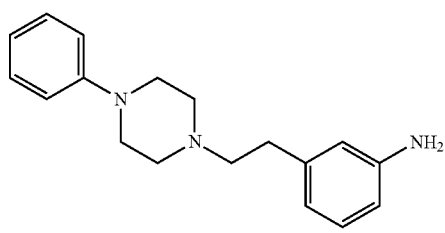 [SMILES: Nc1cccc(CCN2CCN(c3ccccc3)CC2)c1]

3-(2-(4-phenylpiperazin-1-yl)ethyl)aniline 5ac. A nitro reduction reaction of 4ac (500 mg, 1.6 mmol) following general procedure B resulted in 5ac as orange yellow semi-solid (450 mg, 99% yield). $^1$H NMR (400 MHz, CDCl$_3$): δ 7.30-7.24 (m, 2H), 7.08 (t, J=7.7 Hz, 1H), 6.97-6.92 (m, 2H), 6.88-6.84 (m, 1H), 6.63 (dt, J=7.6, 1.2 Hz, 1H), 6.56-6.52 (m, 2H), 3.60 (bs, 2H), 3.26-3.22 (m, 4H), 2.79-2.74 (m, 2H), 2.71-2.62 (m, 6H). $^{13}$C NMR (101 MHz, CDCl$_3$): δ 151.3, 146.4, 141.4, 129.3, 129.1 (2C), 119.7, 119.0, 116.0, 115.4 (2C), 112.9, 60.4, 53.2 (2C), 49.1 (2C), 33.6.

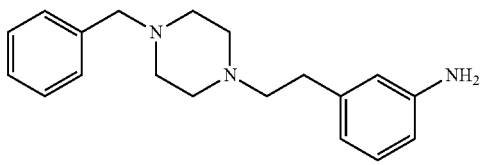

3-(2-(4-benzylpiperazin-1-yl)ethyl)aniline 5ad. A nitro reduction reaction of 4ad (700 mg, 2.1 mmol) following general procedure B resulted in 5ad as yellow oil (550 mg, 86% yield). $^1$H NMR (400 MHz, CDCl$_3$): δ 7.32-7.29 (m, 4H), 7.28-7.20 (m, 1H), 7.04 (td, J=7.3, 1.4 Hz, 1H), 6.58 (dt, J=7.3, 1.3 Hz, 1H), 6.50 (dd, J=7.1, 1.1 Hz, 2H), 3.91 (bs, 2H), 3.52 (s, 2H), 2.76-2.66 (m, 2H), 2.57 (ddd, J=23.4, 12.1, 4.9 Hz, 1OH). $^{13}$C NMR (101 MHz, CDCl$_3$): δ 146.4, 141.3, 137.8, 129.2, 129.2 (2C), 128.1 (2C), 127.0, 118.9, 115.4, 112.9, 62.9, 60.2, 52.9 (2C), 52.7 (2C), 33.3.

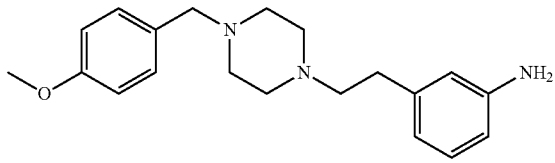 [SMILES: COc1ccc(CN2CCN(CCc3cccc(N)c3)CC2)cc1]

3-(2-(4-(4-methoxybenzyl)piperazin-1-yl)ethyl)aniline 5ae. A nitro reduction reaction of 4ae (1.0 g, 3.0 mmol) following general procedure B resulted in 5ae as orange yellow semi-solid (820 mg, 90% yield). $^1$H NMR (400 MHz, CDCl$_3$): δ 7.20 (t, J=8.4 Hz, 2H), 7.03 (t, J=7.7 Hz, 1H), 6.83 (dd, J=8.4, 5.8 Hz, 2H), 6.57 (d, J=7.6 Hz, 1H), 6.49 (d, J=7.0 Hz, 2H), 3.77 (s, 3H), 3.43 (s, 2H), 2.69 (dd, J=10.6, 5.7 Hz, 2H), 2.64-2.39 (m, 10H). $^{13}$C NMR (101 MHz, CDCl$_3$): δ 158.6, 146.4, 141.4, 130.3 (2C), 129.9, 129.2, 118.8, 115.3, 113.5 (2C), 112.8, 62.3, 60.3, 55.1, 53.0 (2C), 52.8 (2C), 33.5.

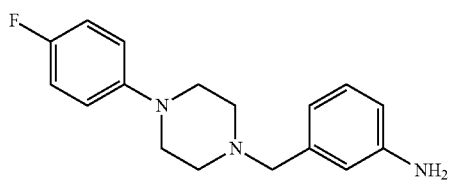 [SMILES: Nc1cccc(CN2CCN(c3ccc(F)cc3)CC2)c1]

3-((4-(4-Fluorophenyl)piperazin-1-yl)methyl)aniline 5aj. A nitro reduction reaction of 4aj (8.4 g, 26.6 mmol) following general procedure B resulted in 5aj as pale yellow solid (7.3 g, 96% yield). $^1$H NMR (400 MHz, methanol-d$_4$): δ 7.04 (t, J=7.7 Hz, 1H), 6.92-6.82 (m, 4H), 6.68 (t, J=2.0 Hz, 1H), 6.65 (dt, J=7.5, 1.3 Hz, 1H), 6.60 (ddd, J=8.0, 2.3, 1.0 Hz, 1H), 3.40 (s, 2H), 3.06-3.01 (m, 4H), 2.58-2.52 (m, 4H). $^{13}$C NMR (101 MHz, methanol-d$_4$) δ 159.5, 157.1, 148.9, 148.2, 138.7, 129.9, 120.4, 118.9, 117.4, 116.2, 116.0, 115.4, 63.9, 53.8 (2C), 50.7 (2C).

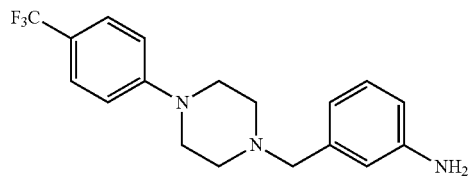 [SMILES: Nc1cccc(CN2CCN(c3ccc(C(F)(F)F)cc3)CC2)c1]

3-((4-(4-(Trifluoromethyl)phenyl)piperazin-1-yl)methyl)aniline 5ap. A nitro reduction reaction of 4ap (2.8 g, 7.55 mmol) following method B resulted in 5ap as a pale orange solid (2.4 g, 94% yield). $^1$H NMR (399 MHz, CDCl$_3$) δ 7.48 (d, J=8.7 Hz, 2H), 7.13 (t, J=7.7 Hz, 1H), 6.92 (d, J=8.7 Hz, 2H), 6.79-6.70 (m, 2H), 6.66-6.57 (m, 1H), 3.66 (bs, 2H), 3.49 (s, 2H), 3.35-3.22 (m, 4H), 2.70-2.56 (m, 4H). $^{13}$C NMR (100 MHz, CDCl$_3$) δ 153.4, 146.6, 139.1, 129.3, 126.4 (q, J=3.6 Hz), 124.9 (d, J=270.6 Hz), 120.3 (d, J=32.5 Hz), 119.6, 115.8, 114.5, 114.2, 63.1, 52.9, 48.0.

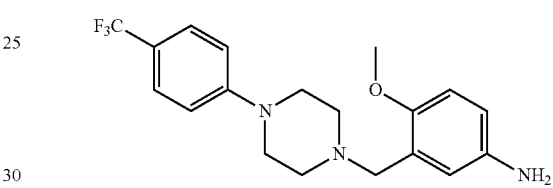

4-Methoxy-3-((4-(4-(trifluoromethyl)phenyl)piperazin-1-yl)methyl)aniline 5as. A nitro reduction reaction of 4as (1.5 g, 3.79 mmol) following method B resulted in 5as, isolated as a crude orange solid which was used in the next step without further purification.

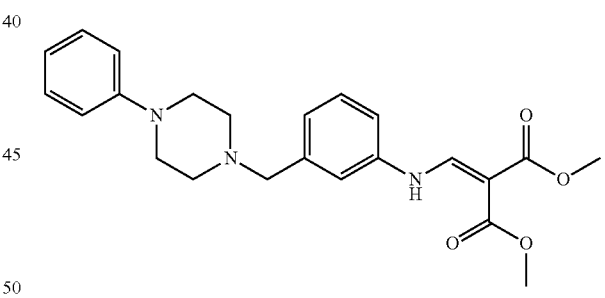

Dimethyl 2-(((3-((4-phenylpiperazin-1-yl)methyl)phenyl)amino)methylene)malonate 7j. A direct reductive amination (DRA) reaction between aldehyde 13a (1.0 g, 3.8 mmol) and 1-phenylpiperazine (740 mg, 4.6 mmol) following general procedure E afforded 7j as brown yellow semi-solid (1.1 g, 72% yield). $^1$H NMR (400 MHz, CDCl$_3$): δ 11.02 (d, J=13.6 Hz, 1H), 8.52 (dd, J=13.7, 2.1 Hz, 1H), 7.31-6.96 (m, 6H), 6.90-6.75 (m, 3H), 3.79 (d, J=2.5 Hz, 3H), 3.73 (d, J=2.2 Hz, 3H), 3.51 (d, J=2.8 Hz, 2H), 3.16 (t, J=4.9 Hz, 4H), 2.57 (t, J=5.0 Hz, 4H). $^{13}$C NMR (101 MHz, CDCl$_3$): δ 169.0, 165.6, 151.9, 150.9, 139.8, 138.9, 129.4, 128.8 (2C), 125.5, 119.4, 117.6, 115.7 (2C), 115.6, 92.6, 62.3, 52.8 (2C), 513, 51.2, 48.7 (2C).

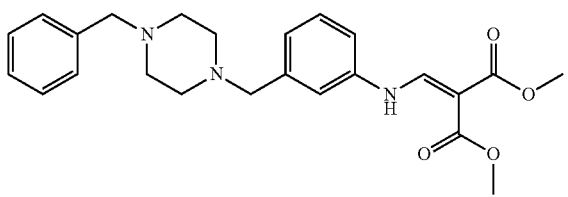 [SMILES: COC(=O)C(=CNc1cccc(CN2CCN(Cc3ccccc3)CC2)c1)C(=O)OC]

Dimethyl 2-(((3-((4-benzylpiperazin-1-yl)methyl)phenyl)amino)methylene)malonate 7k. A direct reductive amination (DRA) reaction between aldehyde 13a (500 mg, 1.9 mmol) and 1-benzylpiperazine (400 mg, 2.3 mmol) following general procedure E afforded 7k as yellow oil (600 mg, 75% yield). $^1$H NMR (400 MHz, CDCl$_3$): δ 11.00 (d, J=13.8 Hz, 1H), 8.52 (dd, J=13.8, 1.2 Hz, 1H), 7.30-7.24 (m, 5H), 7.20 (ddt, J=5.9, 4.8, 2.4 Hz, 1H), 7.11 (t, J=1.8 Hz, 1H), 7.06 (dt, J=7.6, 1.2 Hz, 1H), 7.02-6.98 (m, 1H), 3.83 (d, J=1.4 Hz, 3H), 3.76 (d, J=1.3 Hz, 3H), 3.49 (d, J=1.2 Hz, 2H), 3.46 (s, 2H), 2.55-2.36 (m, 8H). $^{13}$C NMR (101 MHz, CDCl$_3$): δ 169.2, 165.9, 152.2, 140.5, 139.0, 137.9, 129.5, 129.1 (2C), 128.1 (2C), 126.9, 125.7, 117.8, 115.6, 92.6, 62.9, 62.5, 53.0 (2C), 52.9 (2C), 51.5, 51.4.

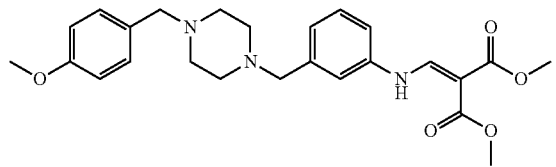

Dimethyl 2-(((3-((4-(4-methoxybenzyl)piperazin-1-yl)methyl)phenyl)amino)methylene)malonate 7l. A DRA reaction between aldehyde 13k (1.0 g, 3.8 mmol) and 1-(4-methoxybenzyl)piperazine (940 mg, 4.6 mmol) following general procedure E afforded 7l as yellow oil (1.2 g, 70% yield). $^1$H NMR (400 MHz, CDCl$_3$): δ 10.99 (d, J=13.8 Hz, 1H), 8.51 (d, J=13.8 Hz, 1H), 7.27-7.23 (m, 1H), 7.19-7.15 (m, 2H), 7.10 (t, J=1.9 Hz, 1H), 7.05 (dt, J=7.6, 1.2 Hz, 1H), 6.99 (ddd, J=8.1, 2.5, 1.0 Hz, 1H), 6.82-6.78 (m, 2H), 3.81 (s, 3H), 3.74 (s, 3H), 3.74 (s, 3H), 3.45 (s, 2H), 3.41 (s, 2H), 2.43 (s, 8H). $^{13}$C NMR (101 MHz, CDCl$_3$): δ 169.2, 165.9, 158.6, 152.1, 140.5, 139.0, 130.3 (2C), 129.8, 129.5, 125.7, 117.7, 115.6, 113.4 (2C), 92.6, 62.5, 62.3, 55.1, 53.0 (2C), 52.7 (2C), 51.5, 51.3.

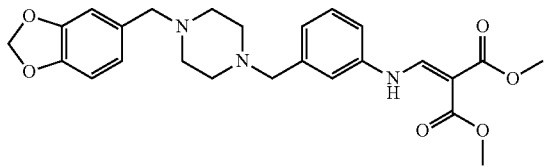 [SMILES: COC(=O)C(=CNc1cccc(CN2CCN(Cc3ccc4c(c3)OCO4)CC2)c1)C(=O)OC]

Dimethyl 2-(((3-((4-(benzo[d][1,3]dioxol-5-ylmethyl)piperazin-1-yl)methyl)phenyl)amino)methylene)malonate 7m. A DRA reaction between aldehyde 13a (500 mg, 1.9 mmol) and 1-piperonylpiperazine (500 mg, 2.3 mmol) following general procedure E afforded 7m as yellow oil (600 mg, 67% yield). $^1$H NMR (400 MHz, CDCl$_3$): δ 11.01 (d, J=13.7 Hz, 1H), 8.53 (d, J=13.9 Hz, 1H), 7.32-7.23 (m, 1H), 7.12 (t, J=1.9 Hz, 1H), 7.07 (dt, J=7.7, 1.1 Hz, 1H), 7.01 (ddd, J=8.0, 2.5, 0.9 Hz, 1H), 6.82 (d, J=1.1 Hz, 1H), 6.75-6.68 (m, 2H), 5.90 (d, J=0.6 Hz, 2H), 3.83 (d, J=0.6 Hz, 4H), 3.76 (d, J=0.5 Hz, 3H), 3.48 (s, 2H), 3.41 (s, 2H), 2.46 (s, 8H). $^{13}$C NMR (101 MHz, CDCl$_3$): δ 169.3, 166.0, 152.2, 147.5, 146.5, 140.5, 139.1, 131.7, 129.6, 125.8, 122.2, 117.8, 115.7, 109.5, 107.8, 100.8, 92.7, 62.6, 62.6, 53.0 (2C), 52.8 (2C), 51.5, 51.4.

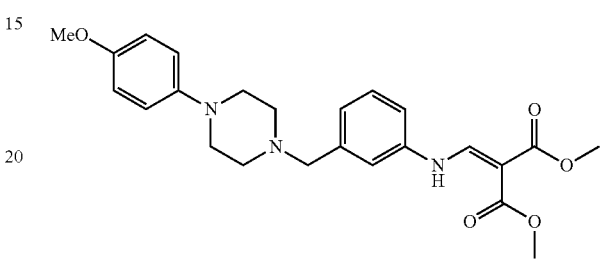

Dimethyl 2-(((3-((4-(4-methoxyphenyl)piperazin-1-yl)methyl)phenyl)amino)methylene)malonate 7n. A DRA reaction between aldehyde 13a (500 mg, 1.9 mmol) and 1-(4-methoxyphenyl)piperazine hydrochloride (604 mg, 2.3 mmol) following general procedure E afforded 7n as pale yellow semi-solid (565 mg, 68% yield). $^1$H NMR (400 MHz, CDCl$_3$): δ 11.03 (d, J=13.8 Hz, 1H), 8.54 (d, J=13.8 Hz, 1H), 7.30 (t, J=7.8 Hz, 1H), 7.16 (t, J=1.9 Hz, 1H), 7.11 (dt, J=7.6, 1.2 Hz, 1H), 7.05-7.01 (m, 1H), 6.89-6.84 (m, 2H), 6.82-6.78 (m, 2H), 3.83 (s, 3H), 3.76 (s, 3H), 3.73 (s, 3H), 3.53 (s, 2H), 3.10-3.05 (m, 4H), 2.59 (dd, J=6.0, 3.8 Hz, 4H). $^{13}$C NMR (101 MHz, CDCl$_3$): δ 169.3, 166.0, 153.7, 152.2, 145.6, 140.4, 139.1, 129.6, 125.8, 118.2 (2C), 117.9, 115.8, 114.3 (2C), 92.7, 62.6, 55.5, 53.2 (2C), 51.5, 51.4, 50.5 (2C).

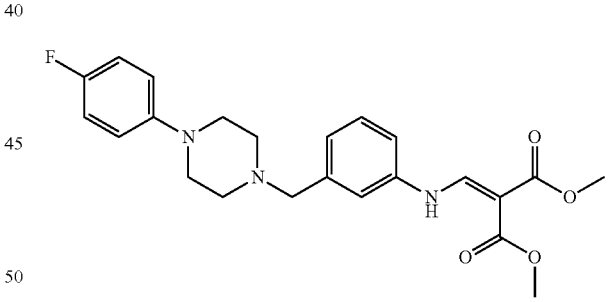

Dimethyl 2-(((3-((4-(4-fluorophenyl)piperazin-1-yl)methyl)phenyl)amino)methylene)malonate 7o. A direct reductive amination (DRA) reaction between aldehyde 13a (500 mg, 1.9 mmol) and 1-(4-florophenyl)piperazine (410 mg, 2.3 mmol) following general procedure E afforded 7o as pale yellow semi-solid (580 mg, 72%). $^1$H NMR (400 MHz, CDCl$_3$): δ 11.04 (d, J=13.6 Hz, 1H), 8.54 (dd, J=13.9, 3.6 Hz, 1H), 7.30 (td, J=7.8, 3.5 Hz, 1H), 7.16 (s, 1H), 7.12 (d, J=7.5 Hz, 1H), 7.06-7.01 (m, 1H), 6.92 (td, J=8.6, 3.5 Hz, 2H), 6.84 (dt, J=9.0, 4.3 Hz, 2H), 3.83 (d, J=3.2 Hz, 3H), 3.76 (d, J=3.2 Hz, 3H), 3.53 (bs, 2H), 3.11-3.08 (m, Hz, 4H), 2.60-2.58 (m, 4H). $^{13}$C NMR (101 MHz, CDCl$_3$) δ 169.2, 165.9, 158.2, 155.8, 152.1, 147.8, 140.3, 139.1, 129.6, 125.6, 117.7, 117.6, 115.7, 115.4, 115.2, 92.7, 62.4, 53.0 (2C), 51.4, 51.3, 50.0 (2C).

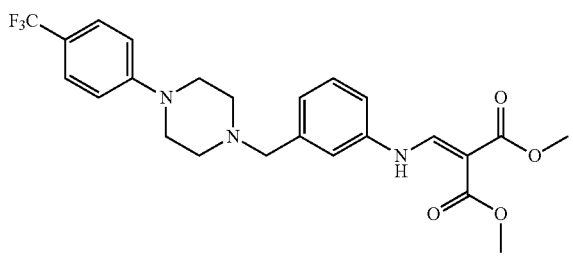 [SMILES: COC(=O)C(=CNc1cccc(CN2CCN(c3ccc(C(F)(F)F)cc3)CC2)c1)C(=O)OC]

Dimethyl 2-(((3-((4-(4-(trifluoromethyl)phenyl)piperazin-1-yl)methyl)phenyl)amino)methylene)malonate 7p. A direct reductive amination (DRA) reaction between aldehyde 13a (500 mg, 1.9 mmol) and 1-(4-trifloromethylphenyl)piperazine (840 mg, 2.3 mmol) following general procedure E afforded 7p as pale yellow semi-solid (980 mg, 68% yield). $^1$H NMR (400 MHz, CDCl$_3$): δ 11.03 (d, J=13.8 Hz, 1H), 8.53 (dd, J=13.8, 1.0 Hz, 1H), 7.41 (d, J=8.7 Hz, 2H), 7.28 (t, J=7.8 Hz, 1H), 7.14 (t, J=1.8 Hz, 1H), 7.09 (dd, J=7.7, 1.3 Hz, 1H), 7.04-7.00 (m, 1H), 6.85 (d, J=8.6 Hz, 2H), 3.81 (s, 3H), 3.74 (s, 3H), 3.50 (s, 2H), 3.23 (t, J=5.1 Hz, 4H), 2.54 (dd, J=6.1, 3.9 Hz, 4H). $^{13}$C NMR (101 MHz, CDCl$_3$) δ 169.1, 165.8, 153.1, 152.0, 140.1, 139.1, 129.6, 126.2, 126.2, 126.1, 126.1, 125.6, 117.6, 115.7, 114.3 (2C), 92.7, 62.4, 52.6 (2C), 51.4, 51.3, 47.7 (2C).

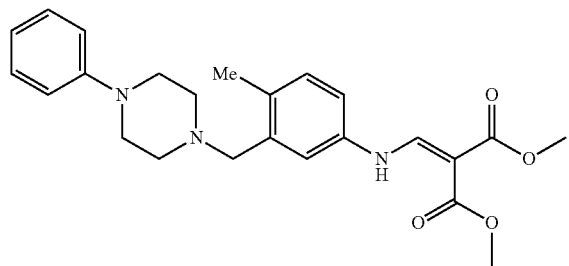 [SMILES: COC(=O)C(=CNc1ccc(C)c(CN2CCN(c3ccccc3)CC2)c1)C(=O)OC]

Dimethyl 2-(((4-methyl-3-((4-phenylpiperazin-1-yl)methyl)phenyl)amino)methylene)malonate 7q. A DRA reaction between aldehyde 13b (600 mg, 2.2 mmol) and 1-phenylpiperazine (430 mg, 2.6 mmol) following general procedure E afforded 7q as white semi solid (700 mg, 77%). $^1$H NMR (400 MHz, CDCl$_3$): δ 11.02 (1H), 8.52 (d, J=13.9 Hz, 1H), 7.23-7.20 (m, 2H), 7.15-7.12 (m, 2H), 6.95 (d, J=8.2 Hz, 2H), 6.91-6.88 (dd, J=8.8, 1.1 Hz, 2H), 6.84-6.80 (m, 1H), 3.83 (s, 3H), 3.75 (s, 3H), 3.47 (s, 2H), 3.19-3.13 (m, 4H), 2.62-2.55 (m, 4H), 2.32 (s, 3H). $^{13}$C NMR (101 MHz, CDCl$_3$) δ 169.2, 165.9, 152.2, 151.1, 138.0, 136.7, 134.1, 131.3, 128.9 (2C), 119.4, 118.5, 115.8 (2C), 115.3, 92.0, 60.2, 53.0 (2C), 51.3, 51.2, 49.0 (2C), 18.6.

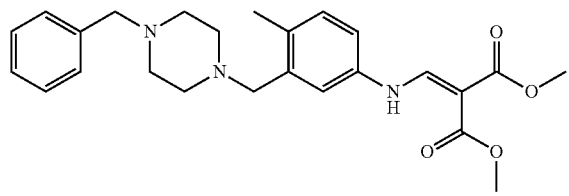 [SMILES: COC(=O)C(=CNc1ccc(C)c(CN2CCN(Cc3ccccc3)CC2)c1)C(=O)OC]

Dimethyl 2-(((3-((4-benzylpiperazin-1-yl)methyl)-4-methylphenyl)amino)methylene)malonate 7r. A DRA reaction between aldehyde 13b (650 mg, 2.3 mmol) and 1-benzylpiperazine (500 mg, 2.8 mmol) following general procedure E afforded 7r as pale yellow semi solid (630 mg, 63%). $^1$H NMR (400 MHz, CDCl$_3$): δ 10.98 (d, J=13.8 Hz, 1H), 8.50 (dd, J=13.9, 0.9 Hz, 1H), 7.32-7.20 (m, 5H), 7.13-7.07 (m, 2H), 6.92 (dd, J=8.1, 2.5 Hz, 1H), 3.83 (s, 3H), 3.76 (s, 3H), 3.50 (s, 2H), 3.41 (s, 2H), 2.47 (m, 8H), 2.28 (s, 3H). $^{13}$C NMR (101 MHz, CDCl$_3$): δ 169.3, 166.0, 152.3, 138.4, 137.9, 136.7, 134.1, 131.3, 129.1 (2C), 128.1 (2C), 126.9, 118.5, 115.2, 92.0, 62.9, 60.1, 53.1 (2C), 53.0 (2C), 51.4, 51.3, 18.5.

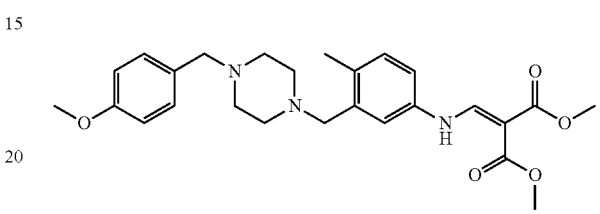

Dimethyl 2-(((3-((4-(4-methoxybenzyl)piperazin-1-yl)methyl)-4-methylphenyl)amino)methylene)malonate 7s. A DRA reaction between aldehyde 13b (200 mg, 1.4 mmol) and 1-(4-methoxybenzyl)piperazine (350 mg, 1.7 mmol) following general procedure E afforded 7s as pale yellow semi-solid (430 mg, 70%). $^1$H NMR (400 MHz, CDCl$_3$): δ 10.95 (d, J=13.9 Hz, 1H), 8.46 (d, J=13.9 Hz, 1H), 7.19-7.12 (m, 2H), 7.07-7.01 (m, 2H), 6.87 (dd, J=8.1, 2.5 Hz, 1H), 6.79-6.75 (m, 2H), 3.78 (s, 3H), 3.71 (s, 3H), 3.70 (s, 3H), 3.38 (s, 2H), 3.36 (s, 2H), 2.40 (s, 8H), 2.23 (s, 3H). $^{13}$C NMR (101 MHz, CDCl$_3$): δ 169.1, 165.8, 158.4, 152.1, 138.3, 136.6, 133.9, 131.1, 130.0 (2C), 129.8, 118.3, 115.0, 113.2 (2C), 91.9, 62.1, 59.9, 54.9, 53.0 (2C), 52.7 (2C), 51.2, 51.1, 18.4.

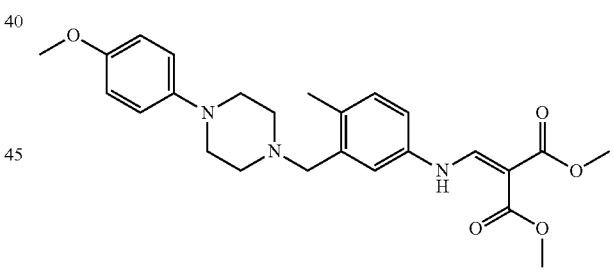

Dimethyl 2-(((3-((4-(4-methoxyphenyl)piperazin-1-yl)methyl)-4-methylphenyl)amino)methylene)malonate 7t. A DRA reaction between aldehyde 13b (600 mg, 2.16 mmol) and 1-(4-methoxyphenyl)piperazine hydrochloride (690 mg, 2.6 mmol) following general procedure E afforded 7t as pale yellow semi-solid (685 mg, 70%). $^1$H NMR (400 MHz, CDCl$_3$): δ 11.00 (d, J=13.9 Hz, 1H), 8.52 (d, J=13.9 Hz, 1H), 7.15-7.11 (m, 2H), 6.95 (dd, J=8.2, 2.5 Hz, 1H), 6.90-6.85 (m, 2H), 6.83-6.78 (m, 2H), 3.83 (s, 3H), 3.75 (s, 3H), 3.73 (s, 3H), 3.48 (s, 2H), 3.09-3.05 (m, 4H), 2.60 (dd, J=6.1, 3.7 Hz, 4H), 2.32 (s, 3H). $^{13}$C NMR (101 MHz, CDCl$_3$): δ 169.4, 166.1, 153.7, 152.4, 145.7, 138.3, 136.8, 134.3, 131.5, 118.7, 118.1 (2C), 115.4, 114.4 (2C), 92.2, 60.3, 55.5, 53.3 (2C), 51.5, 51.4, 50.7 (2C), 18.7.

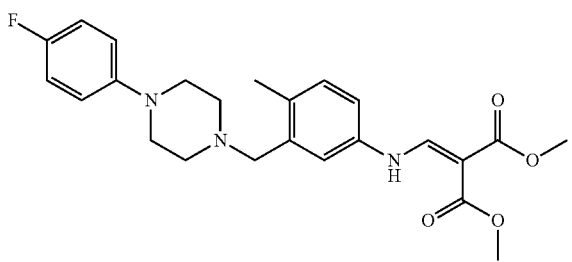 [SMILES: COC(=O)C(=CNc1ccc(C)c(CN2CCN(c3ccc(F)cc3)CC2)c1)C(=O)OC]

Dimethyl 2-(((3-((4-(4-fluorophenyl)piperazin-1-yl)methyl)-4-methylphenyl)amino)methylene)malonate 7u. A DRA reaction between aldehyde 13b (600 mg, 2.16 mmol) and 1-(4-florophenyl)piperazine (470 mg, 2.6 mmol) following general procedure E afforded 7u as yellow semi-solid (800 mg, 84% yield). $^1$H NMR (400 MHz, CDCl$_3$): δ 11.00 (d, J=13.9 Hz, 1H), 8.49-8.42 (m, 1H), 7.46-7.39 (m, 2H), 7.22 (d, J=2.9 Hz, 1H), 7.00 (dd, J=8.8, 2.9 Hz, 1H), 6.89-6.82 (m, 3H), 3.81 (s, 3H), 3.79 (s, 3H), 3.73 (s, 3H), 3.57 (s, 2H), 3.27 (t, J=5.0 Hz, 4H), 2.61 (t, J=5.0 Hz, 4H). $^{13}$C NMR (101 MHz, CDCl$_3$) δ 169.4, 166.1, 158.3, 155.9, 152.4, 148.0, 138.1, 136.9, 134.3, 131.5, 118.7, 117.8, 117.7, 115.6, 115.5, 115.3, 92.2, 60.3, 53.2 (2C), 51.5, 51.4, 50.2 (2C), 18.7.

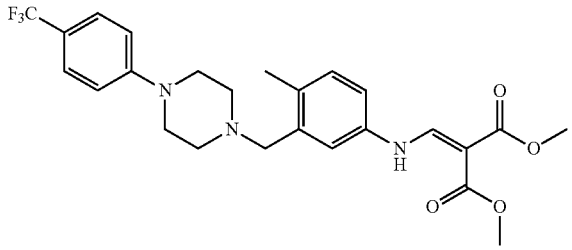 [SMILES: COC(=O)C(=CNc1ccc(C)c(CN2CCN(c3ccc(C(F)(F)F)cc3)CC2)c1)C(=O)OC]

Dimethyl 2-(((4-methyl-3-((4-(4-(trifluoromethyl)phenyl)piperazin-1-yl)methyl)phenyl)amino)methylene)malonate 7v. A DRA reaction between aldehyde 13b (1.0 g, 3.6 mmol) and 1-(4-trifloromethylphenyl)piperazine (1.0 g, 4.4 mmol) following general procedure E afforded 7v as pale yellow semi-solid (1.17 g, 66% yield). $^1$H NMR (400 MHz, CDCl$_3$): δ 10.98 (d, J=13.8 Hz, 1H), 8.47 (d, J=13.9 Hz, 1H), 7.37 (d, J=8.6 Hz, 2H), 7.09-7.05 (m, 2H), 6.89 (dd, J=8.2, 2.5 Hz, 1H), 6.80 (d, J=8.6 Hz, 2H), 3.76 (s, 3H), 3.70 (s, 3H), 3.40 (s, 2H), 3.17 (dd, J=6.2, 3.7 Hz, 4H), 2.51 (t, J=5.0 Hz, 4H), 2.26 (s, 3H). $^{13}$C NMR (101 MHz, CDCl$_3$): δ 169.0, 165.7, 153.0, 151.9, 137.7, 136.6, 134.0, 131.2, 126.0, 126.0, 125.9, 125.9, 118.3, 115.2, 114.0 (2C), 92.0, 59.9, 52.5 (2C), 51.1, 51.0, 47.6 (2C), 18.3.

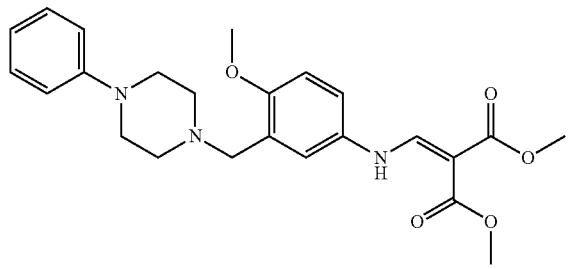 [SMILES: COC(=O)C(=CNc1ccc(OC)c(CN2CCN(c3ccccc3)CC2)c1)C(=O)OC]

Dimethyl 2-(((4-methoxy-3-((4-phenylpiperazin-1-yl)methyl)phenyl)amino)methylene)malonate 7w. A DRA reaction between aldehyde 13c (300 mg, 1.0 mmol) and 1-phenylpiperazine (200 mg, 1.22 mmol) following general procedure E afforded 7w as pale yellow semi-solid (305 mg, 68% yield). $^1$H NMR (400 MHz, CDCl$_3$): δ 11.00 (d, J=13.9 Hz, 1H), 8.46 (d, J=14.0 Hz, 1H), 7.27-7.18 (m, 3H), 7.01 (dd, J=8.7, 2.9 Hz, 1H), 6.94-6.88 (m, 2H), 6.85-6.78 (m, 2H), 3.82 (s, 3H), 3.80 (s, 3H), 3.74 (s, 3H), 3.58 (s, 2H), 3.22-3.19 (m, 4H), 2.66-2.62 (m, 4H). $^{13}$C NMR (101 MHz, CDCl$_3$): δ 169.5, 166.1, 155.4, 152.9, 151.3, 132.4, 129.0 (2C), 128.0, 119.8, 119.5, 116.7, 116.0 (2C), 111.4, 91.65, 55.8, 55.6, 53.1 (2C), 51.4, 51.3, 49.1 (2C).

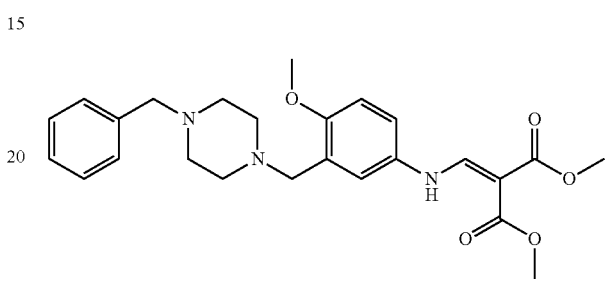

Dimethyl 2-(((3-((4-benzylpiperazin-1-yl)methyl)-4-methoxyphenyl)amino)methylene)malonate 7x. A DRA reaction between aldehyde 13c (500 mg, 1.7 mmol) and 1-benzylpiperazine (360 mg, 2.0 mmol) following general procedure E afforded 7x as pale yellow semi-solid (500 mg, 65% yield). $^1$H NMR (400 MHz, CDCl$_3$): δ 10.97 (d, J=14.0 Hz, 1H), 8.44 (d, J=13.9 Hz, 1H), 7.30-7.26 (m, J=2.6 Hz, 4H), 7.23-7.18 (m, 2H), 6.97 (dd, J=8.7, 2.9 Hz, 1H), 6.80 (d, J=8.7 Hz, 1H), 3.83 (s, 3H), 3.77 (s, 3H), 3.75 (s, 3H), 3.52 (s, 2H), 3.49 (s, 2H), 2.50 (m, 8H). $^{13}$C NMR (101 MHz, CDCl$_3$): δ 169.5, 166.1, 155.4, 152.9, 138.0, 132.3, 129.2 (2C), 128.2, 128.1 (2C), 126.9, 119.8, 116.6, 111.3, 91.6, 63.0, 55.7, 55.5, 53.1 (2C), 53.0 (2C), 51.4, 51.3.

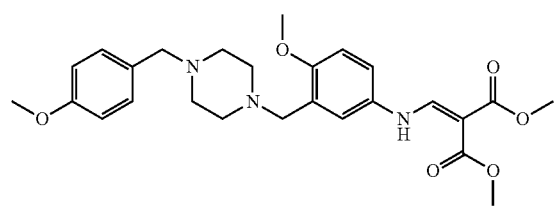

Dimethyl 2-(((4-methoxy-3-((4-(4-methoxyphenyl)piperazin-1-yl)methyl)phenyl)amino)methylene)malonate 7y. A DRA reaction between aldehyde 13c (350 mg, 1.2 mmol) and 1-(4-methoxybenzyl)piperazine (295 mg, 1.4 mmol) following general procedure E afforded 7y as pale yellow semi-solid (350 mg, 61%). $^1$H NMR (400 MHz, CDCl$_3$) δ 11.02-10.91 (m, 1H), 8.44 (d, J=14.0 Hz, 1H), 7.25-7.17 (m, 3H), 6.98 (dd, J=8.7, 2.9 Hz, 1H), 6.85-6.77 (m, 3H), 3.83 (s, 3H), 3.77 (s, 3H), 3.76 (s, 3H), 3.75 (s, 3H), 3.54 (s, 2H), 3.46 (s, 2H), 2.52 (s, 8H). $^{13}$C NMR (101 MHz, CDCl$_3$) δ 169.5, 166.2, 158.8, 155.4, 153.0 (2C), 132.4 (2C), 130.5 (2C), 119.9, 116.8, 113.6 (2C), 111.4, 91.6, 62.3, 55.7, 55.4, 55.2, 55.2, 52.9, 52.8, 51.5, 51.4, 51.4.

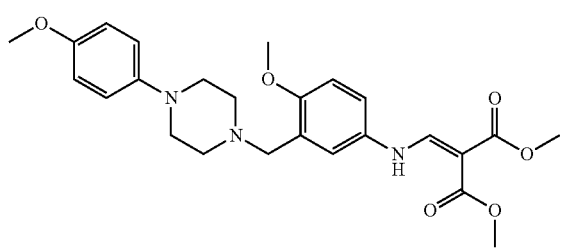

Dimethyl 2-(((4-methoxy-3-((4-(4-methoxyphenyl)piperazin-1-yl)methyl)phenyl)amino)methylene)malonate 7z. A DRA reaction between aldehyde 13c (200 mg, 0.7 mmol) and 1-(4-methoxyphenyl)piperazine hydrochloride (220 mg, 0.82 mmol) following general procedure E afforded 7z as pale yellow semi-solid (250 mg, 78%). $^1$H NMR (400 MHz, CDCl$_3$): δ 11.00 (d, J=13.9 Hz, 1H), 8.47 (d, J=13.9 Hz, 1H), 7.28-7.24 (m, 1H), 7.02 (dd, J=8.7, 2.9 Hz, 1H), 6.92-6.77 (m, 5H), 3.83 (s, 4H), 3.82 (s, 3H), 3.75 (s, 3H), 3.74 (s, 3H), 3.61 (s, 2H), 3.14-3.08 (m, 4H), 2.67 (t, J=5.0 Hz, 4H). $^{13}$C NMR (101 MHz, CDCl$_3$) δ 169.5, 166.2, 155.5, 153.8, 153.0 (2C), 145.7, 132.4, 119.9, 118.2 (2C), 116.8, 114.4 (2C), 111.5, 91.7, 55.8, 55.6, 55.5, 53.2, 51.5, 51.4, 50.6.

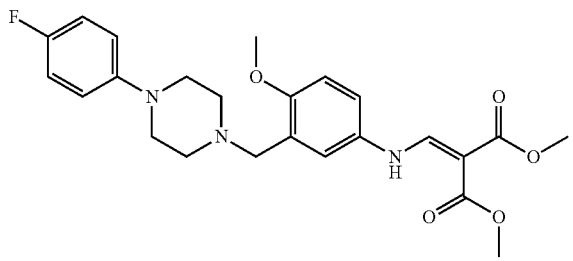 [SMILES: COC(=O)C(=CNc1ccc(OC)c(CN2CCN(c3ccc(F)cc3)CC2)c1)C(=O)OC]

Dimethyl 2-(((3-((4-(4-fluorophenyl)piperazin-1-yl)methyl)-4-methoxyphenyl)amino)methylene)malonate 7aa. A DRA reaction between aldehyde 13c (500 mg, 1.7 mmol) and 1-(4-florophenyl)piperazine (220 mg, 2.0 mmol) following general procedure E afforded 7aa as pale yellow semi-solid (550 mg, 71%). $^1$H NMR (400 MHz, CDCl$_3$): δ 11.03-10.94 (m, 1H), 8.44 (dd, J=13.9, 12.3 Hz, 1H), 7.25-7.14 (m, 1H), 7.03-6.97 (m, 1H), 6.96-6.89 (m, 2H), 6.87-6.82 (m, 3H), 3.82 (s, 3H), 3.80 (s, 3H), 3.74 (s, 3H), 3.59 (s, 2H), 3.15-3.10 (m, 4H), 2.68-2.61 (m, 4H). $^{13}$C NMR (101 MHz, CDCl$_3$) δ 169.5, 166.2, 158.3, 155.9, 155.4, 154.6, 152.9, 152.8, 148.0, 132.5, 132.4, 131.0, 127.8, 119.9, 117.8, 117.7, 117.6, 117.5, 116.8, 115.5, 115.3, 111.5, 111.0, 91.7, 60.9, 55.8, 55.6, 55.5, 53.1, 51.5, 51.4, 51.3, 50.1.

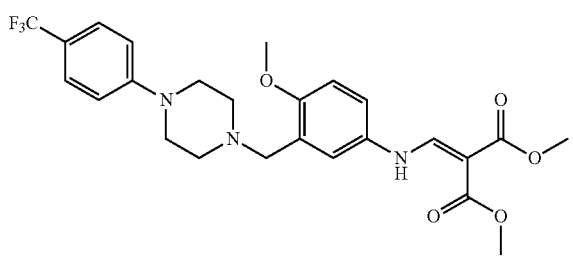 [SMILES: COC(=O)C(=CNc1ccc(OC)c(CN2CCN(c3ccc(C(F)(F)F)cc3)CC2)c1)C(=O)OC]

Dimethyl 2-(((4-methoxy-3-((4-(4-(trifluoromethyl)phenyl)piperazin-1-yl)methyl)phenyl)amino)methylene)malonate 7ab. A DRA reaction between aldehyde 13c (1.0 g, 3.4 mmol) and 1-(4-trifloromethylphenyl)piperazine (950 mg, 4.1 mmol) following general procedure E afforded 7ab as pale yellow semi-solid (1.2 g, 70% yield). 1H NMR (400 MHz, CDCl$_3$): δ 11.00 (d, J=13.9 Hz, 1H), 8.48-8.42 (m, 1H), 7.46-7.40 (m, 2H), 7.22 (d, J=2.9 Hz, 1H), 7.00 (dd, J=8.8, 2.9 Hz, 1H), 6.89-6.81 (s, 3H), 3.81 (m, 3H), 3.79 (s, 3H), 3.73 (S, 3H), 3.57 (s, 2H), 3.27 (t, J=5.0 Hz, 4H), 2.61 (t, J=5.0 Hz, 4H). $^{13}$C NMR (101 MHz, CDCl$_3$) δ 169.5, 166.2, 155.4, 153.3, 152.9, 132.4, 127.9, 126.3, 126.3, 126.3, 126.2, 119.8, 116.8, 114.4 (2C), 111.5, 91.7, 55.8, 55.6, 52.8 (2C), 51.4, 51.4, 47.9 (2C).

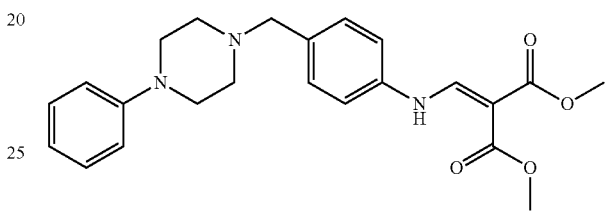

Dimethyl 2-(((4-((4-phenylpiperazin-1-yl)methyl)phenyl)amino)methylene)malonate 7af. A DRA reaction of aldehyde 13d (500 mg, 1.89 mmol) with 1-phenylpiperazine hydrochloride (370 mg, 2.3 mmol) following general procedure E furnished 7af as pale yellow semi-solid (520 mg, 67% yield). $^1$H NMR (400 MHz, CDCl$_3$): δ 11.04 (d, J=13.9 Hz, 1H), 8.52 (d, J=13.7 Hz, 1H), 7.34 (d, J=8.0 Hz, 2H), 7.23 (t, J=7.7 Hz, 2H), 7.09 (d, J=8.0 Hz, 2H), 6.90 (d, J=8.1 Hz, 2H), 6.82 (t, J=7.3 Hz, 1H), 3.84 (s, 3H), 3.76 (s, 3H), 3.52 (s, 2H), 3.17 (t, J=4.8 Hz, 4H), 2.58 (t, J=4.8 Hz, 4H). $^{13}$C NMR (101 MHz, CDCl$_3$): δ 169.3, 165.9, 152.2, 151.2, 138.1, 135.1, 130.5 (2C), 129.0 (2C), 119.6, 117.1 (2C), 116.0 (2C), 92.7, 62.2, 53.0 (2C), 51.5, 51.4, 49.1 (2C).

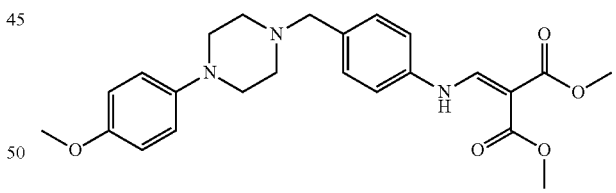

Dimethyl 2-(((4-((4-(4-methoxyphenyl)piperazin-1-yl)methyl)phenyl)amino)methylene)malonate 7ag. A DRA reaction of aldehyde 13d (850 mg, 3.2 mmol) with 1-(4-methoxyphenyl)piperazine hydrochloride (1.0 g, 3.86 mmol) following general procedure E furnished 7ag as pale yellow solid (1.0 g, 71% yield). $^1$H NMR (400 MHz, CDCl$_3$): δ 11.01 (d, J=13.8 Hz, 1H), 8.49 (dd, J=13.7, 1.1 Hz, 1H), 7.31 (d, J=8.0 Hz, 2H), 7.07 (d, J=8.1 Hz, 2H), 6.84 (d, J=9.1 Hz, 2H), 6.80-6.76 (m, 2H), 3.81 (s, 3H), 3.73 (s, 3H), 3.70 (s, 3H), 3.49 (s, 2H), 3.04 (t, J=4.8 Hz, 4H), 2.55 (t, J=4.8 Hz, 4H). $^{13}$C NMR (101 MHz, CDCl$_3$): δ 169.2, 165.8, 153.6, 152.1, 145.5, 138.0, 135.0, 130.4 (2C), 118.0 (2C), 117.1, 117.0, 114.2 (2C), 92.5, 62.1, 55.3, 53.0 (2C), 51.4, 51.3, 50.4 (2C).

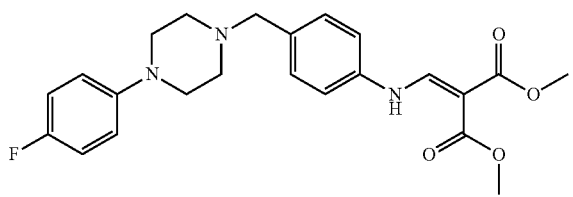 [SMILES: COC(=O)C(=CNc1ccc(CN2CCN(c3ccc(F)cc3)CC2)cc1)C(=O)OC]

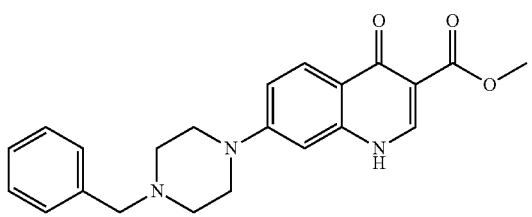

Dimethyl 2-(((4-((4-(4-fluorophenyl)piperazin-1-yl)methyl)phenyl)amino)methylene)malonate 7ah. A DRA reaction of aldehyde 13d (850 mg, 3.2 mmol) with 1-(4-florophenyl)piperazine (695 mg, 3.86 mmol) following general procedure E furnished 7ah as pale white solid (900 mg, 66% yield). $^1$H NMR (400 MHz, CDCl$_3$): δ 11.01 (d, J=13.7 Hz, 1H), 8.49 (d, J=13.8 Hz, 1H), 7.33-7.29 (m, 2H), 7.07 (dd, J=9.0, 2.5 Hz, 2H), 6.92-6.87 (m, 2H), 6.84-6.79 (m, 2H), 3.81 (s, 3H), 3.73 (s, 3H), 3.49 (s, 2H), 3.06 (t, J=5.0 Hz, 4H), 2.54 (dd, J=6.1, 3.9 Hz, 4H). $^{13}$C NMR (101 MHz, CDCl$_3$): δ 169.2, 165.8, 158.1, 155.7, 152.1, 147.8, 147.8, 138.0, 135.0, 130.4, 117.6, 117.5, 117.0, 115.4, 115.2, 92.6, 62.1, 52.9 (2C), 51.4, 51.3, 50.0 (2C).

Methyl 7-(4-benzylpiperazin-1-yl)-4-oxo-1,4-dihydroquinoline-3-carboxylate 8b was synthesized from amine 5b following general procedures C and F in 16% yield over two steps. $^1$H NMR (500 MHz, DMSO-d$_6$) δ 11.92 (s, 1H), 8.41 (s, 1H), 7.93 (d, J=9.1 Hz, 1H), 7.34 (d, J=4.8 Hz, 4H), 7.30-7.24 (m, 1H), 7.09 (dd, J=9.2, 2.4 Hz, 1H), 6.79 (d, J=2.4 Hz, 1H), 3.70 (s, 3H), 3.53 (s, 2H), 3.30 (t, J=5.1 Hz, 4H), 2.53 (d, J=5.4 Hz, 4H). $^{13}$C NMR (126 MHz, DMSO-d$_6$) δ 172.8, 165.5, 153.4, 144.7, 140.7, 137.9, 128.9, 128.2, 127.0, 126.7, 119.1, 113.7, 109.0, 100.0, 62.0, 52.2, 51.0, 47.0.

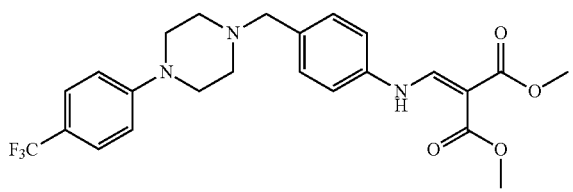 [SMILES: COC(=O)C(=CNc1ccc(CN2CCN(c3ccc(C(F)(F)F)cc3)CC2)cc1)C(=O)OC]

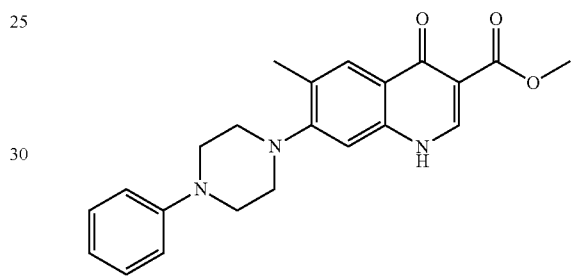

Dimethyl 2-(((4-((4-(4-(trifluoromethyl)phenyl)piperazin-1-yl)methyl)phenyl)amino)methylene)malonate 7ai. A DRA reaction of aldehyde 13d (500 mg, 1.9 mmol) with 1-(4-trifloromethylphenyl)piperazine (523 mg, 2.3 mmol) following general procedure E furnished 7ai as pale yellow solid (570 mg, 63% yield). $^1$H NMR (400 MHz, CDCl$_3$): δ 11.03 (d, J=13.7 Hz, 1H), 8.52 (dd, J=13.7, 1.1 Hz, 1H), 7.43 (d, J=1.2 Hz, 2H), 7.34 (d, J=7.4 Hz, 2H), 7.12-7.08 (m, 2H), 6.90-6.86 (m, 2H), 3.83 (s, 3H), 3.76 (s, 3H), 3.51 (s, 2H), 3.27-3.23 (m, 4H), 2.56 (dd, J=6.1, 4.1 Hz, 4H). $^{13}$C NMR (101 MHz, CDCl$_3$): δ 169.4, 165.9, 153.3, 152.2, 138.2, 134.9, 130.5 (2C), 126.4, 126.3, 126.3, 126.3, 117.2 (2C), 114.4 (2C), 92.8, 62.2, 52.7 (2C), 51.6, 51.4, 47.9 (2C).

Methyl 6-methyl-4-oxo-7-(4-phenylpiperazin-1-yl)-1,4-dihydroquinoline-3-carboxylate 8c was synthesized from commercially available 10a following general procedure H, followed by general procedures B, C and F in 5% overall yield. $^1$H NMR (400 MHz, DMSO-d$_6$) δ 12.12 (s, 1H), 8.46 (d, J=5.9 Hz, 1H), 7.90 (s, 1H), 7.21 (d, J=7.8 Hz, 2H), 7.11 (s, 1H), 6.98 (d, J=8.2 Hz, 2H), 6.79 (t, J=7.2 Hz, 1H), 3.69 (s, 3H), 3.07 (dd, J=6.2, 3.7 Hz, 4H), 2.51 (t, J=5.0 Hz, 4H), 2.35 (s, 3H).

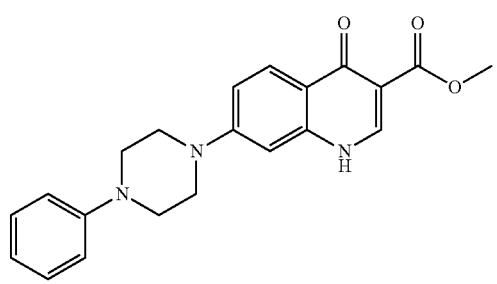 [SMILES: COC(=O)c1c[nH]c2cc(N3CCN(c4ccccc4)CC3)ccc2c1=O]

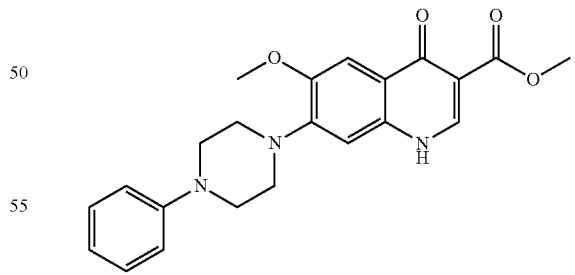

Methyl 4-oxo-7-(4-phenylpiperazin-1-yl)-1,4-dihydroquinoline-3-carboxylate 8a was synthesized from amine 5a following general procedures C and F in 12% yield over two steps. $^1$H NMR (500 MHz, DMSO-d$_6$) δ 11.95 (s, 1H), 8.44 (s, 1H), 7.97 (d, J=9.1 Hz, 1H), 7.25 (t, J=7.8 Hz, 2H), 7.17 (dd, J=9.1, 2.3 Hz, 1H), 7.01 (d, J=8.1 Hz, 2H), 6.88 (d, J=2.4 Hz, 1H), 6.82 (t, J=7.4 Hz, 1H), 3.71 (s, 3H), 3.46 (t, J=5.0 Hz, 4H), 3.30 (d, J=5.2 Hz, 4H).

Methyl 6-methoxy-4-oxo-7-(4-phenylpiperazin-1-yl)-1,4-dihydroquinoline-3-carboxylate 8d was synthesized from commercially available 10a following general procedure H, followed by general procedures B, C and F in 4% overall yield. $^1$H NMR (400 MHz, DMSO-de) b 12.14 (s, 1H), 8.47 (s, 1H), 7.53 (s, 1H), 7.26-7.22 (m, 2H), 7.06 (s, 1H), 7.00 (d, J=8.0 Hz, 2H), 6.81 (t, J=7.2 Hz, 1H), 3.90 (s, 3H), 3.72 (s, 3H), 3.31-3.25 (m, 8H).

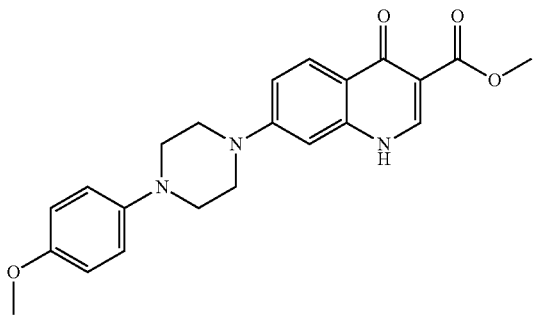 [SMILES: COC(=O)c1c[nH]c2cc(N3CCN(c4ccc(OC)cc4)CC3)ccc2c1=O]

Methyl 7-(4-(4-methoxyphenyl)piperazin-1-yl)-4-oxo-1,4-dihydroquinoline-3-carboxylate 8e was synthesized from 10b following general procedure H, followed by general procedures B, C and F in 6% overall yield. 1H NMR (500 MHz, DMSO-d6) δ 11.93 (s, 1H), 8.43 (d, J=6.0 Hz, 1H), 7.97 (d, J=9.0 Hz, 1H), 7.16 (dd, J=9.1, 2.3 Hz, 1H), 6.96 (d, J=8.8 Hz, 2H), 6.90-6.82 (m, 3H), 3.70 (d, J=9.7 Hz, 6H), 3.44 (t, J=5.1 Hz, 4H), 3.17 (t, J=5.1 Hz, 4H).

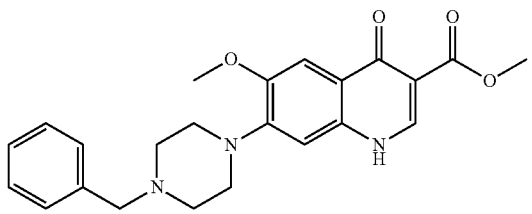

Methyl 7-(4-benzylpiperazin-1-yl)-6-methoxy-4-oxo-1,4-dihydroquinoline-3-carboxylate 8h was synthesized from commercially available 10c following general procedure H, followed by general procedures B, C and F in 8% overall yield. $^1$H NMR (500 MHz, DMSO-d$_6$) δ 12.12 (s, 1H), 8.11 (s, 1H), 7.46 (s, 1H), 7.21 (d, J=3.9 Hz, 4H), 7.19-7.11 (m, 1H), 6.89 (s, 1H), 3.58 (s, 3H), 3.51 (s, 2H), 3.37 (t, J=5.1 Hz, 4H), 3.01 (s, 3H) 2.64 (d, J=5.4 Hz, 4H).

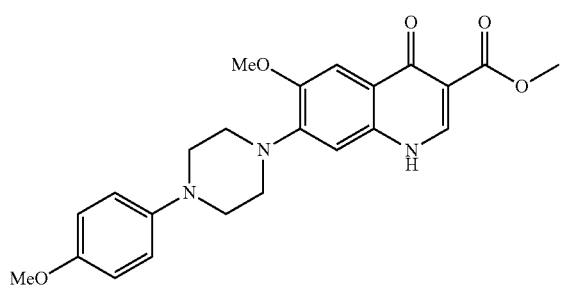 [SMILES: COC(=O)c1c[nH]c2cc(N3CCN(c4ccc(OC)cc4)CC3)c(OC)cc2c1=O]

Methyl 6-methoxy-7-(4-(4-methoxyphenyl)piperazin-1-yl)-4-oxo-1,4-dihydroquinoline-3-carboxylate 8f was synthesized from 10b following general procedure H, followed by general procedures B, C and F in 4% overall yield. $^1$H NMR (400 MHz, DMSO-d$_6$) δ 12.41 (s, 1H), 8.65 (s, 1H), 8.01 (s, 1H), 6.96 (d, J=8.0 Hz, 2H), 7.11 (s, 1H), 7.08 (d, J=8.2 Hz, 2H), 3.84 (s, 3H), 3.78 (s, 3H), 3.61 (s, 3H), 3.48-3.38 (m, 8H).

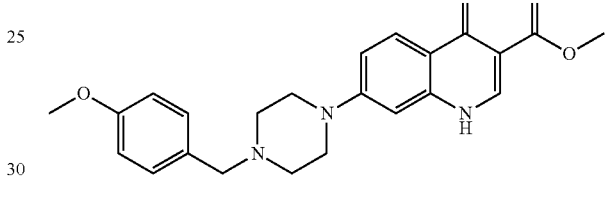

Methyl 7-(4-(4-methoxybenzyl)piperazin-1-yl)-4-oxo-1,4-dihydroquinoline-3-carboxylate 8i was synthesized from 10d following general procedure H, followed by general procedures B, C and F 10% overall yield. $^1$H NMR (400 MHz, DMSO-d) δ 11.90 (s, 1H), 8.41 (s, 1H), 7.93 (d, J=9.2 Hz, 1H), 7.26-7.22 (m, 2H), 7.08 (dd, J=9.2, 2.3 Hz, 1H), 6.91-6.88 (m, 2H), 6.78 (d, J=2.4 Hz, 1H), 3.72 (d, J=14.9 Hz, 10H), 3.46 (s, 2H), 3.28 (d, J=6.8 Hz, 4H). $^{13}$C NMR (126 MHz, DMSO-d$_6$) δ 172.8, 165.5, 158.4, 153.3, 144.7, 140.7, 130.2, 126.7, 119.1, 113.7, 113.6, 109.0, 99.9, 61.3, 55.0, 52.1, 51.0, 47.0.

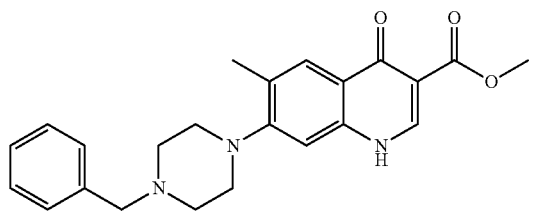 [SMILES: COC(=O)c1c[nH]c2cc(N3CCN(Cc4ccccc4)CC3)c(C)cc2c1=O]

Methyl 7-(4-benzylpiperazin-1-yl)-6-methyl-4-oxo-1,4-dihydroquinoline-3-carboxylate 8g was synthesized from commercially available 10c following general procedure H, followed by general procedures B, C and F in 6% overall yield. $^1$H NMR (500 MHz, DMSO-d$_6$) δ 11.85 (s, 1H), 8.37 (s, 1H), 7.88 (s, 1H), 7.7 (d, J=4.2 Hz, 4H), 7.27-7.21 (m, 1H), 6.99 (s, 1H), 3.70 (s, 3H), 3.62 (s, 2H), 3.42 (t, J=5.1 Hz, 4H), 3.08 (s, 3H) 2.66 (d, J=5.4 Hz, 4H). $^{13}$C NMR (126 MHz, DMSO-d$_6$) δ 172.8, 165.5, 155.3, 144.5, 138.4, 138.0, 129.0, 128.2, 127.5, 127.0, 122.3, 109.1, 106.7, 103.2, 62.1, 52.8, 51.0, 50.9, 18.0.

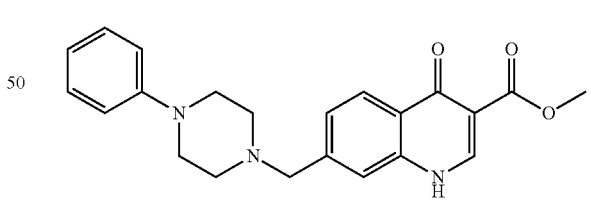

Methyl 4-oxo-7-((4-phenylpiperazin-1-yl)methyl)-1,4-dihydroquinoline-3-carboxylate 8j was synthesized from 7j following general procedure F as a pale yellow solid in 32% yield. $^1$H NMR (400 MHz, DMSO-d$_6$): δ 12.58 (s, 1H), 8.57 (d, J=6.4, 1H), 8.22 (d, J=7.9, 1H), 7.69 (s, 1H), 7.51 (d, J=8.0, 1H), 7.22 (t, J=7.9, 2H), 6.94 (d, J=8.1, 2H), 6.82 (t, J=7.2, 1H), 3.78 (s, 2H), 3.72 (s, 3H), 3.53 (m, 4H), 3.21 (s, 4H). $^{13}$C NMR (101 MHz, DMSO-d$_6$): δ 173.7, 165.9, 151.4, 145.7, 143.8, 139.8, 129.3 (2C), 126.8, 126.1, 125.8, 119.3, 118.7, 115.8 (2C), 109.8, 61.8, 53.1 (2C), 51.5, 48.7 (2C).

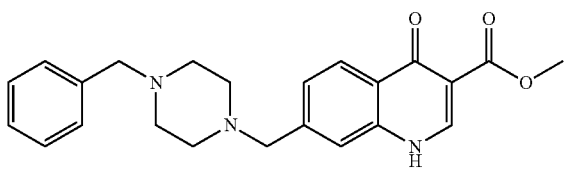 [SMILES: COC(=O)c1c[nH]c2cc(CN3CCN(Cc4ccccc4)CC3)ccc2c1=O]

Methyl 7-((4-benzylpiperazin-1-yl)methyl)-4-oxo-1,4-dihydroquinoline-3-carboxylate 8k was synthesized from 7k following general procedure F as a pale yellow solid in 26% yield. $^1$H NMR (400 MHz, methanol-$d_4$): δ 8.67 (s, 1H), 7.95 (d, J=8.3, 1 H), 7.61 (s, 1H), 7.47-7.34 (m, 6H), 4.41 (s, 2H), 4.30 (s, 2H), 3.83 (s, 3H), 3.61 (s, 4H), 3.49 (s, 4H). $^{13}$C NMR (101 MHz, methanol-$d_4$): δ 175.3, 165.6, 145.8 (2C), 138.8, 137.6, 130.9 (2C), 129.8, 128.8 (2C), 127.1, 126.4, 120.6, 117.7, 108.5, 60.0, 59.7, 50.9, 50.0 (2C), 48.9 (2C).

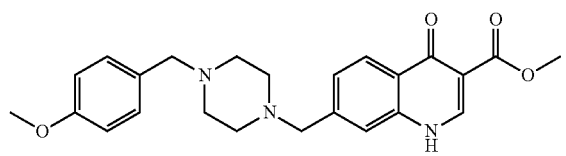

Methyl 7-((4-(4-methoxybenzyl)piperazin-1-yl)methyl)-4-oxo-1,4-dihydroquinoline-3-carboxylate 8l was synthesized from 7l following general procedure F as a light brown solid in 21% yield. $^1$H NMR (400 MHz, DMSO-$d_6$): δ 12.27 (s, 1H), 8.52 (s, 1H), 8.08 (d, J=8.0, 1H), 7.52 (s, 1H), 7.32 (d, J=8.1, 1H), 7.17 (d, J=7.0, 2H), 6.85 (d, J=6.8, 2H), 3.74 (s, 2H), 3.57 (s, 3H), 3.36 (m, 4H), 2.38 (m, 4H). $^{13}$C NMR (126 MHz, DMSO-$d_6$) δ 173.8, 165.6, 159.5, 145.4, 139.4, 132.0, 131.7, 126.8, 126.1, 125.8, 118.7, 114.8, 114.1, 109.8, 79.6, 79.3, 78.9, 61.2, 55.4 (2C), 51.7 (2C), 51.4 (2C).

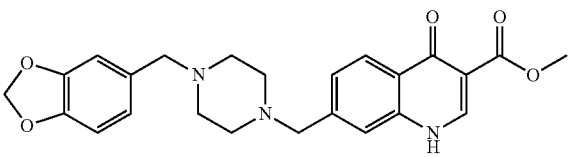 [SMILES: COC(=O)c1c[nH]c2cc(CN3CCN(Cc4ccc5c(c4)OCO5)CC3)ccc2c1=O]

Methyl 7-((4-(benzo[d][1,3]dioxol-5-ylmethyl)piperazin-1-yl)methyl)-4-oxo-1,4-dihydroquinoline-3-carboxylate 8m was synthesized from 7m following general procedure F as a pale yellow solid in 15% yield. $^1$H NMR (400 MHz, DMSO-$d_6$): δ 12.33 (bs, 1H), 8.51 (s, 1H), 8.10 (s, 1H), 7.52 (s, 1H), 7.35 (s, 1H), 6.98-6.89 (m, 3H), 6.00 (s, 2H), 3.92 (m, 4H), 3.70 (s, 3H), 2.82 (m, 8H). $^{13}$C NMR (126 MHz, DMSO-$d_6$) δ 173.24, 165.39, 147.16, 146.10, 145.01, 143.62, 139.05, 131.94, 126.27, 125.63, 125.27, 121.90, 117.89, 109.45, 109.02, 107.80, 100.74, 61.71, 61.39, 52.72 (2C), 52.42 (2C), 51.09.

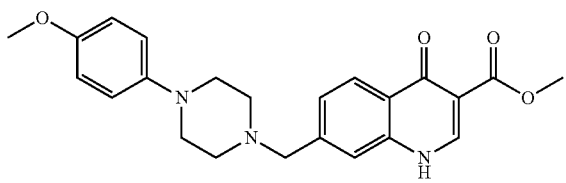

Methyl 7-((4-(4-methoxyphenyl)piperazin-1-yl)methyl)-4-oxo-1,4-dihydroquinoline-3-carboxylate 8n was synthesized from 7n following general procedure F as a pale yellow solid in 20% yield. $^1$H NMR (400 MHz, DMSO-$d_6$): δ 12.31 (s, 1H), 8.55 (s, 1H), 8.12 (d, J=8.2 Hz, 1H), 7.60 (s, 1H), 7.38 (d, J=8.3 Hz, 1H), 6.88 (d, J=8.7 Hz, 2H), 6.81 (d, J=9.1 Hz, 2H), 3.74 (s, 3H), 3.68 (s, 3H), 3.65 (s, 2H), 3.03 (t, J=4.6 Hz, 4H), 2.58-2.53 (m, 4H). $^{13}$C NMR (101 MHz, DMSO-$d_6$): δ 173.7, 165.9, 153.3, 145.8, 145.5, 143.9, 139.5, 126.8, 126.1, 125.8, 118.5, 117.8 (2C), 114.7 (2C), 109.9, 61.9, 55.6, 53.2 (2C), 51.6, 50.1 (2C).

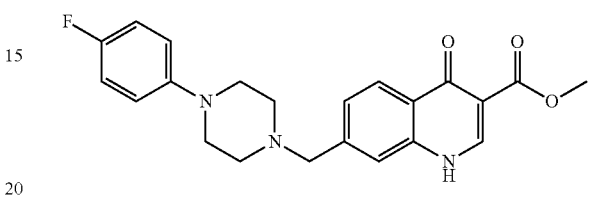

Methyl 7-((4-(4-fluorophenyl)piperazin-1-yl)methyl)-4-oxo-1,4-dihydroquinoline-3-carboxylate 8o was synthesized from 7o following general procedure F as a pale yellow solid in 20% yield. $^1$H NMR (400 MHz, DMSO-$d_6$): δ 12.29 (s, 1H), 8.53 (s, 1H), 8.10 (d, J=8.3 Hz, 1H), 7.57 (d, J=1.4 Hz, 1H), 7.35 (dd, J=8.2, 1.5 Hz, 1H), 7.04-6.98 (m, 2H), 6.93-6.89 (m, 2H), 3.72 (s, 3H), 3.63 (s, 2H), 3.07 (t, J=4.9 Hz, 4H), 2.53 (t, J=4.9 Hz, 4H). $^{13}$C NMR (101 MHz, DMSO-$d_6$): δ 173.7, 165.8, 157.6, 155.3, 148.3, 145.5, 143.8, 139.5, 126.8, 126.1, 125.8, 118.5, 117.6, 117.5, 115.8, 115.6, 109.9, 61.8, 53.1 (2C), 51.5, 49.5 (2C).

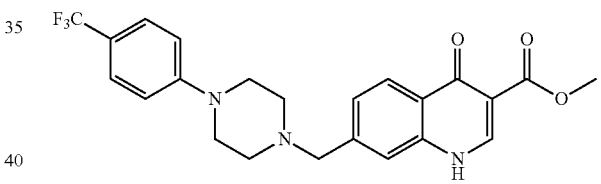

Methyl 4-oxo-7-((4-(4-(trifluoromethyl)phenyl)piperazin-1-yl)methyl)-1,4-dihydroquinoline-3-carboxylate 8p was synthesized from 7p following general procedure F as a pale yellow solid in 35% yield. $^1$H NMR (400 MHz, DMSO-$d_6$): δ 12.30 (s, 1H), 8.54 (s, 1H), 8.12 (d, J=8.2 Hz, 1H), 7.58 (s, 1H), 7.48 (d, J=8.5 Hz, 2H), 7.37 (dd, J=8.2, 1.5 Hz, 1H), 7.04 (d, J=8.6 Hz, 2H), 3.73 (s, 3H), 3.65 (s, 2H), 3.32-3.27 (m, 4H), 2.54 (t, J=5.0 Hz, 4H).

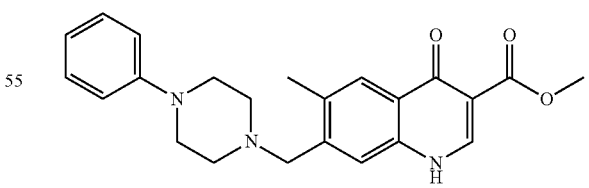

Methyl 6-methyl-4-oxo-7-((4-phenylpiperazin-1-yl)methyl)-1,4-dihydroquinoline-3-carboxylate 8q was synthesized from 7q following general procedure F as a pale yellow solid in 30% yield. $^1$H NMR (400 MHz, DMSO-$d_6$): δ 12.22 (s, 1H), 8.48 (s, 1H), 7.89 (s, 1H), 7.58 (s, 1H), 7.16 (t, J=7.8 Hz, 2H), 6.89 (d, J=8.1 Hz, 2H), 6.73 (t, J=7.3 Hz, 1H), 3.69 (s, 3H), 3.56 (s, 2H), 3.11 (m, 4H), 2.55 (t, J=5.0

Hz, 4H), 2.37 (s, 3H). $^{13}$C NMR (101 MHz, DMSO-d$_6$): δ 173.6, 165.9, 151.4, 145.0, 137.6, 134.3, 129.4 (2C), 126.5 (2C), 119.3, 118.8 (2C), 115.8 (2C), 109.6, 59.7, 53.3 (2C), 51.5, 48.8 (2C), 19.2.

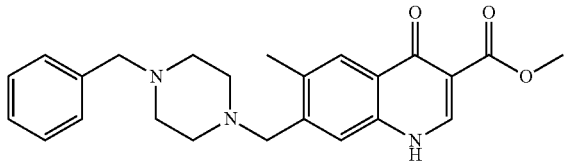 [SMILES: COC(=O)c1c[nH]c2cc(CN3CCN(Cc4ccccc4)CC3)c(C)cc2c1=O]

Methyl 7-((4-benzylpiperazin-1-yl)methyl)-6-methyl-4-oxo-1,4-dihydroquinoline-3-carboxylate 8r was synthesized from 7r following general procedure F as a pale yellow solid in 23% yield. $^1$H NMR (400 MHz, DMSO-d$_6$): δ 12.20 (s, 1H), 8.47 (s, 1H), 7.89 (d, J=1.0 Hz, 1H), 7.52 (s, 1H), 7.33-7.17 (m, 5H), 3.72 (s, 3H), 3.51 (s, 2H), 3.46 (s, 2H), 2.45-2.40 (m, 8H), 2.37 (s, 3H). $^{13}$C NMR (126 MHz, DMSO-d$_6$) δ 173.07, 165.53, 144.62, 142.18, 138.07, 137.18, 133.88, 128.86 (2C), 128.16 (2C), 126.92, 126.01, 125.94, 118.24, 109.14, 62.07, 59.35, 52.91 (2C), 52.67 (2C), 51.05, 18.68.

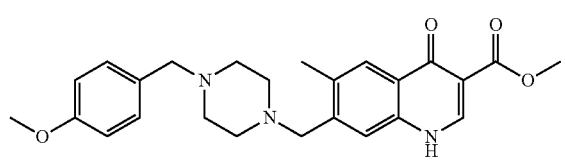

Methyl 7-((4-(4-methoxybenzyl)piperazin-1-yl)methyl)-6-methyl-4-oxo-1,4-dihydroquinoline-3-carboxylate 8s was synthesized from 7s following general procedure F as a pale yellow solid in 20% yield. $^1$H NMR (400 MHz, DMSO-d$_6$): δ 12.27 (s, 1H), 8.51 (s, 1H), 7.91 (s, 1H), 7.56 (s, 1H), 7.20 (d, J=7.8 Hz, 2H), 6.88 (d, J=8.0 Hz, 2H), 3.74 (s, 6H), 3.52 (s, 2H), 3.41 (s, 2H), 2.45 (bs, 8H), 2.38 (s, 3H). $^{13}$C NMR (101 MHz, DMSO-d$_6$) δ 173.6, 165.9, 158.7, 145.0 (2C), 142.6, 137.6, 134.4, 130.6 (2C), 126.5, 126.5, 118.7, 114.0 (2C), 109.6, 61.9, 59.8, 55.4 (2C), 53.3, 53.0 (2C), 51.5, 19.1.

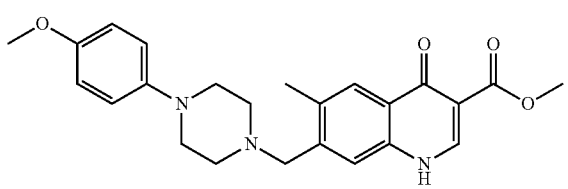

Methyl 7-((4-(4-methoxyphenyl)piperazin-1-yl)methyl)-6-methyl-4-oxo-1,4-dihydroquinoline-3-carboxylate 8t was synthesized from 7t following general procedure F as a pale yellow solid in 22% yield. $^1$H NMR (400 MHz, DMSO-d$_6$): δ 12.26 (s, 1H), 8.55-8.45 (m, 1H), 7.93 (d, J=4.8 Hz, 1H), 7.59 (d, J=4.8 Hz, 1H), 6.87-6.84 (m, 2H), 6.81-6.78 (m, 2H), 3.73 (s, 3H), 3.67 (s, 3H), 3.66 (s, 2H), 3.04 (bs, 4H), 2.66 (bs, 4H), 2.41 (s, 3H). $^{13}$C NMR (101 MHz, DMSO-d$_6$): δ 173.2, 165.4, 153.0, 144.6 (2C), 137.1 (2C), 133.9, 126.2, 117.4 (2C), 114.2 (2C), 114.2 (2C), 109.1, 79.2, 78.9, 78.5, 55.1, 52.8 (2C), 51.0, 49.6 (2C), 18.8.

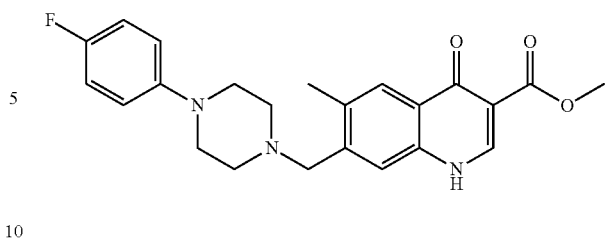

Methyl 7-((4-(4-fluorophenyl)piperazin-1-yl)methyl)-6-methyl-4-oxo-1,4-dihydroquinoline-3-carboxylate 8u was synthesized from 7u following general procedure F as a pale yellow solid in 30% yield. $^1$H NMR (400 MHz, DMSO-d$_6$): δ 12.23 (s, 1H), 8.50 (s, 1H), 7.92 (s, 1H), 7.59 (s, 1H), 7.03 (t, J=8.7 Hz, 2H), 6.93 (dd, J=9.2, 4.6 Hz, 2H), 3.72 (s, 3H), 3.59 (s, 2H), 3.10 (t, J=4.8 Hz, 4H), 2.58 (t, J=4.7 Hz, 4H), 2.41 (s, 3H). $^{13}$C NMR (101 MHz, DMSO-d$_6$) δ 173.12, 165.48, 157.15, 154.81, 147.91, 144.57, 141.99, 137.19, 133.87, 126.08, 118.38, 117.10, 117.02, 115.36, 115.14, 109.19, 59.30, 52.81 (2C), 51.05, 49.13 (2C), 18.71.

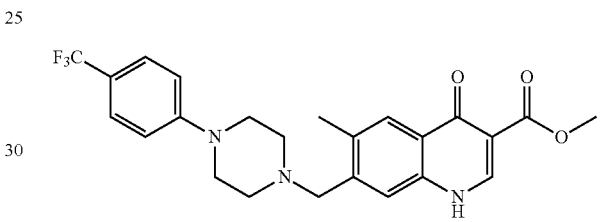

Methyl 6-methyl-4-oxo-7-((4-(4-(trifluoromethyl)phenyl)piperazin-1-yl)methyl)-1,4-dihydroquinoline-3-carboxylate 8v was synthesized from 7v following general procedure F as a pale yellow solid in 35% yield. $^1$H NMR (400 MHz, DMSO-d$_6$): δ 12.25 (s, 1H), 8.51 (s, 1H), 7.92 (s, 1H), 7.60 (s, 1H), 7.49 (d, J=8.5 Hz, 2H), 7.05 (d, J=8.6 Hz, 2H), 3.72 (s, 3H), 3.59 (s, 2H), 3.29 (m, 4H), 2.62-2.54 (m, 4H), 2.40 (s, 3H).

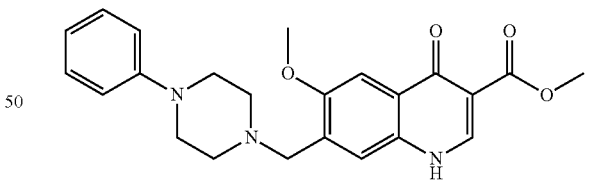

Methyl 6-methoxy-4-oxo-7-((4-(4-phenylpiperazin-1-yl)methyl)-1,4-dihydroquinoline-3-carboxylate 8w was synthesized from 7w following general procedure F as a pale yellow solid in 16% yield. $^1$H NMR (400 MHz, DMSO-d$_6$): δ 12.29 (s, 1H), 8.52-8.42 (m, 1H), 7.72 (d, J=14.8 Hz, 1H), 7.59-7.51 (m, 1H), 7.25-7.12 (m, 2H), 6.93 (d, J=8.3 Hz, 2H), 6.76 (t, J=7.2 Hz, 1H), 3.87 (s, 3H), 3.70 (m, 3H), 3.61 (d, J=13.9 Hz, 2H), 3.21-3.12 (m, 4H), 2.61 (t, J=5.0 Hz, 4H). $^{13}$C NMR (126 MHz, DMSO-d$_6$) δ 172.79, 165.56, 154.83, 151.04, 143.70, 133.30, 133.24, 128.95 (2C), 127.12, 119.10, 118.85, 115.34 (2C), 108.33, 104.08, 55.65, 55.22, 52.93 (2C), 51.06, 48.36 (2C).

83

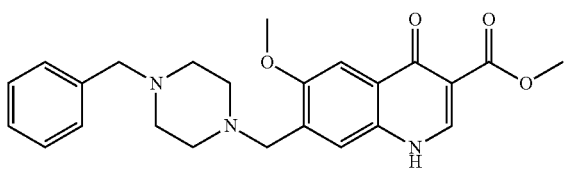 [SMILES: COC(=O)c1c[nH]c2cc(CN3CCN(Cc4ccccc4)CC3)c(OC)cc2c1=O]

Methyl 7-((4-benzylpiperazin-1-yl)methyl)-6-methoxy-4-oxo-1,4-dihydroquinoline-3-carboxylate 8x was synthesized from 7x following general procedure F as a pale yellow solid in 15% yield. $^1$H NMR (500 MHz, DMSO-d$_6$): 12.30 (bs, 1H), δ 8.48 (s, 1H), 7.67 (s, 1H), 7.53 (s, 1H), 7.33-7.23 (m, 5H), 3.85 (s, 3H), 3.72 (s, 3H), 3.55 (s, 2H), 3.47 (s, 2H), 2.44 (m, 8H).

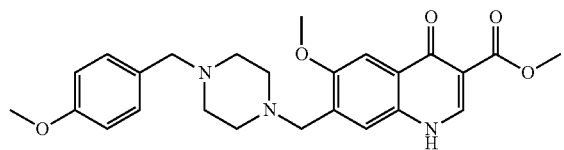

Methyl 6-methoxy-7-((4-(4-methoxybenzyl)piperazin-1-yl)methyl)-4-oxo-1,4-dihydroquinoline-3-carboxylate 8y was synthesized from 7y following general procedure F as a pale yellow solid in 15% yield. $^1$H NMR (500 MHz, DMSO-d$_6$) δ 12.30 (s, 1H), 8.49 (s, 1H), 7.68 (s, 1H), 7.54 (s, 1H), 7.20 (d, J=8.1 Hz, 2H), 6.88 (d, J=8.1 Hz, 2H), 3.87 (s, 3H), 3.74 (s, 3H), 3.72 (s, 3H), 3.56 (s, 2H), 3.42 (s, 2H), 2.44 (bs, 8H). $^{13}$C NMR (126 MHz, DMSO-d$_6$) δ 172.6, 165.5, 158.3, 154.6, 143.5, 133.3, 133.2, 130.1 (2C), 129.9, 126.9, 118.7, 113.5 (2C), 108.3, 104.0, 61.5, 55.6, 55.2, 55.0, 53.0 (2C), 52.5 (2C), 51.0.

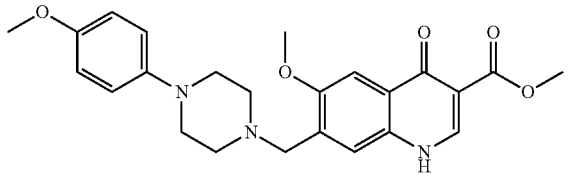

Methyl 6-methoxy-7-((4-(4-methoxyphenyl)piperazin-1-yl)methyl)-4-oxo-1,4-dihydroquinoline-3-carboxylate 8z was synthesized from 7z following general procedure F as a pale yellow solid in 20% yield. $^1$H NMR (400 MHz, DMSO-d$_6$): δ 12.29 (s, 1H), 8.48 (s, 1H), 7.72 (s, 1H), 7.55 (s, 1H), 6.91-6.85 (m, 2H), 6.80 (d, J=9.0 Hz, 2H), 3.87 (s, 3H), 3.71 (s, 3H), 3.66 (s, 3H), 3.62 (s, 2H), 3.05 (t, J=4.7 Hz, 4H), 2.60 (t, J=4.8 Hz, 4H). $^{13}$C NMR (101 MHz, DMSO-d$_6$): δ 173.2, 165.9, 155.2, 153.3, 145.8, 144.1, 133.7 (2C), 127.5, 119.5, 117.7 (2C), 114.7 (2C), 108.8, 104.5, 56.1, 55.6, 53.4 (2C), 51.5, 50.2 (2C).

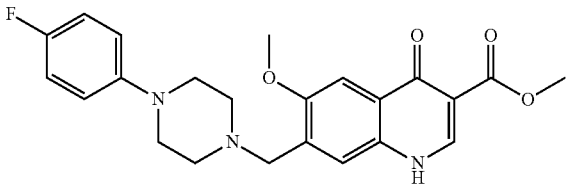 [SMILES: COC(=O)c1c[nH]c2cc(CN3CCN(c4ccc(F)cc4)CC3)c(OC)cc2c1=O]

Methyl 7-((4-(4-fluorophenyl)piperazin-1-yl)methyl)-6-methoxy-4-oxo-1,4-dihydroquinoline-3-carboxylate 8aa was synthesized from 7aa following general procedure F as a pale yellow solid in 28% yield. $^1$H NMR (400 MHz, DMSO-d$_6$): δ 12.29 (s, 1H), 8.49 (s, 1H), 7.73 (s, 1H), 7.56 (s, 1H), 7.03 (t, J=8.7 Hz, 2H), 6.94 (dd, J=9.2, 4.7 Hz, 2H), 3.88 (s, 3H), 3.72 (s, 3H), 3.63 (s, 2H), 3.12 (t, J=4.6 Hz, 4H), 2.61 (t, J=4.8 Hz, 4H). $^{13}$C NMR (101 MHz, DMSO-d$_6$): δ 173.2, 166.0, 157.6, 155.2, 148.4, 144.1, 133.7, 133.6, 127.6, 119.5, 117.5, 117.4, 115.8, 115.6, 108.8, 104.5, 56.1, 55.6, 53.3 (2C), 51.5, 49.6 (2C).

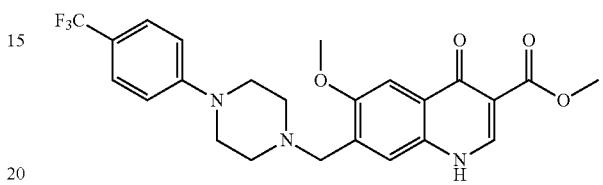

Methyl 6-methoxy-4-oxo-7-((4-(4-(trifluoromethyl)phenyl)piperazin-1-yl)methyl)-1,4-dihydroquinoline-3-carboxylate 8ab was synthesized from 7ab following general procedure F as a pale yellow solid in 30% yield. $^1$H NMR (400 MHz, DMSO-d$_6$): δ 12.29 (s, 1H), 8.49 (s, 1H), 7.73 (s, 1H), 7.56 (s, 1H), 7.49 (d, J=8.5 Hz, 2H), 7.06 (d, J=8.6 Hz, 2H), 3.88 (s, 3H), 3.72 (s, 3H), 3.63 (s, 2H), 3.32 (m, 4H), 2.61 (t, J=4.8 Hz, 4H). $^{13}$C NMR (101 MHz, DMSO-d$_6$) δ 172.78, 165.40, 154.77 (2C), 153.10, 143.78, 143.61, 133.17 (2C), 126.08 (2C), 126.03 (2C), 114.07 (2C), 108.26, 104.07, 55.56, 55.02, 52.45 (2C), 50.92, 46.98 (2C).

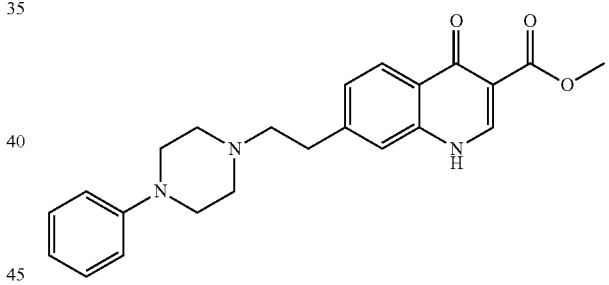

Methyl 4-oxo-7-(2-(4-phenylpiperazin-1-yl)ethyl)-1,4-dihydroquinoline-3-carboxylate 8ac was synthesized from 5ac following general procedures C and F as a pale brown solid in 23% yield over two steps. $^1$H NMR (400 MHz, DMSO-d$_6$): δ 12.59 (bs, 1H), 8.55 (s, 1H), 8.25 (m, 1H), 7.49 (s, 1H), 7.35 (d, J=10.5, 1H), 7.26 (t, J=7.9, 2H), 7.01 (d, J=8.1, 2H), 6.86 (t, J=7.3, 1H), 3.85 (m, 2H), 3.73 (s, 3H), 3.51-3.43 (m, 4H), 3.24-3.16 (m, 4H), 3.02 (m, 2H).

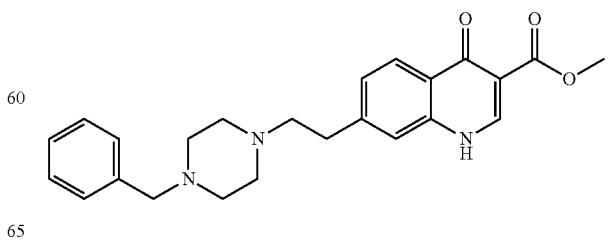

Methyl 7-(2-(4-benzylpiperazin-1-yl)ethyl)-4-oxo-1,4-dihydroquinoline-3-carboxylate 8ad was synthesized from 5ad following general procedures C and F as a brown solid in 15% yield over two steps. $^1$H NMR (400 MHz, DMSO-d$_6$): δ 12.22 (s, 1H), 8.50 (s, 1H), 8.04 (s, 1H), 7.41 (s, 1H), 7.28 (m, 6H), 3.72 (s, 3H), 3.44 (s, 2H), 3.31 (s, 2H), 2.84 (m, 2H), 2.48-2.37 (m, 8H).

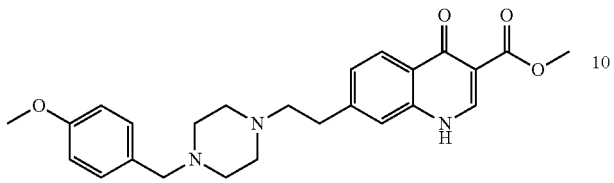

Methyl 7-(2-(4-(4-methoxybenzyl)piperazin-1-yl)ethyl)-4-oxo-1,4-dihydroquinoline-3-carboxylate 8ae was synthesized from 5ae following general procedures C and F as a brown solid in 11% yield over two steps. $^1$H NMR (400 MHz, DMSO-d$_6$) δ 12.24 (bs, 1H), 8.52 (s, 1H), 8.05 (d, J=7.9 Hz, 1H), 7.42 (s, 1H), 7.29 (s, 1H), 7.19 (d, J=7.9 Hz, 2H), 6.87 (d, J=8.1 Hz, 2H), 3.77 (m, 6H), 3.46-3.36 (m, 4H), 2.85 (t, J=7.4 Hz, 2H), 2.60-2.37 (m, 8H).

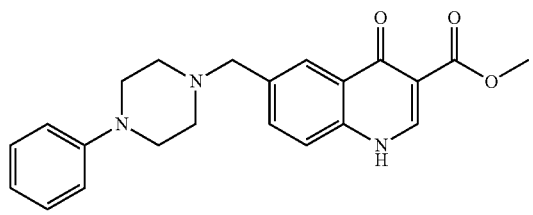 [SMILES: COC(=O)c1c[nH]c2ccc(CN3CCN(c4ccccc4)CC3)cc2c1=O]

Methyl 4-oxo-6-((4-phenylpiperazin-1-yl)methyl)-1,4-dihydroquinoline-3-carboxylate 8af was synthesized following general procedure F as a pale yellow solid in 42% yield. $^1$H NMR (400 MHz, DMSO-d$_6$): δ 12.36 (s, 1H), 8.55 (s, 1H), 8.09 (s, 1H), 7.67 (s, 1H), 7.61 (s, 1H), 7.19 (s, 2H), 6.91 (d, J=7.2 Hz, 2H), 6.76 (s, 1H), 3.74 (s, 3H), 3.64 (s, 2H), 3.13 (m, 4H), 2.50 (m, 4H).

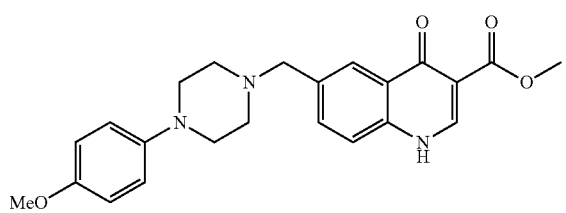 [SMILES: COC(=O)c1c[nH]c2ccc(CN3CCN(c4ccc(OC)cc4)CC3)cc2c1=O]

Methyl 6-((4-(4-methoxyphenyl)piperazin-1-yl)methyl)-4-oxo-1,4-dihydroquinoline-3-carboxylate 8ag was synthesized following general procedure F as a pale yellow solid in 36% yield. $^1$H NMR (400 MHz, DMSO-d$_6$): δ 12.34 (s, 1H), 8.53 (s, 1H), 8.07 (s, 1H), 7.68-7.63 (m, 1H), 7.57 (d, J=8.4 Hz, 1H), 6.85 (d, J=9.1 Hz, 2H), 6.78 (d, J=9.1 Hz, 2H), 3.72 (s, 3H), 3.65 (s, 3H), 3.61 (s, 2H), 2.99 (m, 4H), 2.49 (m, 4H).

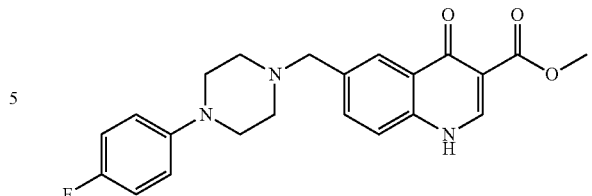

Methyl 6-((4-(4-fluorophenyl)piperazin-1-yl)methyl)-4-oxo-1,4-dihydroquinoline-3-carboxylate 8ah was synthesized following general procedure F as a pale yellow solid in 45% yield. $^1$H NMR (400 MHz, DMSO-d$_6$): δ 12.36 (s, 1H), 8.54 (s, 1H), 8.08 (s, 1H), 7.67 (d, J=7.7 Hz, 1H), 7.58 (d, J=8.4 Hz, 1H), 7.01 (t, J=8.3 Hz, 2H), 6.92 (d, J=4.1 Hz, 2H), 3.73 (s, 3H), 3.62 (s, 2H), 3.06 (s, 4H), 2.50 (s, 4H).

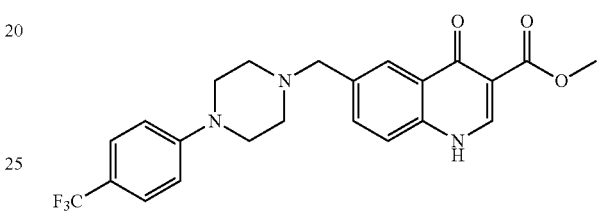

Methyl 4-oxo-6-((4-(4-(trifluoromethyl)phenyl)piperazin-1-yl)methyl)-1,4-dihydroquinoline-3-carboxylate 8ai was synthesized following general procedure F as a pale yellow solid in 45% yield. $^1$H NMR (400 MHz, DMSO-d$_6$): δ 12.29 (s, 1H), 8.50 (s, 1H), 8.06 (s, 1H), 7.63 (d, J=8.5 Hz, 1H), 7.54 (d, J=8.5 Hz, 1H), 7.42 (d, J=8.6 Hz, 2H), 6.97 (d, J=8.7 Hz, 2H), 3.69 (d, J=10.0 Hz, 3H), 3.60 (s, 2H), 3.23 (m, 4H), 2.49 (m, 4H).

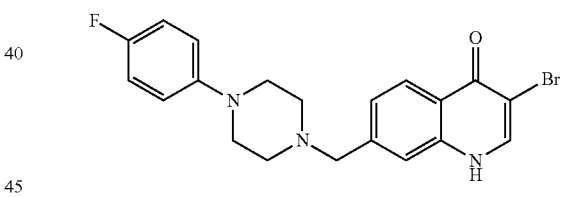

3-Bromo-7-((4-(4-fluorophenyl)piperazin-1-yl)methyl) quinolin-4(1H)-one 8ak. The enamine intermediate 15aj (270 mg, 0.61 mmol) in toluene was subjected to microwave heating at 260° C. for 5 min. The reaction was allowed to cool to RT and concentrated under reduced pressure. The resultant crude was an inseparable mixture of quinolone regio-isomers. To a stirred solution of quinolone isomers in anhydrous CH$_2$Cl$_2$ was added freshly recrystallized NBS (127.0 mg, 0.71 mmol) at RT and the resulting mixture was stirred overnight. The reaction mixture was concentrated under reduced pressure and the residue was purified by preparative HPLC to give the desired 8ak as pale yellow solid (40 mg, 16% over two steps). $^1$H NMR (400 MHz, DMSO-d$_6$): δ 12.50 (d, J=6.4 Hz, 1H), 8.53 (d, J=6.3 Hz, 1H), 8.24 (d, J=8.3 Hz, 1H), 7.73 (s, 1H), 7.54 (d, J=8.4 Hz, 1H), 7.13-7.06 (m, 2H), 7.02-6.97 (m, 2H), 3.74 (d, J=13.3 Hz, 2H), 3.44 (d, J=12.2 Hz, 3H), 3.25 (d, J=11.1 Hz, 3H), 2.97 (d, J=12.6 Hz, 2H). $^{13}$C NMR (126 MHz, DMSO-d$_6$) δ 171.16, 155.72, 146.31, 140.70, 139.13, 133.29, 126.48, 126.21, 124.56, 121.79, 117.98, 117.92, 115.65, 115.48, 104.77, 58.11, 50.69 (2C), 46.23 (2C).

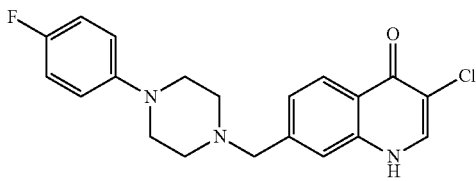 [SMILES: O=c1c(Cl)c[nH]c2cc(CN3CCN(c4ccc(F)cc4)CC3)ccc12]

3-Chloro-7-((4-(4-fluorophenyl)piperazin-1-yl)methyl) quinolin-4(1H)-one 8al. The enamine intermediate 15aj (270 mg, 0.61 mmol) in toluene was subjected to microwave heating at 260° C. for 5 min. The reaction was allowed to cool to RT and concentrated under reduced pressure. The resultant crude was an inseparable mixture of quinolone regio-isomers. To a stirred solution of quinolone isomers in anhydrous $CH_2Cl_2$ was added freshly recrystallized NCS (94.0 mg, 0.71 mmol) at RT, and the resulting mixture was stirred overnight. The reaction mixture was concentrated under reduced pressure and the residue was purified by preparative HPLC to give the desired 8al as pale yellow solid (34 mg, 15% over two steps). $^1$H NMR (400 MHz, DMSO-$d_6$): δ 12.71 (s, 1H), 8.39 (d, J=4.8 Hz, 1H), 8.20 (d, J=8.3 Hz, 1H), 7.86 (d, J=1.5 Hz, 1H), 7.65 (dd, J=8.4, 1.5 Hz, 1H), 7.08 (dd, J=9.9, 7.8 Hz, 2H), 7.01-6.94 (m, 2H), 3.70 (d, J=12.5 Hz, 2H), 3.37 (d, J=11.5 Hz, 2H), 3.26-3.03 (m, 6H). $^{13}$C NMR (101 MHz, methanol-$d_6$ and 3 drops of $CDCl_3$) δ 173.02, 160.83, 158.42, 145.88, 140.41, 139.95, 133.89, 128.07, 127.54, 125.78, 123.04, 120.55, 120.47, 116.84, 116.61, 110.91, 60.34, 52.47 (2C), 48.94 (2C).

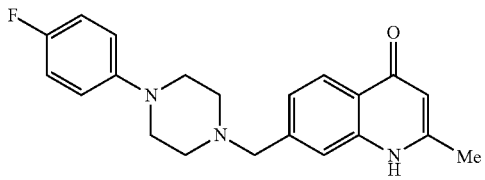 [SMILES: Cc1cc(=O)c2ccc(CN3CCN(c4ccc(F)cc4)CC3)cc2[nH]1]

7-((4-(4-Fluorophenyl)piperazin-1-yl)methyl)-2-methylquinolin-4(1H)-one 8am. A mixture of aniline 5aj (2.0 g, 7.01 mmol) and ethyl acetoacetate (1.34 mL, 10.5 mmol) in benzene (20 mL) and AcOH (cat.) was heated to reflux in an oven dried round bottom flask equipped with Dean-Stark trap and a reflux condenser until no water separates out (usually overnight). The solvents were removed under reduced pressure and the resulting crude intermediate after thorough drying under vacuo was used in next step without further purification. The enamine intermediate in toluene was subjected to microwave heating at 260° C. for 5 min. The reaction mixture was allowed to cool to RT. The crude mixture containing quinolone regio-isomers was then refluxed in methanol for 1 h and filtered to give the unwanted isomer as white solid. The methanolic solution (filtrate) after evaporation gave 950 mg (39% yield) of light brown amorphous 8am in pure form. $^1$H NMR (400 MHz, methanol-$d_6$): δ 8.14 (t, J=5.5 Hz, 1H), 7.54 (s, 1H), 7.38 (dd, J=8.4, 1.4 Hz, 1H), 6.94 (d, J=2.2 Hz, 2H), 6.93 (d, J=2.4 Hz, 2H), 6.17 (s, 1H), 3.69 (s, 2H), 3.13-3.09 (m, 4H), 2.67-2.62 (m, 4H), 2.44 (s, 3H).

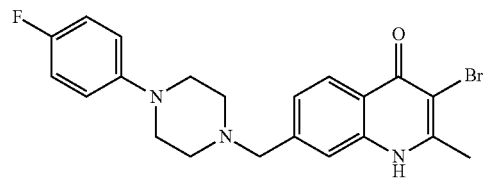 [SMILES: Cc1[nH]c2cc(CN3CCN(c4ccc(F)cc4)CC3)ccc2c(=O)c1Br]

3-Bromo-7-((4-(4-fluorophenyl)piperazin-1-yl)methyl)-2-methylquinolin-4(1H)-one 8an. To a stirred solution of quinolone 8am (50.0 mg, 0.14 mmol) in anhydrous $CH_2Cl_2$ was added freshly recrystallized NBS (30.0 mg, 0.17 mmol) at RT and the resulting mixture was stirred overnight. The reaction mixture was filtered and the solid was washed with EtOAc followed by MeOH to give the purest 8an as off-white solid (25 mg, 42% yield). $^1$H NMR (400 MHz, DMSO-$d_6$): δ 12.07 (s, 1H), 8.04 (d, J=8.3 Hz, 1H), 7.54 (s, 1H), 7.31 (d, J=8.3 Hz, 1H), 7.03 (t, J=8.7 Hz, 2H), 6.93 (dd, J=9.3, 4.6 Hz, 2H), 3.65 (s, 2H), 3.10-3.08 (m, 4H), 2.58-2.55 (m, 4H), 2.54 (s, 3H). $^{13}$C NMR (126 MHz, DMSO-$d_6$) δ 171.20, 158.04, 156.16, 149.85, 146.83, 138.97, 126.62, 126.46, 123.53, 118.42, 118.36, 116.09, 115.92, 109.99, 106.97, 58.70, 51.19 (2C), 46.83 (2C), 21.86.

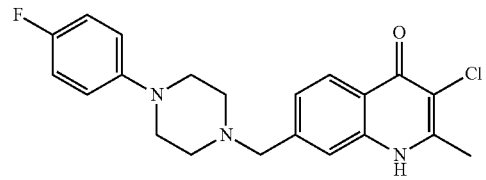 [SMILES: Cc1[nH]c2cc(CN3CCN(c4ccc(F)cc4)CC3)ccc2c(=O)c1Cl]

3-Chloro-7-((4-(4-fluorophenyl)piperazin-1-yl)methyl)-2-methylquinolin-4(1H)-one 8ao: To a stirred solution of quinolone 8am (50.0 mg, 0.14 mmol) in anhydrous $CH_2Cl_2$ was added freshly recrystallized NCS (23.0 mg, 0.17 mmol) at RT, and the resulting mixture was stirred overnight. The reaction mixture was concentrated under reduced pressure and the residue was purified by preparative HPLC to give the purest 8ao as white solid (30 mg, 55% yield). $^1$H NMR (400 MHz, DMSO-$d_6$): δ 12.03 (s, 1H), 8.05 (d, J=8.2 Hz, 1H), 7.54 (s, 1H), 7.30 (d, J=8.3 Hz, 1H), 7.03 (t, J=8.9 Hz, 2H), 6.97-6.85 (m, 2H), 3.65 (s, 2H), 3.09 (t, J=4.7 Hz, 4H), 2.55 (t, J=4.6 Hz, 4H), 2.50 (s, 3H).

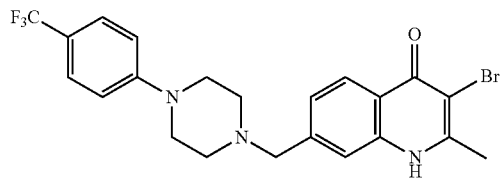

3-Bromo-2-methyl-7-((4-(4-(trifluoromethyl)phenyl)piperazin-1-yl)methyl)quinolin-4(1H)-one 8aq. A mixture of aniline 5ap (380 mg, 1.12 mmol), ethyl acetoacetate (280 µL, 2.98 mmol) and acetic acid (cat.) were stirred overnight in benzene (2 mL) at 100° C. in an oven-dried round bottom equipped with a Dean-Stark trap and reflux condenser. Solvents were removed under reduced pressure and the resulting crude intermediate was transferred with toluene (2 mL) into a microwave vessel and subjected to 260° C. in the microwave for 5 min. The resulting crude was a mixture of 2 quinolone isomers. The quinolone mixture (100 mg, 0.249 mmol) was brominated using NBS (53 mg, 0.299 mmol) according to the general method G. The reaction mixture was filtered and the solid was recrystallized in methanol to give 8aq as a pale brown solid (6 mg, 5% yield). $^1$H NMR (399 MHz, DMSO) δ 12.10 (s, 1H), 8.05 (d, J=8.2 Hz, 1H), 7.54 (s, 1H), 7.49 (d, J=8.6 Hz, 2H), 7.32 (d, J=8.4 Hz, 1H), 7.05 (d, J=8.7 Hz, 2H), 3.66 (s, 2H), 3.30 (s, 4H), 2.55 (s, 7H).

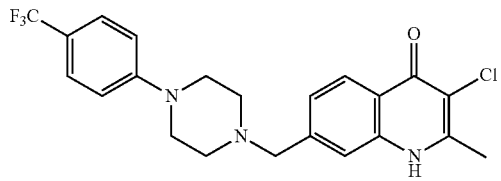 [SMILES: Cc1[nH]c2cc(CN3CCN(c4ccc(C(F)(F)F)cc4)CC3)ccc2c(=O)c1Br]

3-Chloro-2-methyl-7-((4-(4-(trifluoromethyl)phenyl)piperazin-1-yl)methyl)quinolin-4(1H)-one 8ar. A mixture of aniline 5ap (380 mg, 1.12 mmol), ethyl acetoacetate (280 μL, 2.98 mmol) and acetic acid (cat.) were stirred overnight in benzene (2 mL) at 100° C. in an oven-dried round bottom equipped with a Dean-Stark trap and reflux condenser. Solvents were removed under reduced pressure and the resulting crude intermediate was transferred with toluene (2 mL) into a microwave vessel and subjected to 260° C. in the microwave for 5 min. The resulting crude was a mixture of 2 quinolone isomers. The quinolone mixture (100 mg, 0.249 mmol) was chlorinated using NCS (40 mg, 0.299 mmol) according to the general method G. The reaction mixture was filtered and the solid was recrystallized in methanol to give 8ar as a pale brown solid (19 mg, 18% yield). $^1$H NMR (399 MHz, DMSO) δ 12.06 (s, 1H), 8.06 (d, J=8.1 Hz, 1H), 7.54 (s, 1H), 7.49 (d, J=8.6 Hz, 2H), 7.31 (d, J=8.4 Hz, 1H), 7.05 (d, J=8.6 Hz, 2H), 3.66 (s, 2H), 3.30 (s, 4H), 2.55 (s, 4H), 2.51 (s, 3H). $^{13}$C NMR (100 MHz, DMSO) δ 170.5, 153.2, 142.6, 138.6, 126.2, 125.2, 122.6, 119.1, 117.1, 115.5, 114.2, 113.7, 61.4, 52.4, 47.1, 18.7.

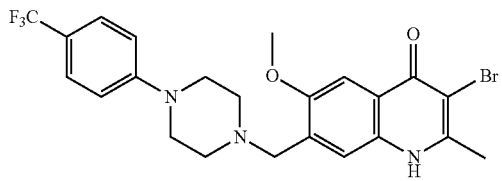 [SMILES: COc1cc2c(=O)c(Br)c(C)[nH]c2cc1CN1CCN(c2ccc(C(F)(F)F)cc2)CC1]

3-Bromo-6-methoxy-2-methyl-7-((4-(4-(trifluoromethyl) phenyl)piperazin-1-yl)methyl)quinolin-4(1H)-one 8at. A mixture of aniline 5as (760 mg, 1.37 mmol), ethyl acetoacetate (520 μL, 2.74 mmol) and acetic acid (cat.) were stirred overnight in benzene (3.5 mL) at 100° C. in an oven-dried round bottom equipped with a Dean-Stark trap and reflux condenser. Solvents were removed under reduced pressure and the resulting crude intermediate was transferred with toluene (3.5 mL) into a microwave vessel and subjected to 260° C. in the microwave for 5 min. The resulting crude was a mixture of 2 quinolone isomers. The quinolone mixture (500 mg, 1.16 mmol) was brominated using NBS (250 mg, 1.39 mmol) according to the general method G. The reaction mixture was filtered, and the solid was recrystallized in methanol to give 8at as a yellow solid (74 mg, 12% yield). $^1$H NMR (399 MHz, CDCl$_3$ and 3 drops TFA-d) δ 11.12 (s, 1H), 8.60 (s, 1H), 7.76 (d, J=8.6 Hz, 2H), 7.73 (s, 1H), 7.59 (d, J=8.7 Hz, 2H), 4.80 (s, 2H), 4.10 (s, 3H), 4.01 (s, 8H), 3.03 (s, 3H). $^{13}$C NMR (100 MHz, CDCl$_3$ and 3 drops TFA-d) δ 162.71, 157.95, 155.49, 132.61, 132.35, 128.12 (d, J=2.9 Hz), 126.5, 121.0, 120.1, 118.8, 116.0, 113.1, 110.3, 105.1, 102.5, 57.2, 55.2, 50.7, 50.1, 22.2.

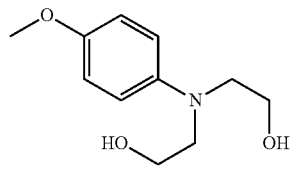

2,2'-((4-Methoxyphenyl)azanediyl)bis(ethan-1-ol) 10b. A mixture of p-anisole (36 mmol) and 2-chloroethan-1-ol (90 mmol) were added to a round bottom flask along with DMF (72 mL) and K$_2$CO$_3$ (72 mmol) and refluxed overnight. The reaction was then concentrated and purified using flash chromatography (hexanes/ethyl acetate) to give the title compound in 85% yield as an off white solid. $^1$H NMR (500 MHz, CDCl$_3$) δ 7.31 (d, J=8.3 Hz, 2H), 6.82-6.77 (m, 2H), 3.62 (dd, J=9.4, 7.9 Hz, 4H), 3.89 (s, 3H), 2.64-2.58 (m, 4H). $^{13}$C NMR (126 MHz, CDCl$_3$) δ 249.2, 239.6, 218.4, 214.9, 178.3, 151.8, 149.6.

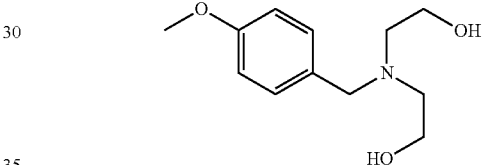

2,2'-((4-Methoxybenzyl)azanediyl)bis(ethan-1-ol) 10d. A mixture of (4-methoxyphenyl)methanamine (36 mmol) and 2-chloroethan-1-ol (90 mmol) were added to a round bottom flask along with DMF (70 mL) and K$_2$CO$_3$ (72 mmol) and refluxed overnight. The reaction was then concentrated and purified using flash chromatography (hexanes/ethyl acetate) to give the title compound in 91% yield as an off white solid. $^1$H NMR (500 MHz, CDCl$_3$) δ 7.20 (d, J=8.7 Hz, 2H), 6.86-6.81 (m, 2H), 3.76 (s, 2H), 3.62 (dd, J=10.3, 8.6 Hz, 4H), 3.47 (s, 3H), 2.70-2.60 (m, 4H). $^{13}$C NMR (126 MHz, CDCl$_3$) δ 260.6, 232.1, 215.6, 210.1, 164.6, 161.3, 157.4, 157.1.

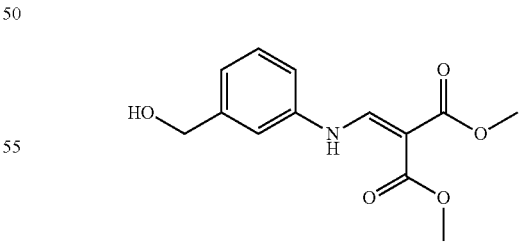

Dimethyl 2-(((3-(hydroxymethyl)phenyl)amino)methylene)malonate 12a was prepared from 3-aminobenzyl alcohol (3 g, 24.4 mmol) according to general procedure C (pale yellow solid, 6.4 g, quantitative yield). $^1$H NMR (400 MHz, CDCl$_3$): δ 10.93 (d, J=13.8 Hz, 1H), 8.44 (d, J=13.8 Hz, 1H), 7.26 (t, J=7.8 Hz, 1H), 7.11-7.04 (m, 2H), 6.97-6.93 (m, 1H), 4.63 (s, 2H), 3.77 (s, 3H), 3.70 (s, 3H), 2.83 (bs, 1H).

$^{13}$C NMR (101 MHz, CDCl$_3$): δ 169.1, 166.0, 151.9, 143.2, 139.1, 129.7, 123.2, 116.0, 115.2, 92.6, 64.3, 51.5, 51.4.

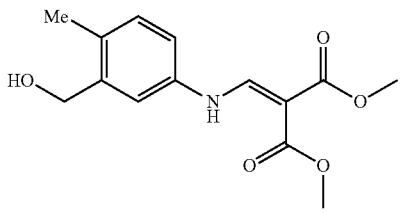 [SMILES: COC(=O)C(=CNc1ccc(C)c(CO)c1)C(=O)OC]

Dimethyl 2-(((3-(hydroxymethyl)-4-methylphenyl)amino)methylene)malonate 12b was prepared from 5-amino-2-methoxybenzyl alcohol (3.0 g, 21.9 mmol) according to general procedure C (pale white solid, 5.5 g, 95% yield). $^1$H NMR (400 MHz, CDCl$_3$): δ 10.94 (d, J=13.9 Hz, 1H), 8.44 (dd, J=13.9, 0.7 Hz, 1H), 7.15 (d, J=2.5 Hz, 1H), 7.07 (d, J=8.1 Hz, 1H), 6.88 (dd, J=8.0, 2.6 Hz, 1H), 4.62 (s, 2H), 3.76 (s, 3H), 3.71 (s, 3H), 2.21 (s, 3H). $^{13}$C NMR (101 MHz, CDCl$_3$): δ 169.2, 166.1, 152.1, 140.8, 137.0, 132.2, 131.2, 115.7, 115.6, 92.0, 62.4, 51.4, 51.3, 17.9.

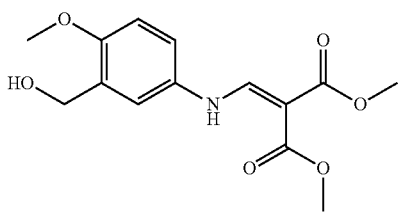 [SMILES: COC(=O)C(=CNc1ccc(OC)c(CO)c1)C(=O)OC]

Dimethyl 2-(((3-(hydroxymethyl)-4-methoxyphenyl)amino)methylene)malonate 12c was prepared from 5-amino-2-methoxybenzyl alcohol (3.0 g, 19.6 mmol) according to general procedure C (violet red semi-solid, 5.3 g, 92% yield). $^1$H NMR (400 MHz, CDCl$_3$) δ 10.96 (d, J=13.8 Hz, 1H), 8.40 (d, J=13.9 Hz, 1H), 7.13 (d, J=2.9 Hz, 1H), 7.01-6.95 (m, 1H), 6.83-6.78 (m, 1H), 4.65 (s, 2H), 3.81 (s, 3H), 3.80 (s, 3H), 3.73 (s, 3H). $^{13}$C NMR (101 MHz, CDCl$_3$): δ 169.4, 166.1, 154.6, 152.8, 132.4, 130.9, 117.6, 117.5, 111.0, 91.8, 61.0, 55.6, 51.4, 51.3.

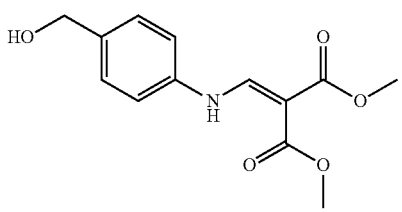 [SMILES: COC(=O)C(=CNc1ccc(CO)cc1)C(=O)OC]

Dimethyl 2-(((4-(hydroxymethyl)phenyl)amino)methylene)malonate 12d was prepared from 4-aminobenzyl alcohol (3 g, 24.4 mmol) according to general procedure C (pale yellow solid, 6.4 g, quantitative yield). $^1$H NMR (400 MHz, CDCl$_3$): δ 10.94 (d, J=13.8 Hz, 1H), 8.43 (ddd, J=13.8, 8.2, 5.5 Hz, 1H), 7.38-7.28 (m, 2H), 7.06-7.02 (m, 2H), 4.60 (s, 2H), 3.79 s, 3H), 3.71 (m, 3H). $^{13}$C NMR (101 MHz, CDCl$_3$): δ 169.2, 166.0, 152.0, 138.1, 138.1, 128.3 (2C), 117.1 (2C), 92.6, 64.2, 51.5, 51.4.

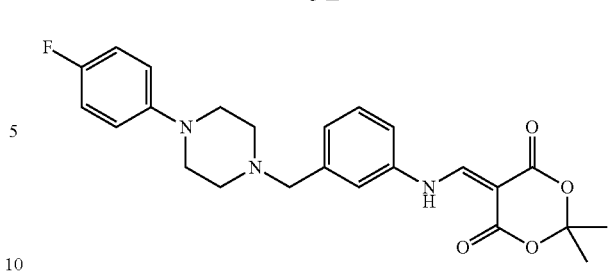

5-(((3-((4-(4-Fluorophenyl)piperazin-1-yl)methyl)phenyl)amino)methylene)-2,2-dimethyl-1,3-dioxane-4,6-dione 15aj. Trimethyl orthoformate (3.7 g, 35.0 mmol.) and Meldrum's acid (0.3 g, 2.10 mmol) were refluxed for 3 h under N$_2$, and then cooled to RT. The aniline 5aj (0.5 g, 1.75 mmol) was then added to the reaction and the resulting mixture was refluxed for another 1 h. The reaction mixture was cooled to RT, ether was added to allow precipitation, and the excess solvents were decanted (the addition of ether and decanting can be repeated couple of times to get rid of excess CH(OCH$_3$)$_3$ and Meldrum's acid). The resulting orange yellow solid was dried under vacuum to give an NMR-pure enamine 15aj in 84% yield (650 mg) that was used directly in next cyclization step without further purification. $^1$H NMR (400 MHz, CDCl$_3$): δ 11.19 (m, 1H), 8.64 (d, J=14.4 Hz, 1H), 7.35 (t, J=7.8 Hz, 1H), 7.28 (s, 1H), 7.21 (d, J=7.6 Hz, 1H), 7.12 (dd, J=7.9, 1.8 Hz, 1H), 6.95-6.87 (m, 2H), 6.86-6.80 (m, 2H), 3.56 (d, J=12.8 Hz, 2H), 3.14-3.04 (m, 4H), 2.63-2.55 (m, 4H), 1.72 (s, 6H). $^{13}$C NMR (101 MHz, CDCl$_3$) δ 165.38, 163.43, 152.43 (2C), 147.81, 140.78, 137.83, 129.83, 127.34, 118.23, 117.76, 117.69, 116.72 (2C), 115.45, 115.23, 105.02, 62.32, 53.04 (2C), 49.97 (2C), 26.90 (2C).

References for Example 1

(1) World Health Organization. World Malaria Report 2015; 2015.
(2) CDC—Centers for Disease Control and Prevention. CDC—Malaria—About Malaria—Biology.
(3) LaCrue, A. N.; Saenz, F. E.; Cross, R. M.; Udenze, K. O.; Monastyrskyi, A.; Stein, S.; Mutka, T. S.; Manetsch, R.; Kyle, D. E. 4(1H)-Quinolones with Liver Stage Activity against *Plasmodium Berghei*. *Antimicrob. Agents Chemother.* 2013, 57 (1), 417-424.
(4) Teixeira, C.; Vale, N.; Pérez, B.; Gomes, A.; Gomes, J. R. B.; Gomes, P. "Recycling" Classical Drugs for Malaria. *Chem. Rev.* 2014, 114 (22), 11164-11220.
(5) Zhang, Y.; Guiguemde, W. A.; Sigal, M.; Zhu, F.; Connelly, M. C.; Nwaka, S.; Guy, R. K. Synthesis and Structure-Activity Relationships of Antimalarial 4-Oxo-3-Carboxyl Quinolones. *Bioorganic Med. Chem.* 2010, 18 (7), 2756-2766.
(6) Zhang, Y.; Clark, J. A.; Connelly, M. C.; Zhu, F.; Min, J.; Guiguemde, W. A.; Pradhan, A.; Iyer, L.; Furimsky, A.; Gow, J.; Parman, T.; El Mazouni, F.; Phillips, M. A.; Kyle, D. E.; Mirsalis, J.; Guy, R. K. Lead Optimization of 3-Carboxyl-4(1H)-Quinolones to Deliver Orally Bioavailable Antimalarials. *J. Med. Chem.* 2012, 55 (9), 4205-4219.
(7) Cross, R. M.; Flanigan, D. L.; Monastyrskyi, A.; LaCrue, A. N.; Saenz, F. E.; Maignan, J. R.; Mutka, T. S.; White, K. L.; Shackleford, D. M.; Bathurst, I.; Fronczek, F. R.; Wojtas, L.; Guida, W. C.; Charman, S. A.; Burrows, J. N.; Kyle, D. E.; Manetsch, R. Orally Bioavailable 6-Chloro- 7-Methoxy-4(1H)-Quinolones Efficacious against Multiple Stages of *Plasmodium*. *J. Med. Chem.* 2014, 57 (21), 8860-8879.

(8) Cross, R. M.; Maignan, J. R.; Mutka, T. S.; Luong, L.; Sargent, J.; Kyle, D. E.; Manetsch, R. Optimization of 1,2,3,4-Tetrahydroacridin-9(10H)-Ones as Antimalarials Utilizing Structure-Activity and Structure-Property Relationships. *J. Med. Chem.* 2011, 54 (13), 4399-4426.

(9) Cross, R. M.; Namelikonda, N. K.; Mutka, T. S.; Luong, L.; Kyle, D. E.; Manetsch, R. Synthesis, Antimalarial Activity, and Structure-Activity Relationship of 7-(2-Phenoxyethoxy)-4(1H)-Quinolones. *J. Med. Chem.* 2011, 54 (24), 8321-8327.

(10) Cross, R. M.; Monastyrskyi, A.; Mutka, T. S.; Burrows, J. N.; Kyle, D. E.; Manetsch, R. Endochin Optimization: Structure-Activity and Structure-Property Relationship Studies of 3-Substituted 2-Methyl-4(1H)-Quinolones with Antimalarial Activity. *J. Med. Chem.* 2010, 53 (19), 7076-7094.

(11) Saenz, F. E.; LaCrue, A. N.; Cross, R. M.; Maignan, J. R.; Udenze, K. O.; Manetsch, R.; Kyle, D. E. 4-(1H)-Quinolones and 1,2,3,4-Tetrahydroacridin-9(10H)-Ones Prevent the Transmission of *Plasmodium Falciparum* to *Anopheles Freeborni*. *Antimicrob. Agents Chemother.* 2013, 57 (12), 6187-6195.

(12) Bueno, J. M.; Manzano, P.; Garcia, M. C.; Chicharro, J.; Puente, M.; Lorenzo, M.; Garcia, A.; Ferrer, S.; Gómez, R. M.; Fraile, M. T.; Lavandera, J. L.; Fiandor, J. M.; Vidal, J.; Herreros, E.; Gargallo-Viola, D. Potent Antimalarial 4-Pyridones with Improved Physico-Chemical Properties. *Bioorg. Med. Chem. Lett.* 2011, 21 (18), 5214-5218.

(13) Winter, R. W.; Kelly, J. X.; Smilkstein, M. J.; Dodean, R.; Hinrichs, D.; Riscoe, M. K. Antimalarial Quinolones: Synthesis, Potency, and Mechanistic Studies. *Exp. Parasitol.* 2008, 118 (4), 487-497.

(14) Winter, R.; Kelly, J. X.; Smilkstein, M. J.; Hinrichs, D.; Koop, D. R.; Riscoe, M. K. Optimization of Endochin-like Quinolones for Antimalarial Activity. *Exp. Parasitol.* 2011, 127 (2), 545-551.

(15) Monastyrskyi, A.; Kyle, D. E.; Manetsch, R. 4(1H)-Pyridone and 4(1H)-Quinolone Derivatives as Antimalarials with Erythrocytic, Exoerythrocytic, and Transmission Blocking Activities. *Curr. Top. Med. Chem.* 2014, 14 (14), 1693-1705.

(16) Ryley, J. F.; Peters, W. Antimalarial Activity of Some Quinolone Esters. *Ann. Trop. Med. Parasitol.* 1970, 64 (2), 209-222.

(17) Puri, S. K.; Dutta, G. P. Quinoline Esters as Potential Antimalarial Drugs: Effect on Relapses of *Plasmodium Cynomolgi* Infections in Monkeys. *Trans. R. Soc. Trop. Med. Hyg.* 1990, 84 (6), 759-760.

(18) Cowley, R.; Leung, S.; Fisher, N.; Al-Helal, M.; Berry, N. G.; Lawrenson, A. S.; Sharma, R.; Shone, A. E.; Ward, S. A.; Biagini, G. A.; O'Neill, P. M. The Development of Quinoloneesters as Novel Antimalarial Agents Targeting the *Plasmodium Falciparum* Bc 1 Protein Complex. *Med. Chem. Commun.* 2012, 3 (1), 39-44.

(19) Maignan, J. R.; Lichorowic, C. L.; Giarrusso, J.; Blake, L.; Casandra, D.; Mutka, T. S.; LaCrue, A. N.; Burrows, J. N.; Willis, P. A.; Kyle, D. E.; Manetsch, R. ICI 56,780 Optimization: Structural-Activity and Relationship Studies of 7-(2-Phenoxyethoxy)-4(1H)-Quinolones with Antimalarial Activity. *J. Med. Chem.* 2016, 4.

(20) Reddy, M. V. R.; Akula, B.; Cosenza, S. C.; Athuluridivakar, S.; Mallireddigari, M. R.; Pallela, V. R.; Billa, V. K.; Subbaiah, D. R. C. V.; Bharathi, E. V.; Vasquez-Del Carpio, R.; Padgaonkar, A.; Baker, S. J.; Reddy, E. P. Discovery of 8-Cyclopentyl-2-[4-(4-Methyl-Piperazin-1-YI)-Phenylamino]-7-Oxo-7,8-Dihydro-pyrido[2,3-D]Pyrimidine-6-Carbonitrile (7x) as a Potent Inhibitor of Cyclin-Dependent Kinase 4 (CDK4) and AMPK-Related Kinase 5 (ARK5). *J. Med. Chem.* 2014, 57 (3), 578-599.

(21) Liu, K. G.; Robichaud, A. J. A General and Convenient Synthesis of N-Aryl Piperazines. *Tetrahedron Lett.* 2005, 46 (46), 7921-7922.

(22) Gould, R. G.; Jacobs, W. A. The Synthesis of Certain Substituted Quinolines and 5,6-Benzoquinolines. *J. Am. Chem. Soc.* 1939, 61 (10), 2890-2895.

(23) Dess, D. B.; Martin, J. C. Readily Accessible 12-I-5 Oxidant for the Conversion of Primary and Secondary Alcohols to Aldehydes and Ketones. *J. Org. Chem.* 1983, 48 (22), 4155-4156.

(24) Kühhorn, J.; Hübner, H.; Gmeiner, P. Bivalent Dopamine D 2 Receptor Ligands: Synthesis and Binding Properties. *J. Med. Chem.* 2011, 54 (13), 4896-4903.

(25) Rossi, C.; Porcelloni, M.; D'Andrea, P.; Fincham, C. I.; Ettorre, A.; Mauro, S.; Squarcia, A.; Bigioni, M.; Parlani, M.; Nardelli, F.; Binaschi, M.; Maggi, C. A.; Fattori, D. Alkyl Piperidine and Piperazine Hydroxamic Acids as HDAC Inhibitors. *Bioorganic Med. Chem. Lett.* 2011, 21 (8), 2305-2308.

(26) Ghosh, B.; Antonio, T.; Reith, M. E. a; Dutta, A. K. Discovery of 4-(4-(2-((5-Hydroxy-1,2,3,4-Tetrahydronaphthalen-2-YI)(propyl)amino)ethyl)piperazin-1-YI) quinolin-8-OI and Its Analogues as Highly Potent Dopamine D2/D3 Agonists and as Iron Chelator: In Vivo Activity Indicates Potential Application in Sympto. *J. Med. Chem.* 2010, 53 (5), 2114-2125.

(27) Nilsen, A.; LaCrue, A. N.; White, K. L.; Forquer, I. P.; Cross, R. M.; Marfurt, J.; Mather, M. W.; Delves, M. J.; Shackleford, D. M.; Saenz, F. E.; Morrisey, J. M.; Steuten, J.; Mutka, T.; Li, Y.; Wirjanata, G.; Ryan, E.; Duffy, S.; Kelly, J. X.; Sebayang, B. F.; Zeeman, A.-M.; Noviyanti, R.; Sinden, R. E.; Kocken, C. H. M.; Price, R. N.; Avery, V. M.; Angulo-Barturen, I.; Jimenez-Diaz, M. B.; Ferrer, S.; Herreros, E.; Sanz, L. M.; Gamo, F.-J.; Bathurst, I.; Burrows, J. N.; Siegl, P.; Guy, R. K.; Winter, R. W.; Vaidya, A. B.; Charman, S. A.; Kyle, D. E.; Manetsch, R.; Riscoe, M. K. Quinolone-3-Diarylethers: A New Class of Antimalarial Drug. *Sci. Transl. Med.* 2013, 5 (177), 177ra37-ra177ra37.

(28) Plowe, C. V. Resistance Nailed. *Nature* 2014, 505, 30-31.

(29) Looareesuwan, S.; Viravan, C.; Webster, H. K.; Kyle, D. E.; Hutchinson, D. B.; Canfield, C. J. Clinical Studies of Atovaquone, Alone or in Combination with Other Antimalarial Drugs, for Treatment of Acute Uncomplicated Malaria in Thailand. *Am. J. Trop. Med. Hyg.* 1996, 54 (1), 62-66.

(30) Milhous, W. K.; Gerena, L.; Kyle, D. E.; Oduola, A. M. In Vitro Strategies for Circumventing Antimalarial Drug Resistance. *Prog. Clin. Biol. Res.* 1989, 313 (Malar. Red Cell, 2), 61-72.

(31) Van Horn, K. S.; Zhu, X.; Pandharkar, T.; Yang, S.; Vesely, B.; Vanaerschot, M.; Dujardin, J.-C.; Rijal, S.; Kyle, D. E.; Wang, M. Z.; Werbovetz, K. A.; Manetsch, R. Antileishmanial Activity of a Series of N 2, N 4-Disubstituted Quinazoline-2,4-Diamines. *J. Med. Chem.* 2014, 57 (12), 5141-5156.

(32) Van Horn, K. S.; Burda, W. N.; Fleeman, R.; Shaw, L. N.; Manetsch, R. Antibacterial Activity of a Series of N 2, N 4-Disubstituted Quinazoline-2,4-Diamines. *J. Med. Chem.* 2014, 57 (7), 3075-3093.

Example 2

Introduction

Figure 5:
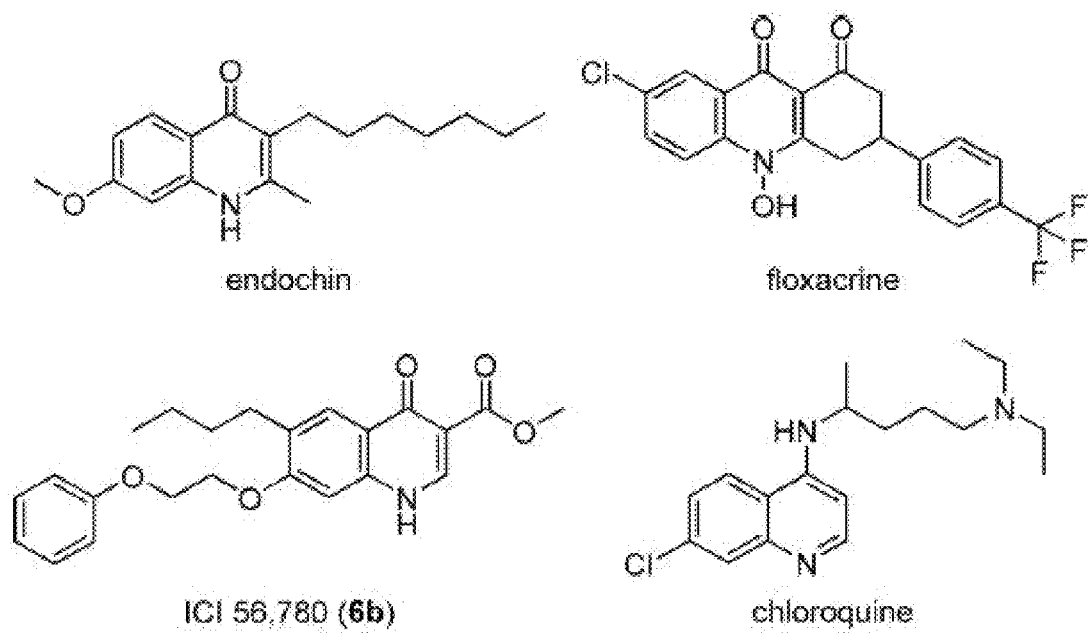
FIG. 5 shows structures of antimalarial compounds that are primed for recycling.

Malaria is considered endemic in 97 countries, and it is estimated that 3.2 billion people are at risk for contracting malaria.[1-3] Although the number of deaths caused by malaria has decreased by 48% since the turn of the century, resistance to current treatments is a mounting problem.[3] Therefore, there is an immediate need to develop new antimalarial agents, which ideally should be active against all developmental stages of the parasite within the host and within the mosquito vector. In humans, malaria is caused by *P. falciparum, P. knowlesi, P. malariae, P. ovale*, and *P. vivax*, of which *P. falciparum* is the most common cause for infections. Malaria begins its life cycle in a host when an infected female *Anopheles* mosquito takes a blood meal from a host. Sporozoites are injected from the salivary gland of the mosquito into the human host and first infect liver cells, which mature into schizonts. Next, schizonts rupture and release merozoites, which rapidly infect red blood cells causing the clinical symptoms of the disease. In stark contrast to the most prevalent *P. falciparum* infections, *P. vivax* parasites can infect and stay dormant in liver cells and reemerge weeks, months or even years later causing a new infection.[4-6] Currently, the only effective treatment for the dormant liver stage of the parasite is primaquine, which is also used as a causal prophylactic agent.[7,8] Effective drug treatment remains the cornerstone of malaria control; 1 nevertheless WHO states that without new therapeutics, all the strides made in reducing the deaths from the disease could be reversed owing to resistance of parasite strains to many of the common antimalarials and artemisinin combination therapies (ACTs).[9] Due to the limited chemotypes active against malaria, researchers have begun to optimize old antimalarial agents or drugs, evaluating these in current preclinical efficacy models and assessing these for proper physicochemical properties.[7,10,11] This approach has been shown to be effective for endochin, a 3-substituted 4(1H)-quinolone,[12-14] floxacrine, a dihydroacridinedione,[7,15-18] chloroquine,[11,19] and other chemotypes (FIG. 5).[7] 4(1H)-Quinolone ester ICI 56,780[15,20,21] (6b) is an example of an old scaffold that is primed for recycling. This analogue was discovered in 1970 by Ryley and Peters to have blood schizonticidal activity against *P. berghei* (Pb) and prophylactic activity against *P. cynomolgi* infections.[21,22] Compound 6b was found to produce radical cures at 15 mg/kg; however, resistance was observed after only one passage in Pb infected mice and the compound was eventually abandoned.[21] Studies by Manetsch, Kyle, Guy, Ward, and O'Neill have shown that considerable optimization can be done to offset some of the liabilities of the 4(1H)-quinolone compound class.[23-26] However, these failed to address the fundamental questions about why 6b has such broad range antimalarial activity or how structural modifications of 6b may reduce the propensity to induce resistance. Given the promise of this scaffold, detailed structure-activity relationship studies against the blood and liver stages of the parasite were conducted in order to gain a deeper understanding of this promising scaffold.\

Results and Discussion

Synthetic Chemistry.

Figure 7:
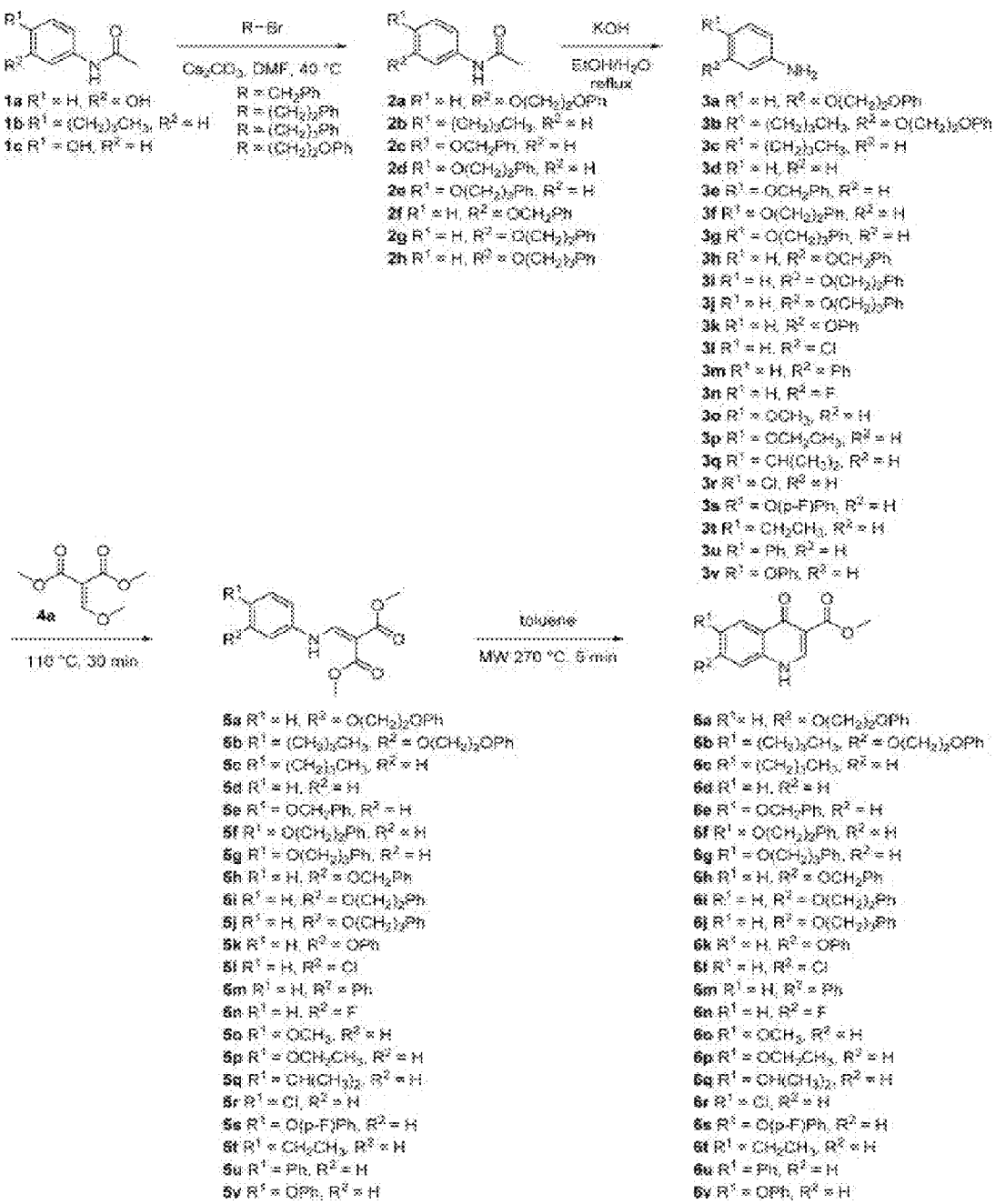
FIG. 7 shows a synthesis scheme of 4(1H)-Quinolones 6a-v from Example 2.
Figure 8:
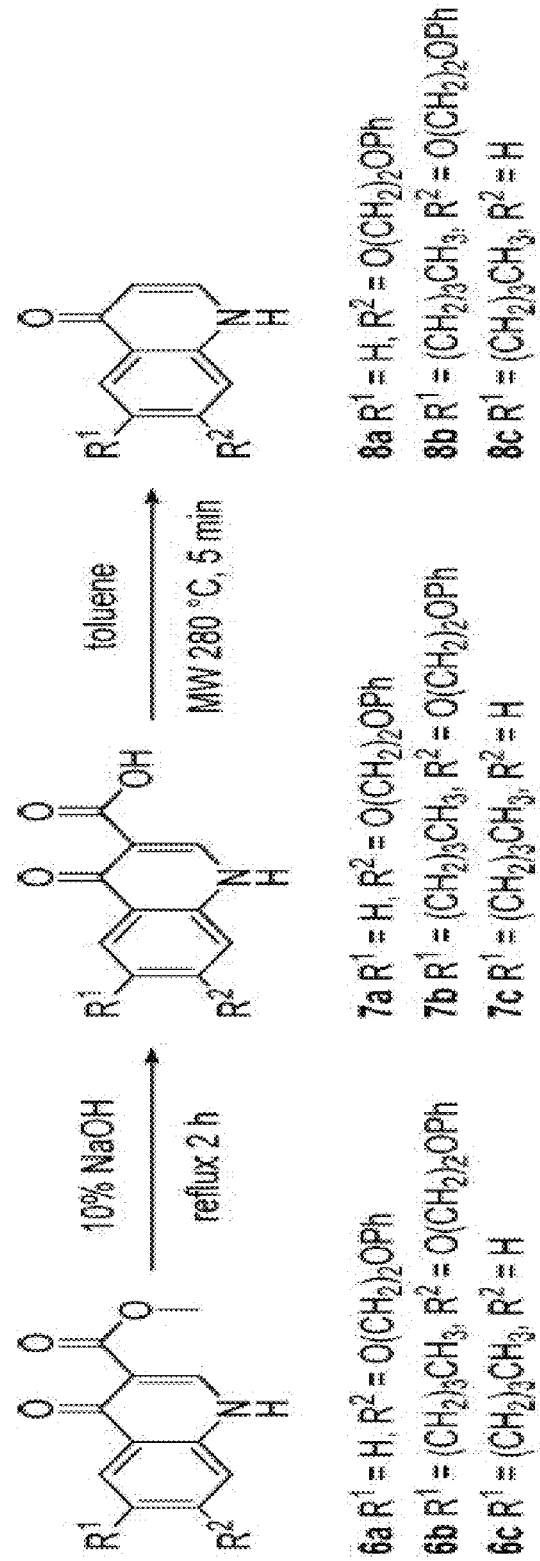
FIG. 8 shows a synthesis scheme of decarboxylated 4(1H)-Quinolones 8a-c of Example 2.

Previous efforts to optimize 6b using Suzuki-Miyaura cross couplings yielded compounds with reduced antimalarial activities, suboptimal atovaquone crossresistance indices, and poor physicochemical properties.[25] In our efforts to improve the bioavailability as well as to better understand the structural reasons for the broad spectrum activity of compound 6b, initially a focused structure-activity relationship (SAR) study was undertaken with a small number of analogues (FIG. 6). The goal was to individually assess the 3-ester, the 6-butyl, and the 7-phenoxyethoxy groups' contribution to the overall activity of 6b. The majority of the compounds have been prepared by a nucleophilic substitution of N-acetyl-protected phenols 1 providing acetamides 2, which under basic conditions were deacetylated to anilines 3. Treatment of anilines 3 with malonate 4a followed by microwave-assisted cyclization furnished 4(1H)-quinolone esters 6 (FIG. 7). Compound 6b was synthesized by an eight-step reaction sequence previously reported.[25] Analogue 6a was synthesized by the alkylation of acetamide 1a followed by acetyl deprotection and Gould-Jacobs cyclization.[27] Compounds 6c and 6d were both prepared using Gould-Jacobs cyclization of the appropriate aniline along with malonate 4a (FIG. 7), while 8a-c were synthesized by the removal of the ester moiety of their corresponding 4(1H)-quinolones 6a-c by a two-step reaction sequence of first refluxing in 10% sodium hydroxide and then heating the intermediate acid in toluene at 270° C. for 5 min (FIG. 8). Due to the limited commercial availability of highly substituted anilines, optimization of the 6- and 7-positions was conducted in parallel using two individual compound series focusing on either the 6-position or 7-position (see FIGS. 9 and 10). Compounds 6k-v and 8a were accessed through commercially available amines as opposed to 4(1H)-quinolones 6e-j, which were synthesized via a reaction sequence similar to the one of compound 6a.

Figure 11:
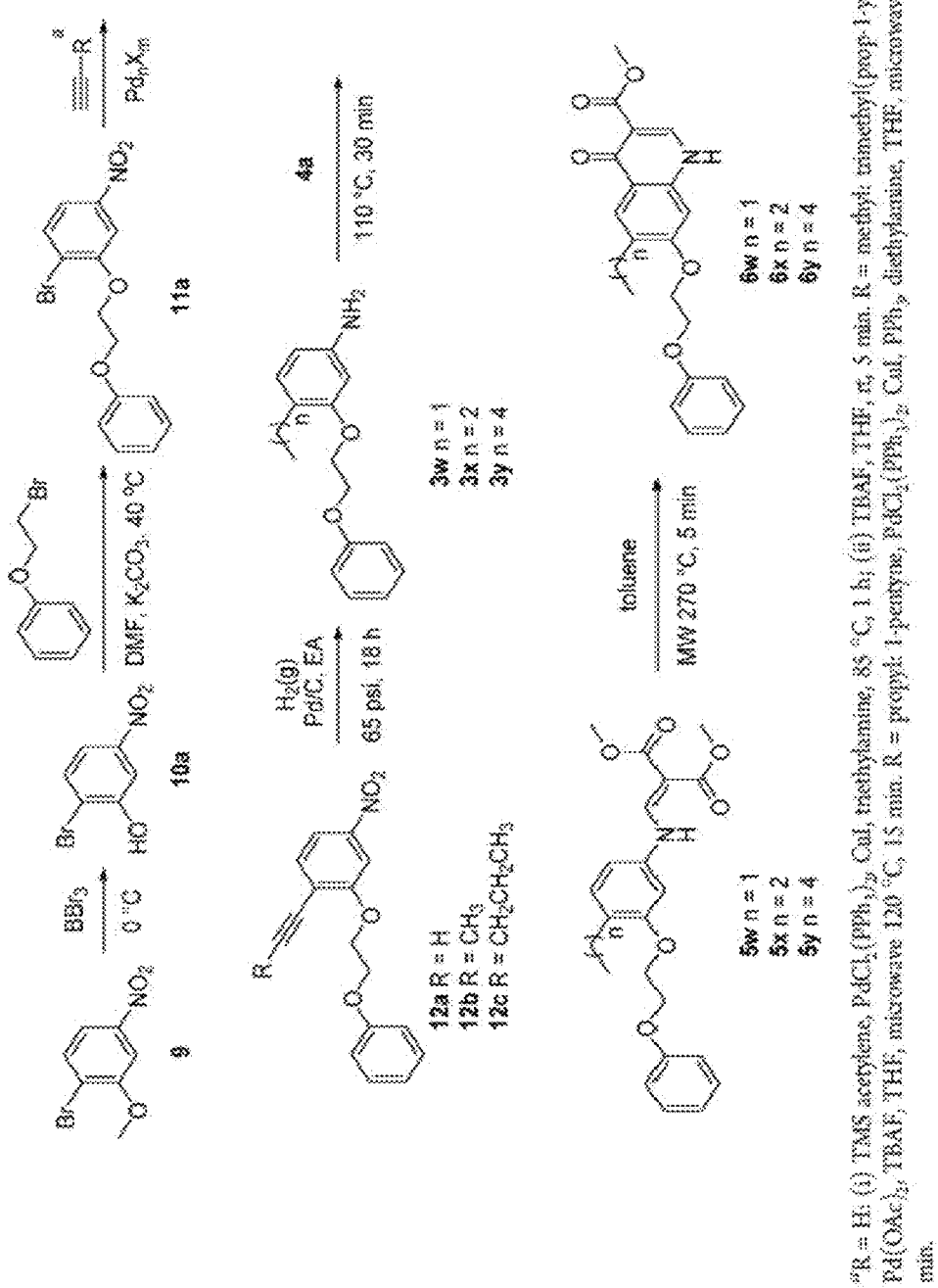
FIG. 11 shows a synthesis scheme for 4(1H)-Quinolones 6w-y with Varying Alkyl Group in 6-Position[a] of Example 2.

To explore the optimal length of the alkyl group in 6-position of compound 6b, a series of 4(1H)-quinolones was prepared whose 6-position was substituted with a variety of groups ranging from one hydrogen to a pentyl chain. Compounds 6w-y were synthesized from 1-bromo-4-nitro-2-(2-phenoxyethoxy)-benzene (11a) via 1-bromo-2-methoxy-4-nitrobenzene (9) (FIG. 11). Phenol 10a was synthesized from anisole 9 via a demethylation with BBr3. Compound 10a was alkylated with (2-bromoethoxy)benzene to give 11a, the needed starting material for the next reaction steps.[25] The alkynyl nitrobenzenes 12 were synthesized via Sonogashira coupling of the available alkynyl starting materials. Nitrobenzene 11a was first subjected to a Sonogashira cross-coupling using TMS-acetylene with PdCl2(PPh3)$_2$, CuI, and TEA, then finally deprotected with TBAF to yield 12a.[28] To access the nitroalkyne 12b, a microwave-assisted deprotection and coupling reaction using trimethyl(prop-1-yn-1-yl)silane, Pd(OAc)2, and TBAF was employed to give the desired product in low yields.[29] Lastly, analogue 12c was obtained in good yields using 1-pentyne, PdCl2(PPh3)$_2$, CuI, PPh3, and diethylamine in a microwave reactor.[30] Each alkyne 12 was reduced using hydrogenation conditions in order to reduce both the alkyne and nitro groups to the corresponding alkyl-substituted anilines 3, which were subjected to standard Gould-Jacobs cyclization conditions furnishing the 4(1H)-quinolones 6w-y.

Figure 12:
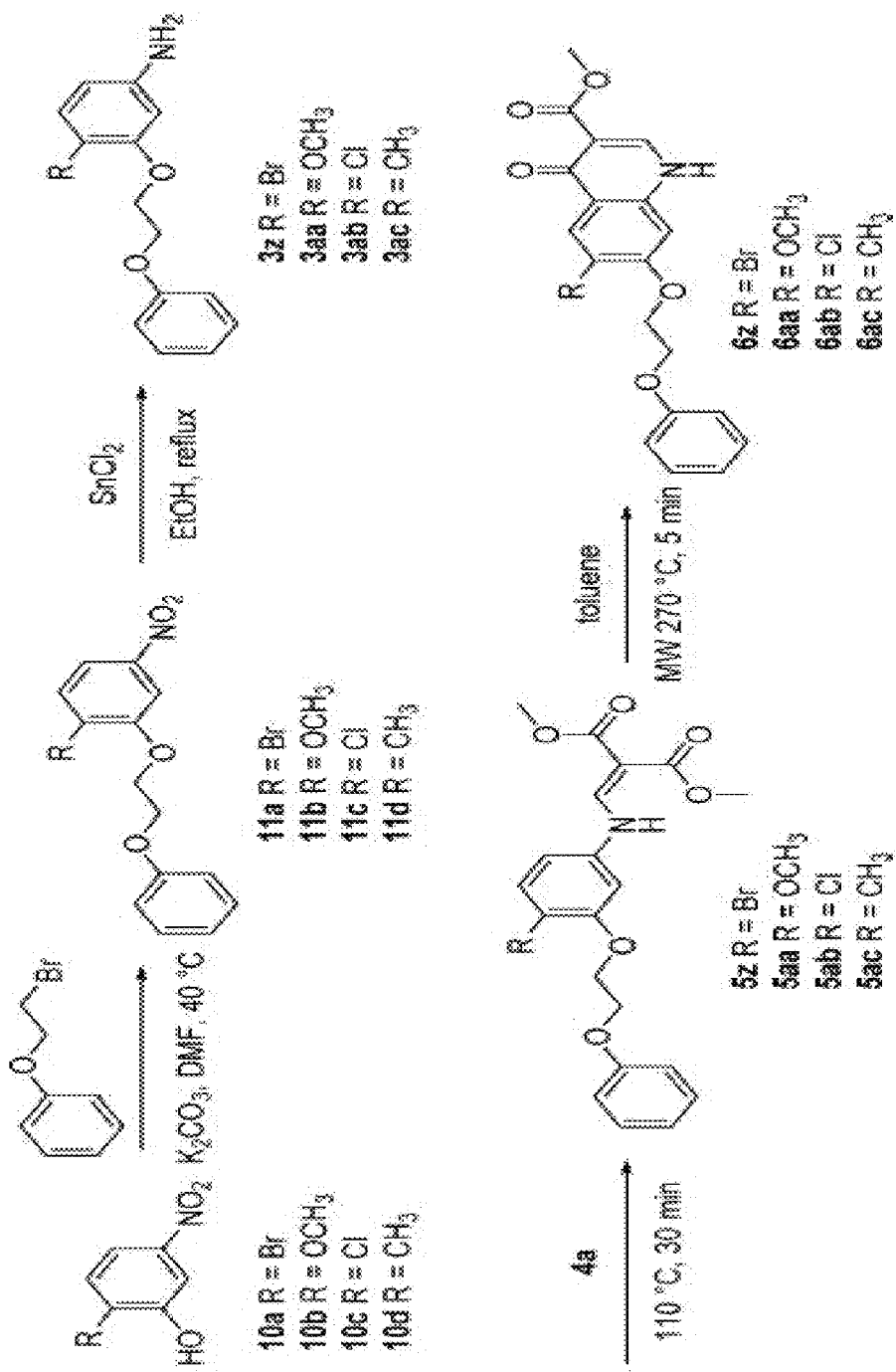
FIG. 12 shows a synthesis scheme for 4(1H)-Quinolones 6z-ac Probing 6-position electronics of Example 2.

Next, a small set of 4(1H)-quinolones with electron donating or electron withdrawing groups were synthesized. This chemistry allowed access to 4(1H)-quinolones 6z, 6aa, 6ab, and 6ac substituted in 6-position with a bromo, methoxy, chloro, or methyl group. These compounds were synthesized starting from the alkylation of corresponding nitrophenols 10 followed by the reduction of the nitrobenzenes 11a-d to give anilines 3z-ac, which were cyclized to give the desired 4(1H)-quinolones 6z-ac (FIG. 12).

Figure 13:
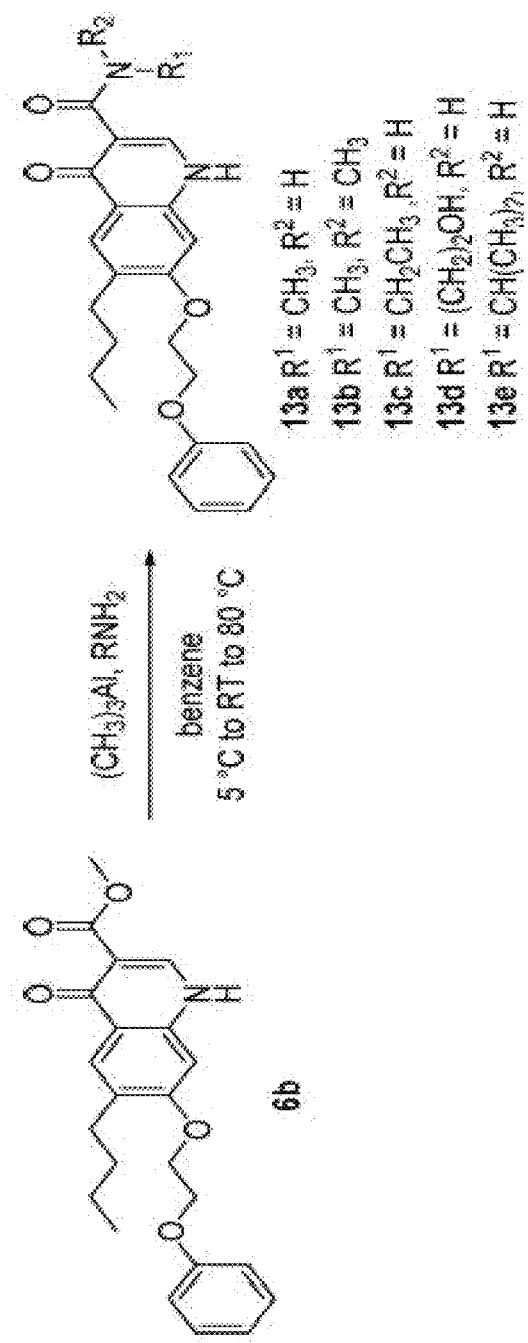
FIG. 13 shows a synthesis scheme for 3-Amide Substituted 4(1H)-Quinolones 13a-e of Example 2.
Figure 14:
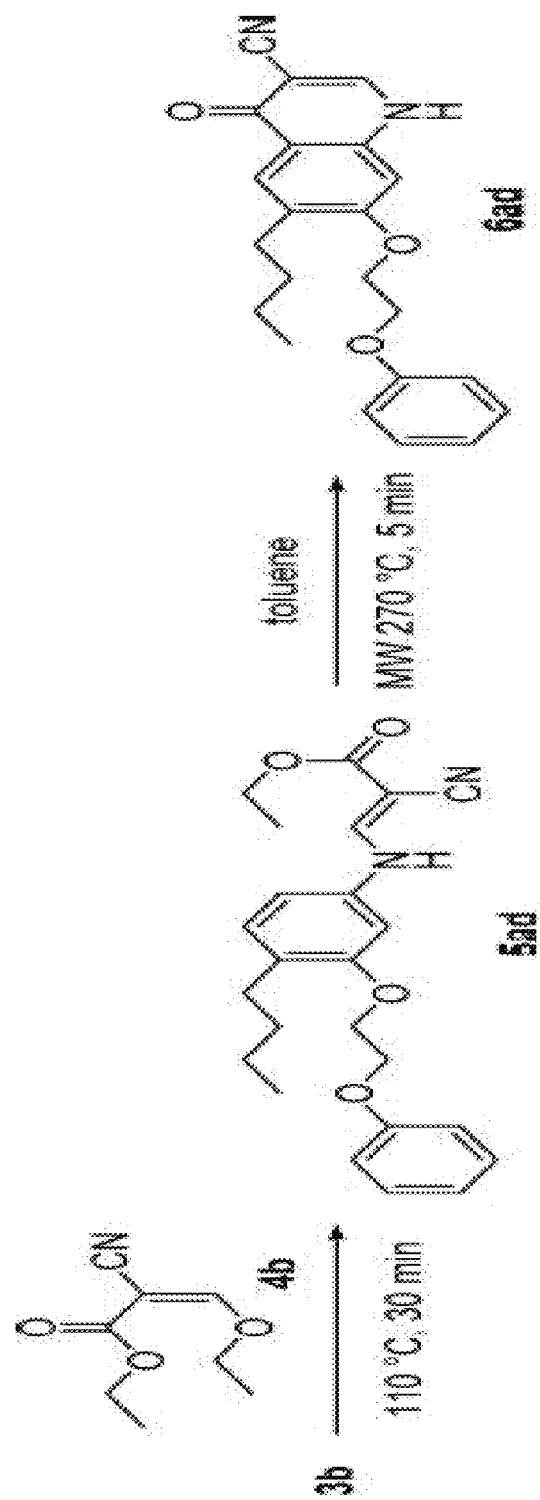
FIG. 14 shows a synthesis scheme for 3-Cyano Substituted 4(1H)-Quinolone 6ad of Example 2.

As the ester group in 3-position of compound 6b was considered to be a potential metabolic liability, 4(1H)- quinolone analogues were prepared in which the methyl ester group was replaced by amides, halides, a nitrile, a keto, an ethyl, or other esters. The amide functionalities were introduced by the aminolysis of 6b using trimethylaluminum and the appropriate amine in dry benzene[31] to yield compounds 13a-e in moderate to low yield after purification using preparative HPLC (FIG. 13). The 3-cyano-4(1H)-quinolone was synthesized from aniline 3b and the commercially available ethyl-2-cyano-3-ethoxyacrylate (4b). Standard Gould-Jacobs cyclization of intermediate N-Narylenamine 5ad afforded the cyano-substituted 4(1H)-quinolone 6ad in low yield (FIG. 14).

Figure 15:
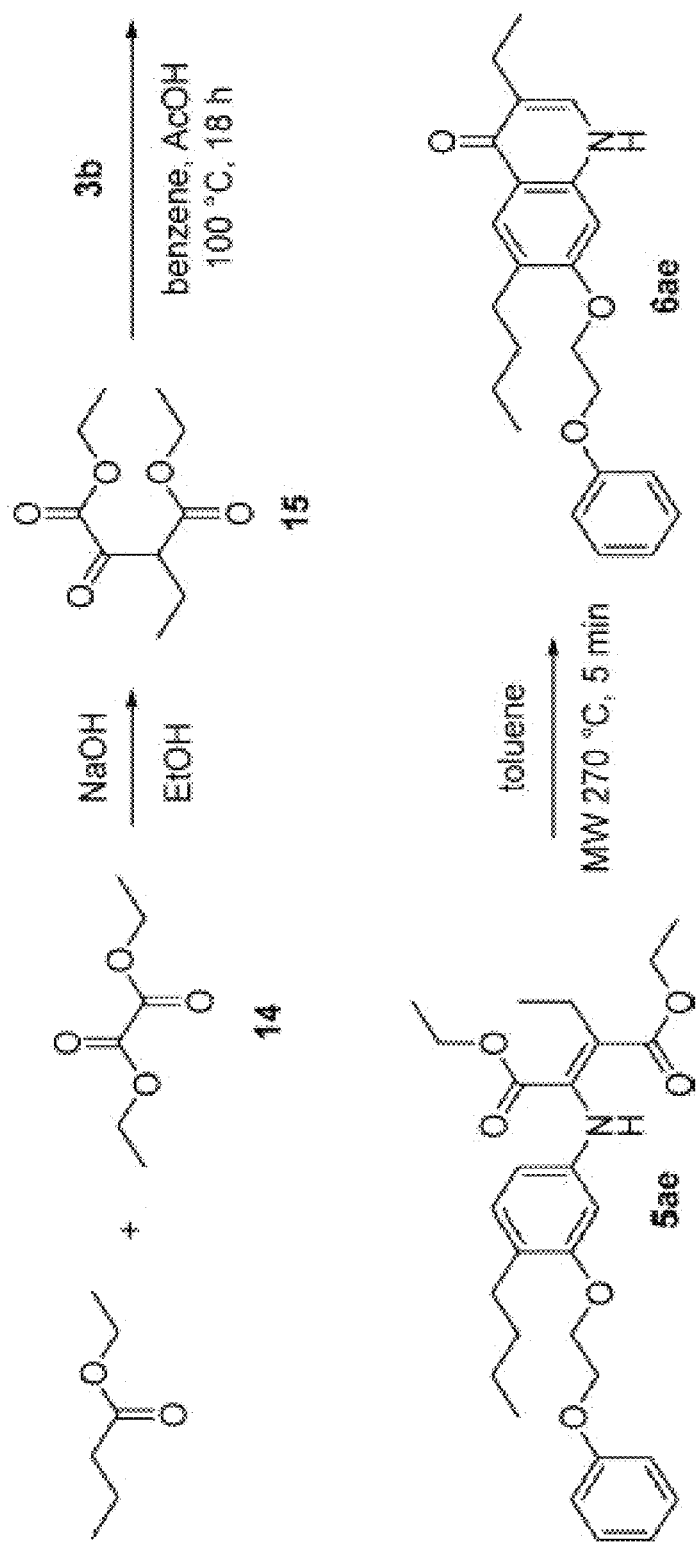
FIG. 15 shows a synthesis scheme for 3-Ethyl Substituted 4(1H)-Quinolone 6af of Example 2.
Figure 16:
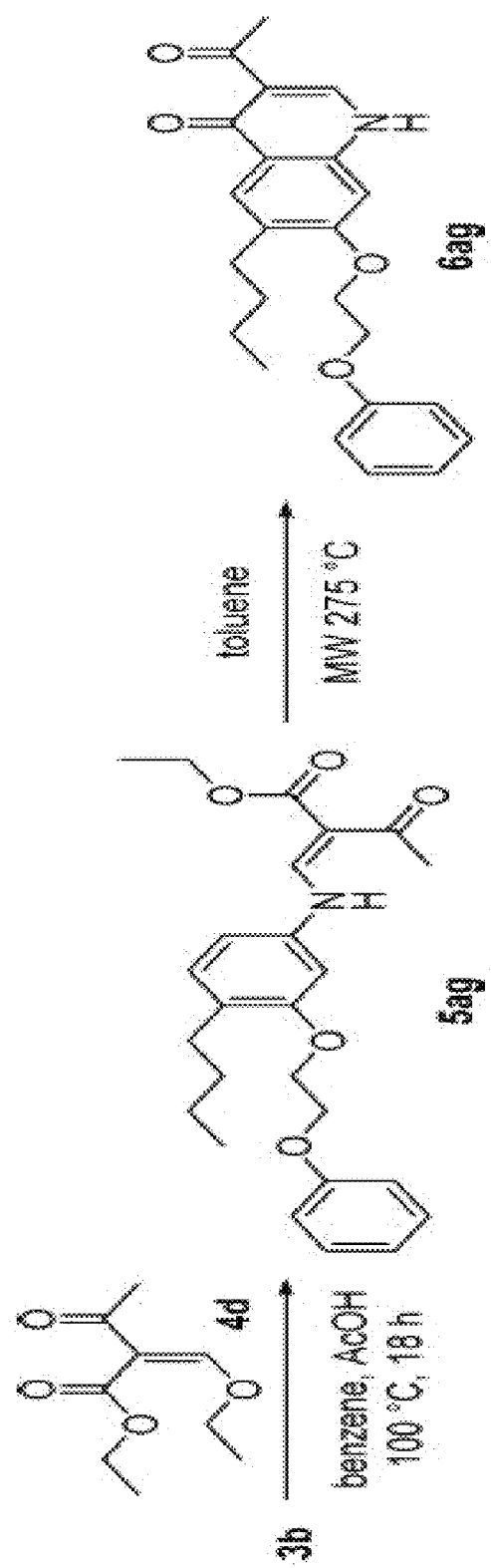
FIG. 16 shows a synthesis scheme for 3-Keto 4(1H)-Quinolone 6ag of Example 2.
Figure 17:
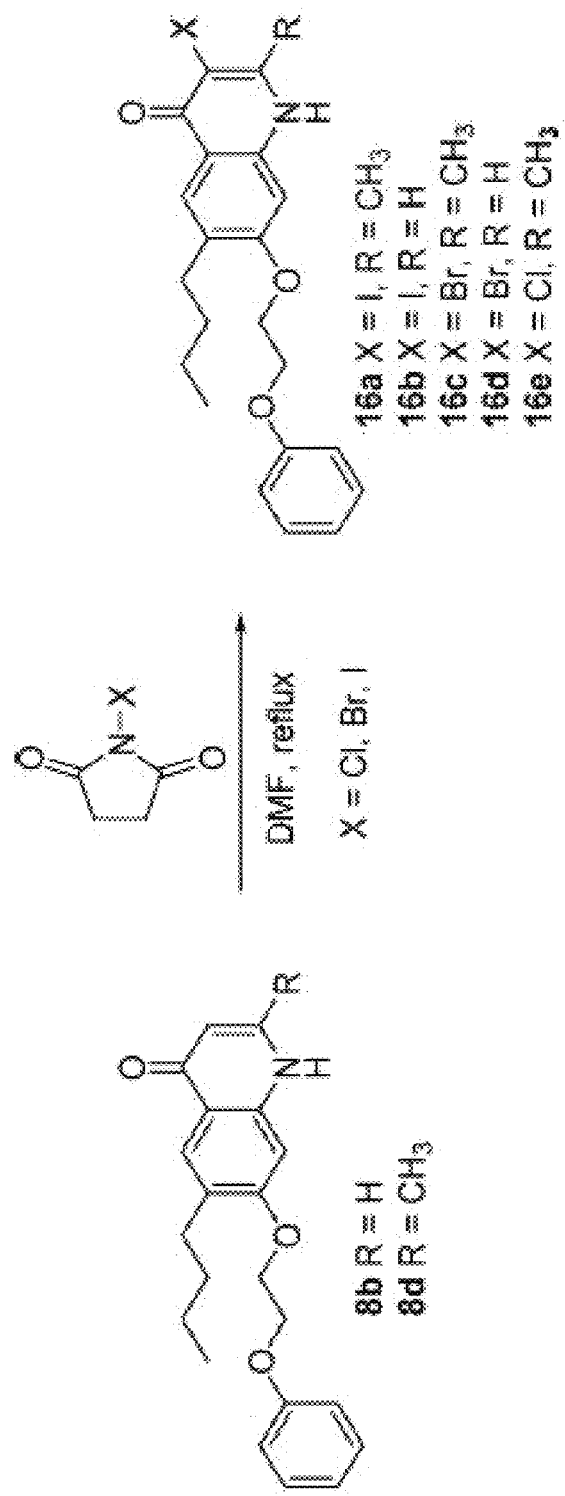
FIG. 17 shows a synthesis scheme for 3-Halide Substituted 4(1H)-Quinolones 16a-e of Example 2.

A three-step reaction sequence was utilized for the preparation of 3-ethyl-substituted 4(1H)-quinolone 6ae. First, ethyl butyrate was reacted with diethyl oxalate (14) to give diester[15,32] which was used as the starting material along with the aniline 3b to furnish intermediate 5ae followed by cyclization to give 3-ethylsubstituted 4(1H)-quinolone 6ae (FIG. 15). 3-Ethyl ester substituted 4(1H)-quinolone 6af was cyclized from enamine 5af following a reaction of aniline 3b with malonate 4c. (FIG. 15). Ketone 6ag was synthesized through a standard Conrad-Limpach[33] cyclization (FIG. 16). 3-Iodo-4(1H)-quinolone 16b was an intermediate for the preparation of 3-aryl-substituted 4(1H)-quinolones previously reported.[25] The remaining halides 16a and 16c-e were synthesized from 4(1H)-quinolone 8b or 2-methyl-4(1H)-quinolone 8d using NBS, NCS, or NIS in DMF (FIG. 17).

Antimalarial Activity and Cytotoxicity

All synthesized compounds were routinely tested against the clinically relevant multidrug resistant malarial strains W2 (pyrimethamine and chloroquine resistant strains) and TM90-C2B (mefloquine, chloroquine, atovaquone, pyrimethamine resistant strains) as previously reported.[12-14] Due to the emergence and rapid acquisition of cross-resistance,[34] each compound was also evaluated on its resistance index (RI), which is the ratio of the effective concentrations needed to kill 50% of the population of parasites (EC50) for TM90-C2B and W2 strains (RI=(EC50 TM90-C2B)/(EC50 W2)). Ideally, the RI of a compound should lie between 0.3 and 3 in order to avoid rapidly inducing resistance in the parasite.[35,36] This range is based upon the natural resistance patterns observed for drugs like chloroquine and mefloquine.[35,36] The target for 4(1H)-quinolones is cytochrome b of the mitochondria; TM90-C2B has a Y268S mutation in cytochrome b that confers high grade resistance to atovaquone. Therefore, the RI values with TM90-C2B reflect potential cross-resistance to atovaquone. Selected compounds were also tested for in vitro liver stage activity using *P. berghei* sporozoites expressing luciferase, harvested from mosquito salivary glands and allowed to infect HEPG2 hepatoma cells in order to assess if the compounds possessed causal prophylactic activity.[13] Similar to the RI, liver blood indices (LBIs) were assessed in order to relate activity against *P. berghei* with activity against W2 or TM90-C2B (LBI=(EC50 W2)/(EC50 Pb) or LBI=(EC50 TM90-C2B)/(EC50 Pb)). This allowed a simplified method for comparing the different assays being simultaneously run. Additionally, each compound was also tested for cytotoxicity using mammalian J774 cell lines in a 96-well plate format.[12-14, 16]

Structure-Activity Relationships

The original compound 6b was found to have an excellent EC50 for W2 at 39.0 pM; however, it suffered from a 2 orders of magnitude drop in activity for the atovaquone resistant strain TM90-C2B with an EC50 value of 7.89 nM. Compound 6b also showed excellent in vitro liver stage activity in *P. berghei* infected cells with an EC50 of 52.0 pM. Initially, each substituent in 3-, 6-, and 7-position was removed sequentially to give compounds 6a, 6c, and 8b. The removal of the 6-butyl or 7-(2-phenoxyethoxy) group provided slightly less potent compounds 6a and 6c with EC50 values against W2 of 2.80 and 1.58 nM, respectively, whereas both maintained subnanomolar liver stage activity. In contrast, removal of the ester functionality in 3-position severely affected the potency, dropping the EC50 values of W2, TM90-C2B, and *P. berghei* to 328 nM, 430 nM, and 5.82 nM, respectively. These data suggest the importance of the ester in liver stage activity. Despite the severe potency reduction for compound 8b, it was noted that the resistance index equaled 1.31, which stands in stark contrast to the large RI values for compounds 6a and 6c which were 26.3 and 141, respectively. Subsequently, compounds 6d, 8a, and 8c were tested, in which two of the 3-, 6-, and 7-substituents were simultaneously removed. Both 6d and 8c retained respectable potency against W2; however, both were devoid of any activity against TM90-C2B. Similar to compound 8b, when the ester group was removed in compounds 8a, inhibition against W2 was lost; however, the RI value converged toward 1. Importantly, it was also observed that compounds 8a, 8b, and 8c, lacking the ester group in 3-position, were the least potent analogues against *P. berghei* of the entire subseries (FIG. 6).

Figure 10:
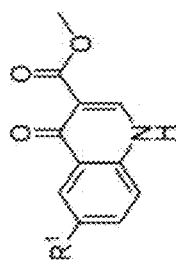
FIG. 10 shows a table demonstrating the structure-activity relationship of the 6-position[a].

Due to the scarcity and costs of commercially available di- and trisubstituted anilines along with the awareness that 3-estersubstituted 4(1H)-quinolones 6a and 6c retained moderate blood stage activity, a set of compounds were synthesized, in which the 7- or 6-position was probed (FIGS. 9-10). Considering possible metabolic instabilities of the 2-phenoxyethoxy substituent in 4(1H)-quinolone 6b, analogue 6j was designed in which one of the oxygens in the 7-(2-phenoxyethoxy) moiety was replaced by a methylene unit. Compound 6j, which in comparison to analogue 6a was 4 times more active against W2 with an EC50 of 0.711 nM, displayed a greater than 10-fold drop in activity against TM90-C2B. This was mirrored in the *P. berghei* activities where there was an 18-fold drop in the activity of 6j as compared to the reference 6a, from EC50 values of 0.286 nM in 6a to 5.26 nM in 6j. The length of the alkyl chain linker was also shortened in hopes of improvement similar to 4(1H)-quinolone 6j; however, analogues 6i, 6h, and 6k were all less active than the reference 6a. Finally, in order to test electronic and steric effects, 4(1H)-quinolones substituted in the 7-position with phenyl, chloro, and fluoro functionalities were tested. 7-Chloro and 7-phenyl substituents were not tolerated, as compounds 6l and 6m were devoid of antimalarial activity, whereas 7-fluoro-4(1H)-quinolone 6n was active against W2 and TM90-C2B with EC50 values of 26.2 nM and 395 nM, respectively.

A similar study was conducted investigating possible moieties in the quinolone's 6-position. The reference compound 6c, which maintains the 6-butyl substituent, proved to be the most active compound of this set, with EC50 values of 1.58 nM for W2, 222 nM for TM90-C2B, and 0.819 nM for *P. berghei*. Among the other compounds tested, substituents derived from the 2-phenoxyethoxy group were shown to be the most potent analogues. Compound 6e, containing the benzyloxy substituent in the 6-position, was the most active analogue against W2, TM90-C2B, and *P. berghei* with EC50 values equaling 11.6 nM, 1100 nM, and 127 nM, respectively. Compounds 6f and 6g, analogues which increase the alkyl chain linker length in comparison to 6e, were the only other analogues of this subseries displaying EC50 with double-digit nM activity against W2. Overall, with the exception of 6-phenyl-substituted 4(1H)-quinolone 6u, which was devoid of activity, probing of the six position gave mediocre compounds leading to the belief that it was overall less tolerant of structural variation than the 7-position.

Figure 18:
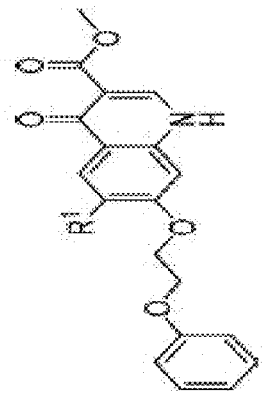
FIG. 18 shows a table demonstrating the effect of aliphatic chain length in 6-Position[a].

In a subseries of close analogues, the optimal length of the 6-alkyl residue was investigated (FIG. 18), leading to the design of compounds 6ac, 6w, 6x, and 6y. 7-Methyl-substituted 4(1H)-quinolone 6ac had modest activity with an EC50 of 2.01 nM for W2, an EC50 of 499 nM for TM90-C2B, and Pb EC50 of 152 nM. Antimalarial potency increased as the number of methylene units were added until the alkyl chain length reached four carbons and decreased as the chain length grew past four carbons, suggesting that the original 6-butyl substituent of 6b was optimal. In general, all compounds in this subseries were potent with most displaying subnanomolar EC50 values for W2 and with the 6-butylsubstituted 4(1H)-quinolone being the most potent.

Figure 19:
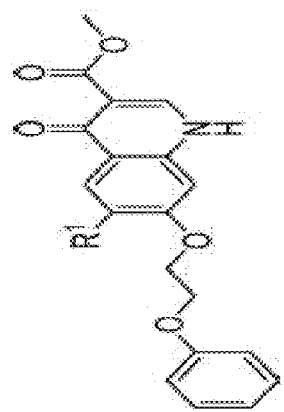
FIG. 19 shows a table demonstrating the structure-activity relationship of 6-position using electron withdrawing and donating groups[a].

In the same vein, analogues in FIG. 19 were designed to probe the same steric and electronic effects of the 6-position. 6-Chloro and 6-bromo compounds, 6ab and 6z, possessed moderate activity with 6ab having an EC50 of 9.93 nM and 617 nM for W2 and TM90-C2B, while 6z had EC50 values of 4.47 nM and 847 nM for W2 and TM90-C2B. Both 6-chloro and 6-bromo compounds, 6ab and 6z, also displayed subnanomolar P. berghei EC50 values of 0.063 nM and 0.336 nM, respectively. Interestingly, 6-methoxy-7-phenoxyethoxy-substituted 4(1H)-quinolone 6aa had an RI of 1.60 with good activities for both blood and liver stages. It was also observed by the direct comparison pairs between compound 6aa and its 7-phenoxyethoxy-omitted analogue 60 and between 6-chloro 4(1H)-quinolone 6ab and its 7-phenoxyethoxy-omitted analogue 6r that the addition of the 7-(2-phenoxyethoxy) group increases the activity for W2 by >60-fold and >130-fold for TM90-C2B.

Following the 6- and 7-positions, the 3-position was probed. A possible metabolite of ester 6b is acid 7b. Therefore, it was synthesized in order to see whether it could be the active form of the compound. With activities of 64.0 nM for W2, 1110 nM for TM90-C2B, and 0.267 nM for Pb, it was not as active as its parent; however, all activity was not lost. Ethyl ester 6af showed potent activity, with aW2 EC50 value of 0.143 nM, and was active against P. berghei with a subnanomolar EC50. Converting the ester to an amide dropped activity slightly. Methylamide 13a was the most active at 13.3 nM for W2 and at 3980 nM for TM90-C2B. As the alkyl chain increased in size, activity decreased with isopropylamide 13e being completely inactive with EC50 values in the μM range. Also, when each amide is compared to its ester counterpart, the ester is in all cases significantly more active. The 2-cyano-substituted compound 6ad had W2 activity in the high double-digit nM range. When the ester was converted to ketone 6ag, the activity dropped by almost 250-fold for W2 moving to 9.67 nM; the change for TM90-C2B was not as pronounced, however, with only a 48-fold difference. Lastly, complete removal of the ketone leaving just an alkyl chain, as with compound 6ae, was potent, having an EC50 of 0.440 nM for W2, 1.92 nM for TM90-C2B, and 2.65 for P. berghei. With an RI of 4.36, it showed once again that removal of the ester left compounds with improved RIs (FIG. 20). Unfortunately, compound 6ae displayed cytotoxicity with an EC50 value of 360 nM against J774.

Figure 21:
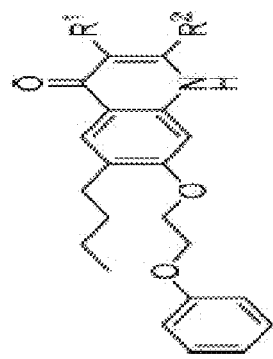
FIG. 21 shows a table demonstrating the 3-halo0substitued (4(1H)-Quinolones with and without 2-Methyl Groups[a].

3-Iodo-substituted 4(1H)-quinolone 16b was synthesized with the intention of replacing the 2-methyl ester substituent with a polarizable group. Interestingly, its testing gave an active compound having EC50 values of 1.23 nM for W2 and 6.04 nM for TM90-C2B with an RI of 4.91 (FIG. 21). Other 3-halo analogues were made, with and without a 2-methyl group. 3-Iodo-2-methyl-4(1H)-quinolone 16a was approximately 2-fold more potent than its reference 16b. The 3-bromo 4(1H)-quinolone 16d and its 2-methyl analogue 16c were slightly less potent than their 3-iodo counterparts with W2 activities of 4.64 nM and 2.60 nM, respectively, and TM90-C2B activities of 48.7 nM and 12.2 nM, respectively. 3-Chloro-2-methyl analogue 16e had EC50 values of 6.92 nM for W2 and 67.7 nM for TM90-C2B with an RI of 9.79. Overall, the 3-halo-substituted subseries followed the trend that the 2-methyl substituted analogues were approximately 2-fold more active than the 2-hydrogen analogues, and with RIs of 4.69-10.5, all five 3-halo substituted PEQs 16a-e consistently had the best RI values identified thus far.

Correlation Between Blood Stage Activity Liver Stage Activity.

In general, 7-phenoxyethoxy-substituted 4(1H)-quinolones display potent in vitro liver stage activity with lownanomolar to subnanomolar EC50 values. The most potent 4(1H)-quinolone esters 6a, 6b, 6c, 6y, and 6af as well as the medium potent compounds follow an activity order similar to the ranking observed for W2 and TM90-C2B, whereby the EC50 values for TM90-C2B are approximately 20- to 200-fold higher than the EC50 values for W2 or in vitro liver stage activity. In order to quantify how efficiently compounds target the liver stages in comparison to the blood stages, a liver blood index (LBI) has been calculated, which is the ratio of the effective concentrations needed to kill 50% of the population of parasites (EC50) for TM90-C2B and W2 strains (LBIC2B=(EC50 TM90-C2B)/(EC50 Pb or LBIW2)=(EC50 TM90-C2B)/(EC50 Pb)).

Aqueous Solubility and Lipophilicity.

In parallel to testing the compounds for in vitro antimalarial activity, a limited structure-property relationship (SPR) study focusing on log D and aqueous solubility was conducted to assess potential physiochemical liabilities (FIG. 22). Solubility at pH 6.5 was determined using an in-house HPLC assay based on UV absorption.24 The log D7.4, the distribution coefficient between octanol and water at pH 7.4, was experimentally determined via a previously described HPLCbased method.37 Overall, solubility continued to be a problem persistent throughout the study, with 13d being the only compound to reach a solubility of greater than 20 μM at any given pH. Along the same lines, the majority of the compounds **displayed a log D7.4 similar to the starting point 6b. For these reasons, physicochemical properties were not strongly considered as selection criteria for in vivo efficacy studies.

In Vivo Efficacy Evaluation of Selected Compounds.

The 12 4(1H)-quinolones with potent in vitro activity against blood stages of P. falciparum were chosen to be screened for in vivo efficacy according to a previously reported P. berghei infected mouse model (FIG. 23).[12] Criteria such as in vitro blood stage activity, in vitro liver stage activity, compound availability, and to a limited extent also physicochemical property data were considered for the selection of the screening candidates 6b, 6e, 6f, 6g, 6j, 6k, 6i, 6ab, 6ae, 13d, 16a, and 16c. The RI values were considered a secondary discrimination factor as most of the presented compounds are extremely potent. The screening was performed by treating two infected mice with a single 50 mg/kg oral dose of test compound suspended in PEG400 on day 1 postexposure (PE) followed by assessing parasitemia on days 3 and 6 PE. Compounds with a parasitemia reduction of greater than 50% on days 3 and 6 PE were considered to be active. The original compound 6b was one of the most active candidates in the group with 76.9% inhibition on day 3 PE and 49% inhibition on day 6 PE (FIG. 23). Quinolone ester 6j and 3-bromo-4(1H)-quinolone 16c were the only other two compounds that displayed a parasitemia reduction similar to the original compound 6b with 47.1% and 49.5% inhibition on day 6 PE. Analogues 6g and 6ae with >65% inhibition on day 3 PE were considered promising, nevertheless, the lack of significant parasitemia reduction on day 6 PE suggested that these compounds may suffer from insufficient bioavailability. A similar outcome has been observed for the previously reported 3-arylsubstituted 6-chloro-7-methoxy-4(1H)-quinolones compound series, for which a long half-life has been detrimental to the development of curative antimalarials.[12]

The two frontrunner compounds, 6b and 16c, displaying the best in vivo efficacy were subjected to a more rigorous in vivo efficacy testing in a modified Thompson test (FIG. 24).[12-14,16] By use of mice infected with 1×106 *Plasmodium berghei*-GFP parasites, compounds were dosed orally on days 3, 4, and 5 at a 10 mg/kg concentration of compound suspended or dissolved in HEC/Tween. On days 3, 6, 9, 13, 21, and 30 PE, parasitemia was monitored by Giemsa-stained blood smears. Both compounds were evaluated by the reduction of parasitemia on day 6 PE and the survival up to day 30 PE. Compound 6b showed no inhibition on day 6 PE, and mice were sacrificed on day 13, the same day as the controls. In comparison to the original compound 6b, 3-bromo-4(1H)-quinolone 16c is approximately 10-fold more soluble, which possibly improved the in vivo efficacy to 61% inhibition on day 6 PE. Nevertheless, parasitemia rapidly rebounded so that mice dosed with compound 16c were sacrificed on day 13 PE.

SUMMARY

In this example, a library of 46 4(1H)-quinolones with a variety of substituents was synthesized, and focus was put primarily on the 3-, 6-, and 7-positions. All compounds were tested in vitro against the two clinically relevant *P. falciparum* strains W2 and TM90-C2B. Furthermore, example compounds with promising activity against W2 and TM90-C2B were evaluated for in vitro liver stage activity against *P. berghei*. Overall, this 4(1H)-quinolone series displays potent erythrocytic and exoerythrocytic activity with many compounds displaying low nanomolar EC50 values. The vast majority of the 4(1H)-quinolones were also shown to be nontoxic in J774 cytotoxicity assays with EC50>20 µM. However, most compounds were not in vivo efficacious, most likely due to poor aqueous solubility and low oral bioavailability.

It was shown that the 3-ester group is very important in addressing atovaquone cross-resistance since 3-halide compounds 16a-e had excellent RI values. It was also determined that the 6 and 7 positions are important for blood stage activity due to the combination of the 6- and 7-substituted compounds being much more active than the 6- or 7-substituted compounds separately. Compounds 6b and 16c were both tested in vivo using a modified Thompson test. There was a marked increase in the parasite inhibition for compound 16c over 6b on day 6 PE showing significant improvements over the original compound 6b. Although bromo-substituted 4(1H)-quinolone 16c showed less in vitro blood and in vitro liver stage activity than the predecessor 6b, the in vivo activity of 16c on day 6 PE clearly proved its superiority overall. The blood and liver stage activities of these quinolone esters along with the discovery of the 3-halo-4(1H)-quinolones lead us to postulate that there is still much potential in this scaffold and further optimization of solubility and stability could lead to orally bioavailable, curative agents with activity across the full spectrum of malaria life cycle stages.

Experimental Section

General.

General. All reagents and solvents were obtained from Aldrich Chemical Co. and used without further purification. NMR spectra were recorded at ambient temperature on a 400 or 500 MHz Varian NMR spectrometer in the solvent indicated. All 1H NMR experiments are reported in δ units, parts per million (ppm) downfield of TMS, and were measured relative to the signals of chloroform (7.26 ppm) and dimethylsulfoxide (39.5 ppm) with 1H decoupled observation. Data for 1HNMR are reported as follows: chemicals shift (δ ppm), multiplicity (s=singlet, d=doublet, t=triplet, q=quartet, p=pentet, sext=sextet, sept=septet, oct=octet, m=multiplet), integration, and coupling constant (Hz), whereas 13C NMR analyses were reported in terms of chemical shift. NMRdata were analyzed by using MestReNova software, version 6.0.2-5475. The purity of the final compounds was determined to be ≥95% by high-performance liquid chromatography (HPLC) using an Agilent 1100 LC/MSD-VL with electrospray ionization. Low resolution mass spectra were acquired on an Agilent 1100 LC/MSD-VL with electrospray ionization. High-resolution mass spectra (HRMS) were acquired on an Agilent LC/MSD TOF system G3250AA. Analytical thin layer chromatography (TLC) was performed on silica gel 60 F254 precoated plates (0.25 mm) from EMD Chemical Inc., and components were visualized by ultraviolet light (254 nm). EMD silica gel 230-400 (particle size 40-63 µm) mesh was used for all flash column chromatography. Microwave heating was performed in a singlemode Anton Paar Monowave 300, and all microwave-irradiated reactions were conducted in heavy-walled glass vials sealed with Teflon septa.

All in vivo studies were conducted in compliance with the Guide for the Care and Use of Laboratory Animals of the National Research Council. The protocol was approved by the University of South Florida Institutional Animal Care and Use Committee.

General Procedure A.

Aniline (5 mmol) and dimethyl methoxy methylene malonate (7.6 mmol) were added to a flask and heated to 110° C. for 30 min (monitored by TLC). After cooling, diethyl ether was added at which point precipitation occurred. This solid was collected by filtration and used in the next step without further purification.

General Procedure B.

Enamine intermediate (5.8 mmol) was added to toluene (11.6 mL) and heated in a microwave reactor for 5 min at 270° C. The precipitated product was filtered and washed with cold methanol. The solid residue was in most cases recrystallized in 4:1 MeOH/DMF to afford the final product.

General Procedure C.

An ester (4 mmol) was refluxed for 2 h in 10% NaOH (10 mL) solution. It was then cooled and acidified to pH 5 where the precipitate was filtered and washed with water. It was dried and used in the next step without further purification.

General Procedure D.

A carboxylic acid (5 mmol) and toluene (10 mL) were refluxed in a microwave for 5 min at 280° C. Diethyl ether was added to the reaction, and the resulting precipitate was collected and washed with cold methanol.

General Procedure E.

To N-(3-hydroxyphenyl)acetamide (15 mmol) was added (2-bromoethoxy)benzene (19.5 mmol) along with Cs2CO3 (45 mmol) and DMF (30 mL). The reaction was heated at 40° C. overnight. The reaction was extracted with DCM, dried over Na2SO4, filtered, and concentrated under reduced pressure. The crude product was recrystallized in hexanes/ethyl acetate.

General Procedure F.

An acetamide (4 mmol) along with KOH (40 mmol) and 9:1 DI water/ethanol (50 mL) was refluxed overnight. After the reaction was complete, the ethanol was removed under reduced pressure. The residue was then dissolved in DCM washed with DI water, dried over Na2SO4, filtered, and concentrated under reduced pressure. The resulting oil could then be used without further purification in most cases. If not, aqueous HCl was added and the solution was washed with EA. The aqueous layer was basified and then washed with EA, and the organic layer was dried over Na2SO4, filtered, and concentrated under reduced pressure.

General Procedure G.

An amine or amine hydrochloride (0.76 mmol) and trimethylaluminum (0.8 mL) were added dropwise at 0° C. The reaction was then stirred at room temperature for 30 min. At that time, 6b (0.38 mmol) was added as a solid and the reaction was allowed to reflux overnight. The reaction was purified using preparative HPLC to yield the title compound.

General Procedure H.

Quinolone (1 mmol) and N-halo succinimide (2.2 mmol) were refluxed in DMF (5 mL) for 2 h. The reaction was concentrated, and water was added. The resulting precipitate was filtered and recrystallized in acetone.

General Procedure I.

An alkyne substituted nitrobenzene was added with palladium on carbon and ethyl acetate to a hydrogenation flask. The flask was shaken under 60 psi hydrogen gas for 24 h. The reaction mixture was filtered over Celite and concentrated under reduced pressure. The title compound was isolated via flash chromatography.

N-(3-(2-Phenoxyethoxy)phenyl)acetamide 2a 2a was synthesized following general procedure E in 91% yield. 1H NMR (400 MHz, DMSO) δ 9.94 (s, 1H), 7.37 (s, 1H), 7.35-7.26 (m, 2H), 7.26-7.10 (m, 2H), 7.02-6.91 (m, 3H), 6.66 (dd, J=8.1, 1.5 Hz, 1H), 4.27 (td, J=5.2, 3.5 Hz, 4H), 2.05 (s, 3H). 13C NMR (101 MHz, DMSO) δ 168.44, 158.60, 158.33, 140.56, 129.56, 120.78, 114.50, 111.63, 108.85, 105.61, 66.27, 66.17, 24.11. HRMS (ESI-TOF) m/z: [M+H]+ calcd for C16H17NO3 272.1281; found 272.1284.

N-(4-(Benzyloxy)phenyl)acetamide 2c 2c was synthesized following general procedure E in 98% yield. 1H NMR (400 MHz, DMSO) δ 9.80 (s, 1H), 7.53-7.47 (m, 2H), 7.45-7.41 (m, 2H), 7.41-7.35 (m, 2H), 7.34-7.29 (m, 1H), 6.97-6.92 (m, 2H), 5.05 (s, 2H), 2.02 (s, 3H). 13C NMR (101 MHz, DMSO) δ 167.73, 154.07, 137.19, 132.76, 128.36, 127.73, 127.63, 120.50, 114.76, 69.35, 23.80. HRMS (ESI-TOF) m/z: [M+H]+ calcd for C15H15NO2 242.1176; found 242.1200.

N-(4-(3-Phenylpropoxy)phenyl)acetamide 2e 2e was synthesized following general procedure E in 94% yield. 1H NMR (400 MHz, DMSO) δ 9.79 (s, 1H), 7.51-7.45 (m, 2H), 7.31-7.14 (m, 5H), 6.88-6.82 (m, 2H), 3.90 (t, J=6.4 Hz, 2H), 2.78-2.68 (m, 2H), 2.05-1.94 (m, 5H). 13C NMR (101 MHz, DMSO) δ 167.62, 154.33, 141.39, 132.50, 128.31, 128.30, 125.79, 120.44, 114.39, 66.75, 31.48, 30.44, 23.76. HRMS (ESI-TOF) m/z: [M+H]+ calcd for C17H19NO2 270.1489; found 270.1471.

N-(3-(Benzyloxy)phenyl)acetamide 2f 2f was synthesized following general procedure E in 98% yield. 1H NMR (400 MHz, DMSO) δ 9.91 (s, 1H), 7.46-7.42 (m, 2H), 7.42-7.36 (m, 3H), 7.35-7.29 (m, 1H), 7.18 (t, J=8.1 Hz, 1H), 7.11 (dt, J=8.1, 1.3 Hz, 1H), 6.71-6.66 (m, 1H), 5.06 (s, 2H), 2.03 (s, 3H). 13C NMR (101 MHz, DMSO) δ 168.76, 159.00, 140.95, 137.50, 129.88, 128.85, 128.22, 128.07, 111.97, 109.55, 106.23, 69.53, 24.52. HRMS (ESI-TOF) m/z: [M+H]+ calcd for C15H15NO2 242.1176; found 242.1162.

N-(3-(3-Phenylpropoxy)phenyl)acetamide 2h 2h was synthesized following general procedure E in 99% yield. 1H NMR (400 MHz, CDCl3) δ 9.24 (s, 1H), 7.37 (d, J=1.9 Hz, 1H), 7.26-7.21 (m, 2H), 7.16-7.11 (m, 5H), 6.59 (dt, J=7.4, 2.1 Hz, 1H), 3.86 (t, J=6.3 Hz, 2H), 2.76-2.68 (m, 2H), 2.12 (s, 3H), 2.00 (tt, J=12.9, 6.3 Hz, 2H). 13C NMR (101 MHz, CDCl3) δ 169.18, 159.14, 141.22, 139.59, 129.15, 128.17, 128.08, 125.58, 111.96, 109.85, 106.19, 66.54, 31.79, 30.52, 24.01. HRMS (ESI-TOF) m/z: [M+H]+ calcd for C17H19NO2 270.1489; found 270.1464.

4-(Benzyloxy)aniline 3e 3e was synthesized following general procedure F in 93% yield. 1 HNMR (400 MHz, CDCl3) δ 7.46-7.36 (m, 4H), 7.35-7.30 (m, 1H), 6.86-6.81 (m, 2H), 6.67-6.62 (m, 2H), 5.00 (s, 2H), 3.31 (s, 2H). 13C NMR (101 MHz, CDCl3) δ 152.04, 140.31, 137.58, 128.57, 127.86, 127.57, 116.46, 116.14, 70.85.

4-(3-Phenylpropoxy)aniline 3g 3g was synthesized following general procedure F in 98% yield. 1HNMR (400 MHz, CDCl3): δ 7.29-7.16 (m, 5H), 6.75-6.60 (m, 4H), 3.88 (t, J=6.4 Hz 2H), 3.40 (s, 2H), 2.79 (t, J=7.4 Hz 2H), 2.06 (dt, J=7.4/6.4 Hz 2H). 13C NMR (100 MHz, CDCl3): δ 152.2, 141.6, 139.9, 128.5, 128.3, 125.8, 116.4, 115.7, 67.6, 32.1, 30.9. HRMS (ESI-TOF) m/z: [M+H]+ calcd for C15H17NO 227.1310; found 227.1310.

3-(Benzyloxy)aniline 3h 3h was synthesized following general procedure E in 91% yield. 1HNMR (500 MHz, CDCl3) δ 7.47 (d, J=7.1 Hz, 2H), 7.45-7.39 (m, 2H), 7.36 (dd, J=8.3, 6.1 Hz, 1H), 7.10 (t, J=8.0 Hz, 1H), 6.48-6.42 (m, 1H), 6.38-6.31 (m, 2H), 5.05 (s, 2H), 3.67 (s, 2H). 13C NMR (126 MHz, CDCl3) δ 160.05, 147.89, 137.29, 130.19, 128.61, 127.93, 127.52, 108.24, 104.88, 102.05, 69.86. HRMS (ESI) calcd for C13H13NO [M+H]+ 200.1070; found 200.1094.

3-(3-Phenylpropoxy)aniline 3j 3j was synthesized following general procedure E in 89% yield. 1H NMR (500 MHz, CDCl3) δ 7.30 (t, J=7.5 Hz, 2H), 7.22 (dd, J=12.6, 7.1 Hz, 3H), 7.06 (t, J=8.0 Hz, 1H), 6.33 (dd, J=8.2, 2.2 Hz, 1H), 6.29 (dd, J=7.9, 1.9 Hz, 1H), 6.25 (t, J=2.1 Hz, 1H), 3.93 (t, J=6.3 Hz, 2H), 3.65 (s, 2H), 2.89-2.75 (m, 2H), 2.10 (dd, J=14.8, 6.6 Hz, 2H). 13C NMR (126 MHz, CDCl$_3$) δ 160.28, 147.84, 141.69, 130.16, 128.63, 128.49, 125.99, 107.93, 104.75, 101.76, 66.74, 32.26, 30.96. HRMS (ESI) calcd for C15H17NO[M+H]+ 228.1383; found 228.1356.

3-(2-Phenoxyethoxy)-4-propylaniline 3x 3x was synthesized from 12b following general procedure I, and the crude product was used without further purification.

4-Pentyl-3-(2-phenoxyethoxy)aniline 3y 3y was synthesized from 12c following general procedure I and the crude product was used without further purification.

4-Bromo-3-(2-phenoxyethoxy)aniline 3z

To a solution of 1-bromo-4-nitro-2-(2-phenoxyethoxy) benzene (572 mg, 1.6916 mmol) in ethanol (5 mL) were added zinc powder (1.1 g, 16.916 mmol) and acetic acid (0.97 mL, 16.916 mmol) at 0° C. The solution was allowed to warm to room temperature and stirred until the disappearance of the starting material was observed as indicated by TLC (4 h). The reaction solution was filtered through Celite and then concentrated under reduced pressure. The residue was dissolved in DCM (10 mL), washed with sodium bicarbonate, DI water, and brine, dried over Na2SO4, filtered, and concentrated under reduced pressure. The crude product was purified by flash chromatography to give the 3z (486 mg, 93% yield). 1H NMR (400 MHz, DMSO) δ 7.33-7.26 (m, 2H), 7.11 (d, J=8.5 Hz, 1H), 7.02-6.98 (m, 2H), 6.97-6.92 (m, 1H), 6.37 (d, J=2.4 Hz, 1H), 6.13 (dd, J=8.5, 2.4 Hz, 1H), 5.28 (s, 2H), 4.35-4.28 (m, 2H), 4.27-4.21 (m, 2H). 13C NMR (101 MHz, DMSO) δ 158.33, 154.94, 149.78, 132.68, 129.51, 120.76, 114.62, 108.01, 99.83, 95.55, 67.11, 66.20. HRMS (ESI) calcd for C14H14BrNO2 [M+H]+ 308.0281; found 308.0268.

4-Methoxy-3-(2-phenoxyethoxy)aniline 3aa

To a solution of 1-methoxy-4-nitro-2-(2-phenoxyethoxy) benzene (3.2 mmol) in ethanol (10 mL) were added zinc powder (32 mmol) and acetic acid (32 mmol) at 0° C. The solution was allowed to warm to room temperature and stirred until the disappearance of the starting material was observed as indicated by TLC (4 h). The reaction solution was filtered through Celite and then concentrated under reduced pressure. The resulting residue was dissolved in DCM, washed with sodium bicarbonate, DI water, and brine, dried over Na2SO4, filtered, and concentrated under reduced pressure. The residue was purified by flash chromatography to give 3aa in 62% yield. 1H NMR (399 MHz, CDCl$_3$) δ 7.33-7.26 (m, 2H), 6.95 (d, J=9.0 Hz, 3H), 6.73 (d, J=8.5 Hz, 1H), 6.40 (d, J=2.6 Hz, 1H), 6.28 (dd, J=8.4, 2.6 Hz, 1H), 4.34 (s, 4H), 3.79 (s, 3H), 3.44 (bs, 2H). 13C NMR (100 MHz, CDCl$_3$) δ 158.72, 142.98, 140.68, 133.86, 129.58, 121.10, 114.77, 114.34, 107.77, 103.41, 67.69, 66.38, 57.08.

4-Chloro-3-(2-phenoxyethoxy)aniline 3ab

3ab was synthesized following general procedure F in 87% yield. 1H NMR (500 MHz, CDCl$_3$) δ 7.36-7.28 (m, 2H), 7.11 (d, J=8.4 Hz, 1H), 7.03-6.95 (m, 3H), 6.33 (d, J=2.5 Hz, 1H), 6.25 (dd, J=8.4, 2.5 Hz, 1H), 4.39-4.27 (m, 4H), 3.68 (s, 2H). 13C NMR (126 MHz, CDCl$_3$) δ 158.58, 154.77, 146.39, 130.59, 129.53, 121.16, 114.81, 112.30, 108.61, 101.72, 67.74, 66.33.

4-Methyl-3-(2-phenoxyethoxy)aniline 3ac

To a flame-dried flask were added 1-methyl-4-nitro-2-(2-phenoxyethoxy)benzene (10 mmol) and SnCl2 (40 mmol) and 300 mL of ethanol. The reaction was refluxed for 3 h. The EtOH was removed, and 4MKOH was added until basic, and the reaction was extracted with EA. The reaction was then dried and concentrated to give the title compound in 75% yield. 1H NMR (500 MHz, CDCl$_3$) δ 7.33 (t, J=8.0 Hz, 2H), 7.01 (t, J=7.7 Hz, 3H), 6.94 (d, J=7.6 Hz, 1H), 6.30-6.23 (m, 2H), 4.37-4.32 (m, 2H), 4.30-4.26 (m, 2H), 3.54 (s, 2H), 2.15 (s, 3H). 13C NMR (126 MHz, CDCl$_3$) δ 158.82, 157.54, 145.56, 131.23, 129.58, 121.10, 117.13, 114.83, 107.55, 100.01, 66.81, 66.64, 15.48. HRMS (ESI) calcd for C15H17NO2 [M+H]+ 244.1332; found 244.1320.

Dimethyl 2-(((3-(2-Phenoxyethoxy)phenyl)amino)-methylene)malonate 5a 5a was synthesized following general procedure A in 86% yield. 1H NMR (400 MHz, DMSO) δ 10.69 (d, J=13.9 Hz, 1H), 8.44 (d, J=13.9 Hz, 1H), 7.30 (tt, J=8.1, 2.5 Hz, 3H), 7.06 (t, J=2.2 Hz, 1H), 7.02-6.91 (m, 4H), 6.78 (dd, J=8.2, 2.2 Hz, 1H), 4.37-4.33 (m, 2H), 4.32-4.28 (m, 2H), 3.73 (s, 3H), 3.66 (s, 3H). 13C NMR (101 MHz, DMSO) δ 167.57, 165.25, 159.40, 158.26, 151.40, 140.63, 130.57, 129.52, 120.74, 114.45, 111.07, 109.85, 104.15, 92.72, 66.53, 66.08, 51.12, 51.09. HRMS (ESI-TOF) m/z [M+H]+ calcd for C20H21NO6 372.1442; found 372.1429.

Dimethyl 2-((Phenylamino)methylene)malonate 5d 5d was synthesized following general procedure A in quantitative yield. 1H NMR (399 MHz, DMSO) δ 10.75 (d, J=14.0 Hz, 1H), 8.43 (d, J=14.0 Hz, 1H), 7.41-7.30 (m, 4H), 7.15 (t, J=6.8 Hz, 1H), 3.72 (s, 3H), 3.66 (s, 3H). 13CNMR (100 MHz, DMSO) δ 167.74, 165.30, 151.60, 139.37, 129.63, 124.76, 117.66, 92.55, 51.10, 51.07.

Dimethyl 2-(((4-(Benzyloxy)phenyl)amino)methylene)-malonate 5e 5e was synthesized following general procedure A in 89% yield. 1H NMR (400 MHz, CDCl$_3$) δ 11.00 (d, J=13.9 Hz, 1H), 8.43 (d, J=13.9 Hz, 1H), 7.45-7.29 (m, 5H), 7.09-7.03 (m, 2H), 6.99-6.93 (m, 2H), 5.03 (s, 2H), 3.84 (s, 3H), 3.76 (s, 3H). 13C NMR (101 MHz, CDCl$_3$) δ 169.51, 166.05, 156.44, 152.87, 136.64, 132.84, 128.64, 128.11, 127.45, 118.89, 116.07, 91.94, 70.38, 51.52, 51.37.

Dimethyl 2-(((4-Phenethoxyphenyl)amino)methylene)-malonate 5f 5f was synthesized following general procedure A in 96% yield. 1H NMR (500 MHz, CDCl$_3$) 1H NMR (500 MHz, CDCl$_3$) δ 11.02 (d, J=13.8 Hz, 1H), 8.46 (d, J=13.9 Hz, 1H), 7.37-7.23 (m, 5H), 7.08 (d, J=8.9 Hz, 2H), 6.91 (d, J=8.9 Hz, 2H), 4.17 (t, J=7.1 Hz, 2H), 3.86 (s, 3H), 3.78 (s, 3H), 3.11 (t, J=7.1 Hz, 2H). 13C NMR (126 MHz, CDCl$_3$) δ 169.67, 166.23, 156.65, 153.06, 138.12, 132.76, 129.10, 128.65, 126.71, 119.02, 115.83, 91.94, 69.21, 51.66, 51.51, 35.88.

Dimethyl 2-(((3-(Benzyloxy)phenyl)amino)methylene)-malonate 5h 5h was synthesized following general procedure A in 97% yield. 1H NMR (400 MHz, CDCl$_3$) δ 10.97 (d, J=13.7 Hz, 1H), 8.47 (d, J=13.7 Hz, 1H), 7.42-7.28 (m, 5H), 7.25-7.20 (m, 1H), 6.72 (d, J=1.4 Hz, 1H), 6.75-6.68 (m, 2H), 5.02 (s, 2H), 3.82 (s, 3H), 3.75 (s, 3H). 13C NMR (101 MHz, CDCl$_3$) δ 169.22, 165.76, 159.97, 151.98, 140.28, 136.40, 130.67, 128.60, 128.09, 127.42, 111.08, 109.84, 104.18, 92.95, 70.09, 51.53, 51.38. HRMS (ESI) [M+H]+ calcd for C19H19NO5 342.1336; found 342.1319.

Dimethyl 2-(((3-Phenethoxyphenyl)amino)methylene)-malonate 5i 5i was synthesized following general procedure A in 97% yield. 1H NMR (400 MHz, CDCl$_3$) δ 10.78 (d, J=13.7 Hz, 1H), 8.29 (d, J=13.8 Hz, 1H), 7.13-7.01 (m, 6H), 6.53-6.42 (m, 3H), 3.96 (t, J=7.0 Hz, 2H), 3.63 (s, 3H), 3.56 (s, 3H), 2.88 (t, J=7.0 Hz, 2H). 13C NMR (101 MHz, CDCl$_3$) δ 169.39, 165.99, 160.17, 152.19, 140.35, 138.02, 130.75, 129.04, 128.61, 126.68, 110.96, 109.72, 104.05, 92.98, 68.93, 51.67, 51.54, 35.77.

Dimethyl 2-(((3-(3-Phenylpropoxy)phenyl)amino)methylene)malonate 5j 5j was synthesized following general procedure A in 96% yield. 1H NMR (500 MHz, CDCl$_3$) δ 11.01 (d, J=13.7 Hz, 1H), 8.54 (d, J=13.8 Hz, 1H), 7.37-7.16 (m, 6H), 6.78-6.65 (m, 3H), 3.98 (t, J=6.2 Hz, 2H), 3.87 (s, J=0.5 Hz, 3H), 3.80 (s, J=0.6 Hz, 3H), 2.83 (t, J=7.6 Hz, 2H), 2.17-2.09 (m, 2H). 13C NMR (126 MHz, CDCl$_3$) δ 169.47, 166.04, 160.41, 152.29, 141.38, 140.38, 130.79, 128.60, 128.57, 126.12, 111.07, 109.63, 104.01, 92.97, 67.19, 51.73, 51.59, 32.19, 30.82.

Dimethyl 2-(((3-Chlorophenyl)amino)methylene)malonate 5l 5l was synthesized following general procedure A in 75% yield. 1H NMR (500 MHz, CDCl$_3$) δ 11.01 (d, J=13.2 Hz, 1H), 8.48 (d, J=13.6 Hz, 1H), 7.30 (t, J=8.1 Hz, 1H), 7.20-7.09 (m, 2H), 7.02 (dd, J=8.1, 1.5 Hz, 1H), 3.86 (s, 3H), 3.79 (s, 3H). 13C NMR (126 MHz, CDCl$_3$) δ 169.35, 165.81, 151.81, 140.46, 135.84, 131.03, 125.12, 117.39, 115.61, 94.10, 51.89, 51.74.

Dimethyl 2-(([1,1'-Biphenyl]-3-ylamino)methylene)-malonate 5m 5m was synthesized from [1,1'-biphenyl]-3-amine following general procedure A in quantitative yield. 1H NMR (399 MHz, CDCl$_3$) δ 11.14 (d, J=14.2 Hz, 1H), 8.61 (d, J=13.7 Hz, 1H), 7.58 (d, J=7.3 Hz, 2H), 7.46 (q, J=14.7, 7.3 Hz, 3H), 7.39 (t, J=6.4 Hz, 2H), 7.34 (bs, 1H), 7.14 (d, J=7.6 Hz, 1H), 3.88 (s, 3H), 3.79 (s, 3H). 13C NMR (100 MHz, CDCl$_3$) δ 169.56, 166.12, 152.44, 143.38, 140.24, 139.70, 130.39, 129.06, 128.09, 127.30, 124.12, 116.30, 116.07, 93.17, 51.81, 51.67.

Dimethyl 2-(((3-Fluorophenyl)amino)methylene)malonate 5n 5n was synthesized following general procedure A in 39% yield. 1H NMR (400 MHz, CDCl$_3$) δ 11.01 (d, J=13.3 Hz, 1H), 8.46 (d, J=13.6 Hz, 1H), 7.32 (dd, J=14.3, 8.0 Hz, 1H), 6.93-6.80 (m, 3H), 3.84 (s, 3H), 3.77 (s, 3H). 13C NMR (101 MHz, CDCl$_3$) δ 169.31, 165.76, 163.71 (d, J=247.4 Hz), 151.81, 140.88 (d, J=9.8 Hz), 131.33 (d, J=9.5 Hz), 113.06, 111.85 (d, J=21.2 Hz), 104.58 (d, J=25.5 Hz), 93.99, 51.83 (s, J=15.0 Hz), 51.68.

Dimethyl 2-(((4-Methoxyphenyl)amino)methylene)-malonate 5o 5o was synthesized following general procedure A in 85% yield. 1H NMR (399 MHz, CDCl$_3$) δ 10.99 (d, J=13.7 Hz, 1H), 8.42 (d, J=13.9 Hz, 1H), 7.05 (d, J=8.9 Hz, 2H), 6.87 (d, J=8.9 Hz, 2H), 3.82 (s, 3H), 3.77 (s, 3H), 3.74 (s, 3H). 13C NMR (100 MHz, CDCl$_3$) δ 169.56, 166.10, 157.31, 152.95, 132.61, 118.94, 115.02, 91.80, 55.59, 51.57, 51.41.

Dimethyl 2-(((4-Ethoxyphenyl)amino)methylene)malonate 5p 5p was synthesized following general procedure A in 97% yield. 1H NMR (400 MHz, DMSO) δ 10.72 (d, J=14.1 Hz, 1H), 8.33 (d, J=14.1 Hz, 1H), 7.32-7.24 (m, 2H), 6.97-6.88 (m, 2H), 4.00-3.95 (m, 2H), 3.71 (s, 3H), 3.64 (s, 3H), 1.30 (t, J=7.0 Hz, 3H). 13C NMR (101 MHz, DMSO) δ 167.78, 165.37, 156.02, 152.22, 132.67, 119.38, 115.22, 91.32, 63.29, 50.93, 50.91, 14.58.

Dimethyl 2-(((4-Isopropylphenyl)amino)methylene)-malonate 5q 5q was synthesized following general procedure A in 96% yield. 1H NMR (400 MHz, DMSO) δ 10.74 (d, J=14.1 Hz, 1H), 8.41 (d, J=14.1 Hz, 1H), 7.32-7.21 (m, 4H), 3.72 (s, 3H), 3.65 (s, 3H), 2.87 (hept, J=6.9 Hz, 1H), 1.19 (s, 3H), 1.17 (s, 3H). 13C NMR (101 MHz, DMSO) δ 167.70, 165.31, 151.78, 145.12, 137.26, 127.40, 117.80, 91.96, 54.90, 51.03, 32.83, 23.82.

Dimethyl 2-(((4-Chlorophenyl)amino)methylene)malonate 5r 5r was synthesized following general procedure A in 56% yield. 1H NMR (400 MHz, DMSO) δ 10.68 (d, J=11.3 Hz, 1H), 8.38 (d, J=11.9 Hz, 1H), 7.42 (s, 4H), 3.73 (s, 3H), 3.66 (s, 3H). 13C NMR (101 MHz, DMSO) δ 167.75, 165.63, 151.66, 138.93, 129.80, 128.99, 119.94, 93.63, 51.61, 51.55.

Dimethyl 2-(((4-(4-Fluorophenoxy)phenyl)amino)methylene)malonate 5s 5s was synthesized following general procedure A in 86% yield. 1H NMR (400 MHz, CDCl$_3$) δ 11.02 (d, J=13.7 Hz, 1H), 8.44 (d, J=13.8 Hz, 1H), 7.11-7.06 (m, 2H), 7.05-6.98 (m, 2H), 6.98-6.91 (m, 4H), 3.83 (s, 3H), 3.75 (s, 3H). 13C NMR (101 MHz, CDCl$_3$) δ 169.58, 166.07, 159.05 (d, J=242.1 Hz), 155.18, 152.87 (d, J=2.6 Hz), 152.77, 134.81, 120.49 (d, J=8.3 Hz), 119.72, 119.04, 116.55 (d, J=23.4 Hz), 92.72, 51.72, 51.58.

Dimethyl 2-(((4-Ethylphenyl)amino)methylene)malonate 5t 5t was synthesized following general procedure A in 50% yield. 1HNMR (400 MHz, DMSO) δ 10.72 (d, J=14.1 Hz, 1H), 8.41 (d, J=14.1 Hz, 1H), 7.28 (d, J=8.5 Hz, 2H), 7.22 (d, J=8.5 Hz, 2H), 3.72 (s, 3H), 3.65 (s, 3H), 2.58 (q, J=7.6 Hz, 2H), 1.16 (t, J=7.6 Hz, 3H). 13C NMR (101 MHz, DMSO) δ 167.66, 165.31, 151.71, 140.49, 137.18, 128.87, 117.78, 91.97, 51.05, 51.03, 27.48, 15.57.

Dimethyl 2-(([1,1'-Biphenyl]-4-ylamino)methylene)-malonate 5u 5u was synthesized following general procedure A in 79% yield. 1H NMR (399 MHz, CDCl$_3$) δ 11.11 (d, J=13.8 Hz, 1H), 8.57 (d, J=13.8 Hz, 1H), 7.57 (dd, J=12.9, 8.0 Hz, 4H), 7.43 (t, J=7.6 Hz, 2H), 7.34 (t, J=7.3 Hz, 1H), 7.19 (d, J=8.5 Hz, 2H), 3.87 (s, 3H), 3.79 (s, 3H). 13C NMR (100 MHz, CDCl$_3$) δ 169.41, 165.94, 151.96, 139.89, 138.27, 138.01, 128.92, 128.44, 127.47, 126.79, 117.54, 93.03, 51.70, 51.55.

Dimethyl 2-(((4-Phenoxyphenyl)amino)methylene)malonate 5v 5v was synthesized following general procedure A in 93% yield. 1H NMR (399 MHz, DMSO) δ 10.75 (d, J=13.9 Hz, 1H), 8.38 (d, J=14.0 Hz, 1H), 7.47-7.35 (m, 4H), 7.13 (t, J=7.4 Hz, 1H), 7.08-6.96 (m, 4H), 3.72 (s, 3H), 3.65 (s, 3H). 13C NMR (100 MHz, DMSO) δ 167.59, 165.35, 156.88, 153.59, 135.37, 130.09, 123.43, 119.91, 119.77, 118.33, 92.16, 51.11, 51.09.

Dimethyl 2-(((4-Bromo-3-(2-phenoxyethoxy)phenyl)amino)-methylene)malonate 5z 5z was synthesized following general procedure A in 91% yield. 1H NMR (400 MHz, DMSO) δ 10.70 (d, J=13.8 Hz, 1H), 8.44 (d, J=13.8 Hz, 1H), 7.55 (d, J=8.6 Hz, 1H), 7.35-7.26 (m, 3H), 7.05-6.91 (m, 4H), 4.49-4.42 (m, 2H), 4.38-4.33 (m, 2H), 3.74 (s, 3H), 3.67 (s, 3H). 13C NMR (100 MHz, DMSO) 13C NMR (100 MHz, DMSO) δ 167.48, 165.29, 158.31, 155.32, 151.18, 140.25, 133.52, 129.55, 120.83, 114.62, 110.82, 106.06, 104.42, 93.28, 67.84, 66.09, 51.23.

Dimethyl 2-(((4-Methoxy-3-(2-phenoxyethoxy)phenyl)-amino)methylene)malonate 5aa 5aa was synthesized from 3aa following general procedure A in 78% yield. 1H NMR (500 MHz, CDCl$_3$) δ 11.03 (d, J=13.9 Hz, 1H), 8.45 (d, J=13.8 Hz, 1H), 7.29 (dd, J=8.7, 7.4 Hz, 2H), 6.99-6.93 (m, 3H), 6.87 (d, J=8.6 Hz, 1H), 6.79 (d, J=2.5 Hz, 1H), 6.74 (dd, J=8.6, 2.6 Hz, 1H), 4.42-4.38 (m, 2H), 4.38-4.35 (m, 2H), 3.86 (s, 3H), 3.85 (s, 3H), 3.77 (s, 3H). 13C NMR (100 MHz, CDCl$_3$) δ 169.68, 166.22, 158.60, 152.96, 149.25, 147.65, 132.96, 129.63, 121.26, 114.77, 112.92, 110.43, 104.91, 92.12, 68.21, 66.44, 56.46, 51.72, 51.58.

Methyl 4-Oxo-7-(2-phenoxyethoxy)-1,4-dihydroquinoline-3-carboxylate 6a 6a was synthesized following general procedure B in 48% yield. 1H NMR (400 MHz, DMSO) δ 12.15 (s, 1H), 8.51 (s, 1H), 8.07 (s, 1H), 7.30 (s, 2H), 7.03 (d, J=27.9 Hz, 5H), 4.39 (d, J=20.9 Hz, 4H), 3.73 (s, 3H). HRMS (ESI-TOF) m/z: [M+H]+ calcd for C19H17NO5 340.1180; found 340.1153.

Methyl 6-Butyl-4-oxo-7-(2-phenoxyethoxy)-1,4-dihydroquinoline-3-carboxylate 6b 6b was synthesized following general procedures A and B as a white powder in 22% yield. 1H NMR (500 MHz, CDCl$_3$ and 3 drops of TFA-d) δ 9.29 (s, 1H), 8.18 (s, 1H), 7.77 (s, 1H), 7.31 (t, J=8.0 Hz, 2H), 6.99 (t, J=7.4 Hz, 1H), 6.96 (d, J=7.9 Hz, 2H), 4.59 (dd, J=5.3, 3.1 Hz, 2H), 4.45 (dd, J=5.2, 3.1 Hz, 2H), 4.12 (s, 3H), 2.83-2.78 (m, 2H), 1.66 (t, J=7.6 Hz, 2H), 1.37 (dd, J=14.9, 7.4 Hz, 2H), 0.92 (t, J=7.4 Hz, 3H). 13C NMR (126 MHz, CDCl$_3$ and 3 drops of TFA-d) δ 170.15, 168.60, 164.87, 158.55, 144.49, 142.02, 138.11, 129.70, 124.16, 121.46, 114.78, 114.05, 103.32, 100.52, 68.51, 65.83, 54.01, 31.20, 30.50, 22.58, 13.97. HRMS (ESI-TOF) m/z: [M+H]+ calcd for C23H25NO5 396.1806; found 396.1780.

Methyl 6-Butyl-4-oxo-1,4-dihydroquinoline-3-carboxylate 6c 6c was synthesized following general procedures A and B as a white powder in 33% yield. 1HNMR (400 MHz, DMSO) δ 8.54 (s, 1H), 7.95 (s, 1H), 7.57 (dd, J=32.1 Hz, 7.9, 2H), 3.73 (s, 3H), 2.69 (t, J=7.1 Hz, 2H), 1.64-1.52 (m, 2H), 1.30 (dd, J=14.1, 7.6 Hz, 2H), 0.89 (t, J=7.2 Hz, 3H). 13CNMR (101 MHz, DMSO) δ 186.05, 184.62, 173.71, 145.35, 138.78, 138.38, 132.78, 127.21, 124.15, 119.68, 51.04, 34.46, 33.05, 21.62, 13.76. HRMS (ESI-TOF) m/z: [M+H]+ calcd for C15H17NO3 260.1281; found 260.1262.

Methyl 4-Oxo-1,4-dihydroquinoline-3-carboxylate 6d 6d was synthesized following general procedure B in 25% yield. 1H NMR (400 MHz, DMSO) δ 12.34 (s, 1H), 8.57 (s, 1H), 8.16 (dd, J=8.1, 0.9 Hz, 1H), 7.75-7.67 (m, 1H), 7.61 (d, J=8.2 Hz, 1H), 7.45-7.38 (m, 1H), 3.74 (s, 3H). 13C NMR (101 MHz, DMSO) δ 173.35, 165.36, 145.06, 138.93, 132.41, 127.25, 125.62, 124.71, 118.77, 109.48, 51.10. HRMS (ESI-TOF) m/z: [M+H]+ calcd for C11H9NO3 204.0655; found 204.0638.

Methyl 6-(Benzyloxy)-4-oxo-1,4-dihydroquinoline-3-carboxylate 6e 6e was synthesized following general procedure B in 13% yield. 1H NMR (400 MHz, DMSO) δ 12.15 (s, 1H), 8.50 (s, 1H), 8.06 (d, J=9.3 Hz, 1H), 7.48 (d, J=7.3 Hz, 2H), 7.42 (t, J=7.2 Hz, 2H), 7.36 (t, J=7.1 Hz, 1H), 7.09 (s, 2H), 5.22 (s, 2H), 3.72 (s, 3H). 13C NMR (101 MHz, DMSO) δ 172.78, 165.37, 161.29, 145.02, 140.56, 136.24, 128.51, 128.07, 127.82, 127.54, 121.42, 114.58, 109.45, 101.25, 69.64, 51.05. HRMS (ESI-TOF) m/z: [M+H]+ calcd for C18H15NO4 310.1074; found 310.1072.

Methyl 4-Oxo-6-phenethoxy-1,4-dihydroquinoline-3-carboxylate 6f 6f was synthesized following general procedure B in 17% yield. 1H NMR (400 MHz, DMSO) δ 12.08 (s, 1H), 8.51 (s, 1H), 8.04 (d, J=8.3 Hz, 1H), 7.34 (s, 4H), 7.23 (s, 1H), 7.05-6.96 (m, 2H), 4.29 (s, 2H), 3.72 (s, 3H), 3.09 (s, 2H). HRMS (ESI-TOF) m/z: [M+H]+ calcd for C19H17NO4 324.1230; found 324.1227

Methyl 4-Oxo-6-(3-phenylpropoxy)-1,4-dihydroquinoline-3-carboxylate 6g 6g was synthesized from the amine following general procedures A and B in 8% yield. 1H NMR (400 MHz, DMSO) δ 12.33 (s, 1H), 8.51 (s, 1H), 7.56 (dd, J=16.3, 5.9 Hz, 2H), 7.35 (dd, J=8.9, 2.9 Hz, 1H), 7.27 (dt, J=8.2, 7.1 Hz, 4H), 7.19 (dd, J=11.3, 4.3 Hz, 1H), 4.05 (t, J=6.3 Hz, 2H), 3.73 (s, 3H), 2.80-2.75 (m, 2H), 2.06 (dd, J=8.4, 6.9 Hz, 2H). 13C NMR (101 MHz, DMSO) δ 172.77, 155.94, 143.84, 140.86, 133.33, 128.34, 128.32, 125.84, 122.01, 120.58, 108.30, 106.21, 92.75, 90.94, 67.13, 51.04, 30.98, 29.79. HRMS (ESI-TOF) m/z: [M+H]+ calcd for C20H19NO4 338.1387; found 338.1381.

Methyl 7-(Benzyloxy)-4-oxo-1,4-dihydroquinoline-3-carboxylate 6h 6h was synthesized following general procedure B in 10% yield. 1H NMR (400 MHz, DMSO) δ 8.52 (s, 1H), 7.66 (d, J=2.7 Hz, 1H), 7.60 (d, J=9.0 Hz, 1H), 7.48 (d, J=7.3 Hz, 2H), 7.40 (t, J=7.4 Hz, 3H), 7.33 (d, J=14.2 Hz, 1H), 5.20 (s, 2H), 3.73 (s, 3H). 13C NMR (126 MHz, DMSO) δ 172.76, 165.56, 155.55, 144.28, 136.75, 128.44, 127.89, 127.71, 122.58, 120.96, 115.37, 108.22, 107.51, 106.81, 69.54, 51.01. HRMS (ESI-TOF) m/z: [M+H]+ calcd for C18H15NO4 310.1074; found 310.1072.

Methyl 4-Oxo-7-phenethoxy-1,4-dihydroquinoline-3-carboxylate 6i 6i was synthesized following general procedure B in 13% yield. 1H NMR (400 MHz, DMSO) δ 12.32 (s, 1H), 8.51 (s, 1H), 7.59-7.54 (m, 2H), 7.36-7.30 (m, 5H), 7.26-7.20 (m, 1H), 4.28 (t, J=6.7 Hz, 2H), 3.73 (s, 3H), 3.07 (t, J=6.7 Hz, 2H). 13C NMR (101 MHz, DMSO) δ 172.75, 165.49, 155.72, 143.84, 138.26, 133.32, 128.94, 128.48, 128.32, 126.30, 122.37, 120.56, 108.32, 106.42, 68.52, 51.04, 34.75. HRMS (ESI-TOF) m/z: [M+H]+ calcd for C19H17NO4 324.1230; found 324.1225.

Methyl 4-Oxo-7-(3-phenylpropoxy)-1,4-dihydroquinoline-3-carboxylate 6j 6j was synthesized following general procedure B in 16% yield. 1H NMR (400 MHz, DMSO) δ 12.09 (s, 1H), 8.50 (s, 1H), 8.05 (d, J=6.5 Hz, 1H), 7.33-7.18 (m, 5H), 6.99 (s, 2H), 4.06 (s, 2H), 3.72 (s, 3H), 2.77 (s, 2H), 2.08 (s, 2H). HRMS (ESI-TOF) m/z: [M+H]+ calcd for C20H19NO4 338.1387; found 338.1384.

Methyl 4-Oxo-7-phenoxy-1,4-dihydroquinoline-3-carboxylate 6k 6k was synthesized following general procedures A and B in 8% yield. 1H NMR (400 MHz, DMSO) δ 12.15 (s, 1H), 8.48 (d, J=28.8 Hz, 1H), 8.14 (d, J=8.9 Hz, 1H), 7.49 (t, J=7.8 Hz, 2H), 7.29 (t, J=7.4 Hz, 1H), 7.19 (d, J=7.9 Hz, 2H), 7.08 (dd, J=8.9 Hz, 2.1 Hz, 1H), 6.99 (d, J=2.0 Hz, 1H), 3.72 (s, 3H). 13C NMR (101 MHz, DMSO) δ 172.80, 165.27, 160.72, 154.69, 145.30, 140.56, 130.42, 128.18, 125.06, 122.69, 120.41, 115.60, 109.59, 104.39, 51.09. HRMS (ESI-TOF) m/z: [M+H]+ calcd for C17H13NO4 296.0917; found 296.0916.

Methyl 7-Chloro-4-oxo-1,4-dihydroquinoline-3-carboxylate 6l 6l was synthesized following general procedure B in 49% yield. 1H NMR (500 MHz, DMSO) δ 12.36 (s, 1H), 8.62 (s, 1H), 8.14 (d, J=8.6 Hz, 1H), 7.67 (d, J=1.9 Hz, 1H), 7.44 (dd, J=8.6, 2.0 Hz, 1H), 3.74 (s, 3H). 13C NMR (126 MHz, CDCl3 and 3 drops of TFA-d) δ 172.36, 168.11, 147.02, 145.30, 140.55, 131.48, 126.24, 120.93, 118.37, 104.90, 54.57. HRMS (ESI-TOF) m/z: [M+H]+ calcd for C11H8NClO3 238.0266; found 238.0247.

Methyl 4-Oxo-7-phenyl-1,4-dihydroquinoline-3-carboxylate 6m 6m was synthesized following general procedure B in 33% yield. 1H NMR (500 MHz, CDCl3 and 3 drops of TFA-d) δ 10.64 (s, 1H), 9.43 (d, J=1.1 Hz, 1H), 8.61 (d, J=8.7 Hz, 1H), 8.41 (d, J=1.6 Hz, 1H), 8.17 (dd, J=8.7, 1.6 Hz, 1H), 7.78-7.74 (m, 2H), 7.56 (ddt, J=7.1, 5.6, 3.7 Hz, 3H), 4.16 (s, 3H). 13C NMR (126 MHz, CDCl3) δ 172.25, 168.28, 151.21, 146.24, 140.54, 137.25, 130.54, 129.78, 129.66, 127.91, 125.43, 118.66, 118.26, 104.44, 54.41. HRMS (ESI-TOF) m/z: [M+H]+ calcd for C17H13NO3 280.0968; found 280.0966.

Methyl 7-Fluoro-4-oxo-1,4-dihydroquinoline-3-carboxylate 6n 6n was synthesized following general procedure B in 21% yield. 1HNMR (400 MHz, CDCl3 and 3 drops of TFA-d) δ 11.61 (s, 1H), 9.43 (s, 1H), 8.60 (dd, J=9.2, 5.4 Hz, 1H), 7.98 (dd, J=8.4, 2.1 Hz, 1H), 7.71-7.57 (m, 1H), 4.14 (s, 3H). 13C NMR (101 MHz, CDCl3 and 3 drops of TFA-d) δ 172.13, 168.20, 167.61 (d, J=264.8 Hz), 147.13, 142.27 (d, J=14.1 Hz), 128.22 (d, J=11.2 Hz), 120.29 (d, J=24.8 Hz), 117.08, 107.28 (d, J=25.5 Hz), 104.63, 54.37. HRMS (ESI-TOF) m/z: [M+H]+ calcd for C11H8NFO3 222.0561; found 222.0551.

Methyl 6-Methoxy-4-oxo-1,4-dihydroquinoline-3-carboxylate 6o 6o was synthesized following general procedure B in 15% yield. 1H NMR (400 MHz, DMSO) δ 12.33 (s, 1H), 8.51 (s, 1H), 7.57 (t, J=6.3 Hz, 2H), 7.34 (dd, J=8.9, 3.0 Hz, 1H), 3.85 (s, 3H), 3.73 (s, 3H). 13C NMR (101 MHz, DMSO) δ 172.79, 165.50, 156.61, 143.83, 133.35, 128.51, 122.22, 120.56, 108.35, 105.50, 55.47, 51.07. HRMS (ESI-TOF) m/z: [M+H]+ calcd for C12H11NO4 234.0761; found 234.0746.

Methyl 6-Ethoxy-4-oxo-1,4-dihydroquinoline-3-carboxylate 6p 6p was synthesized following general procedure B in 24% yield. 1H NMR (400 MHz, DMSO) δ 12.31 (s, 1H), 8.50 (s, 1H), 7.55 (dd, J=10.4, 5.9 Hz, 2H), 7.32 (dd, J=9.0, 2.9 Hz, 1H), 4.10 (dd, J=13.8, 6.9 Hz, 2H), 3.73 (s, 3H), 1.36 (t, J=6.9 Hz, 3H). 13C NMR (126 MHz, CDCl3) δ 170.69, 168.42, 160.02, 142.67, 135.39, 130.07, 122.95, 121.73, 104.41, 102.91, 65.13, 54.25, 14.47.

Methyl 6-Isopropyl-4-oxo-1,4-dihydroquinoline-3-carboxylate 6q 6q was synthesized following general procedure B in 23% yield. 1H NMR (400 MHz, DMSO) δ 12.26 (s, 1H), 8.49 (s, 1H), 7.95 (d, J=1.8 Hz, 1H), 7.59 (dd, J=8.5, 2.1 Hz, 1H), 7.51 (d, J=8.5 Hz, 1H), 3.69 (s, 3H), 3.05-2.93 (m, 1H), 1.21 (s, 3H), 1.20 (s, 3H). 13C NMR (101 MHz, DMSO) δ 173.36, 165.44, 145.03, 144.64, 137.28, 131.33, 127.20, 122.14, 118.89, 109.18, 51.08, 33.15, 23.82. HRMS (ESI-TOF) m/z: [M+H]+ calcd for C20H19NO6 246.1125; found 246.1105.

Methyl 6-Chloro-4-oxo-1,4-dihydroquinoline-3-carboxylate 6r 6r was synthesized following general procedure B in 23% yield. 1H NMR (400 MHz, DMSO) δ 12.51 (s, 1H), 8.62 (s, 1H), 8.08 (d, J=2.4 Hz, 1H), 7.76 (dd, J=8.8, 2.5 Hz, 1H), 7.67 (d, J=8.8 Hz, 1H), 3.75 (s, 3H). 13C NMR (101 MHz, CDCl3 and 3 drops of TFA-d) δ 171.31, 167.96, 145.95, 138.62, 137.98, 136.69, 123.65, 123.18, 120.89, 105.05, 54.29. HRMS (ESI-TOF) m/z: [M+H]+ calcd for C11H18NClO3 238.0266; found 238.0241.

Methyl 6-(4-Fluorophenoxy)-4-oxo-1,4-dihydroquinoline-3-carboxylate 6s 6s was synthesized following general procedure B in 31% yield. 1H NMR (400 MHz, CDCl3 and 3 drops of TFA-d) δ 13.92 (s, 1H), 9.31 (d, J=10.0 Hz, 1H), 8.33 (dd, J=9.3, 1.6 Hz, 1H), 7.83 (dt, J=9.3, 2.3 Hz, 1H), 7.69 (s, J=2.6 Hz, 1H), 7.26-7.06 (m, 4H), 4.12 (s, 3H). 13C NMR (101 MHz, CDCl3 and 3 drops of TFA-d) δ 176.01, 171.21, 168.27, 159.69, 150.20, 143.88, 135.97, 129.62, 123.65, 122.30 (d, J=8.2 Hz), 121.62, 117.51 (d, J=23.6 Hz), 107.75, 104.58, 54.37. HRMS (ESI-TOF) m/z: [M+H]+ calcd for C17H12NFO4 314.0823; found 314.0794.

Methyl 6-Ethyl-4-oxo-1,4-dihydroquinoline-3-carboxylate 6t 6t was synthesized following general procedure B in 14% yield. 1H NMR (400 MHz, DMSO) δ 12.30 (s, 1H), 8.53 (s, 1H), 7.97 (d, J=1.2 Hz, 1H), 7.56 (dt, J=14.4, 5.2 Hz, 2H), 3.73 (s, 3H), 2.72 (t, J=7.5 Hz, 2H), 1.22 (t, J=7.6 Hz, 3H). 13C NMR (101 MHz, DMSO) δ 173.74, 165.89, 145.06, 140.91, 137.61, 133.07, 127.69, 124.12, 119.27, 109.63, 51.51, 28.29, 16.00. HRMS (ESI-TOF) m/z: [M+H]+ calcd for C13H13NO3 232.0968; found 232.0965.

Methyl 4-Oxo-6-phenyl-1,4-dihydroquinoline-3-carboxylate 6u 6u was synthesized following general procedure B in 21% yield. 1H NMR (400 MHz, DMSO) δ 12.44 (s, 1H), 8.60 (s, 1H), 8.38 (d, J=2.1 Hz, 1H), 8.04 (dd, J=8.6, 2.2 Hz, 1H), 7.72 (ddd, J=5.8, 4.1, 0.8 Hz, 3H), 7.54-7.49 (m, 2H), 7.43-7.38 (m, 1H), 3.76 (s, 3H). 13C NMR (101 MHz, CDCl3 and 3 drops of TFA-d) δ 172.37, 168.39, 145.35, 143.47, 139.29, 137.83, 137.06, 129.63, 129.52, 127.69, 122.02, 121.85, 120.47, 104.72, 54.36. HRMS (ESI-TOF) m/z: [M+H]+ calcd for C17H13NO3 280.0968; found 280.0947.

Methyl 4-Oxo-6-phenoxy-1,4-dihydroquinoline-3-carboxylate 6v 6v was synthesized following general procedure B in 11% yield. 1H NMR (400 MHz, DMSO) δ 12.45 (s, 1H), 8.56 (s, 1H), 7.69 (d, J=8.6 Hz, 1H), 7.56-7.41 (m, 4H), 7.21 (t, J=7.4 Hz, 1H), 7.09 (d, J=7.9 Hz, 2H), 3.72 (s, 3H). 13C NMR (101 MHz, DMSO) δ 172.62, 165.32, 156.12, 154.28, 144.58, 134.92, 130.24, 128.50, 124.35, 124.12, 121.22, 119.24, 112.00, 108.64, 51.09. HRMS (ESI-TOF) m/z: [M+H]+ calcd for C17H13NO4 296.0917; found 296.0907.

Methyl 6-Ethyl-4-oxo-7-(2-phenoxyethoxy)-1,4-dihydroquinoline-3-carboxylate 6w 6w was synthesized following general procedures A and B in 21% yield. 1H NMR (399 MHz, CDCl3 and 3 drops of TFA-d) δ 9.28 (s, 1H), 8.21 (s, 1H), 7.72 (s, 1H), 7.31 (t, J=7.6 Hz, 2H), 7.07-6.90 (m, 3H), 4.60 (s, 2H), 4.45 (s, 2H), 4.12 (s, 3H), 2.85 (dd, J=14.5, 7.2 Hz, 2H), 1.31 (t, J=7.4 Hz, 3H). 13C NMR (100 MHz, CDCl3 and 3 drops of TFA-d) δ 170.26, 168.53, 164.92, 158.53, 141.88, 139.38, 129.72, 123.39, 123.36, 121.48, 114.79, 114.12, 103.40, 100.25, 68.53, 65.81, 54.05, 23.94, 13.16. HRMS (ESI-TOF) m/z: [M+H]+ calcd for C21H21NO5 368.1493; found 368.1471.

Methyl 4-Oxo-7-(2-phenoxyethoxy)-6-propyl-1,4-dihydroquinoline-3-carboxylate 6x 6x was synthesized following general procedures A and B in 38% yield. 1H NMR (399 MHz, CDCl3 and 3 drops of TFA-d) δ 11.77 (s, 1H), 9.22 (s, 1H), 8.22 (s, 1H), 7.56 (s, 1H), 7.32 (t, J=7.9 Hz, 2H), 7.01 (t, J=7.4 Hz, 1H), 6.97 (d, J=8.1 Hz, 2H), 4.57 (d, J=4.3 Hz, 2H), 4.53-4.41 (m, 2H), 4.13 (s, 3H), 2.80 (t, J=7.7 Hz, 2H), 1.73 (sex, J=7.5 Hz, 2H), 0.97 (t, J=7.3 Hz, 3H). 13C NMR (100 MHz, CDCl3 and 3 drops of TFA-d) δ 170.63, 168.48, 165.27, 158.46, 141.56, 138.26, 129.86, 124.57, 124.56, 121.80, 115.00, 114.15, 103.65, 99.99, 68.51, 66.07, 54.22, 32.73, 22.26, 13.98.

Methyl 4-Oxo-6-pentyl-7-(2-phenoxyethoxy)-1,4-dihydroquinoline-3-carboxylate 6y 6y was synthesized following general procedures A and B in 27% yield. 1H NMR (600 MHz, CDCl3 and 3 drops of TFA-d) δ 12.33 (s, 1H), 9.25 (s, 1H), 8.14 (s, 1H), 7.78 (s, 1H), 7.31-7.25 (m, 2H), 7.00-6.89 (m, 3H), 4.57 (d, J=3.5 Hz, 2H), 4.42 (d, J=1.9 Hz, 2H), 4.11-4.00 (m, 3H), 2.82-2.73 (m, 2H), 1.70-1.60 (m, 2H), 1.34-1.25 (m, 4H), 0.90-0.79 (m, 3H). 13C NMR (151 MHz, CDCl3 and 3 drops of TFA-d) δ 170.10, 168.65, 164.76, 158.59, 144.54, 142.17, 138.01, 129.68, 124.10, 121.44, 114.81, 114.09, 103.30, 100.66, 68.50, 65.88, 53.93, 31.62, 30.75, 28.74, 22.52, 14.03.

Methyl 6-Bromo-4-oxo-7-(2-phenoxyethoxy)-1,4-dihydroquinoline-3-carboxylate 6z 6z was synthesized following general procedure B in 27% yield. 1H NMR (400 MHz, CDCl3 and 3 drops of TFA-d) δ 12.86 (s, 1H), 9.36 (s, 1H), 8.68 (s, J=2.7 Hz, 1H), 7.83 (s, 1H), 7.33-7.23 (m, 2H), 7.03-6.91 (m, 3H), 4.67-4.61 (m, 2H), 4.50-4.44 (m, 2H), 4.12 (s, J=2.6 Hz, 3H). 13C NMR (101 MHz, CDCl3 and 3 drops of TFA-d) δ 180.98, 170.22, 168.22, 162.47, 158.44, 145.88, 141.88, 129.74, 129.09, 121.68, 118.49, 115.03, 104.05, 101.90, 69.79, 65.94, 54.33. HRMS (ESI-TOF) m/z: [M+H]+ calcd for C19H16NBrO5 418.0285; found 418.0249.

Methyl 6-Methoxy-4-oxo-7-(2-phenoxyethoxy)-1,4-dihydroquinoline-3-carboxylate 6aa 6aa was synthesized following general procedure B in 34% yield. 1H NMR (600 MHz, CDCl3 and 3 drops of TFA-d) δ 10.68 (s, 1H), 9.18 (s, 1H), 7.81 (s, 1H), 7.59 (s, 1H), 7.30-7.22 (m, 2H), 7.00-6.89 (m, 3H), 4.60 (dd, J=5.3, 3.3 Hz, 2H), 4.44 (dd, J=5.2, 3.3 Hz, 2H), 4.10 (s, 3H), 4.04 (s, 3H). 13C NMR (151 MHz, CDCl$_3$ and 3 drops of TFA-d) δ 168.94, 168.57, 158.48, 157.88, 152.20, 142.64, 138.26, 129.65, 121.50, 114.98, 114.88, 103.65, 101.80, 101.74, 69.08, 65.88, 56.70, 54.03. HRMS (ESI-TOF) m/z: [M+H]+ calcd for C20H19NO6 370.1285; found 370.1272.

Methyl 6-Chloro-4-oxo-7-(2-phenoxyethoxy)-1,4-dihydroquinoline-3-carboxylate 6ab 6ab was synthesized from the amine following general procedures A and B in 15% yield. 1HNMR (399 MHz, CDCl$_3$ and 3 drops of TFA-d) δ 12.48 (s, 1H), 9.34 (s, 1H), 8.51 (s, 1H), 7.81 (s, 1H), 7.31 (t, J=7.3 Hz, 2H), 6.97 (d, J=7.6 Hz, 3H), 4.65 (s, 2H), 4.49 (s, 2H), 4.14 (s, 3H). 13C NMR (100 MHz, CDCl$_3$ and 3 drops of TFA-d) δ 170.44, 168.12, 161.89, 158.31, 141.13, 129.75, 129.26, 125.59, 125.50, 121.78, 115.01, 114.29, 104.11, 102.01, 69.64, 65.97, 54.36.

Methyl 6-Methyl-4-oxo-7-(2-phenoxyethoxy)-1,4-dihydroquinoline-3-carboxylate 6ac 6ac was synthesized following general procedures A and B in 26% yield. 1H NMR (500 MHz, DMSO) δ 12.10 (d, J=6.6 Hz, 1H), 8.48 (d, J=6.6 Hz, 1H), 7.90 (s, 1H), 7.31 (t, J=7.8 Hz, 2H), 7.05 (s, 1H), 7.01 (d, J=8.1 Hz, 2H), 6.96 (t, J=7.3 Hz, 1H), 4.41 (s, 4H), 3.72 (s, 3H), 2.21 (s, 3H). 13C NMR (126 MHz, DMSO) δ 172.71, 159.84, 158.37, 144.42, 139.05, 129.54, 126.82, 124.75, 121.00, 120.84, 114.63, 109.34, 100.43, 99.10, 67.17, 66.05, 51.04, 15.98.

6-Butyl-4-oxo-7-(2-phenoxyethoxy)-1,4-dihydroquinoline-3-carbonitrile 6ad

6ad was synthesized following general procedures A and B in 21% yield. 1H NMR (400 MHz, DMSO) δ 12.56 (s, 1H), 8.55 (d, J=51.3 Hz, 1H), 7.79 (d, J=36.7 Hz, 1H), 7.29 (d, J=7.0 Hz, 2H), 7.13-6.83 (m, 4H), 4.41 (s, 4H), 2.61 (s, 2H), 1.52 (s, 2H), 1.24 (d, J=7.2 Hz, 2H), 0.83 (t, J=6.8 Hz, 3H). 13C NMR (101 MHz, DMSO) δ 173.63, 160.22, 158.35, 145.92, 139.34, 130.23, 129.50, 125.36, 120.79, 118.89, 117.02, 114.52, 99.57, 93.32, 67.14, 65.97, 31.10, 29.21, 21.80, 13.69. HRMS (ESI-TOF) m/z: [M+H]+ calcd for C22H22N2O3 363.1703; found 363.1708

6-Butyl-3-ethyl-7-(2-phenoxyethoxy)quinolin-4(1H)-one 6ae

Ethyl butyrate (82 mmol) and diethyl oxalate (14) (82 mmol) were stirred in sodium ethoxide and ethanol to give diethyl 2-ethyl-3-oxosuccinate (15). 15 (3g, 13.889 mmol) was then combined with 3b (3g, 10.68 mmol), a catalytic amount of acetic acid and stirred in benzene (22 mL) at 100° C. for 18 h to give 5ae. Benzene and acetic acid were then removed from the reaction mixture with reduced pressure and the crude was cyclized following general procedure B to give 6ae in 39% yield. 1H NMR (400 MHz, DMSO) δ 11.36 (s, 1H), 7.82 (s, 1H), 7.68 (s, 1H), 7.34-7.27 (m, 2H), 7.01-6.91 (m, 4H), 4.38 (q, J=5.1 Hz, 4H), 2.59 (t, J=7.5 Hz, 2H), 2.41 (q, J=7.4 Hz, 2H), 1.57-1.48 (m, 2H), 1.25 (h, J=7.4 Hz, 2H), 1.09 (t, J=7.4 Hz, 3H), 0.83 (t, J=7.3 Hz, 3H). 13C NMR (101 MHz, DMSO) δ 176.04, 159.38, 158.88, 140.24, 135.56, 129.96, 127.76, 125.92, 122.35, 121.22, 119.07, 114.99, 98.47, 67.25, 66.54, 31.85, 29.75, 22.28, 21.02, 14.20, 10.69. HRMS (ESI-TOF) m/z: [M+H]+ calcd for C23H27NO3 366.2064; found 366.2044.

Ethyl 6-Butyl-4-oxo-7-(2-phenoxyethoxy)-1,4-dihydroquinoline-3-carboxylate 6af

6af was synthesized following general procedures A and B in 5% yield. 1H NMR (400 MHz, DMSO) δ 8.45 (s, 1H), 7.87 (s, 1H), 7.31 (t, J=7.9 Hz, 2H), 7.05 (s, 1H), 7.03-6.90 (m, 3H), 4.41 (s, 4H), 4.19 (q, J=7.2 Hz, 2H), 3.38 (dd, J=14.0, 7.0 Hz, 3H), 3.17 (d, J=4.7 Hz, 2H), 2.61 (t, J=7.5 Hz, 2H), 1.60-1.46 (m, 2H), 1.09 (t, J=7.0 Hz, 3H).

3-Acetyl-6-butyl-7-(2-phenoxyethoxy)quinolin-4(1H)-one 6ag 3b (1g, 3.5 mmol) was combined with ethyl-2-(ethoxymethylene)-3-oxobutanoate (848 mg, 4.6 mmol), a catalytic amount of acetic acid and stirred in benzene (7 mL) at 100° C. for 18 h to give 5ag. Benzene and acetic acid were then removed from the reaction mixture with reduced pressure and the crude was cyclized following general procedure B to give 6ag in 31% yield. 1H NMR (400 MHz, DMSO) δ 11.53 (s, 1H), 7.74 (s, 1H), 7.30 (t, J=7.8 Hz, 2H), 7.03-6.91 (m, 4H), 5.79 (s, 1H), 4.38 (q, J=5.2 Hz, 4H), 2.58 (t, J=7.6 Hz, 2H), 2.29 (s, 3H), 1.52 (p, J=7.5 Hz, 2H), 1.24 (h, J=7.4 Hz, 2H), 0.83 (t, J=7.3 Hz, 3H). 13C NMR (101 MHz, DMSO) δ 176.60, 159.48, 158.84, 149.06, 140.68, 133.75, 129.93, 127.61, 125.65, 121.20, 118.86, 114.96, 108.41, 98.66, 67.23, 66.51, 31.78, 29.64, 22.27, 19.78, 14.18.

4-Oxo-7-(2-phenoxyethoxy)-1,4-dihydroquinoline-3-carboxylic-Acid 7a 7a was synthesized following general procedure C in 77% yield. 1H NMR (400 MHz, DMSO) δ 13.29 (s, 1H), 8.82 (s, 1H), 8.20 (d, J=8.9 Hz, 1H), 7.29 (ddd, J=8.2, 7.3, 4.9 Hz, 4H), 6.98 (dd, J=13.1, 7.6 Hz, 3H), 4.48 (dd, J=5.5, 2.8 Hz, 2H), 4.39 (dd, J=5.3, 2.9 Hz, 2H). 13C NMR (101 MHz, DMSO) δ 177.62, 166.46, 162.41, 158.17, 144.98, 141.47, 129.55, 126.99, 120.86, 118.53, 116.40, 114.49, 107.29, 101.33, 67.16, 65.88.

6-Butyl-4-oxo-7-(2-phenoxyethoxy)-1,4-dihydroquinoline-3-carboxylic Acid 7b 7b synthesized following general procedure C as yellow powder in 68% yield. 1H NMR (500 MHz, DMSO) δ 13.62 (s, 1H), 11.79 (s, 1H), 8.73 (s, 1H), 7.98 (s, 1H), 7.30 (t, J=7.6 Hz, 3H), 7.00 (d, J=7.9 Hz, 2H), 6.95 (t, J=7.2 Hz, 1H), 4.43 (s, 4H), 2.69-2.61 (m, 2H), 1.54 (dt, J=14.8, 7.5 Hz, 2H), 1.25 (dd, J=14.5, 7.3 Hz, 2H), 0.83 (t, J=7.3 Hz, 3H). 13C NMR (126 MHz, DMSO) δ 214.93, 204.35, 198.46, 196.01, 181.60, 177.76, 169.00, 167.17, 162.74, 158.47, 155.69, 152.20, 144.81, 137.36, 104.96, 103.59, 68.67, 66.98, 59.48, 51.36.

7-(2-Phenoxyethoxy)quinolin-4(1H)-one 8a 8a was synthesized following general procedure D in 45% yield. 1H NMR (400 MHz, DMSO) δ 11.54 (d, J=5.4 Hz, 1H), 7.99 (d, J=8.6 Hz, 1H), 7.81 (dd, J=7.3, 6.0 Hz, 1H), 7.33-7.28 (m, 2H), 7.01-6.94 (m, 5H), 5.97-5.92 (m, 1H), 4.43-4.38 (m, 2H), 4.38-4.34 (m, 2H). 13C NMR (101 MHz, DMSO) δ 176.42, 160.81, 158.23, 141.68, 139.08, 129.55, 126.89, 120.81, 120.34, 114.49, 113.23, 108.58, 99.94, 66.69, 66.00. HRMS (ESI-TOF) m/z: [M+H]+ calcd for C17H15NO3 282.1125; found 282.1120.

6-Butyl-7-(2-phenoxyethoxy)quinolin-4(1H)-one 8b 8b was synthesized by general procedure D as an off white solid in 21% yield. 1H NMR (600 MHz, CDCl$_3$) δ 13.07 (s, 1H), 8.02-7.93 (m, 1H), 7.60 (d, J=7.2 Hz, 1H), 7.13-7.04 (m, 2H), 6.89 (s, 1H), 6.76 (dd, J=10.7 Hz, 4.1 Hz, 1H), 6.74-6.68 (m, 2H), 6.13 (t, J=12.5 Hz, 1H), 4.04 (dd, J=11.4 Hz, 7.6 Hz, 2H), 3.97-3.90 (m, 2H), 2.53-2.40 (m, 2H), 1.41-1.30 (m, 2H), 1.08 (dq, J=14.8 Hz, 7.4 Hz, 2H), 0.67-0.58 (m, 3H). 13C NMR (151 MHz, CDCl$_3$) δ 178.69, 160.55, 158.71, 141.11, 139.38, 130.77, 129.67, 125.53, 121.32, 120.27, 114.78, 108.63, 98.75, 67.01, 66.21, 31.89, 30.13, 22.64, 14.09. HRMS (ESI-TOF) m/z: [M+H]+ calcd for C21H23NO3 338.1751; found 338.1729.

6-Butylquinolin-4(1H)-one 8c 8c was synthesized following general procedures C and D in 39% yield. 1H NMR (400 MHz, DMSO) δ 7.94-7.80 (m, 2H), 7.55 (d, J=8.5 Hz, 1H), 7.46 (dd, J=8.5, 2.0 Hz, 1H), 6.01 (d, J=7.3 Hz, 1H), 2.64 (t, J=7.6 Hz, 2H), 1.60-1.51 (m, 2H), 1.27 (dd, J=14.8, 7.4 Hz, 2H), 0.87 (t, J=7.3 Hz, 3H).

2-Bromo-5-nitrophenol 10a

To a charged round-bottom flask, backfilled with argon, was added 1-bromo-2-methoxy-4-nitrobenzene (10 g, 43.098 mmol) followed by boron tribromide solution (1.0 M in DCM, 107.5 mL) at 0° C. The reaction mixture was stirred for 24 h at room temperature before quenching with DI water. The organic layer was washed with DI water, dried over Na2SO4, filtered, and concentrated under reduced pressure. It was used in the next step without further purification (9.2 g, 99% yield). 1H NMR (400 MHz, CDCl$_3$) δ 7.84 (s, 1H), 7.79-7.59 (m, 2H), 5.92 (bs, 1H). 13C NMR (101 MHz, CDCl$_3$) δ 152.97, 148.49, 132.62, 117.44, 116.43, 111.20.

1-Bromo-4-nitro-2-(2-phenoxyethoxy)benzene 11a

To a solution of 2-bromo-5-nitrophenol (9g, 0.041 28 mol) in anhydrous DMF (90 mL) at room temperature was added sodium hydride (1.82 g, 0.0454 mol). After stirring the resulting solution for 10 min, (2-bromoethoxy)benzene (9.96g, 0.04954 mol) was added slowly. The reaction was then stirred for 24 h and then quenched with water and diluted with DCM (150 mL). The organic layer was dried over Na2SO4, filtered, and concentrated under reduced pressure. The residue was purified by recrystallization from ethyl acetate to afford the title compound (6.95 g, 50% yield). 1H NMR (399 MHz, DMSO) δ 7.94 (s, 1H), 7.87 (d, J=8.1 Hz, 1H), 7.76 (d, J=8.3 Hz, 1H), 7.29 (t, J=6.8 Hz, 2H), 6.99 (d, J=7.6 Hz, 2H), 6.95 (s, 1H), 4.57 (s, 2H), 4.37 (s, 2H). 13C NMR (100 MHz, DMSO) δ 158.22, 155.20, 147.77, 133.77, 129.54, 120.87, 119.20, 116.83, 114.56, 108.28, 68.56, 66.10. HRMS (ESI) calcd for C14H12BrNO4 [M+Na]+ 359.9842; found 359.9855.

1-Methoxy-4-nitro-2-(2-phenoxyethoxy)benzene 11b

To a solution of 2-methoxy-5-nitrophenol (3g, 0.017 74 mol) in anhydrous DMF (50 mL) at room temperature was added sodium hydride (850 mg, 0.021 28 mol). After stirring the resulting solution for 10 min, (2-bromoethoxy)benzene (4.3 g, 0.021 28 mol) was added slowly. The reaction was then stirred for 24 h and then quenched with water and diluted with DCM (100 mL). The organic layer was dried over Na2SO4, filtered, and concentrated under reduced pressure. The residue was purified by recrystallization from ethyl acetate to afford the title compound in 90% yield (4.62 g). 1H NMR (400 MHz, CDCl$_3$) δ 7.94 (dd, J=8.9, 2.6 Hz, 1H), 7.89 (d, J=2.6 Hz, 1H), 7.33-7.25 (m, 2H), 7.01-6.94 (m, 3H), 6.92 (d, J=8.9 Hz, 1H), 4.49-4.44 (m, 2H), 4.42-4.37 (m, 2H), 3.95 (s, 3H). 13C NMR (101 MHz, CDCl$_3$) δ 158.54, 155.17, 148.13, 141.42, 129.64, 121.35, 118.44, 114.78, 110.40, 108.73, 68.23, 66.35, 56.51.

1-Methoxy-4-nitro-2-(2-phenoxyethoxy)benzene 11c

To a solution of 2-methoxy-5-nitrophenol (3g, 0.017 74 mmol) in N,Ndimethylformamide (50 mL) was added sodium hydride (0.85g, 0.02128 mmol) followed by (2-bromoethoxy)benzene. The reaction was stirred overnight at 40° C. Upon completion, the reaction was quenched with DI H2O and extracted with dichloromethane. The organic extracts were dried over Na2SO4, filtered, and concentrated under reduced pressure. The crude material was recrystallized in ethyl acetate to give the title product in 90% yield. 1H NMR (400 MHz, CDCl$_3$) δ 7.92 (dd, J=8.9, 2.6 Hz, 1H), 7.87 (d, J=2.6 Hz, 1H), 7.32-7.24 (m, 2H), 6.99-6.92 (m, 3H), 6.90 (d, J=8.9 Hz, 1H), 4.47-4.42 (m, 2H), 4.40-4.36 (m, 2H). 13C NMR (101 MHz, CDCl$_3$) δ 158.54, 155.17, 148.13, 141.42, 129.64, 121.35, 118.44, 114.78, 110.40, 108.73, 68.23, 66.35.

1-Methyl-4-nitro-2-(2-phenoxyethoxy)benzene 11d 11d was synthesized following general procedure E in 96% yield. 1H NMR (500 MHz, CDCl$_3$) δ 7.83-7.78 (m, 1H), 7.76 (s, 1H), 7.33 (t, J=7.8 Hz, 2H), 7.28 (d, J=8.3 Hz, 1H), 7.04-6.96 (m, 3H), 4.42 (dd, J=10.3, 4.5 Hz, 4H), 2.32 (s, 3H). 13C NMR (126 MHz, CDCl$_3$) δ 158.63, 157.05, 147.19, 135.56, 130.76, 129.67, 121.37, 116.18, 114.78, 106.01, 67.50, 66.37, 16.78.

1-Ethynyl-4-nitro-2-(2-phenoxyethoxy)benzene 12a

To a flame-dried Schlenk tube, 11a (500 mg, 1.48 mmol), PdCl2(PPH3)2 (52.1 mg, 5 mol %), and Cu(I)I (14.13 mg, 5 mol %) were added in triethylamine (10 mL). The reaction mixture was bubbled with argon for 5 min. Trimethylsilylacetylene (0.23 mL, 1.63 mmol) was added under argon, and the flask was sealed. The mixture was stirred and heated to 85° C. for 2 h or until the starting material was no longer visible by TLC. The reaction mixture was filtered through Celite, and the Celite was washed with DCM. The filtrate was washed with 50 mL of saturated ammonium chloride and then 50 mL of DI water. The organic layer was dried over sodium sulfate and then concentrated under reduced pressure. The product was isolated by flash column chromatography with hexanes/ethyl acetate gradient to yield 88% product. 1H NMR (600 MHz, CDCl$_3$) δ 7.84-7.74 (m, 2H), 7.52 (d, J=8.4 Hz, 1H), 7.28 (dd, J=8.6, 7.4 Hz, 2H), 6.94 (dd, J=9.3, 8.3 Hz, 3H), 4.46 (dd, J=5.7, 3.8 Hz, 2H), 4.38 (dd, J=5.6, 3.9 Hz, 2H), 0.19 (s, 9H). 13C NMR (100 MHz, CDCl$_3$) δ 160.00, 158.50, 148.08, 133.89, 129.63, 121.35, 120.01, 116.03, 114.74, 107.30, 105.07, 99.10, 68.06, 66.35, −0.22. To the intermediate (790 mg, 2.23 mmol) were then added THF (3.7 mL) and TBAF (8.9 mL, 1 M). The reaction was stirred at room temperature for 5 min, when the starting material is no longer visible by TLC. Crude was washed through a short silica plug with DCM and then concentrated under reduced pressure. 12a was isolated by flash chromatography with hexanes/ethyl acetate gradient in 56% yield. 1H NMR (400 MHz, CDCl$_3$) δ 7.86 (d, J=2.1 Hz, 1H), 7.80 (dd, J=8.4, 2.1 Hz, 1H), 7.57 (d, J=8.4 Hz, 1H), 7.34-7.25 (m, 2H), 6.96 (dd, J=12.3, 4.9 Hz, 3H), 4.48 (dd, J=5.7, 3.6 Hz, 2H), 4.40 (dd, J=5.8, 3.6 Hz, 2H), 3.47 (s, 1H). 13C NMR (100 MHz, CDCl$_3$) δ 160.24, 158.51, 148.51, 134.49, 129.67, 121.44, 118.90, 116.03, 114.86, 107.40, 86.32, 78.23, 68.31, 66.38.

4-Nitro-2-(2-phenoxyethoxy)-1-(prop-1-yn-1-yl)benzene 12b

In a flame-dried 5 mL round-bottom flask, 100 mg (0.30 mmol) of 11a, PdCl$_2$(PPh$_3$)$_2$(10.4 mg, 5 mol %), Cu(I)I (2.8 mg, 5 mol %), PPh3 (15.5 mg, 0.059 mmol), and diethylamine (1 mL) were combined with 0.5 mL of DMF under argon. A balloon of propyne gas was attached, and the reaction vessel was flushed with propyne. The mixture was stirred at 80° C. for 2 h or until starting material was no longer visible by TLC. The reaction mixture was filtered through Celite, the Celite washed with ethyl acetate. The filtrate was washed with DI water and then with brine. The organic layer was then dried over sodium sulfate, filtered, then concentrated under reduced pressure. The target molecule was isolated via flash chromatography with hexanes and ethyl acetate to give the title compound in 70% yield. 1H NMR (400 MHz, CDCl$_3$) δ 7.81 (d, J=2.0 Hz, 1H), 7.77 (dd, J=8.4, 2.1 Hz, 1H), 7.45 (d, J=8.4 Hz, 1H), 7.34-7.25 (m, 2H), 6.98 (dd, J=10.1, 4.4 Hz, 3H), 4.44 (dd, J=5.7, 3.3 Hz, 2H), 4.39 (dd, J=5.7, 3.3 Hz, 2H), 2.08 (s, 3H).

4-Nitro-1-(pent-1-yn-1-yl)-2-(2-phenoxyethoxy)benzene 12c

In a 30 mL microwave vial, 500 mg (1.48 mmol) of 11a, PdCl2(PPh3)2 (51.9 mg, 5 mol %), Cu(I)I (51.9 mg, 5 mol %), PPh3 (77.6 mg, 0.3 mmol), pent-1-yne (0.16 mL, 1.63 mmol), and diethylamine (2 mL) were combined in 10 mL of DMF. The mixture was stirred and irradiated at 120° C. for 25 min or until starting material was no longer visible by TLC. The reaction mixture was filtered through Celite, the Celite washed with ethyl acetate. The filtrate was washed with DI water and then with brine. The organic layer was then dried over sodium sulfate, filtered, then concentrated under reduced pressure. The target molecule was isolated via flash chromatography with hexanes and ethyl acetate to give the title compound in 70% yield. 1H NMR (600 MHz, CDCl$_3$) δ 7.81-7.75 (m, 2H), 7.47-7.43 (m, 1H), 7.28 (t, J=7.9 Hz, 2H), 7.01-6.89 (m, 3H), 4.46-4.42 (m, 2H), 4.39-4.35 (m, 2H), 2.40 (t, J=6.9 Hz, 2H), 1.57 (sextet, J=7.2 Hz, 2H), 0.98 (t, J=7.4 Hz, 3H).

6-Butyl-N-methyl-4-oxo-7-(2-phenoxyethoxy)-1,4-dihydroquinoline-3-carboxamide 13a 13a was synthesized following general procedure G in 25% yield. 1H NMR (600 MHz, DMSO) δ 12.41 (s, 1H), 9.94 (d, J=4.6 Hz, 1H), 8.63 (s, 1H), 7.95 (s, 1H), 7.30 (t, J=7.9 Hz, 2H), 7.10 (s, 1H), 6.99 (d, J=8.1 Hz, 2H), 6.95 (t, J=7.3 Hz, 1H), 4.41 (d, J=1.5 Hz, 4H), 2.84 (d, J=4.5 Hz, 3H), 2.66-2.59 (m, 2H), 1.53 (dt, J=15.1, 7.6 Hz, 2H), 1.25 (dq, J=14.8, 7.4 Hz, 2H), 0.83 (t, J=7.4 Hz, 3H). 13C NMR (151 MHz, DMSO) δ 175.35, 172.00, 165.22, 159.90, 158.39, 142.52, 139.36, 129.66, 129.51, 125.67, 120.80, 114.54, 110.71, 99.11, 67.08, 66.01, 31.20, 29.34, 25.30, 21.83, 13.70. HRMS (ESI-TOF) m/z: [M+H]+ calcd for C23H26N2O4 395.1965; found 395.1941.

6-Butyl-N, N-dimethyl-4-oxo-7-(2-phenoxyethoxy)-1,4-dihydroquinoline-3-carboxamide 13b 13b was synthesized following general procedure G in 20% yield. 1H NMR (600 MHz, DMSO) δ 11.90 (s, 1H), b 7.95 (s, 1H), 7.85 (s, 1H), 7.30 (t, J=7.9 Hz, 2H), 7.04-6.98 (m, 3H), 6.95 (t, J=7.3 Hz, 1H), 4.40 (s, 4H), 2.95 (s, 3H), 2.87 (s, 3H), 2.61 (t, J=7.6 Hz, 2H), 1.57-1.50 (m, 2H), 1.28-1.23 (m, 2H), 0.84 (t, J=7.3 Hz, 3H). 13CNMR (151 MHz, DMSO) δ 172.02, 167.33, 159.45, 158.39, 139.51, 139.03, 129.50, 128.68, 125.66, 120.78, 119.63, 118.04, 114.54, 98.73, 66.95, 66.05, 37.84, 34.60, 31.34, 29.30, 21.88, 13.73. HRMS (ESI-TOF) m/z: [M+H]+ calcd for C24H28N2O4 409.2122; found 409.2108.

6-Butyl-N-ethyl-4-oxo-7-(2-phenoxyethoxy)-1,4-dihydroquinoline-3-carboxamide 13c 13c was synthesized following general procedure H in 17% yield. 1H NMR (400 MHz, DMSO) δ 10.07 (t, J=5.5 Hz, 1H), 8.63 (s, 1H), 7.95 (s, 1H), 7.39-7.24 (m, 2H), 7.10 (s, 1H), 6.99 (d, J=8.0 Hz, 2H), 6.95 (t, J=7.4 Hz, 1H), 4.41 (s, 4H), 2.68-2.58 (m, 2H), 1.60-1.48 (m, 2H), 1.33-1.17 (m, 4H), 1.13 (t, J=7.2 Hz, 3H), 0.83 (t, J=7.3 Hz, 3H).

6-Butyl-N-(2-hydroxyethyl)-4-oxo-7-(2-phenoxyethoxy)-1,4-dihydroquinoline-3-carboxamide 13d 13d was synthesized following general procedure G in 22% yield. 1H NMR (400 MHz, DMSO) δ 12.56 (d, J=5.7 Hz, 1H), 10.20 (s, 1H), 8.63 (d, J=6.0 Hz, 1H), 7.96 (s, 1H), 7.30 (dd, J=8.4, 7.4 Hz, 2H), 7.13 (s, 1H), 7.00 (d, J=8.4 Hz, 2H), 6.95 (t, J=7.4 Hz, 1H), 4.42 (s, 4H), 3.51 (t, J=5.7 Hz, 2H), 3.38 (dd, J=10.5, 5.4 Hz, 2H), 2.67-2.58 (m, 2H), 1.60-1.49 (m, 2H), 1.25 (dd, J=14.8, 7.4 Hz, 3H), 0.84 (t, J=7.3 Hz, 3H). HRMS (ESI-TOF) m/z: [M+H]+ calcd for C24H28N2O5 425.2071; found 425.2043.

6-Butyl-N-isopropyl-4-oxo-7-(2-phenoxyethoxy)-1,4-dihydroquinoline-3-carboxamide 13e 13e was synthesized following general procedure H in 35% yield. 1HNMR (400 MHz, DMSO) δ 12.38 (s, 1H), 10.08 (d, J=7.4 Hz, 1H), 8.62 (s, 1H), 7.94 (s, 1H), 7.29 (t, J=7.6 Hz, 2H), 7.08 (s, 1H), 7.01-6.91 (m, 3H), 4.40 (s, 4H), 4.06 (dq, J=13.4, 6.7 Hz, 1H), 2.60 (t, J=7.5 Hz, 2H), 1.59-1.46 (m, 2H), 1.27-1.21 (m, 2H), 1.17 (d, J=6.5 Hz, 6H), 0.82 (t, J=7.3 Hz, 3H). 13CNMR (126 MHz, DMSO) δ 175.41, 163.73, 159.83, 158.39, 142.76, 139.55, 129.51, 125.60, 120.79, 119.94, 114.54, 110.61, 99.23, 67.07, 66.01, 31.06, 29.27, 22.83, 21.78, 13.73.

6-Butyl-3-iodo-2-methyl-7-(2-phenoxyethoxy)quinolin-4(1H)-one 16a 16a was synthesized following general procedure H in 65% yield. 1H NMR (400 MHz, DMSO) δ 12.16 (s, 1H), 8.51 (s, 1H), 7.91 (s, 1H), 7.34 (s, 1H), 7.02 (s, 4H), 4.44 (s, 4H), 3.76 (s, 2H), 2.64 (s, 3H), 1.56 (s, 2H), 1.28 (s, 2H), 0.87 (s, 3H). HRMS (ESI-TOF) m/z: [M+H]+ calcd for C22H24NIO3 478.0874; found 478.0852.

6-Butyl-3-iodo-7-(2-phenoxyethoxy)quinolin-4(1H)-one 16b 16b was synthesized following general procedure H in 57% yield. 1H NMR (400 MHz, DMSO) δ 11.96 (s, 1H), 8.38 (s, 1H), 7.82 (s, 1H), 7.32-7.28 (m, 2H), 7.01-6.93 (m, 4H), 4.39 (s, 4H), 2.60 (t, J=7.5 Hz, 2H), 1.52 (t, J=7.4 Hz, 2H), 1.27-1.21 (m, 2H), 0.83 (t, J=7.3 Hz, 3H). 13C NMR (101 MHz, DMSO) δ 172.27, 159.35, 158.38, 143.78, 139.68, 129.50, 129.00, 125.86, 120.78, 116.63, 114.53, 98.47, 80.51, 66.94, 66.03, 31.25, 29.27, 21.80, 13.72.

3-Bromo-6-butyl-2-methyl-7-(2-phenoxyethoxy)quinolin-4(1H)-one 16c 16c was synthesized following general procedure H in 74% yield. 1H NMR (400 MHz, DMSO) δ 11.85 (s, 1H), 7.72 (s, 1H), 7.22 (t, J=7.8 Hz, 2H), 7.07-6.73 (m, 4H), 4.32 (s, 4H), 2.52 (t, J=7.6 Hz, 2H), 2.43 (s, 3H), 1.57-1.35 (m, 2H), 1.16 (q, J=7.3 Hz, 2H), 0.75 (t, J=7.3 Hz, 3H). 13C NMR (101 MHz, DMSO) δ 170.81, 159.78, 158.82, 147.92, 139.17, 129.94, 128.90, 126.04, 121.22, 117.20, 114.96, 106.03, 98.41, 67.35, 66.48, 31.68, 29.68, 22.26, 21.71, 14.16. HRMS (ESI-TOF) m/z: [M+H]+ calcd for C22H24NBrO3 430.1012; found 430.1010.

3-Bromo-6-butyl-7-(2-phenoxyethoxy)quinolin-4(1H)-one 16d 16d was synthesized following general procedure H in 66% yield. 1H NMR (400 MHz, DMSO) δ 12.06 (s, 1H), 7.85 (s, 1H), 7.30 (ddd, J=8.7, 5.7, 2.0 Hz, 2H), 7.07-6.90 (m, 5H), 4.39 (s, 4H), 2.65-2.58 (m, 2H), 1.56-1.48 (m, 2H), 1.26 (dd, J=12.4, 5.1 Hz, 2H), 0.83 (t, J=7.3 Hz, 3H). HRMS (ESI-TOF) m/z: [M+H]+ calcd for C21H22NBrO3 416.0856; found 416.0842.

6-Butyl-3-chloro-2-methyl-7-(2-phenoxyethoxy)quinolin-4(1H)-one 16e 16e was synthesized following general procedure G in 52% yield. 1H NMR (400 MHz, DMSO) δ 11.89 (s, 1H), 7.78 (d, J=23.4 Hz, 1H), 7.34-7.27 (m, 2H), 7.02-6.90 (m, 4H), 4.40 (q, J=6.7, 5.7 Hz, 4H), 3.34 (s, 3H), 2.59 (q, J=7.7 Hz, 2H), 1.58-1.47 (m, 2H), 1.25 (q, J=7.4 Hz, 2H), 0.83 (t, J=7.3 Hz, 3H). 13C NMR (101 MHz, DMSO) δ 170.49, 159.76, 158.84, 146.44, 139.02, 129.94, 128.78, 127.79, 125.88, 121.22, 114.97, 109.99, 98.44, 67.37, 66.48, 31.69, 29.68, 22.27, 18.96, 14.17. HRMS (ESI-TOF) m/z: [M+H]+ calcd for C22H24NClO3 386.1518; found 386.1513.

Abbreviations for Example 2

Ac, acetyl; ACT, artemisinin combination therapy; DMF, N,Ndimethylformamide; EC50, half maximal effective concentration; ED50, half maximal effective dose; HPLC, high performance liquid chromatography; LBI, liver blood index; NBS, Nbromosuccinimide; NCS, N-chlorosuccinimide; ND, not determined; NIS, N-iodosuccinimide; Pb, *P. berghei*; PE, postexposure; RI, resistance index; rt, room temperature; SAR, structure-activity relationship; SPR, structure-property relationship; TBAF, tetra-n-butylammonium fluoride; TEA, triethylamine; TMS, trimethylsilyl; WHO, World Health Organization.

References for Example 2

(1) Gamo, F.-J. Antimalarial Drug Resistance: New Treatments Options for *Plasmodium*. Drug Discovery Today: Technol. 2014, 11, 81-88.

(2) World Health Organization. Malaria Fact Sheet (accessed Jun. 22, 2015).

(3) World Malaria Report 2015; World Health Organization: Geneva, Switzerland, 2015.

(4) Centers for Disease Control and Prevention. Biology. (accessed Jun. 22, 2015).

(5) Fujioka, H.; Aikawa, M. Structure and Life Cycle. Chem. Immunol. 2002, 80, 1-26.

(6) Centers for Disease Control and Prevention. Malaria. (accessed Jun. 22, 2015).

(7) Teixeira, C.; Vale, N.; Perez, B.; Gomes, A.; Gomes, J. R. B.; Gomes, P. "Recycling" Classical Drugs for Malaria. Chem. Rev. 2014, 114, 11164-11220.

(8) White, N. J. Primaquine to Prevent Transmission of *Falciparum* Malaria. Lancet Infect. Dis. 2013, 13, 175-181.

(9) World Malaria Report 2013; World Health Organization: Geneva, Switzerland, 2013.

(10) Monastyrskyi, A.; Kyle, D.; Manetsch, R. 4(1H)-Pyridone and 4(1H)-Quinolone Derivatives as Antimalarials with Erythrocytic, Exoerythrocytic, and Transmission Blocking Activities. Curr. Top. Med. Chem. 2014, 14, 1693-1705.

(11) University of the Sciences, Techniques and Technologies of Bamako. Phase 2 Proof of Concept Study of a Candidate Aminoquinoline Antimalarial (AQ-13). NLM Identifier: NCT01614964. (cited Jun. 22, 2015).

(12) Cross, R. M.; Flanigan, D. L.; Monastyrskyi, A.; LaCrue, A. N.; Saenz, F. E.; Maignan, J. R.; Mutka, T. S.; White, K. L.; Shackleford, D. M.; Bathurst, I.; Fronczek, F. R.; Wojtas, L.; Guida, W. C.; Charman, S. a; Burrows, J. N.; Kyle, D. E.; Manetsch, R. Orally Bioavailable 6-Chloro-7-Methoxy-4(1H)-Quinolones Efficacious against Multiple Stages of *Plasmodium*. J. Med. Chem. 2014, 57, 8860-8879.

(13) Nilsen, A.; et al., Quinolone-3-Diarylethers: A New Class of Antimalarial Drug. Sci. Transl. Med. 2013, 5, 177ra37.

(14) Cross, R. M.; Monastyrskyi, A.; Mutka, T. S.; Burrows, J. N.; Kyle, D. E.; Manetsch, R. Endochin Optimization: Structure-Activity and Structure-Property Relationship Studies of 3-Substituted 2-Methyl-4(1H)-Quinolones with Antimalarial Activity. J. Med. Chem. 2010, 53, 7076-7094.

(15) Saenz, F. E.; LaCrue, A. N.; Cross, R. M.; Maignan, J. R.; Udenze, K. O.; Manetsch, R.; Kyle, D. E. 4-(1H)-Quinolones and 1,2,3,4-Tetrahydroacridin-9(10H)-Ones Prevent the Transmission of *Plasmodium Falciparum* to *Anopheles Freeborni*. Antimicrob. Agents Chemother. 2013, 57, 6187-6195.

(16) Cross, R. M.; Maignan, J. R.; Mutka, T. S.; Luong, L.; Sargent, J.; Kyle, D. E.; Manetsch, R. Optimization of 1,2,3,4-Tetrahydroacridin-9(10H)-ones as Antimalarials Utilizing Structure-Activity and Structure-Property Relationships. J. Med. Chem. 2011, 54, 4399-4426.

(17) Durckheimer, W.; Raether, W.; Seliger, H. G. Tetrahydroacridones Having Chemotherapeutic Action and Process for Preparing Them. U.S. Pat. No. 3,947,449, Mar. 30, 1976.

We claim:

1. A compound having a structure according to Formula A

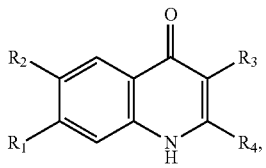

Formula A wherein $R_1$ is

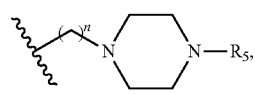

wherein $R_2$ is selected from the group consisting of: $CH_3$, $OCH_3$, $OCH_2Ph$, $O(CH_2)_mPh$ wherein m can be 1-4, Ph, $CH_2CH_3$, $(CH_2)_2CH_3$, $(CH_2)_3CH_3$, $(CH_2)_4CH_3$, OPh, O(p-F)Ph, $CH(CH_3)_2$, Br, Cl, $OCH_2CH_3$, $O(CH_2)_3Ph$, and

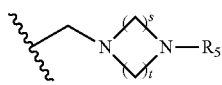

wherein s is 1-4 and t is 1-4,
wherein $R_3$ is selected from the group of H, Cl, Br, I, $CO_2$, $CH_3$, $CO_2CH_2CH_3$, $CO_2CH_3$, $CH_2CH_3$, CN, $CONHCH_3$, $CON(CH_3)_2$, $CONHCH_2CH_3$, $CONH(CH_2)_2OH$, $CONHCH(CH_3)_2$, and $COCH_3$,
wherein $R_4$ is selected from the group of H and $CH_3$,
wherein $R_5$ is selected from the group consisting of: H, F, Bn, para-methoxybenzyl, a piperonyl, 4-$OCH_3$Ph, 4-F-Ph, 4-$CF_3$-Ph, $OCH_3$, $CF_3$,

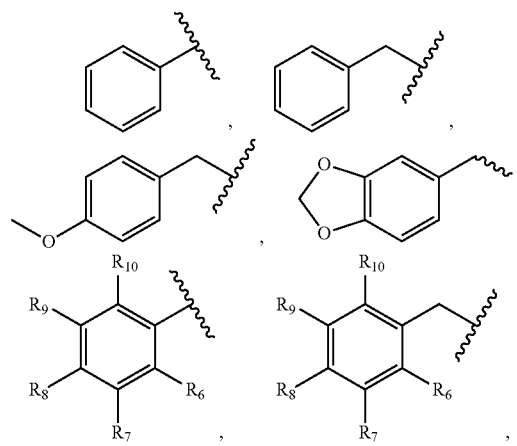

an alkyl, an alkylene, an alkenyl, a heterocycle, a heteroaryl, a heteroalkyl, an alkoxyl, an alkoxy, an amine, an amido, an aryl, an alkyl, an aralkyloxy, a carbocycle, a carbonyl, a nitro, a halogen, a sulfhydryl, a hydroxyl, and a sulfonyl, wherein $R_5$ is further optionally substituted, wherein $R_6$, $R_7$, $R_8$, $R_9$, and $R_{10}$ are each independently selected from the group consisting of: F, $OCH_3$, $CF_3$, H, an alkyl, an alkylene, an alkenyl, a heterocycle, a heteroaryl, a heteroalkyl, an alkoxyl, an alkoxy, an amine, an amido, an aryl, an alkyl, an aralkyloxy, a carbocycle, a carbonyl, a nitro, a halogen, a sulfhydryl, a hydroxyl, a sulfonyl, wherein $R_6$, $R_7$, $R_8$, $R_9$, and $R_{10}$ are each further optionally substituted, and
wherein n is 0, 1, or 2, and
wherein the compound is not according to Formula B

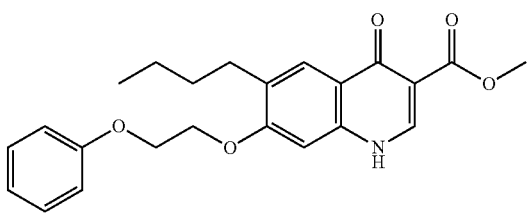

Formula B

2. The compound of claim 1, wherein the compound has a structure according to Formula C

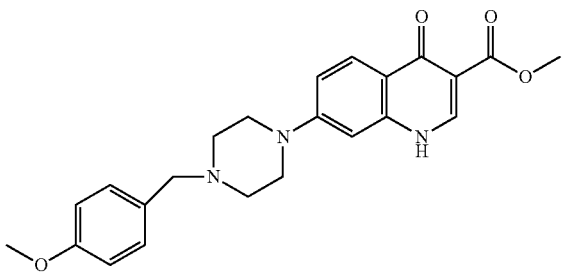

Formula C

3. The compound of claim 1, wherein the compound has a structure according to Formula D

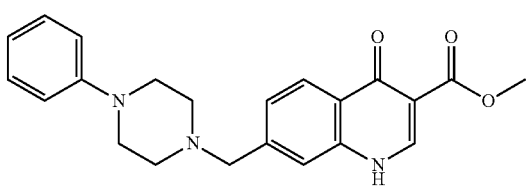

Formula D

4. The compound of claim 1, wherein the $EC_{50}$ against malarial strain W2 of the compound ranges from 0 to about 1 μM.

5. The compound of claim 4, wherein the $EC_{50}$ against malarial strain W2 of the compound ranges from 0 to about 100 nM.

6. The compound of claim 1, wherein the $EC_{50}$ against malarial strain TM90-C2B of the compound ranges from 0 to about 1 μM.

7. The compound of claim 1, wherein the resistive index (RI) ranges from about 0 to 200, wherein the resistive index is ($EC_{50}$ for TM90C2B)/($EC_{50}$ for W2).

8. A pharmaceutical formulation comprising:
a compound having a structure according to Formula A

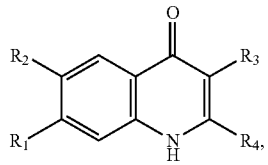

Formula A wherein $R_1$ is

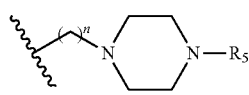

wherein $R_2$ is selected from the group consisting of: $CH_3$, $OCH_3$, $OCH_2Ph$, $O(CH_2)_mPh$ wherein m can be 1-4, Ph, $CH_2CH_3$, $(CH_2)_2CH_3$, $(CH_2)_3CH_3$, $(CH_2)_4CH_3$, OPh, O(p-F)Ph, $CH(CH_3)_2$, Br, Cl, $OCH_2CH_3$, $O(CH_2)_3Ph$, and

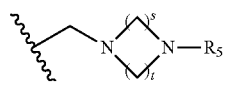

wherein s is 1-4 and t is 1-4,
wherein $R_3$ is selected from the group consisting of H, Cl, Br, I, $CO_2$, $CH_3$, $CO_2CH_2CH_3$, $CO_2CH_3$, $CH_2CH_3$, CN, $CONHCH_3$, $CON(CH_3)_2$, $CONHCH_2CH_3$, $CONH(CH_2)_2OH$, $CONHCH(CH_3)_2$, and $COCH_3$,
wherein $R_4$ is selected from the group of H and $CH_3$,
wherein $R_5$ is selected from the group consisting of: H, F, Bn, para-methoxybenzyl, a piperonyl, 4-$OCH_3$Ph, 4-F-Ph, 4-$CF_3$-Ph, $OCH_3$, $CF_3$,

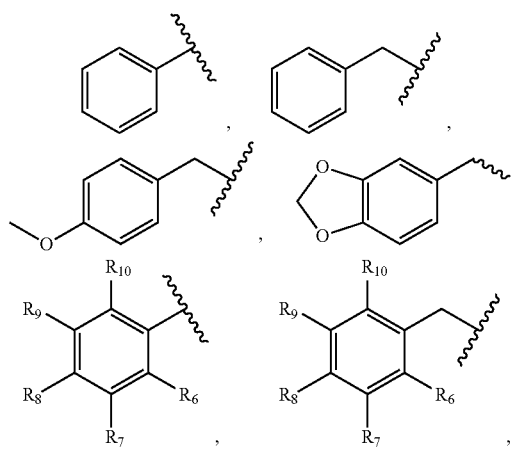

an alkyl, an alkylene, an alkenyl, a heterocycle, a heteroaryl, a heteroalkyl, an alkoxyl, an alkoxy, an amine, an amido, an aryl, an aralkyl, an aralkyloxy, a carbocycle, a carbonyl, a nitro, a halogen, a sulfhydryl, a hydroxyl, and a sulfonyl, wherein $R_5$ is further optionally substituted,
wherein $R_6$, $R_7$, $R_8$, $R_9$, and $R_{10}$ are each independently selected from the group consisting of: F, $OCH_3$, $CF_3$, H, an alkyl, an alkylene, an alkenyl, a heterocycle, a heteroaryl, a heteroalkyl, an alkoxyl, an alkoxy, an amine, an amido, an aryl, an aralkyl, an aralkyloxy, a carbocycle, a carbonyl, a nitro, a halogen, a sulfhydryl, a hydroxyl, a sulfonyl, wherein $R_6$, $R_7$, $R_8$, $R_9$, and $R_{10}$ are each further optionally substituted, and wherein n is 0, 1, or 2,
wherein the compound is not according to Formula B

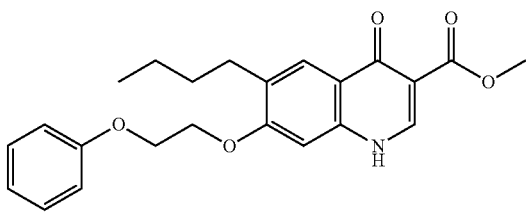

Formula B and a pharmaceutically acceptable carrier.

9. The pharmaceutical formulation of claim 8, wherein the compound has a structure according to Formula C

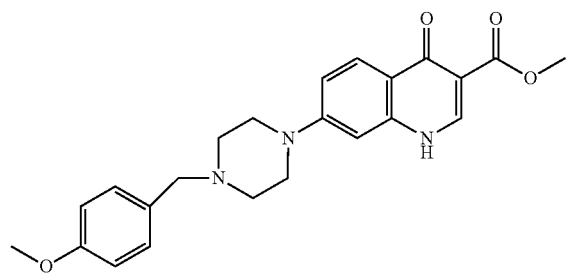

Formula C

10. The pharmaceutical formulation of claim 8, wherein the compound has a structure according to Formula D

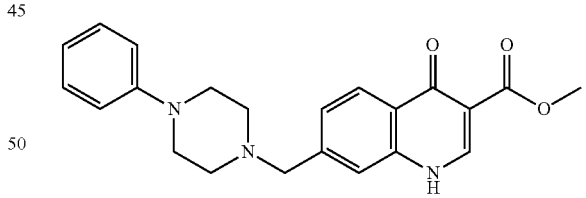

Formula D

11. The pharmaceutical formulation of claim 8, wherein the $EC_{50}$ against malarial strain W2 of the compound ranges from 0 to about 1 µM.

12. The pharmaceutical formulation of claim 8, wherein the $EC_{50}$ against malarial strain W2 of the compound ranges from 0 to about 100 nM.

13. The pharmaceutical formulation of claim 8, wherein the $EC_{50}$ against malarial strain TM90-C2B of the compound ranges from 0 to about 1 µM.

14. The pharmaceutical formulation of claim 8, wherein the resistive index (RI) ranges from about 0 to 200, wherein the resistive index is ($EC_{50}$ for TM90C2B)/($EC_{50}$ for W2).

15. A method of treating malaria in a subject, the method comprising:

administering an amount of a compound having a structure according to Formula A to the subject

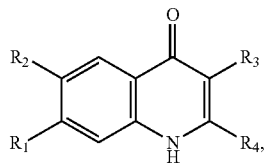

Formula A wherein $R_1$ is

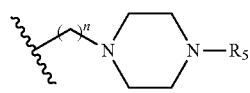

wherein $R_2$ is selected from the group consisting of: $CH_3$, $OCH_3$, $OCH_2Ph$, $O(CH_2)_mPh$ wherein m can be 1-4, Ph, $CH_2CH_3$, $(CH_2)_2CH_3$, $(CH_2)_3CH_3$, $(CH_2)_4CH_3$, OPh, O(p-F)Ph, $CH(CH_3)_2$, Br, Cl, $OCH_2CH_3$, $O(CH_2)_3Ph$, and

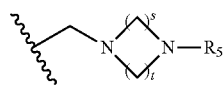

wherein s is 1-4 and t is 1-4,
wherein $R_3$ is selected from the group consisting of H, Cl, Br, I, $CO_2$, $CH_3$, $CO_2CH_2CH_3$, $CO_2CH_3$, $CH_2CH_3$, CN, $CONHCH_3$, $CON(CH_3)_2$, $CONHCH_2CH_3$, $CONH(CH_2)_2OH$, $CONHCH(CH_3)_2$, and $COCH_3$,
wherein $R_4$ is selected from the group of H and $CH_3$,
wherein $R_5$ is selected from the group consisting of: H, F, Bn, para-methoxybenzyl, a piperonyl, 4-$OCH_3$Ph, 4-F-Ph, 4-$CF_3$-Ph, $OCH_3$, $CF_3$,

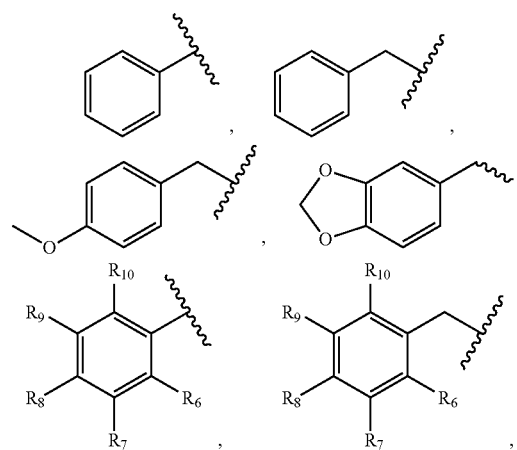

an alkyl, an alkylene, an alkenyl, a heterocycle, a heteroaryl, a heteroalkyl, an alkoxyl, an alkoxy, an amine, an amido, an aryl, an aralkyl, an aralkyloxy, a carbocycle, a carbonyl, a nitro, a halogen, a sulfhydryl, a hydroxyl, and a sulfonyl, wherein $R_5$ can be further optionally substituted,
wherein $R_6$, $R_7$, $R_8$, $R_9$, and $R_{10}$ are each independently selected from the group consisting of: F, $OCH_3$, $CF_3$, H, an alkyl, an alkylene, an alkenyl, a heterocycle, a heteroaryl, a heteroalkyl, an alkoxyl, an alkoxy, an amine, an amido, an aryl, an aralkyl, an aralkyloxy, a carbocycle, a carbonyl, a nitro, a halogen, a sulfhydryl, a hydroxyl, a sulfonyl, wherein $R_6$, $R_7$, $R_8$, $R_9$, and $R_{10}$ are each further optionally substituted, and
wherein n is 0, 1, or 2, and
wherein the compound is not according to Formula B

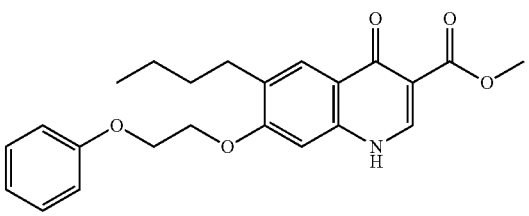

Formula B

16. The method of claim 15, wherein the compound has a structure according to Formula C

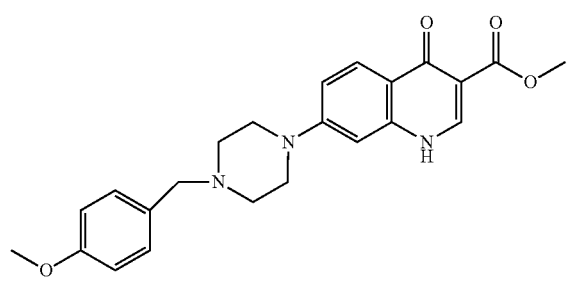

Formula C

17. The method of claim 15, wherein the compound has a structure according to Formula D

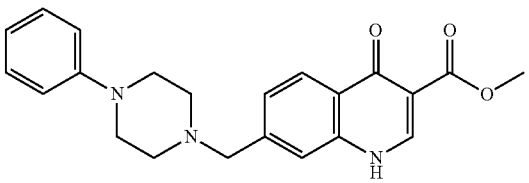

Formula D

* * * * *